US010022355B2

(12) United States Patent
Friedhoff et al.

(10) Patent No.: US 10,022,355 B2
(45) Date of Patent: Jul. 17, 2018

(54) DIARYL AND ARYLHETEROARYL UREA DERIVATIVES AS MODULATORS OF THE 5-HT2A SEROTONIN RECEPTOR USEFUL FOR THE PROPHYLAXIS AND TREATMENT OF REM SLEEP BEHAVIOR DISORDER

(71) Applicant: Axovant Sciences GmbH, Basel (CH)

(72) Inventors: Lawrence Tim Friedhoff, Rivervale, NJ (US); Shankar Ramaswamy, Cincinnati, OH (US); Yandong Wen, Weston, CT (US)

(73) Assignee: Axovant Sciences GmbH, Basel (CH)

( * ) Notice: Subject to any disclaimer, the term of this patent is extended or adjusted under 35 U.S.C. 154(b) by 0 days.

(21) Appl. No.: 15/179,926

(22) Filed: Jun. 10, 2016

(65) Prior Publication Data

US 2016/0361296 A1  Dec. 15, 2016

Related U.S. Application Data

(60) Provisional application No. 62/174,983, filed on Jun. 12, 2015, provisional application No. 62/194,084, filed on Jul. 17, 2015, provisional application No. 62/236,562, filed on Oct. 2, 2015, provisional application No. 62/263,967, filed on Dec. 7, 2015, provisional application No. 62/278,198, filed on Jan. 13, 2016.

(51) Int. Cl.
*A61K 31/415* (2006.01)
*A61K 45/06* (2006.01)
*A61K 31/554* (2006.01)
*A61K 31/5513* (2006.01)
*A61K 31/27* (2006.01)
*A61K 31/4045* (2006.01)
*A61K 31/445* (2006.01)
*A61K 31/55* (2006.01)
*A61K 31/135* (2006.01)
*A61K 9/00* (2006.01)
*A61K 31/198* (2006.01)

(52) U.S. Cl.
CPC .......... *A61K 31/415* (2013.01); *A61K 9/0053* (2013.01); *A61K 31/135* (2013.01); *A61K 31/198* (2013.01); *A61K 31/27* (2013.01); *A61K 31/4045* (2013.01); *A61K 31/445* (2013.01); *A61K 31/55* (2013.01); *A61K 31/554* (2013.01); *A61K 31/5513* (2013.01); *A61K 45/06* (2013.01)

(58) Field of Classification Search
None
See application file for complete search history.

(56) References Cited

U.S. PATENT DOCUMENTS

| | | |
|---|---|---|
| 4,099,012 A | 7/1978 | Gschwend |
| 4,405,644 A | 9/1983 | Kabbe et al. |
| 4,409,231 A | 10/1983 | Stenzel et al. |
| 4,482,534 A | 11/1984 | Blank |
| 4,555,399 A | 11/1985 | Hsiao |
| 4,985,352 A | 1/1991 | Julius et al. |
| 5,077,409 A | 12/1991 | Wissner |
| 5,128,351 A | 7/1992 | Wissner |
| 5,346,906 A | 9/1994 | Baker et al. |
| 5,523,280 A | 6/1996 | Chene et al. |
| 5,576,338 A | 11/1996 | Friesen et al. |
| 5,596,001 A | 1/1997 | Hamanaka |
| 5,661,024 A | 8/1997 | Kao et al. |
| 5,856,326 A | 1/1999 | Anthony et al. |
| 5,861,431 A | 1/1999 | Hildebrand et al. |
| 5,885,785 A | 3/1999 | Kao et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,083 A | 2/2000 | Carr et al. |
| 6,028,085 A | 2/2000 | Bromidge |
| 6,054,472 A | 4/2000 | Armistead et al. |
| 6,063,808 A | 5/2000 | Fabiano et al. |
| 6,107,324 A | 8/2000 | Behan et al. |
| 6,110,498 A | 8/2000 | Rudnic et al. |
| 6,140,509 A | 10/2000 | Smith et al. |
| 6,150,393 A | 11/2000 | Behan et al. |
| 6,172,084 B1 | 1/2001 | Cuny et al. |
| 6,180,138 B1 | 1/2001 | Engh et al. |
| 6,187,805 B1 | 2/2001 | Pineiro et al. |
| 6,204,285 B1 | 3/2001 | Fabiano et al. |
| 6,207,679 B1 | 3/2001 | Cuny et al. |
| 6,271,261 B1 | 8/2001 | Widdowson |
| 6,284,269 B1 | 9/2001 | Struengmann et al. |
| 6,297,261 B1 | 10/2001 | Christophersen et al. |
| 6,310,212 B1 | 10/2001 | Yuan et al. |
| 6,316,450 B1 | 11/2001 | Bromidge et al. |
| 6,358,698 B1 | 3/2002 | Weiner et al. |
| 6,376,670 B1 | 4/2002 | Cuny et al. |
| 6,380,199 B1 | 4/2002 | Reavill et al. |
| 6,383,762 B1 | 5/2002 | Kao et al. |
| 6,403,808 B1 | 6/2002 | Glennon et al. |
| 6,417,393 B1 | 7/2002 | Christophersen et al. |
| 6,420,541 B1 | 7/2002 | Behan et al. |
| 6,469,006 B1 | 10/2002 | Blair et al. |
| 6,479,480 B1 | 11/2002 | Moyes et al. |
| 6,479,519 B1 | 11/2002 | Astles et al. |

(Continued)

FOREIGN PATENT DOCUMENTS

| | | |
|---|---|---|
| CA | 2135253 | 5/1996 |
| CA | 2169231 A1 | 8/1996 |

(Continued)

OTHER PUBLICATIONS

J. M. Monti, Drugs of Today, (2010), 46(3), 183-193.*

(Continued)

*Primary Examiner* — Yong Chu
(74) *Attorney, Agent, or Firm* — Pepper Hamilton LLP

(57) ABSTRACT

The present invention relates to certain pyrazole derivatives of Formula (I) and pharmaceutical compositions thereof that modulate the activity of the 5-HT$_{2A}$ serotonin receptor and their uses for the treatment of REM sleep behavior disorder.

68 Claims, 2 Drawing Sheets

(56) References Cited

U.S. PATENT DOCUMENTS

| | | |
|---|---|---|
| 6,489,488 B2 | 12/2002 | Glennon et al. |
| 6,518,297 B2 | 2/2003 | Glennon et al. |
| 6,531,291 B1 | 3/2003 | Kabbash et al. |
| 6,541,209 B1 | 4/2003 | Behan et al. |
| 6,541,477 B2 | 4/2003 | Goehring et al. |
| 6,548,504 B1 | 4/2003 | Bromidge et al. |
| 6,608,085 B1 | 8/2003 | Gillespie et al. |
| 6,627,661 B2 | 9/2003 | Reavill et al. |
| 6,696,475 B2 | 2/2004 | Dahl et al. |
| 6,706,749 B2 | 3/2004 | Dahl et al. |
| 6,753,442 B1 | 6/2004 | Benedini et al. |
| 6,784,183 B2 | 8/2004 | Lavielle et al. |
| 6,787,535 B2 | 9/2004 | Beard et al. |
| 6,846,919 B2 | 1/2005 | Behan et al. |
| 6,849,644 B2 | 2/2005 | Bromidge et al. |
| 7,084,169 B2 | 8/2006 | Zhao |
| 7,087,750 B2 | 8/2006 | Caldirola et al. |
| 7,091,236 B1 | 8/2006 | Roberts et al. |
| 7,098,233 B2 | 8/2006 | Di Cesare et al. |
| 7,262,188 B2 | 8/2007 | MacDonald et al. |
| 7,368,539 B2 | 5/2008 | Behan et al. |
| 7,452,888 B2 | 11/2008 | Ahmed et al. |
| 7,601,837 B2 | 10/2009 | Ahmed et al. |
| 7,754,724 B2 | 7/2010 | Lorsbach et al. |
| 7,799,774 B2 | 9/2010 | Ahmed et al. |
| 7,943,639 B2 | 5/2011 | Johansson et al. |
| 7,977,337 B2 | 7/2011 | Ahmed et al. |
| 8,236,947 B2 | 8/2012 | Ahmed et al. |
| 8,404,690 B2 | 3/2013 | Page et al. |
| 8,481,535 B2 | 7/2013 | Gharbaoui et al. |
| 9,029,379 B2 | 5/2015 | Korenberg et al. |
| 9,034,911 B2 | 5/2015 | Selvey et al. |
| 9,084,742 B2 | 7/2015 | Chuang et al. |
| 9,353,064 B2 | 5/2016 | Carlos et al. |
| 2001/0022963 A1 | 9/2001 | Klaveness et al. |
| 2001/0051719 A1 | 12/2001 | Bromidge et al. |
| 2002/0025965 A1 | 2/2002 | Lavielle et al. |
| 2002/0025967 A1 | 2/2002 | Smith |
| 2002/0098548 A1 | 7/2002 | Kao et al. |
| 2002/0115670 A1 | 8/2002 | Kelly et al. |
| 2003/0037274 A1 | 2/2003 | Shikata et al. |
| 2003/0144505 A1 | 7/2003 | Bromidge et al. |
| 2004/0024210 A1 | 2/2004 | Johansson et al. |
| 2004/0034036 A1 | 2/2004 | Bromidge et al. |
| 2004/0077654 A1 | 4/2004 | Bouillot et al. |
| 2004/0082644 A1 | 4/2004 | Korsten |
| 2004/0092528 A1 | 5/2004 | Kelly et al. |
| 2004/0102636 A1 | 5/2004 | Miller et al. |
| 2004/0122076 A1 | 6/2004 | Bobb et al. |
| 2004/0132742 A1 | 7/2004 | Bromidge et al. |
| 2004/0167030 A1 | 8/2004 | Bernotas et al. |
| 2005/0054691 A1 | 3/2005 | Potter et al. |
| 2005/0080124 A1 | 4/2005 | Teegarden et al. |
| 2005/0090485 A1 | 4/2005 | Bromidge et al. |
| 2005/0090496 A1 | 4/2005 | Ahmed et al. |
| 2005/0124628 A1 | 6/2005 | Ahmend et al. |
| 2005/0176705 A1 | 8/2005 | Bromidge |
| 2005/0176759 A1 | 8/2005 | Ahmed et al. |
| 2005/0215526 A1 | 9/2005 | Hulme et al. |
| 2005/0267097 A1 | 12/2005 | Pinto et al. |
| 2006/0014705 A1 | 1/2006 | Howitz et al. |
| 2006/0018839 A1 | 1/2006 | Ieni et al. |
| 2006/0035888 A1 | 2/2006 | Jonas et al. |
| 2006/0063754 A1 | 3/2006 | Edgar et al. |
| 2006/0142241 A1 | 6/2006 | Yoo |
| 2006/0148818 A1 | 7/2006 | Johansson et al. |
| 2006/0172992 A1 | 8/2006 | Yokoyama et al. |
| 2006/0205792 A1 | 9/2006 | Wong et al. |
| 2006/0229335 A1 | 10/2006 | Teegarden et al. |
| 2006/0287334 A1 | 12/2006 | Johnson et al. |
| 2007/0004750 A1 | 1/2007 | Lorsbach et al. |
| 2007/0027139 A1 | 2/2007 | Johnson et al. |
| 2007/0032504 A1 | 2/2007 | Gladwin |
| 2007/0037827 A1 | 2/2007 | Nunes et al. |
| 2007/0043058 A1 | 2/2007 | Bang-Andersen et al. |
| 2007/0072857 A1 | 3/2007 | Teegarden et al. |
| 2007/0078134 A1 | 4/2007 | Teegarden et al. |
| 2007/0167431 A1 | 7/2007 | Comery et al. |
| 2007/0191345 A1 | 8/2007 | Ahmed et al. |
| 2007/0207994 A1 | 9/2007 | Teegarden et al. |
| 2007/0244086 A1 | 10/2007 | Teegarden et al. |
| 2007/0249603 A1 | 10/2007 | Johnson et al. |
| 2007/0275979 A1 | 11/2007 | MacDonald et al. |
| 2007/0293539 A1 | 12/2007 | Lansbury et al. |
| 2007/0293685 A1 | 12/2007 | Fitch et al. |
| 2008/0015223 A1 | 1/2008 | Strah-Pleynet et al. |
| 2008/0114014 A1 | 5/2008 | Rich |
| 2008/0194836 A1 | 8/2008 | Gharbaoui et al. |
| 2008/0200530 A1 | 8/2008 | Unett et al. |
| 2008/0255359 A1 | 10/2008 | Wade |
| 2009/0053306 A1 | 2/2009 | Agarwal et al. |
| 2009/0076254 A1 | 3/2009 | Behan et al. |
| 2009/0186895 A1 | 7/2009 | Teegarden et al. |
| 2009/0197935 A1 | 8/2009 | Teegarden et al. |
| 2010/0004264 A1 | 1/2010 | Xiong et al. |
| 2010/0041672 A1 | 2/2010 | Bruton et al. |
| 2010/0069367 A1 | 3/2010 | Boren et al. |
| 2010/0226855 A1 | 9/2010 | Nangia et al. |
| 2010/0240653 A1 | 9/2010 | Santora et al. |
| 2010/0267691 A1 | 10/2010 | Chuang et al. |
| 2011/0021538 A1 | 1/2011 | Krishnan et al. |
| 2011/0178094 A1 | 7/2011 | Holm et al. |
| 2011/0207790 A1 | 8/2011 | Carlos et al. |
| 2011/0207791 A1* | 8/2011 | Selvey ................. A61K 31/415 514/406 |
| 2011/0263592 A1 | 10/2011 | Xiong et al. |
| 2012/0088785 A1 | 4/2012 | Rich |
| 2013/0172379 A1 | 7/2013 | Rich |
| 2013/0172398 A1 | 7/2013 | Rich |
| 2013/0217700 A1 | 8/2013 | Xiong et al. |
| 2013/0237541 A1 | 9/2013 | Teegarden et al. |
| 2013/0331399 A1 | 12/2013 | Leahy et al. |
| 2014/0073681 A1 | 3/2014 | Schmidt et al. |
| 2014/0142140 A1 | 5/2014 | Bird |
| 2014/0349976 A1 | 11/2014 | Hacksell et al. |
| 2015/0031897 A1 | 1/2015 | Rich |
| 2015/0045372 A1 | 2/2015 | Krishnan et al. |
| 2015/0073141 A1 | 3/2015 | Teegarden et al. |
| 2015/0210648 A1 | 7/2015 | Carlos et al. |
| 2015/0233698 A1 | 8/2015 | Huang et al. |
| 2016/0067216 A1 | 3/2016 | Selvey et al. |
| 2016/0075660 A1 | 3/2016 | Xiong et al. |
| 2016/0324851 A1 | 11/2016 | Friedhoff et al. |
| 2016/0324852 A1 | 11/2016 | Friedhoff et al. |
| 2017/0014385 A1 | 1/2017 | Friedhoff et al. |

FOREIGN PATENT DOCUMENTS

| | | |
|---|---|---|
| DE | 102004061593 | 6/2006 |
| EP | 0030023 A2 | 6/1981 |
| EP | 0371431 | 11/1989 |
| EP | 0605981 B1 | 2/1996 |
| EP | 0818449 A1 | 1/1998 |
| EP | 0631176 B1 | 12/2000 |
| EP | 1108720 | 12/2000 |
| EP | 0867477 B1 | 5/2002 |
| EP | 1734039 | 6/2005 |
| EP | 1558582 B1 | 12/2005 |
| EP | 1683516 | 1/2006 |
| EP | 1695966 A1 | 8/2006 |
| EP | 1727803 B1 | 3/2012 |
| EP | 1956004 B1 | 6/2012 |
| EP | 2190844 B1 | 4/2013 |
| EP | 2066641 B1 | 6/2014 |
| FR | 2722369 A | 1/1996 |
| GB | 1147379 | 4/1969 |
| GB | 2341549 A | 3/2000 |
| JP | 02262627 | 10/1990 |
| JP | 04334357 B2 | 3/2010 |
| WO | WO 1995/11592 A1 | 5/1995 |
| WO | WO 1996/02138 | 2/1996 |
| WO | WO 1996/10559 | 4/1996 |
| WO | WO 1996/23783 | 8/1996 |
| WO | WO 1996/032931 | 10/1996 |

(56) References Cited

FOREIGN PATENT DOCUMENTS

| | | |
|---|---|---|
| WO | WO 1997/03967 | 2/1997 |
| WO | WO 1997/32858 A1 | 9/1997 |
| WO | WO 1997/45111 | 12/1997 |
| WO | WO 1998/24785 | 6/1998 |
| WO | WO 1998/27081 A1 | 6/1998 |
| WO | WO 1998/47874 A1 | 10/1998 |
| WO | WO 1998/54157 A1 | 12/1998 |
| WO | WO 1998/54158 A1 | 12/1998 |
| WO | WO 1998/57931 A2 | 12/1998 |
| WO | WO 1998/57952 A1 | 12/1998 |
| WO | WO 1999/06354 | 2/1999 |
| WO | WO 1999/32436 | 7/1999 |
| WO | WO 1999/32463 | 7/1999 |
| WO | WO 1999/32927 | 7/1999 |
| WO | WO 1999/42465 A2 | 8/1999 |
| WO | WO 1999/47516 A1 | 9/1999 |
| WO | WO 1999/52927 A | 10/1999 |
| WO | WO 1999/65906 A1 | 12/1999 |
| WO | WO 2000/012073 A1 | 3/2000 |
| WO | WO 2000/013681 | 3/2000 |
| WO | WO 2000/034265 A2 | 6/2000 |
| WO | WO 2000/042026 A1 | 7/2000 |
| WO | WO 2000/57877 | 10/2000 |
| WO | WO 2000/058303 A1 | 10/2000 |
| WO | WO 2000/058313 A1 | 10/2000 |
| WO | WO 2000/063203 A1 | 10/2000 |
| WO | WO 2000/64866 | 11/2000 |
| WO | WO 2000/064877 A1 | 11/2000 |
| WO | WO 2001/007436 | 2/2001 |
| WO | WO 2001/016108 A2 | 3/2001 |
| WO | WO 2001/017963 A2 | 3/2001 |
| WO | WO 2001/21160 | 3/2001 |
| WO | WO 2001/29008 | 4/2001 |
| WO | WO 2001/029008 A | 4/2001 |
| WO | WO 2001/032646 A2 | 5/2001 |
| WO | WO 2001/032660 A1 | 5/2001 |
| WO | WO 2001/040217 A1 | 6/2001 |
| WO | WO 2001/046166 | 6/2001 |
| WO | WO 2001/064676 | 9/2001 |
| WO | WO 2001/098279 A2 | 12/2001 |
| WO | WO 2002/008178 A1 | 1/2002 |
| WO | WO 2002/020489 A2 | 3/2002 |
| WO | WO 2002/028837 A1 | 4/2002 |
| WO | WO 2002/036562 A2 | 5/2002 |
| WO | WO 2002/39987 | 5/2002 |
| WO | WO 2002/044170 A2 | 6/2002 |
| WO | WO 2002/051833 | 7/2002 |
| WO | WO 2002/076464 A | 10/2002 |
| WO | WO 2002/078693 A2 | 10/2002 |
| WO | WO 2002/089811 A1 | 11/2002 |
| WO | WO 2002/098857 A1 | 12/2002 |
| WO | WO 2002/102774 A1 | 12/2002 |
| WO | WO 2003/002097 | 1/2003 |
| WO | WO 2003/011284 A1 | 2/2003 |
| WO | WO 2003/013510 A1 | 2/2003 |
| WO | WO 2003/014097 A1 | 2/2003 |
| WO | WO 2003/020707 A1 | 3/2003 |
| WO | WO 2003/035061 A1 | 5/2003 |
| WO | WO 2003/037872 A1 | 5/2003 |
| WO | WO 2003/062206 | 7/2003 |
| WO | WO 2003/066056 A1 | 8/2003 |
| WO | WO 2003/072558 A2 | 9/2003 |
| WO | WO 2003/080580 A2 | 10/2003 |
| WO | WO 2003/080608 A2 | 10/2003 |
| WO | WO 2003/095434 A1 | 11/2003 |
| WO | WO 2003/104193 A1 | 12/2003 |
| WO | WO 2004/000828 A1 | 12/2003 |
| WO | WO 2004/026830 A1 | 4/2004 |
| WO | WO 2004/026831 A1 | 4/2004 |
| WO | WO 2004/028450 A2 | 4/2004 |
| WO | WO 2004/035047 A1 | 4/2004 |
| WO | WO 2004/041792 A1 | 5/2004 |
| WO | WO 2004/045118 | 5/2004 |
| WO | WO 2004/046110 | 6/2004 |
| WO | WO 2004/050085 A1 | 6/2004 |
| WO | WO 2004/058722 | 7/2004 |
| WO | WO 2004/071426 | 8/2004 |
| WO | WO 2004/074243 A2 | 9/2004 |
| WO | WO 2004/078176 A1 | 9/2004 |
| WO | WO 2004/080969 A1 | 9/2004 |
| WO | WO 2004/085433 | 10/2004 |
| WO | WO 2004/096771 | 11/2004 |
| WO | WO 2005/012254 | 2/2005 |
| WO | WO 2005/021530 A1 | 3/2005 |
| WO | WO 2005/021545 A | 3/2005 |
| WO | WO 2005/026125 A1 | 3/2005 |
| WO | WO 2005/030724 A2 | 4/2005 |
| WO | WO 2005/040124 A1 | 5/2005 |
| WO | WO 2005/066157 A | 7/2005 |
| WO | WO 2005/077345 | 8/2005 |
| WO | WO 2005/095346 A1 | 10/2005 |
| WO | WO 2005/103011 | 11/2005 |
| WO | WO 2005/113539 A1 | 12/2005 |
| WO | WO 2005/121140 A1 | 12/2005 |
| WO | WO 2006/018662 | 2/2006 |
| WO | WO 2006/038006 A2 | 4/2006 |
| WO | WO 2006/049734 | 5/2006 |
| WO | WO 2006/049941 | 5/2006 |
| WO | WO 2006/053785 A1 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO 2006/081335 A2 | 8/2006 |
| WO | WO 2006/086705 A | 8/2006 |
| WO | WO 2006/089871 | 8/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/039219 A1 | 4/2007 |
| WO | WO 2007/039220 A1 | 4/2007 |
| WO | WO 2007/039238 A1 | 4/2007 |
| WO | WO 2007/041409 A1 | 4/2007 |
| WO | WO 2007/120600 | 10/2007 |
| WO | WO 2007/129111 | 11/2007 |
| WO | WO 2007/136680 | 11/2007 |
| WO | WO 2007/136689 | 11/2007 |
| WO | WO 2007/136703 | 11/2007 |
| WO | WO 2007/136875 | 11/2007 |
| WO | WO 2007/147883 A1 | 12/2007 |
| WO | WO 2008/027483 | 3/2008 |
| WO | WO 2008/042388 | 4/2008 |
| WO | WO 2008/054748 | 5/2008 |
| WO | WO 2008/113818 A1 | 9/2008 |
| WO | WO 2009/023253 | 2/2009 |
| WO | WO 2009/074607 A1 | 6/2009 |
| WO | WO 2009/123714 | 10/2009 |
| WO | WO 2010/062321 | 6/2010 |
| WO | WO 2010/062323 | 6/2010 |
| WO | WO 2014/065437 | 5/2014 |
| WO | WO 2014/085362 | 6/2014 |
| WO | WO 2015/012554 | 1/2015 |
| WO | WO 2017/011767 | 1/2017 |

OTHER PUBLICATIONS

Ancoli-Israel et al. Sleep Med (2011), 12(2), p. 134-141.*
"The Merck Manual of Diagnosis and Therapy", Merck Research Laboratories, pp. 1769-1781 (2006).
Adams et al. "Antithrombotic and Vascular effects of AR246686, a novel 5-$HT_{2A}$ receptor antagonist" 2007 *EJM*, pp. 1-22.
Affolter, H., "CA2+ as Messenger of 5HT2-Receptor Stimulation in Human Blood Platelets," (1984) *Naunyn Schmiedebergs Arch. Pharmacol.* 325(4):337-42.

(56) References Cited

OTHER PUBLICATIONS

Ahmed et al., "Bicylic heteroarylpiperazines as selective brain penetrant 5-HT6 receptor antagonists," (2005) *Bioorganic & Medicinal Chem. Letters*, 15:4867-4871.
Al-Shamma "APD125: A 5-HT$_{2A}$ Inverse Agonist for the Treatment of Sleep Maintenance Insomnia," 2008 *DDST* 1-7.
Al-Shamma et al, "The Selective Serotonin 5HT2A Inverse Agonist APD125 Promotes Sleep Onset and Consolidation in Male Wistar Rats During the Normal Active Phase" (2005) APSS Abstract 0005.
Al-Shamma et al., "Nelotanserin, a Novel Selective Human 5-Hydroxytryptamine$_{2A}$ Inverse Agonist for the Treatment of Insomnia,"(2010)*J. Pharmacol. Exp. Ther*. 332:281-290.
Al-Shamma et al; "The Selective Serotonin 5HT$_{2A}$ Inverse Agonist APD125 Promotes Sleep Onset and Consolidation in Male Wistar Rats During the Normal Active Phase," 1994 APSS Slides, 1-5.
Ancelin, et al. "Non-degenerative mild cognitive impairment in elderly people and use of anticholinergic drugs: longitudinal cohort study" (Feb. 1, 2006) *BMJ*, doi:10.1136/bmj.38740.439664.DE.
Andrzejewska-Buczko et al. "[Serotonin in diabetic retinopathy]," *Klin Oczna*. Feb. 1996;98(2):101-4 (abstract).
Anonymous "Drug treats severe Alzheimer's". http://newsvote.bbc.co.uk/mpapps/pagetools/print/news.bbc.co.uk/2/hi/health/4832574.stm. Mar. 23, 2006.
Anonymous "Prevention of Atherosclerotic Complications: Controlled Trial of Ketanserin" (1989) *Br. Med. J*. 298:424-430.
Antinori et al., "Diagnosis of AIDS-related Focal Brain Lesions: A decision-making analysis based on clinical and neuroadiiologic characteristics combined with polymerase chain reaction assays in CSF" (1997) *Neurology* 48:687-694.
Arena Pharmaceuticals Announces Preliminary Results of Phase 2b Clinical Trial of APD125 for the Treatment of Insomnia, PRNewswire-FirstCall via Comtex News Network, Press Release dated Dec. 9, 2008.
ARICEPT® Label Jul. 2015.
Aschenbrenner et al., Drug Therapy in Nursing, 2009, TOC.
Barluenga, Jr. et al., "A New and Specific Method for the Monomethylation of Primary Amines," (1984) *J. Chem. Soc. Chem. Commun*. 20:1334-1335.
Batey et al., "An Efficient New Protocol for the Formation of Unsymmetrical Tri- and Tretrasubstituted Ureas," (1998) *Tetra. Lett*. 39:6267-6270.
Bentley et al. "5-HT$_6$ Antisense Oligonucleotide I.C.V. Affects Rat Performance in the Water Maze and Feeding" (1997) *Journal of Psychopharma.(Supplement)* A64:255 (abstract).
Bentley et al. "Effect of the 5-HT6 Antagonist, Ro 04-6790 on Food Consumption in Rats Trained to a Fixed Feeding Regime" (1999) *British Journal of Pharmacol*. 126(Suppl.):66 (abstract).
Bentley et al., "Investigation of stretching behavior induced by the selective 5-HT6 receptor antagonist, Ro 04-6790, in rats" (1999) *British Journal of Pharmacol*. 126:1537-1542.
Berge et al. "Pharmaceutical salts" (1977) *J. of Pharmaceutical Sciences* 66(1):1-19.
Berger et al. "Progressive Multifocal Leukoencephalopathy" (1999) *Seminars in Neurology* 19:193-200.
Bernatowicz et al. "A Comparison of Acid Labile Linkage Agents for the Synthesis of Peptide C-Terminal Amides" (1989) *Tetra. Let*. 30(35):4645-4648.
Birks et al. "Donepezil for dementia due to Alzheimer's disease", The Cochrane Library. http://onlinelibrary.wiley.com/store/10.1002/14651858.CD001190.pub2/asset/CD001190.pdf?v=1&t=h5uxf9xk&s=991bffcda40d23d5edf561ab6543198f531afl6d [retrieved Aug. 14, 2012).
Blier et al. "Putative mechanisms of action of antidepressant drugs in affective and anxiety disorders and pain," (2001) *Journal of Psychiatry and Neuroscience* 26(1):37-43.
Bos et al. "5-HT6 receptor antagonists lead optimization and biological evaluation of N-aryl and B-heteroaryl 4-amino-benzene sulfonamides" (2001) *Eur. J. Med. Chem*. 36(2):165-178.

Bourson et al. "Determination of the Role of the 5-HT6 Receptor in the Rat Brain: A Study Using Antisense Oligonucelotides" (1995) *The Journal of Pharmacology & Experimental Therapeutics* 274(1): 173-180.
Bourson et al. "Involvement of 5-HT6 receptors in nigro-striatal function in rodents" (1998) *British J. of Pharmacol*. 125:1562-1566.
Branchek et al. "5-HT6 Receptors as Emerging Targets for Drug Discovery" (2000) *Annu. Rev. Pharmcol. Toxicol*. 40: 319-334.
Bromidge et al. "Phenyl Benzenesulfonamides are Novel and Selective 5-HT6 Antagonists: Identification of N-(2,50Dibromo-3-fluoropheny1)-4-methoxy-3-piperazin-l-ylbenzensulfonamide (SB-357134)" (2001) *Bioorganic & Medicinal Chemistry Letters* 11:55-58.
Burger "Isosterism and bioisosterism in drug design" (1991) *Prog. Drug Res*. 37:287-371 (abstract).
Burla et al. "SIR2004: an improved tool for crystal structure determination and refinement" (2005)*J. Appl. Cryst*. 38: 381-388 (abstract).
Buysse et al. "The Pittsburgh Sleep Quality Index: A New Instrument for Psychiatric Practice and Researach" (1989) *Psychiatry Research* 28(2):193-213.
Byrn "Solid-State Chemistry of Drugs" $2^{nd}$ Ed. (1999), Chapter 11—Hydrates and Solvates, 233-247 (TOC).
Byrn et al. "Pharmaceutical Solids: A Strategic Approach to Regulatory Considerations" (1995) *Pharm. Res*. 12(7):945-954 (abstract).
Callahan et al. "Characterization of the Selective 5-HT6 Receptor Antagonist SB 271046 in Behavioral Models of Cognition", $34^{th}$ Annual Scientific Meeting of the Soc. for Neurosci., San Diego. Oct. 2004.
Cameron et al. "The effects of 5-hydroxytryptamine 5-HT2 receptor antagonists on nerve conduction velocity and endoneurial perfusion in diabetic rats" (Jun. 2003) *Naunyn Schmiedebergs Arch Pharmacol*. 367(6):607-614.
Campbell et al. "Use of anticholinergics and the risk of cognitive impairment in an African American population" (2010) *Neurology* 75:152-159.
Carnahan et al. "The Concurrent Use of Anticholinergics and Cholinesterase Inhibitors: Rare Event or Common Practice?" (2004) JAGS 52(12):2082-2087 (abstract).
Carter et al. "Carbobenzoxy Chloride and Derivatives" (1995) *Org. Syn. Coll*. 3:167-169.
Casey et al. "Constitutively active mutant 5HT2, serotonin receptors: inverse agonist activity of classical 5HT.sub.2A antagonists" (1996) *Society for Neuroscience Abstracts* 22:699 (abstract).
Castaneda-Corral et al. "Role of Peripheral and Spinal 5-HT6 Receptors According to the Rat Formalin Test" (2009) *Neuroscience* 162:444-452.
Catalan et al. "New Ultraviolet Stabilizers: 3- and 5-(2'-Hydroxyphenyl)pyrazoles" (1992) *J. Am. Chem. Soc*. 114:5039-5048.
Cazzola et al. "5-HT modifiers as a potential treatment of asthma" (2000) TIPS, 21:13-6 (2000).
Cazzola et al. "Central 5-HT$_{1A}$ Receptors and Vagal Tone to the Airways" (2000) *Trends Pharmacol. Sci*. 21:201-202.
Chambers et al. "Translocation of the 5-Alkoxy Substituent of 2,5-Dialkoxyarylalkylamines to the 6-Position: Effect of 5-HT$_{2A/2C}$ Receptor Affinity" (2002) *Bioog. Med. Chem. Lett*. 12:1997-1999.
Chang et al. "Isapirone and Ketanserin Protects Against Circulatory Shock, Intracranial Hypertension, and Cerebral Ischemia During Heatstroke" (2005) *Shock* 24(4): 336-340.
Chang et al. "Mechanism of the ocular hypotensive action of ketanserin" (1985, Summer) *J. Ocul Pharmacol*. 1(2): 137-147.
Chang-Fong et al. "1,2,3,4-Tetrahydrocarbazoles as 5-HT6 serotonin receptor ligands" (2004) *Bioorg. Med. Chem. Lett*. 14(8):1961-1964.
Chuang et al. "5-HT6 Receptor Antagonist SB-742457 as a Novel Cognitive Enhancing Agent for Alzheimer's Disease" (2006) *Alzheimer's & Dementia, The Journal of the Alzheimer's Association*, 2(3/Supp. 1):S631-S632.
Clinical Trial Protocol Summaries (Five studies). http://www.gsk-clinicalstudyregister.com/quick-search-list.jsp?item=SB742457

(56) References Cited

OTHER PUBLICATIONS

&type=Compound&letterrange=Q-U&studyType=All&phase=All&population=All&marketing=All (accessed Mar. 9, 2012).
Collier et al. "Radiosynthesis and in-vivo evaluation of the psuedopeptide 6-opioid antagonist [.sub.125I]-ITIPP(.PSI.)"] (1999) Labeled Compd. Radiopharm. 42:S264-S266.
Cooke "Glycopyrrolate in Bladder Dysfunction", Jan. 1, 1983 South African Medical Journal 63(1):3 (abstract).
CUVPOSA glycopyrrolate oral solution Product Information Sheet, Rev. Jul. 2010.
Database Beilstein [Online] Beilstein Institute for Organic Chem., Frankfurt-Main, DE; XP002535545 Database Accession No. 5926580 (BRN), the whole document.
Davies et al. "Drug discovery targets: 5-HT$_6$ receptor" (2005) Drugs of the Future 30(5):479-495.
De Bie et al. "Modulation of airway hyperresponsiveness and eosinophilia by selective histamine and 5-HT receptor antagonists in a mouse model of allergic asthma" (1998) British Journal of Pharmacology 124:857-864.
DeFilippi et al. "Drug Interactions with Cholinesterase Inhibitors" (2003) Drugs Aging 20(6):437-444 (abstract).
Deuchar et al. "The role of 5-hydroxytryptamine in the control of pulmonary vascular tone in a rabbit model of pulmonary hypertension secondary to left ventricular dysfunction" (2005) Pulm. Pharmacol. Ther. 18(1):23-31.
Diagnostic and Statistical Manual of Mental Disorders, Fourth Edition, Text Revision: DSM-IV-TR, Washington, DC, American Psychiatric Association, 2000 (abstract).
Dosa et al. "Solubilized phenyl-pyrazole ureas as potent, selective 5-HT2A inverse-agonists and their application as antiplatelet agents" (2010) BMCL pp. 1-15.
Dosa et al. "Synthesis and SAR of Pyridinyl-Pyrazole Derivatives as Selective 5HT$_{2A}$ Inverse-Agonists for Platelet Aggregation" 2008 ACS, 235th ACS National Meeting, Medi 44, poster.
Dosa et al. "Synthesis and SAR of Solubilized Pyrazole Derivatives as 5HT2A Inverse-Agonists for Platelet Aggregation" 2006 ACS 232nd ACS National Meeting, Medi 431, poster.
Douaud et al. "Preventing Alzheimer's disease-related gray matter atrophy by B-vitamin treatment" (2013) PNAS 110:9523-9528.
Drinka "Antimuscarinic Drugs for Overactive Bladder and Their Potential Effects on Cognitive Function in Older Patients" 2006 JAGS 54(6):1004-1005 (abstract).
East et al. "5HT6 receptor binding sites in schizophrenia and following antipsychotic drug administration: Autoradiographic studies with '125ISB-258585" (2002) Synapse 45:191-199.
Edwards et al. "Risk of delirium with concomitant use of tolterodine and and acetycholinesterase inhibitors". 2002 J Amer Geriatric Society 50(6):1165-1166 (abstract).
Elliott et al. "4-Oxospiro[benzopyran-2,4'-piperidines] as Class III Antiarrhythmic Agents. Pharmacological Studies on 3,4-Dihydro-1'-[2-(benzofurazan-5-yl)-ethyl]-6methanesulfonamidospiro [(2H- )-1-benzopyran-2,4'-piperidin]-4-one(L-691,121)" (1992) J. Med. Chem. 35:3973-3976.
Elphick et al. "The human polyomavirus, JCV, uses serotonin to infect cells" (2004) Science 306:1380-1383.
European Search Report for EP05025004.2 dated Jun. 30, 2006.
European Search Report for EP08157490.7 dated Jul. 8, 2008.
European Search Report for EP12170019.9 dated Aug. 16, 2012.
Ferguson "Modulation of lymphatic smooth muscle contraction responses by the endothelium" (1992) Journal of Surgical Research 52:359-363 (abstract).
File "Anxiolytic Action of a Neurokinin, Receptor Antagonist in the Social Interaction Test" (Nov. 1997) Pharmacol. Biochem. Behav. 58(3):747-752.
File "The Use of Social Interaction as a Method for Detecting Anxiolytic Activity of Chlordiazepoxide-llike Drugs" (Jun. 1980) J. Neuro. Methods 2(3):219-238.
Foley et al. "The 5-HT6 Receptor Antagonist SB-271046 Reverses Scopolamine-Disrupted Consolidation of a Passive Avoidance Task and Ameliorates Spatial Task Deficits in Aged Rats" (2004) Neuropsychopharmacology 29:93-100.
Fujita et al. "Sarpogrelate Treatment Reduces Restenosis After Coronary Stenting" (2003) Am. Heart J. 145:e16.
Fujiwara "Augmented Responses to 5-HT2-Receptor-Mediated Vascoconstrictions in Atherosclerotic Rabbit Common Carotid Arteries" (1995) Journal of Cardiovascular Pharmacology 26:503-510.
Fullerton et al. "A phase 2 clinical trial of PF-05212377 (SAM-760) in subjects with mild to moderate Alzheimer's Disease with existing neuropsychiatric symptoms on a stable daily dose of Donepezil" Pfizer AAIC 2016 Poster Presentation, Cambridge, MA.
Garcia-Alloza et al. "Differential Involvement of 5-HT IB/ID and 5-HT6 Receptors in Cognitive and Non-cognitive Symptoms in Alzheimer's Disease" (2004) Neuropsychopharmacology 29:410-416.
Gardner "Distress Vocalization in Rat Pups a Simple Screening Method for Anxiolytic Drugs" (Nov. 1985) J. Pharma. Meth. 14(3):181-187 (Nov. 1985).
Geldmacher "Donepezil (Aricept®) for treatment of Alzheimer's disease and other dementing conditions" (2004) Expert Rev. Neurotherapeutics 4(1):5-16.
Gill et al. "A Prescribing Cascade Involving Cholinesterase Inhibitors and Anticholinergic Drugs" (2005) Arch Intern Med 165:808-813.
Gish et al. "Memorandum: Age-dependent manifestations of central anticholinergic effects" Department of Health and Human Services Public Health Service Food and Drug Administration Center for Drug Evaluation and Research, Mar. 5, 2007.
Glaxosmithkline Clinical Trial, http://www.gsk-clinicalstudyregister.com/result_comp_list.jsp?compound=SB742457&studyType=All&phase=All&population=All&marketing=All. Sep. 21, 2011.
Glaxosmithkline Pharmacology Study Report—A study in healthy volunteers to characterise [$^{11}$C]GSK215083A as a positron emission tomography (PET) tracer ligand for the 5-HT$_6$ receptor and to assess the occupancy at the 5-HT$_6$ receptor of SB-742457 in the brain using PET and a tracer dose of [$^{11}$C]GSK215083A (Sep. 24, 2009).
Glaxosmithkline, A Dose Ranging Study to Investigate the Efficacy and Safety of SB-742457 in Alzheimer's Disease NCT ID No. NCT00224497 (Verified 2007) Clinical Study.
Glaxosmithkline, SB-742457 and Donepezil in Alzheimer's Disease. NCT ID No. NCT00348192 (2006) Clinical Study.
Glennon et al. "2-Substituted Tryptamines: Agents with Selectivity for 5-HT6 Serotonin Receptors" (2000) J. Med. Chem., 43: 1011-1018.
Glennon et al. "Behavioral and Serotonin receptor properties of 4-substituted Derivatives of the Hallucinogen 1-2,5-dimethoxyphenyl)-2-aminopropane" (1982)J. Med. Chem. 25(10):1163-1168.
Gottlieb et al. "NMR Chemical Shifts of Common Laboratory Solvents as Trace Impurities" (1997) J. Org. Chem. 62:7512-7515.
Greene et al. "Protecting Groups in Organic Synthesis" 3rd Edition, 1999 (Wiley) (abstract).
Griesser "The Importance of Solvates, in Polymorphism in the Pharmaceutical Industry" 211-233; Rolf Hilfiker, ed., 2006.
Grotewiel et al. "Receptors Exhibit Constitutive Activity that is Blocked by Inverse Agonists," (May 21-25, 1994) Faseb J., Abstract 353:8(7) (1 page).
Grunder et al. "Time course of 5-HT2A receptor occupancy in the human brain after a single oral dose of the putative antipsychotic drug MDL 100,907 measured by positron emission tomography" (Sep. 1997) Neuropsychopharmacology 17(3):175-185.
Guillory "Generation of Polymorphs, Hydrates, Solvates, and Amorphous Solids, in Polymorphism in the Pharmaceutical Industry" (1999) Harry G. Britain ed. 183-226, 202-209.
Gutsche et al. "2-Phenylcycloheptanone" (1963) Org. Syn. Coll. 4:780-783.
Guy "Clinical Global Impression (CGI)—Severity of Depression Rating Scale" ECDEU Assessment Manual for Psychopharmacology (Rev. Ed. U.S. Dept. of Health, Education and Welvare, Bethesda, MD 1976).

(56) References Cited

OTHER PUBLICATIONS

Halberstadt et al. "5-$HT_{2A}$ and 5-$HT_{2C}$ Receptors Exert Opossing Effects on Locomotor Activity in Mice" (Jul. 2009) *Neuropsychopharmacology* 34(8):1958-1967.
Hamilton "A Rating Scale for Depression" (1960) *J. Neurol. Neurosurg. Psychiat.* 23:56-62.
Hamilton "Development of a Rating Scale for Primary Depressive Illness" (Dec. 1967) *Br. J Clin. Psych.* 6(4):278-296.
Hashimoto et al. "Urinary Incontinence: an Unrecognised Adverse Effect with Donepezil" (Aug. 12, 2000) *The Lancet* 356:568 (abstract).
Hayashi et al. "Sarpogrelate HC1, a selective 5-HT2A Antagonist, Retards the Progression of Atherosclerosis Through a Novel Mechanism" (2003) *Atherosclerosis* 168:23-31.
Helm et al. "GABAb receptor antagonist SGS742 improves spatial memory and reduces protein binding to the cAMP response element (CRE) in the hippocampus" (2005) *Neuropharmacology* 48:956-964.
Herrick-Davis et al. "Activating mutations of the serotonin 5-HT2C receptor" (Sep. 1997) *J. Neurochem* 69(3): 1138-44.
Herrick-Davis et al. "Constitutively active 5HT2C serotonin receptor created by site-directed mutagenesis" *Society for Neuroscience Abstracts* 22:699.18.
Higuchi et al. "Pro-Drugs as Novel Delivery Systems" vol. 14 of the ACS Symposium Series; and in Bioreversible Carriers in Drug Design, ed. Edward B. Roche, American Pharmaceutical Association and Pergamon Press, 1987.
Hirst et al. "Characterization of [25I]-SB-258585 binding to human recombinant and native 5-HT6 receptors in rat, pig and human brain tissue" (2000) *British Journal of Pharmacology* 130:1597-1605.
Hirst et al. "Differences in the Central Nervous System Distribution and Pharmacology of the Mouse 5-Hydroxytryptamine-6 Receptor Compared with Rat and Human Receptors Investigated by Radioligand Binding, Site-Directed Mutagenesis, and Molecular Building" (2003) *Mol. Pharmacol.* 64:1295-1308.
Hittner et al. "A Selective 5-HT.sub.2A Receptor Inverse Agonist with Preclinical Antipsychotic Profile in Rats" 2000 *Neuro*, poster.
Holenz et al. "Medicinal Chemistry Driven Approaches Toward Novel and Selective Serontonin 5-HT6 Receptor Ligands" (2005) *J. Med. Chem.* 48(6):1781-1795.
Holtje "Pharmacophore Identification and Receptor Mapping" (2003) The Practice of Medicinal Chemistry, 2nd ed., Wermuth (editor), Academic Press, Chap. 24, pp. 387-403.
Horibe et al. "Sarpogrelate, a 5-HT2 Receptor Blocker, may Have a Preconditioning-Like Effect in Patients with Coronary Artery Disease" (2004) *Circulation Research* 68:68-72.
Ibach et al. "Acetylcholinesterase Inhibition in Alzheimer's Disease" (2004) *Current Pharmaceutical Design* 10:231-251.
ICSD-International Classification of Sleep Disorders: Revied Diagnostic and Coding Manual, American Academy of Sleep Medicine (2001) pp. 1-336 (also includes table of contents and glossary.
Ieni et al. "The 5-HT1A Receptor Probe[3H]8-OH-DPAT Labels. The 5-HT Transporter in Human Platelets" (1988) *Life Sciences* 42:311-320.
Ikeguchi et al. "Mianserin Treatment of Patients with Pyschosis Induced by Antiparkinsonian Drugs" (1995) *Eur. Arch. Psych. Clin. Neurosci.* 244:320-324.
Iliff et al. "A Paravascular Pathway Facilitates CSF Flow Through the Brain Parenchyma and the Clearance of Interstitial Solutes, Including Amyloid β." (2012) *Sci. Transl. Med.* 4(147):147ra111.
International Preliminary Report on Patentability for International Application No. PCT/US2005/041726 dated Sep. 21, 2006 by Authorized Officer Stefan Hartinger.
International Preliminary Report on Patentability for International Application No. PCT/US2007/011810 dated Jul. 16, 2008 by Authorized Officer Bart De Jong.
International Preliminary Report on Patentability; PCT/US2007/021182 dated Nov. 4, 2008 by Authorized Officer P. Lauro.
International Search Report and Written Opinion for PCT/EP008/067225 dated Mar. 23, 2009.
International Search Report and Written Opinion for PCT/EP2004/010843 dated Mar. 14, 2005.
International Search Report and Written Opinion for PCT/EP2005/012463 dated Feb. 20, 2006.
International Search Report and Written Opinion for PCT/EP2006/009460 dated Dec. 14, 2006.
International Search Report and Written Opinion for PCT/EP2008/053285 dated Jul. 29, 2008.
International Search Report and Written Opinion for PCT/US2004/023488 dated Oct. 12, 2004.
International Search Report and Written Opinion for PCT/US2004/023880 dated Nov. 15, 2004.
International Search Report and Written Opinion for PCT/US2007/021182 dated Mar. 14, 2005.
International Search Report and Written Opinion for PCT/US2008/009740 dated Feb. 18, 2009.
International Search Report and Written Opinion for PCT/US2009/005811 dated Jul. 8, 2010.
International Search Report and Written Opinion for PCT/US2009/005809 dated Apr. 28, 2010.
International Search Report and Written Opinion for PCT/US2009/002019 dated Dec. 14, 2009.
International Search Report and Written Opinion for PCT/US2016/031359 dated Jul. 29, 2016.
International Search Report and Written Opinion for PCT/US2016/037090 dated Sep. 9, 2016.
International Search Report for International Application No. PCT/US2006/002721 dated Feb. 20, 2007.
International Search Report for International Application No. PCT/US2005/041726 dated May 18, 2006 by Authorized Officer Stefan Hartinger.
International Search Report for International Application No. PCT/US2006/001516 dated Jun. 7, 2006.
International Search Report for International Application No. PCT/US2007/011810 dated Oct. 30, 2007 by Authorized Officer Bart De Jong.
International Search Report for PCT/EP2003/003197 dated Dec. 11, 2003.
Isaac et al. "6-Bicyclopiperazinyl-1-arylsulfonylindoles and 6-Bicyclopiperidinyl-1-arylsulfonylindoles Derivatives as Novel, Potent, and Selective 5-HT6 Receptor Antagonists" (2000) *Bioorganic& Med. Chem. Letters* 10:1719-1721.
Janos et al. "Overactive bladder medicines and cognitive testing" (Nov. 2008) *Int J Clin Pract* 62(11):1637-1642 (abstract).
Jayakumar et al. "Synthesis and SAR of Alkoxyphenyl Pyrazole as 5-HT2A Inverse Agonists" (2006) ACS, 232nd ACS National Meeting, Medi 430, poster.
Jayakumar et al. "Synthesis and SAR of Novel-Phenyl-Pyrazole Urea derivatives" (2006) ACS, abstract.
Jayakumar et al; "Synthesis and SAR of Substituted Diphenylamines as 5HT2A Inverse-Agonists" (2004) ACS, meeting abstract.
Jayakumar et al; "Synthesis and SAR of Substituted Diphenylamines as 5HT2A Inverse-Agonists" (2005) ACS, 229 th ACS National Meeting, Medi 049, poster.
Jeon et al. "The synthesis of a new pyrazolylimidazolinone via 1,3-dipolar cycloaddition reaction of N-methyl sydnone with methyl propiolate" (1998) *Bull. Korean Chem. Soc.* 19(7):725-726.
Jewart et al. "Cognitive, Behavioral and Physiological Changes in Alzheimer Disease Patients as a Function of Incontinence Medications" (Apr. 2005) *Am J Geriatr Psychiatry* 13(4):324-328 (abstract).
Jhee et al. "Centrally Acting Antiemetics Mitigate Nausea and Vomiting in Patients with Alzheimer's Disease Who Receive Rivastigmine" (Mar./Apr. 2002) *Clinical Neuropharmacology* 25(2):122-123 (abstract).
Johnell et al. "Concurrent Use of Anticholinergic Drugs and Cholinesterase Inhibitors" (2008) *Drugs Aging* 25(10):871-877 (abstract).
Johnson et al. "5-HT6 receptor antagonists: Prospects for the treatment of cognitive disorders including dementia" (2008) *Current Opinion in Drug Discovery and Development* 11(5): 642-654.

(56) References Cited

OTHER PUBLICATIONS

Julius et al. "The 5HT2 Receptor Defines a Family of Structurally Distinct but Functionally Conserved Serotonin Receptors" (1990) PNAS USA 87:928-932.
Kaduszkiewicz et al. "Cholinesterase inhibitors for patients with Alzheimer's disease: systematic review of randomised clinical trials" (2005) BMJ online 331-321.
Kan et al. "Association of the HTR6 Polymorphism C267T With Late-Onset Alzheimer's Disease in Chinese" (1995) J. Pharmacol. & Exp. Therapeutics 274:173-180.
Kanayama et al. "New treatment of lumbar disc herniation using 5-hydroxytryptamine.sub.2a receptor inhibitor: a randomized controlled trial" (2005) Journal of Neurosurgery: Spine 2:441-446.
Kaneniwa et al. "Solubilization of Water-Insoluble Organic Powders by Ball-Milling in the Presence of Polyvinylpyrrolidone" (1975) Chem. Pharm. Bull. 23(11):2973-2986.
Katz et al. "Comparison of risperidone and placebo for psychosis and behavioral disturbances associated with dementia: a randomized, double-blind trial. Risperidone Study Group" (Feb. 1999) J Clin Psychiatry. 60(2):107-15.
Kay et al. "Antimuscarinic Drugs for Overactive Bladder and Their Potential Effects on Cognitive Function in Older Patients" (2005) JAGS 53:2195-2201 (abstract).
Kay et al. "Preserving cognitive function for patients with overactive bladder: evidence for a differential effect with darifenacin" (Nov. 2008) Int J Clin Pract. 62(11):1792-1800.
Khoshkhoo et al. "Crystallization of polymorphs: the effect of solvent" (1993) J. Phys. DD Appl.Phys. 26:B90-B93.
Khullar et al. "Prevalence of Faecal Incontinence Among Women with Urinary Incontinence" (1998) Br. J Obstet. Gynaecol. 105:1211-1213.
Kitagawa et al. "Beckmann Rearrangement of O-4 Pentenyl Oxime through N-Bromosuccinimide-Mediated Activating Process" (1997) Chem. Pharm. Bull. 45(1) 32-35.
Konig et al. "A New Method for Synthesis of Peptides: Activation of the Carboxyl Group with Dicyclohexylcarbodiimide using 1-Hydroxybenzotriazoles as Additives" (1970) Chem. Ber. 103:788-798 (English abstract included).
Koss et al. "Assessing patterns of agitation in Alzheimer's disease patients with the Cohen-Mansfield Agitation Inventory. The Alzheimer's Disease Cooperative Study" (1997) Alzheimer Dis Assoc Disord. 11(Suppl 2):S45-S50.
Krieger et al. "Novel Immunosuppressants" (2004) Pediatr. Transplantation 8:594-599.
Krystal et al. "The effects of APD125, a selective serotonin 5-HT2A, on sleep quality and sleep maintenance in a subjective study in patients with primary insomnia" (2009) Sleep pp. 1-23.
Kubinyi "3D QSAR in Drug Design: Ligand-Protein Interactions and Molecular Similarity" (1998) Springer, 800 pages. p. 2-3:243 (abstract).
Landolt et al. "Serotonin-2 receptors and human sleep: effect of a selective antagonist on EEG power spectra" (1999) Neuropsychopharmacology 21(3):455-66.
Le Bas et al. "Radioiodinated analogs of EP 00652218 for the exploration of the tachykinin NK1 receptor by spect" (2001) J. Labeled Compd. Radiopharm. 44:S280-S282.
Levin et al. "Direct measurement of the anticholinergic activity of a series of pharmacological compounds on the canine and rabbit urinary bladder" (1982) J. Urology 128(2):396-398 (abstract).
Lewy Body Dementia Association, Inc., treatment options page, http://www.lbda.org/content/treatment-options, at least as early as Apr. 10, 2015.
Liang et al. "Olanzapine in the treatment of schizophrenia: a open trial clinical study" (1999) Chinese Journal of Psychiatry vol. 04, Title page/TOC only.
Lieben et al. "The Selective 5-HT6 Receptor Antagonist Ro4368554 Restores Memory Performance in Cholinergic and Serotonergic Models of Memory Deficiency in the Rat" (2005) Neuropsychopharmacology 30: 2169-2179.
Liem-Moolenaar et al. "Central Nervous System Effects of the Interaction Between Risperidone (single dose) and the 5-HT6 Antagonist SB742457 (repeated doses) in Healthy Men" (2010) Br. I Clin. Pharma. 71(6):907-916.
Lightowler et al. "Anxiolytic-like Effect of Paroxetine in a Rat Social Interaction Test" Oct. 1994) Pharmacol. Biochem. Behav. 49(2):281-285 (abstract).
Lindner et al. "An Assessment of the Effects of Serontonin 6 (5-HT6) Receptor Antagonists in Rodent Models of Learning" (2003) J. Pharmacol. Exp. Ther. 307(2): 682-691.
Lombardo et al "CTAD Poster Presentation Figure 4 entitled Phase 1 PET Study to Evaluate the Receptor Occupancy of RVT-101" Sep. 21, 2011.
London Stock Exchange Announcement—GlaxoSmithKline (GSK) plc, Issued on Thursday, Dec. 13, 2007, New York, New York.
Lopez et al. "Predictors of progression in patients with AD and Lewy bodies" (2000) Neurology 54:1774-1779 (abstract).
Lu et al. "Chronic Exposure to Anticholinergic Medications Adversely Affects the Course of Alzheimer Disease" (Jul.-Aug. 2003) Am J Geriatr Psychiatry 11(4):458-461 (abstract).
Luthringer et al. "Pharmacokinetic and Pharmacodynamic Effects of the Selective 5HT.sub.2A Inverse Agonist APD125 in Healthy Adults" 2005 APSS, abstract.
Maher-Edwards et al "Double-blind, controlled phase II study of a 5-HT6 receptor antagonist, SB-742457, in Alzheimer's disease" (2010) Current Alzheimer Research 7:374-385.
Maher-Edwards et al. "SB-742457 and donepezil in Alzheimer disease: a randomized, placebo-controlled study" (2011) Int. J. Geriatr. Psychiatry 26:536-544.
Major et al. "Establishment of a Line of Human Fetal Glial Cells That Supports JC Virus Multiplication" (1985) PNAS USA 82:1257-1261.
Mandel "Statistical Analysis of Experimental Data," Chapter 3, pp. 28-57, Toronto, Ontario, (1964).
Mandel "Statistical Analysis of Experimental Data," Chapter 9, pp. 204-207, Toronto, Ontario, (1964).
Marchini et al. "Sodium Borohydride-Carboxylic Acid Systems. Useful Reagents for the Alkylation of Amines" (1975) J Org. Chem. 40(23) :3453-3456.
Marcos "Serotonin-Induced Smooth Muscle Hyperplasia in Various Forms of Human Pulmonary Hypertension" (2004) Circ. Res. 94(9):1263-1270.
Martarello et al. "Radiolabelling and in vivo evaluation of [11C]GSK215083 as a potential PET radioligand for the 5-HT6 receptor in the porcine brain" (2005) J. Label Compd. Radiopharm. 48:S7.
Martarello et al.. "Radiolabelling and in vivo evaluation of [11C]GSK215083 as potential PET radioligand for the 5-HT6 receptor in the porcine brain" (2005) Journal of Cerebral Blood Flow & Metabolism 25:S598.
Mastropasqua et al. "Ocular hypotensive effect of ketanserin in patients with primary open angle glaucoma" (1997) Acta Ophthalmol Scand Suppl. (224):24-5.
McKeith et al. "Efficacy of rivastigmine in dementia with Lewy bodies: a randomised, double-blind, placebo-controlled international study" (2000) The Lancet 356:2031-2036 (abstract).
MedlinePlus, MedlinePlus Medical Encyclopedia, 2009, pp. 1-5 (abstract).
Menzaghi et al. "AR116081, a Novel Selective 5-HT2A Inverse Agonist As a Putative Atypical Antipsychotic: Comparative Studies with Clozapine and Haloperidol" 2000 CINP, poster.
Menzaghi et al. "AR118081, a Novel High Affinity 5-HT2A Receptor Inverse Agonist With in Vivo Efficacy" Nov. 1999 Neuro, poster.
Menzaghi et al. "Identification of Novel Selective 5-HT2A Inverse Agonists As Putative Atypical Antipsychotics Using Constitutively Activated Human 5-HT Receptors" Jun. 2000 ASPET, poster.
Menzaghi et al. "Therapeutic Potential of Selective Serotonin 5HT2A Receptor Inverse Agonists: Pre-Clinical Evaluation of AR116081 As Antipsychotics in Rodents" 2002 FESN, abstract.
Mestre et al. "5-Hydroxytryptamine 2A receptor antagonists as potential treatment for psychiatric disorders" (2013) Expert Opin. Investig Drugs 22(4):411-421.

(56) References Cited

OTHER PUBLICATIONS

Miao et al. "Ketanserin Stabilizes Blood Pressure in Conscious Spontaneously Hypertensive Rats" (2003) *Clin. Exp. Pharmacol. Physiol.* 30(3):189-193.
Mitchell et al. "5-HT6 receptors: a novel target for cognitive enhancement" (2005) *Pharmacol & Therapeutics* 108:320-333.
Mizuki et al. "Effects of Mianserin on Negative Symptoms in Schizophrenia" (1990) *Int. Clinical Psychopharmacology* 5:83-95.
Montgomery et al. "A New Depression Scale Designed to be Sensitive to Change" (Apr. 1979) *Br. J. Psychiatry* 134(4):382-389.
Morairty et al. "Selective 5HT2A and 5HT6 Receptor Antagonists Promote Sleep in Rats" (2008) *Sleep* 31(1).
Morissette et al. "High-throughput crystallization: polymorphs, salts, co-crystals and solvates of pharmaceutical solids" (2004) *Advanced Drug Delivery Review* 56:275-300.
Mueller "Drug Immunosuppression Therapy for Adult Heart Transplantation. Part 1:.Immune Response to Allograft and Mechanism of Action of Immunosuppressents" (2004) *Ann. Thorac. Surg.* 77:354-362.
Müller, Inorganic Structural Chemistry, Apr. 15, 1993, John Wiley and Sons, 274 pages, pp. 14-15.
Muto et al. "Protective effects of sarpogrelate, a 5HT2A antagonist, against postischemic myocardial dysfunction in guinea-pig hearts" (2005) *Molecular and Cellular Biochemistry* 272:119-32.
National Institutes of Health, National Heart, Lung and Blood Institute, "Facts about Insomnia" (Oct. 1995) NIH Publication No. 95-3801:1-4.
Newton et al. "Mianserin-Induced Down-Regulation of Human 5-Hydroxytryptamine2A and 5-Hydroxytryptamine2c Receptors Stably Expressed in the Human Neuroblastoma Cell Line SH-SY5Y" (1997) *Journal of Neurochemistry* 69:1031-1038.
Nichols et al. "2,3-Dihydrobenzofuran Analogs of Hallucinogenic Phenethylamines" (Jan. 1, 1991) *J. Med. Chem.* 34(1):276-281.
Nishiyama "Effects of 5HT2A receptor antagonist, sarpogrelate on thermal or inflammatory pain" (2005) *European Journal of Pharmacology* 516:18-22.
Nomura et al. "5-HT2A receptor antagonist increases circulating adiponectin in patients with type 2 diabetes" (2005) *Blood Coagulation and Fibrinolysis* 16(6):423-428.
Nordberg et al. "Cholinesterase Inhibitors in the Treatment of Alzheimer's Disease" (1998) *Drug Safety* 19(6):465-480.
Office Action for U.S. Appl. No. 11/883,043, dated Sep. 8, 2009.
Oken "Antihistamines, a Possible Risk Factor for Alzheimer's Disease" (1995) *Medical Hypotheses* 44:47-48 (abstract).
Olichney et al. "Cognitive Decline is Faster in Lewy Body Variant than in Alzheimer's Disease" (1998) *Neurology* 51:351-357 (abstract).
Ono Pharmaceutical Co., Ltd. "Launch of Rivistach.RTM. Patch, for the Treatment of Dementia of Alzheimer's Type" (2011) 2 pages.
Otwinowski et al. "Processing of x-ray diffraction data collected in oscillation mode" (1997) *Methods Enzymology* 276:307-326 (abstract).
Parker et al. "Human Kinetic Modeling of the 5HT6 PET Radioligand 11C-GSK215083 and Its Utility for Determining Occupancy at Both 5HT6 and 5HT2A Receptors by SB742457 as a Potential Therapeutic Mechanism of Aaction in Alzheimer Disease" (2015) *J. Nucl. Med.* 56:1901-1909.
Pawlak et al. "A Potent 5-Hydroxytryptamine Receptor (5-HT2A) Antagonist, DV-7028, Delays Arterial Thrombosis Development in Rats" (1998) *Thrombosis Research* 90:259-270.
Phase 1 Study, result summary. Study AZ3105822, a single-blind, randomized, placebo-controlled study to evaluate the effect of repeated dosing of an investigational product on the pharmacokinetics and pharmacodynamics of Warfarin in healthy adult subjects. http://www.gsk-.clinicalstudyregister.com/result_detail.jsp-?protocolId=105822&studyId=BC2066FF-1606-487D-B093-189458F0AE76&compound=SB742457 (undated).
Phase 2, Study 1, result summary. Study AZ3110865, a study comparing SB-74257 or donepezil versus placebo in subjects with mild-to-moderate Alzheimer's disease. http:..www.gsk-clinicalstudyregister.com/result_detail.jsp?protocolId=AZ3110865&studyId=242C4974-9729-4D30-8F91-327CF0631014&compound=SB742457 (undated).
Phase 2, Study 2, result summary Study AZ3110866, a fixed dose study of SB-742457 versus placebo when added to existing donepezil treatment in subjects with mild-to-moderate Alzheimer's disease. http://www.gsk-clinicalstudyresgister.com/result_detail.jsp?protocolID=AZ3110866&studyId=B8176D5B-C331-4621-9303-2BBF51E4690B&compound=SB742457 (undated).
Pietraszek et al., "Blood serotonergic mechanisms in type 2 (non-insulin-dependent) diabetes mellitus," Thromb Res., Jun. 15, 1992;66(6):765-74.
Pineiro-Nunez et al., "Discovery and SAR studies of 2,6-difluorobenzenesulfonic acid 1-methyl-3-(methylopiperidin-4-y1)-1H-indo1-5-y1 ester, a novel and potent 5-HT6 antagonist treatment of cognitive deficit", 299$^{th}$ ACS Natl. Mtg., Mar. 13-17, San Diego, Abst. Medi 282 (2005).
Porsolt et al. "Behavioral despair in mice: a primary screening test for antidepressants" (1977) *Arch. Int. Pharmac. Ther.* 229(2):327-336 abstract.
Portegies et al. "Guidelines for the Diagnosis and Management of Neuroogical Complications of HIV Infection" (2004) *Eur. J. Neurol.* 11:297-304.
Product Information Sheet, Detrol.RTM. LA (tolterodine tartrate) capsules, Rev. Mar. 2008.
Product Information Sheet, Enablex.RTM. (darifenacin) tablets, T2010-XX.
Product Information Sheet, Exelon.RTM. Patch (rivastigmine transdermal system), LTS Lohmann Therapie Systems AG, 2000.
Product Information Sheet, Sanctura.RTM. (trospium chloride), Rev. Jan. 2011.
Product Information Sheet, VESIcare.RTM. (solifenacin succinate) tablets, Rev. Apr. 2010.
Prosser et al. "Selective serotonin 5-HT2A, inverse agonists promote sleep consolidation in male Wistar rats during the normal inactive phase" #29, Arena Pharmaceuticals, Inc., APSS Meeting Jun. 2004 1 page.
Przyklenk et al. "Targeted inhibition of the serotonin 5HT2A receptor improves coronary patency in an in vivo model of recurrent thrombosis" (2010) *J. Thromb Haemost.* 8(2):331-340.
QuaSAR—Quantitative Structure Activity Relationships of Analgesics, Narcotic Antagonists, and Hallucinogens, Research Monograph 22, 1978, NIDA, Barnett and Willette (eds.), 1-487.
Querbes et al. "A JC Virus-Induced Signal is Required for Infection ofGlial Cells by a Clathrin- and eps15-Dependent Pathway" (2004) *J. Virology* 78:250-256.
Raschetti et al. "Cholinesterase Inhibitors in Mild Cognitive Impairment: A Systematic Review of Randomised Trials" (2007) *PloS Med.* 4(11):1818-1828.
Ray et al. "Central Anticholinergic Hypersensitivity in Aging" (Apr.-Jun. 1992) *Journal of Geriatric Psychiatry and Neurology* 5:72-77 (abstract).
Remington, The Science and Practice of Pharmacy, 20th Edition, 2000 (Lippincott Williams & Wilkins) TOC.
Riemer et al. "Influence of the 5-HT6 Receptor on Acetylcholine Release in the Cortex: Pharmacological Characterization of 4-(2-Bromo-6-pyrrolidin-l-ylpyridine-4-sulfonyl)phenylamine, a Potent and Selective 5-HT6 Receptor Antagonist" (2003) *Brief Articles, J. Med. Chem.* 46:1273-1276.
Roberts et al. "The distribution of 5-HT6 receptors in rat brain: an autoradiographic binding study using the radiolabeled 5-HT6 receptor antagonist 1251SB-258585" (2002) *Brain Research* 934:49-57.
Robichaud et al. "Ch. 2: Recent Advances in Selective Serotonin Receptor Modulation" (2000) *Annual Reports in Medicinal Chemistry* 36:11-20.
Robinul RTM. glycopyrrolate tablets Product Information Sheet, Rev. Apr. 2010.
Roche Bioreversible Carriers in Drug Design ed. (1987) (TOC only).
Roe et al. "Use of Anticholinergic Medications by Older Adults with Dementia" (2002) *JAGS* 50:836-842 (abstract).

(56) References Cited

OTHER PUBLICATIONS

Rogers et al. "5-HT6 Receptor Antagonists Enhance Retention of a Water Maze Task in the Rat" (2001) *Psychopharmacology* 158:114-119.
Rojas-Fernandez "Successful Use of Donepezil for the Treatment of Dementia with Lewy Bodies" (2001) *Annals of Pharmacotherapy* 35(2):202-205.
Rosenberg et al APD125, a selective serotonin 5-HT2A receptor inverse agonist, significantly improves the key PSG parameters of sleep maintenance in patients with primary insomnia (2008) *Sleep*, poster.
Rosenberg et al. "APD125, a selective serotonin 5-HT2A receptor inverse agonist, significantly improves the key parameters of sleep maintenance in patients with primary insomnia" (2007) *AASM* (abstract).
Rosenberg et al. "APD125, a selective serotonin 5-HT2A receptor inverse agonist, significantly improves sleep maintenance in primary insomnia" (2008) *APA* pp. 1-37.
Roth et al. "APD125, a selective serotonin 5-HT2A receptor inverse agonist, significantly improves the key parameters of sleep maintenance in patients with primary insomnia" (2008) *APSS* pp. 1-19.
Roth et al. "Serotonin receptors represent highly favorable molecular targets for cognitive enhancement in schizophrenia and other disorders" (2004) *Psychopharmacology* 174:17-24.
Rudolph et al. "The Anticholinergic Risk Scale and Anticholinergic Adverse Effects in Older Persons" (Mar. 10, 2008) *Arch Intern Med* 168(5):508-513.
Russell et al. "N-Arylsulfonylindole Derrivatives as Serotonin 5-HT6 Receptor Ligands" (2001)*J. Med. Chem.* 44(23):3881-3895.
Sahgal "Practical behavioural neuroscience: problems, pitfalls and suggestions," (1993) *Behavioral Neuroscience: A Practical Approach*, IRL Press, New York, 1:1-8.
Satomura et al. "Sarpogrelate, a specific 5HT2-receptor antagonist, improves the coronary microcirculation in coronary artery disease" (Jan. 2002) *Clin Cardiol.* 25(1):28-32.
Sawnyok et al. "Antidepressants as analgesics: an overview of central and peripheral mechanisms of action" (2001) *Journal of Psychiatry and Neurosciences* 26(1):21-29.
Schmidt et al. "The Role of 5-HT.sub.2A Receptors in Antipsychotic Activity" (1995) *Life Sciences* 56(25):2209-2222.
Shan et al. "Investigation of Non-Aqueous Vehicles for a Poorly Soluble Compound Intended for Softgel Dosage Form Development" 2005 APSS, abstract.
Shan et al. "Physicochemical Characterization During Salt Selection Process" 2005 AAPS, poster.
Shan et al; "Physicochemical Characterization During Salt Selection Process" 2006 AAPS, poster.
Sharpley et al. "Slow wave sleep in humans: role of 5HT2A and 5-HT2C receptors" (Mar.-Apr. 1994) *Neuropharmacology*.33(3-4):467-471.
Sheehan et al. "1-Ethyl-3-(3-Dimethylamiono) Proplycarbodimide Hydrochloride and Methiodide" (1973) *Org. Syn. Coll.* 5:555-558.
Shibata et al. "Adiponectin protects against myocardial ischemiareperfusion injury through AMPK- and COX-2 dependent mechanisms" (2005) *Nature Medicine* pp. 1-8.
Shua-Haim et al. "Safety, Tolerability, and Caregiver's Impressions of Combination Therapy With Rivastigmine and Memantine for the Treatment of Alzheimer's Disease" (2004) *Neurobiology& Aging* S205: P1-377.
Silva et al. "Chronic treatment with mianserin prevents DOCA-salt hypertension in rats—evidence for the involvement of central 5-HT2 receptors" (2005) *J. Pharmacol.* 518(2-3):152-157, 2005.
Singh et al "Immunosuppresive-aassociated Leukoencephalopathy in Organ Transplant Recipients" (2000) *Transplantation* 69:467-472.
Sink et al. "Dual Use of Bladder Anticholinergics and Cholinesterase Inhibitors: Long-Term Functional and Cognitive Outcomes" (2008) *JAGS* 56:847-853.

Sleight et al. "Characterization of Ro 04-6790 and Ro 63-0563: potent and selective antagonists at human and rat 5-HT6 receptors" (1998) *British Journal of Phamacol.* 124:556-562.
Smith et al. "Test-retest variability of serotonin 5-HT2A receptor binding measured with positron emission tomography and [18F]altanserin in the human brain" (1998) *Synapse, Dec.* 30(4):380-392.
Sorenson et al. "Characterization of the 5-HT2 Receptor Antagonist MDL 100907 as Putative Atypical Antipsychotic: Behavioral, Electrophysiological and Neurochemical Studies" (1993) *J. Pharacol. Exp. Ther.* 266(2):684-691.
Speer et al "Intrinsic Dissolution Characterization of Different Morphic Forms of a Poorly Water Soluble Compound" 2006, AAPS, abstract.
Speer et al. "Influence of Digestive Enzymes Combined with Sodium Lauryl Sulfate on Dissolution of Cross-linked Gelatin Capsules" 2005 AAPS, poster.
Speer et al. "Influence of Digestive Enzymes on Dissolution of a Poorly Water Soluble Compound From Cross-Linked Gelatin Capsules in Sodium Lauryl Sulfate Medium" 2005 AAPS, abstract.
Stadler et al. "5-HT6 antagonists: a novel approach for the symptomatic treatment of Alzheimer's Disease", 37th IUPAC Cong. Aug. 14-19, 1999, Berlin, Abst. MM-7.
Staley et al. Comparison of [(18)F]altanserin and [(18)F]deuteroaltanserin for PET imaging of serotonin(2A) receptors in baboon brain: pharmacological studies (Apr. 2001) *Nucl Med Biol.* 28(3):271-279.
Storey et al. "Automation of Solid Form Screening Procedures in the Pharmaceutical Industry—How to Avoid the Bottlenecks" (2004) *Crystallography Reviews* 10(1):45-56.
Strah-Pleynet et al. "5HT2A Receptor Inverse Agonists: Design and SAR of Novel Pyrazole Derivatives" (2006) meeting abstract.
Strah-Pleynet et al. "5-HT2A Receptor Inverse-Agonists: Design and Structure-Activity Relationship of Novel Pyrazole Derivatives" 2005 ACS, 231st ACS National Meeting, Medi 145, poster.
Strah-Pleynet et al. "Bioisosteric Modifications of Urea Derivatives as 5HT2A Inverse-Agonists" 2004 ACS, meeting abstract.
Strah-Pleynet et al. "Bioisosteric Modifications of Urea Derivatives as 5HT2A Inverse-Agonists" 2005 ACS, meeting poster.
Strah-Pleynet et al. "Discovery and SAR of novel 5-HT.sub.2A, inverse-agonists" 227th ACS National Meeting, MED1 270, Arena Pharmaceutical Inc. (Mar. 2004), 1 page, poster.
Strah-Pleynet et al. "Discovery and SAR of Novel 5-HT2A Inverse-Agonists" 2004 ACS, 227th ACS National Meeting, Medi 270, abstract.
Street et al. "Olanzapine treatment of psychotic and behavioral symptoms in patients with Alzheimer disease in nursing care facilities: a double-blind, randomized, placebo-controlled trial. The HGEU Study Group." (Oct. 2000) *Arch Gen Psychiatry.* 57(10):968-976.
Takahashi et al. "Sarpogrelate hydrochloride, a serotonin2A receptor antagonist, reduces albuminuria in diabetic patients with early-stage diabetic nephropathy" (Nov. 2002) *Diabetes Res Clin Pract.* 58(2): 123-129.
Takenaka et al. "The effect of anplag (sarpogrelate HCl), novel selective 5-HT.sub.2 antagonist on intraocular pressure in glaucoma patients" (1995) *Investig Ophthalmol Iris Sci.* 36(4):S724 (abstract 3390-377).
Talvik-Lotfi et al. "High 5HT2A receptor occupancy in M100907-treated schizophrenic patients" (2000) *Phychopharmacology* 148:400-403.
Tang et al. "Anilinopyrazole as selective CDK2 inhibitors: design, synthesis, biological evaluation, and x-ray crystallographic analysis" (2003) *Bioorg. Med. Chem. Letters* 13(18):2985-2988 (abstract).
Teegarden et al. "5HT.sub.2A Inverse-Agonists for the Treatment of Insomnia" (2008) *CTMC* pp. 1-28.
Teegarden et al. "Discovery of 1-[3-(4-Bromo-2-methyl-2H-pyrazol-3-yl)-4-methoxyphenyl]-3-(2,4-difluorophenyl(urea(Nelotanserin) and Related 5-Hydroxytryptamine.sub.2A Inverse Agonists for the Treatment of Insomnia" (2003) *J. Med. Chem.* 53:1923-1936.

(56) References Cited

OTHER PUBLICATIONS

Teegarden et al. "Discovery of 1-[3-(4-Bromo-2-methyl-2H-pyrazol-3-yl)-4-methoxy-phenyl[-3-(2,4-difluoro—phenyl)-urea (APD125) and Related 5-HT.sub.2A Inverse Agonists for the Treatment of Insomnia" (2009) *JMC* pp. 1-50.
Teramura-Gronblad et al. "Use of Anticholinergic Drugs and Cholinesterase Inhibitors and Their Association with Psychological Well-Being Among Frail Older Adults in Residential Care Facilities" (2011) *Ann Pharmacotherapy* 45:596-602 (abstract).
Terry et al. "The Cholinergic Hypothesis of Age and Alzheimer's Disease-Related Cognitive Deficits: Recent Challenges and Their Implications for Novel Drug Development"(2003) *JPET* 306(3):821-827.
Thome et al. "Association analysis of HTR6 and HTR2A polymorphisms in sporadic Alzheimer's disease" (2001) *Journal of Neural Transmission* 108:1175-1180.
Topliss "A Manual Method for Applying the Hansch Approach to Drug Design" (Apr. 1, 1977)*J. Med. Chem.* 20(4):463-469.
Totterdell "Synaptic Circutry of Interactions Between Limbic and Dopaminergic Afferents to the Ventral Striatum" (2004) *International Journal of Neuropsychopharmacology* 7:S14 SP.11.01.
Tsai et al. "Association Analysis of the 5-HT6 Receptor Polymorphism C267T in Alzheimer's Disease" (1999) *Neuroscience Letters* 276:138-139.
Tsao et al. "Transient Memory Impairment and Hallucinations Associated with Tolterodine Use" (Dec. 4, 2003) *New England Journal of Medicine* 349(23):2274-2275 (abstract).
Upton et al. "5-HT$_6$ Receptor antagonists as novel cognitive enhancing agents for Alzheimer's Disease" (2008) *Neurotherapeutics* 5(3):458-469.
Vacante et al. "Extension of JC Virus Host Range to Monkey Cells by Insertion of a Simian Virus 40 Enhancer into the JC Virus Regulatory Region" *Virology* 170:353-361.
Van Eijk et al. "Effect of rivastigmine as an adjunct to usual care with haloperidol on duration of delirium and mortality in critically ill patients: a multicentre, double-blind, placebo-controlled randomised trial" (2010) *The Lancet* 376:1829-1837 (abstract).
Van Zwieten "Receptors Involved in the Regulation of Vascular Tone" (1985) *Arzneimittelforschung.* 35(12A): 1904-1909.
Vanover et al. "Role of 5-HT2A receptor antagonists in the treatment of insomnia" (2010) *Nature and Science of Sleep* 2:139-150.
Vasilevskii "Oxidative Iodination of Substituted N-Methylpyrazoles," (1980) *Bull. Acad. Sci. USSR* 29(5):778-784.
Vasilevsky et al. "Study of the Heterocyclization of vic-Substituted Hydrazides of Actylenylpyrazolecarboxylic Acids into N-Amino Pyrazolpyridinones" (2002)*J. Hetercycl. Chem.* 39:1229-1233.
Verdejo et al. "Tratamiento con propantelina de la incontinencia urinaria por inestabilidad vesical en pacientes ancianos" (1992) *Anales de Medicina* 9(3):1160120.
Verstraete "Prevention of atherosclerotic complications: controlled trial of ketanserin" (1989) *British Medical Journal* 298:424-430.
Vikenes et al "Serotonin is Associated with Coronary Artery Disease and Cardiac Events" (1999) *Circulation* 100:483-489.
Vippagunta "Crystalline Solids" (2001) *Advanced Drug Delivery Reviews* 48:3-26.
Westkaemper et al. "Application of Ligand SAR, Receptor Modeling and Receptor Mutagenesis to the Discovery and Development of a New Class of 5-HT2A Ligands" (2002) *Curr. Topics Med. Chem.* 2:575-598 (abstract).
White "Deamination of Amines. 2-Phenylethyl Benzoate Via the Nitrosoamide Decomposition" (1973) *Org. Syn. Coll.* 5:336-339.
Wikstrom et al. "Synthesis and Pharmacological Testing of 1, 2, 3, 4, 10, 14b-Hexahydro-6-methoxy-2-methyldibenzo[cf]pyrazino[1,2-.alpha.]azepin and Its Enantiomers in Comparison with the Two Antidepressants Mianserin and Mirtazapine" (2002)*J. Med. Chem.*45:3280-3285.
Williams et al. "Survival and mortality differences between dementia with Lewy bodies vs Alzheimer disease" (1935) *Neurology* 67:1935-1941 (abstract).

Willner "Animal Models as Simulations of Depression" (1991) *Trends Pharmacol. Sci.* 12(4):131-136 (abstract).
Wilson et al "LY53857, a 5HT2 receptor antagonist, delays occlusion and inhibits platelet aggregation in a rabbit model of carotid artery occlusion" (Sep. 2, 1991) *Thromb Haemost.* 66(3):355-360.
Winokur et al. "Acute effects of mirtazapine on sleep continuity and sleep architecture in depressed patients: a pilot study" (Jul. 1, 2000) *Biol Psychiatry* 48(1):75-78.
Woolley et al. "5-HT6 Receptors" (2004) *Current Drug Targets— CNS & Neurological Disorders* 3:59-79.
Woolley et al. "A role for 5-HT6 Receptors in Retention of Spatial Learning in the Morris Water Maze" (2001) *Neuropharmacology* 41:210-219.
Woolley et al. "Reversal of a cholinergic-induced deficit in a rodent model of recognition memory by the selective 5-HT6 receptor antagonist, Ro 04-6790" (2003) *Psychopharmacology* 170:358-367.
Xiong et al. "Discovery and SAR of Highly Selective 5-HT.sub.2A Receptor Subtype Inverse-Agonists for Inhibition of Platelet Aggregation" 2008 ACS, 235th National Meeting, Medi 45, poster.
Xiong et al. "Synthesis and in Vivo Evaluation of Phenethylpiperazine Amides: Selective 5-Hydroxytryptamine2A Receptor Antagonists for the Treatment of Insomnia" (2010) *Journal of Medical Chemistry* 53:5696-5706.
Yamada et al. "Phase I/II trial of didanosine (2',2'-dideoxyinosine) in hemophiliac patients with AIDS or AIDS-related complex" (1993) *Clin. Diagn. Virol.* 1:245-256.
Yamashita et al. "Conjunctive effects of the 5HT2 receptor antagonist, sarpogrelate, on thrombolysis with modified tissue plasminogen activator in different laser-induced thrombosis models" (2000) *Haemostatis* 30:321-332 (abstract).
Yevich et al. "Second generation antimigraine 5-HT1B/D agonists: structure activity relationship and preclinical pharmacological distinctions" (1997) *Curr. Med. Chem.* 4(5):295-312 (abstract).
Zhu et al. "Synthesis and mode of action of 125I- and 3H-labeled Thieno[2,3-c]pyridine antagonists of cell adhesion molecule expression" (2000) *J. Org. Chem.* 67:943-948.
Gillman, The serotonin syndrome and its treatment, *Journal of Phychopharmacology* (1999), 31(1):100-109.
Kalueff et al., Hypolocomotion, anxiety and serotonin syndrome-like behavior contribute to the complex phenotype of serotonin transporter knockout mice, *Genes, Brain and Behavior* (2007), 6:389-400.
Chew et al. "Serum Anticholinergic Activity and Cognition in Patients with Moderate-to-Severe Dementia" (Jun. 2005) *Am J Geriatr Psychiatry* 13:6 (abstract).
Cohen-Mansfield et al. "Agitated behaviors in the elderly. I. A conceptual review" (Oct. 1986) *J Am Geriatr Soc.* 34(10):711-21.
Collier et al. "Radiosynthesis and in-vivo evaluation of the psuedopeptide 6-opioid antagonist [.sub.125I]-ITIPP(PSI.) ]" (1999) *Labeled Compd. Radiopharm.* 42:S264-S266.
Collins et al. "N-Phenylamidines as Selective Inhibitors of Human Neuronal Nitric Oxide Sythase: Structure-Activity Studies and Demonstration of in Vivo Activity" (1998) *J. Med. Chem., Amer. Chem. Soc.* 41(15):2858-2871.
Dosa et al. "Synthesis and SAR of solubilized pyrazole derivatives as 5-HT2A inverse-agonists for platelet aggregation" 232nd ACS National Meeting, Sep. 2006, Medi 431, 1 page (abstract).
International Search Report and Written Opinion for PCT/US16/42556 dated Dec. 23, 2016.
Vanover et al., Pharmacological and Behavioral Profile of N-(4-Fluorophenylmethyl)-N-(1-methylpiperidin-4-yl)-N'-(4-(2-methylpropyloxy)phenylmethyl) Carbamide (2R,3R)-Dihydroxybutanedioate (2:1) (ACP-103), a Novel 5-Hydroxytryptamine2A Receptor Inverse Agonist, (2006) J Pharmacol Exp Ther. 317:910-918.
Vanover et al., Pharmacokinetics, Tolerability, and Safety of ACP-103 Following Single or Multiple Oral Dose Administration in Healthy Volunteers, (2007) J Clinical Pharmacol. 47;6:704-714.

\* cited by examiner

DIARYL AND ARYLHETEROARYL UREA DERIVATIVES AS MODULATORS OF THE 5-HT2A SEROTONIN RECEPTOR USEFUL FOR THE PROPHYLAXIS AND TREATMENT OF REM SLEEP BEHAVIOR DISORDER

CROSS REFERENCE TO RELATED APPLICATIONS

This application claims the priority benefit under 35 U.S.C. 119(e) of U.S. Provisional Application No. 62/174,983 filed Jun. 12, 2015, U.S. Provisional Application No. 62/194,084, filed Jul. 17, 2015, U.S. Provisional Application No. 62/236,562 filed Oct. 2, 2015, U.S. Provisional Application No. 62/263,967 filed Dec. 7, 2015 and U.S. Provisional Application No. 62/278,198 filed Jan. 13, 2016, the disclosures of which are incorporated by reference in their entireties.

SUMMARY

The present invention relates to certain diaryl and arylheteroaryl urea derivatives of Formula (I) and pharmaceutical compositions thereof that modulate the activity of the 5-HT$_{2A}$ serotonin receptor. Compounds and pharmaceutical compositions thereof are directed to methods useful in the prophylaxis or treatment of rapid eye movement (REM) sleep behavior disorder.

One aspect of the present invention encompasses certain diaryl and arylheteroaryl urea derivatives as shown in Formula I:

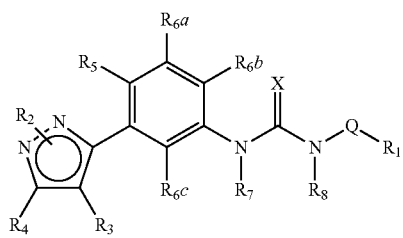

I or a pharmaceutically acceptable salt, hydrate or solvate thereof;
wherein:
i) $R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$dialkylsulfonamide, halogen, $C_{1-6}$ haloalkoxy, $C_{1-6}$ haloalkyl, $C_{1-6}$haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$alkynyl, $C_{1-6}$ alkylsulfonamide, $C_{1-6}$ alkylsulfinyl, $C_{1-6}$alkylsulfonyl, $C_{1-6}$ alkylthio, $C_{1-6}$ alkylureyl, amino, $C_{1-6}$alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$haloalkylsulfonyl, $C_{1-6}$ haloalkylthio, hydroxyl, thiol and nitro;

ii) $R_2$ is selected from the group consisting of H, $C_{1-6}$ alkyl, $C_{2-6}$alkenyl, $C_{2-6}$ alkynyl and $C_{3-7}$ cycloalkyl;

iii) $R_3$ is selected from the group consisting of H, $C_{2-6}$ alkenyl, $C_{1-6}$alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$dialkylamino, $C_{1-4}$ alkylcarboxamide, $C_{2-6}$ alkynyl, $C_{1-4}$alkylsulfonamide, $C_{1-4}$ alkylsulfinyl, $C_{1-4}$ alkylsulfonyl, $C_{1-4}$alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$haloalkylsulfonyl, $C_{1-4}$ haloalkylthio, hydroxyl, nitro and sulfonamide;

iv) $R_4$ is selected from the group consisting of H, $C_{1-6}$ acyl, $C_{1-6}$acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$dialkylcarboxamide, $C_{2-8}$ dialkylsulfonamide, halogen, $C_{1-6}$haloalkoxy, $C_{1-6}$ haloalkyl, $C_{1-6}$ haloalkylsulfinyl, $C_{1-6}$haloalkylsulfonyl, $C_{1-6}$ haloalkylthio, hydroxyl, thiol, nitro and sulfonamide;

v) $R_5$ is selected from the group consisting of $C_{1-6}$ acyl, $C_{1-6}$acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$dialkylcarboxamide, $C_{2-8}$ dialkylsulfonamide, halogen, $C_{1-6}$haloalkoxy, $C_{1-6}$ haloalkyl, $C_{1-6}$haloalkylsulfinyl, $C_{1-6}$haloalkylsulfonyl, $C_{1-6}$ haloalkylthio, hydroxyl, thiol, nitro and sulfonamide, wherein said $C_{1-6}$ alkoxy group can be optionally substituted with 1 to 5 substituents selected independently from the group consisting of $C_{1-5}$ acyl, $C_{1-5}$ acyloxy, $C_{2-6}$ alkenyl, $C_{1-4}$alkoxy, $C_{1-8}$ alkyl, amino, $C_{1-6}$ alkylamino, $C_{2-8}$dialkylamino, $C_{1-4}$alkylcarboxamide, $C_{2-6}$ alkynyl, $C_{1-4}$alkylsulfonamide, $C_{1-4}$alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$cycloalkyl, $C_{2-6}$ dialkylcarboxamide, halogen, $C_{1-4}$ haloalkoxy, $C_{1-4}$haloalkyl, $C_{1-4}$ haloalkylsulfinyl, $C_{1-4}$ haloalkylsulfonyl, $C_{1-4}$haloalkylthio, hydroxyl, nitro and phenyl; and wherein said amino and phenyl are each optionally substituted with 1 to 5 further substituents selected from the group consisting of halogen and carbo-$C_{1-6}$-alkoxy;

vi) $R_{6a}$, $R_{6b}$, and $R_{6c}$ are each independently selected from the group consisting of H, $C_{1-6}$ acyl, $C_{1-6}$ acyloxy, $C_{2-6}$alkenyl, $C_{1-6}$alkoxy, $C_{1-6}$ alkyl, $C_{1-6}$ alkylcarboxamide, $C_{2-6}$ alkynyl, $C_{1-6}$alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

vii) $R_7$ and $R_8$ are independently H or $C_{1-8}$ alkyl;

viii) X is O or S; and ix) Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

One aspect of the present invention encompasses pharmaceutical compositions comprising a compound of the present invention and a pharmaceutically acceptable carrier.

One aspect of the present invention encompasses methods for the prophylaxis and/or treatment of REM sleep behavior disorder, idiopathic REM sleep behavior disorder, or a combination thereof, in an individual comprising administering to said individual in need thereof a therapeutically effective amount of a compound according to any of the embodiments described herein or a pharmaceutical composition.

Some embodiments are directed to methods for the prophylaxis and/or treatment of REM sleep behavior disorder, idiopathic REM sleep behavior disorder, or a combination thereof, in a subject in need thereof comprising administering to said subject a therapeutically effective amount of a 5-$HT_{2A}$ inverse agonist. In some embodiments, administration of a therapeutically effective amount of a 5-$HT_{2A}$ inverse agonist results in treatment, and/or prophylaxis of REM sleep behavior disorder, idiopathic REM sleep behavior disorder, or a combination thereof.

In some embodiments, the 5-$HT_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof. In some embodiments, the 5-$HT_{2A}$ inverse agonist is nelotanserin or a pharmaceutically acceptable salt, hydrate, polymorph, or solvate thereof. In some embodiments, the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof. In some embodiments, the therapeutically effective amount of nelotanserin or a pharmaceutically acceptable salt, hydrate, polymorph, or solvate thereof is from about 0.001 mg to about 1,000 mg, about 0.001 mg to about 160 mg or about 10 to about 160 mg. In some embodiments, the therapeutically effective amount of nelotanserin or a pharmaceutically acceptable salt, hydrate, polymorph, or solvate thereof is about 20 mg, about 40 mg, or about 80 mg. In some embodiments, the therapeutically effective amount of the 5-$HT_{2A}$ inverse agonist is administered once a day, twice a day, or three times a day. In some embodiments, the 5-$HT_{2A}$ inverse agonist is configured for immediate release, for extended release, for delayed release, or any combination thereof. In some embodiments, the 5-$HT_{2A}$ inverse agonist is in a pharmaceutical composition, wherein the pharmaceutical composition is formulated for oral, nasal, sublingual, buccal, transdermal, vaginal or rectal administration. In some embodiments, the therapeutically effective amount of the 5-$HT_{2A}$ inverse agonist is administered about 1 hour prior to the subject's bedtime.

In some embodiments, the subject is a human. In some embodiments, the subject is an elderly adult human. In some embodiments, the human is an adult diagnosed with a neurodegenerative disease. In some embodiments, the neurodegenerative disease is selected from the group consisting of probable dementia with Lewy Bodies, dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, and any combination thereof. In some embodiments, the human is an adult with a diagnosis of a condition selected from probable dementia with Lewy Bodies, dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof. In some embodiments, the human has a concurrent diagnosis of REM Sleep Behavior disorder, idiopathic REM Sleep Behavior disorder, or a combination thereof. In some embodiments, the human has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof. In some embodiments, the human has a Mini Mental State Examination score of greater than, or equal to, about 18. In some embodiments, the human is an adult with a diagnosis of REM sleep behavior disorder, idiopathic REM sleep behavior disorder, or a combination thereof, associated with Dementia with Lewy Bodies. In some embodiments, the human is an adult aged 50-85 inclusive. In some embodiments, the human has experienced frequent episodes of REM sleep behavior disorder. In some embodiments, the human has experienced REM sleep behavior disorder on at least three to four days in a week.

In some embodiments, the subject is concurrently receiving a therapeutically effective amount of at least one additional therapeutic agent selected from the group consisting of melatonin, quetiapine, clonazepam, levodopa, carbidopa, an antiparkinsonian drug, an acetylcholinesterase inhibitor, NMDA receptor antagonist, and a combination thereof. In some embodiments, the therapeutically effective amount of melatonin is about 1 mg to about 5 mg. In some embodiments, the therapeutically effective amount of quetiapine is about 12.5 mg to about 100 mg. In some embodiments, the therapeutically effective amount of clonazepam is about 0.0625 mg to about 5 mg. In some embodiments, the antiparkinsonian drug is selected from an MAO-B inhibitor, a COMT inhibitor, a dopamine agonist or any combination thereof. In some embodiments, the therapeutically effective amount of levodopa or a pharmaceutically acceptable salt, hydrate, polymorph, or solvate thereof is from about 0.001 mg to about 10,000 mg, or about 0.001 mg to about 8,000 mg. In some embodiments, the therapeutically effective amount of levodopa or a pharmaceutically acceptable salt, hydrate, polymorph, or solvate thereof is about 285 mg, about 300 mg, about 400 mg, about 435 mg, 500 mg, about 585 mg, about 600 mg, about 700 mg, about 735 mg, about 750 mg, about 800 mg, about 980 mg, about 1,000 mg, about 1,225 mg, about 1,250 mg, about 1,470 mg, about 1,500 mg, about 1,715 mg, about 1,750 mg, about 1,960 mg, about 2,000 mg, about 2,205 mg, about 2,250 mg, about 2,450 mg, about 2,500 mg, about 2,750 mg, about 3,000 mg, about 3,250 mg, about 3,500 mg, about 3,750 mg, about 4,000 mg, about 4,250 mg, about 5,000 mg, about 5,250 mg, about 5,500 mg, about 5,750 mg, about 6,000 mg, about 6,250 mg, about 6,500 mg, about 6,750 mg, about 7,000 mg, about 7,250 mg, about 7,500 mg, about 7,750 mg, or about 8,000 mg. In some embodiments the therapeutically effective amount of carbidopa or a pharmaceutically acceptable salt, hydrate, polymorph, or solvate thereof is configured for immediate release, extended release, for delayed release, or any combination thereof. In some embodiments, the therapeutically effective amount of carbidopa is from about 0.001 mg to about 1,000 mg, or from about 0.001 mg to about 700 mg. In some embodiments, the therapeutically effective amount of carbidopa is about 30 mg, about 40 mg, about 50 mg, about 60 mg, about 70 mg, about 71.25 mg, about 80 mg, about 108.75 mg, about 146.25 mg, 183.75 mg, about 245 mg, about 245 mg, about 306.25 mg, about 367.5 mg, about 428.75 mg, about 490 mg, about 551.25 mg, or about 612.5 mg. In some embodiments, carbidopa and levodopa are administered concurrently.

In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, the therapeutically effective amount of donepezil or a pharmaceutically acceptable salt, hydrate, polymorph, or solvate thereof is configured for immediate release, extended release, for delayed release, or any combination thereof. In some embodiments, the therapeutically effective amount of donepezil or a pharmaceutically acceptable salt, hydrate, polymorph, or solvate thereof is from about 0.001 mg to about 1,000 mg, or about 0.001 mg to about 30 mg. In some embodiments, the therapeutically effective amount of donepezil or a pharmaceutically acceptable salt, hydrate, polymorph, or solvate thereof is about 5 mg, 10 mg, or 23 mg. In some embodiments, the acetylcholinesterase inhibitor is rivastigmine or a pharmaceutically acceptable salt, hydrate, polymorph, or solvate thereof. In some embodiments, the therapeutically effective amount of rivastigmine or a pharmaceutically acceptable salt, hydrate, polymorph, or solvate thereof is from about 0.001 mg to about 1,000 mg, or about 0.001 mg to about 15 mg. In some embodiments, the therapeutically effective amount of rivastigmine or a pharmaceutically acceptable salt, hydrate, polymorph, or solvate thereof is about 1.5 mg, about 3 mg, about 4.5 mg, about 6 mg, about 9 mg, about 9.5 mg, about 12 mg, or about 13.3 mg. In some embodiments, the therapeutically effective amount of rivastigmine or a pharmaceutically acceptable salt, hydrate, polymorph, or solvate thereof is configured for immediate release, for extended release, for delayed release, or any combination thereof. In some embodiments, the acetylcholinesterase inhibitor is galantamine or a pharmaceutically acceptable salt, hydrate, polymorph, or solvate thereof. In some embodiments, the therapeutically effective amount of galantamine or a pharmaceutically acceptable salt, hydrate, polymorph, or solvate thereof is configured for immediate release, extended release, for delayed release, or any combination thereof. In some embodiments, the therapeutically effective amount of galantamine or a pharmaceutically acceptable salt, hydrate, polymorph, or solvate thereof is from about 0.001 mg to about 1,000 mg, or about 0.001 mg to about 30 mg. In some embodiments, the therapeutically effective amount of galantamine or a pharmaceutically acceptable salt, hydrate, polymorph, or solvate thereof is about 4 mg, about 8 mg, about 12 mg, about 16 mg, or about 24 mg. In some embodiments, NMDA receptor antagonist is selected from the group consisting of memantine, amantadine, ketamine, and pharmaceutically acceptable salts, hydrates, polymorphs, or solvates thereof. In some embodiments, the NMDA receptor antagonist is memantine or a pharmaceutically acceptable salt, hydrate, polymorph, or solvate thereof. In some embodiments, the therapeutically effective amount of memantine or a pharmaceutically acceptable salt, hydrate, polymorph, or solvate thereof is configured for immediate release, extended release, for delayed release, or any combination thereof. In some embodiments, the therapeutically effective amount of memantine or a pharmaceutically acceptable salt, hydrate, polymorph, or solvate thereof is from about 0.001 mg to about 1,000 mg, or about 0.001 mg to about 30 mg. In some embodiments, the therapeutically effective amount of memantine or a pharmaceutically acceptable salt, hydrate, polymorph, or solvate thereof is about 5 mg, about 7 mg, about 10 mg, about 14 mg, about 20 mg, about 21 mg, or about 28 mg. In some embodiments, the therapeutically effective amount of memantine or a pharmaceutically acceptable salt, hydrate, polymorph, or solvate thereof is configured for extended release, for delayed release or a combination thereof. In some embodiments, the NMDA receptor antagonist is amantadine or a pharmaceutically acceptable salt, hydrate, polymorph, or solvate thereof. In some embodiments, the therapeutically effective amount of amantadine or a pharmaceutically acceptable salt, hydrate, polymorph, or solvate thereof is configured for immediate release, extended release, for delayed release, or any combination thereof. In some embodiments, the therapeutically effective amount of amantadine or a pharmaceutically acceptable salt, hydrate, polymorph, or solvate thereof is from about 0.001 mg to about 1,000 mg, or about 0.001 mg to about 500 mg. In some embodiments, the therapeutically effective amount of amantadine or a pharmaceutically acceptable salt, hydrate, polymorph, or solvate thereof is from about 100 mg to about 400 mg. In some embodiments, the therapeutically effective amount of amantadine or a pharmaceutically acceptable salt, hydrate, polymorph, or solvate thereof is about 100 mg, 200 mg, 300 mg or about 400 mg.

In some embodiments, treating or prophylaxis results in a decrease in the frequency, severity, or a combination thereof of REM sleep behavior disorder episodes. In some embodiments, treating or prophylaxis results in a decrease in the frequency of abnormal vocalizations and motor behavior per sleep period. In some embodiments, treatment results in a decrease in the amount of nightmare content per sleep period. In some embodiments, treating or prophylaxis results in a decrease in the potential for injury or injury to said subject during a sleep period. In some embodiments, treating or prophylaxis results in an increase in quality of partner sleep. In some embodiments, treating or prophylaxis results in an improvement in subjective sleep quality and objective sleep measures. In some embodiments, treating or prophylaxis results in an improvement in the clinician assessment of global change pertaining to REM sleep behavior disorder. In some embodiments, treating or prophylaxis results in a decrease in the frequency of REM sleep behavior disorder behaviors. In some embodiments, REM sleep behavior disorder behaviors are selected from the group consisting of vocalizations, simple and complex motor behaviors, and any combination thereof. In some embodiments, treating or prophylaxis results in a decrease in the severity of REM sleep behavior disorder behaviors. In some embodiments, treating or prophylaxis results in a decrease in the number of nights with injurious behaviors to subject or bed partner per week. In some embodiments, injurious behaviors are selected from a group consisting of vocalizations, simple and complex motor behaviors, and any combination thereof. In some embodiments, treating or prophylaxis results in a decrease in the number of nightmares per week. In some embodiments, treating or prophylaxis results in an improvement in Clinician's Global Impression of Change related to REM sleep behavior disorder behaviors. In some embodiments, treating or prophylaxis results in an improvement in the subject's Mini-Mental State Examination score.

Some embodiments are directed to methods for the prophylaxis and/or treatment of REM sleep behavior disorder, idiopathic REM sleep behavior disorder, or a combination thereof, in a subject in need thereof comprising administering to said subject a daily dose of about 40 mg of nelotanserin. In some embodiments, the daily dose of about 40 mg of nelotanserin is administered once a day, twice a day, three times a day or four times a day. In some embodiments, the subject has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, mild cognitive impairment, Parkinson's disease psychosis, Alzheimer's disease psychosis, a sleep disturbance, insomnia and a combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a daily oral dose of about 40 mg of nelotanserin. In some embodiments, the daily dose of about 40 mg of nelotanserin is administered once a day, twice a day, three times a day or four times a day. In some embodiments, the subject has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, mild cognitive impairment, Parkinson's disease psychosis, Alzheimer's disease psychosis, a sleep disturbance, insomnia and a combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a daily dose of about 80 mg of nelotanserin. In some embodiments, the daily dose of about 80 mg of nelotanserin is administered once a day, twice a day, three times a day or four times a day. In some embodiments, the subject has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, mild cognitive impairment, Parkinson's disease psychosis, Alzheimer's disease psychosis, a sleep disturbance, insomnia and a combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a daily oral dose of about 80 mg of nelotanserin. In some embodiments, the daily dose of about 80 mg of nelotanserin is administered once a day, twice a day, three times a day or four times a day. In some embodiments, the subject is a human adult with a diagnosis of a condition selected from probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a dose of about 40 mg of nelotanserin for a first time period followed by administering to said subject a dose of about 80 mg of nelotanserin for a second time period. In some embodiments, the subject is a human adult with a diagnosis of a condition selected from probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

These and other aspects of the invention disclosed herein will be set forth in greater detail as the patent disclosure proceeds.

DETAILED DESCRIPTION

Figure 1:
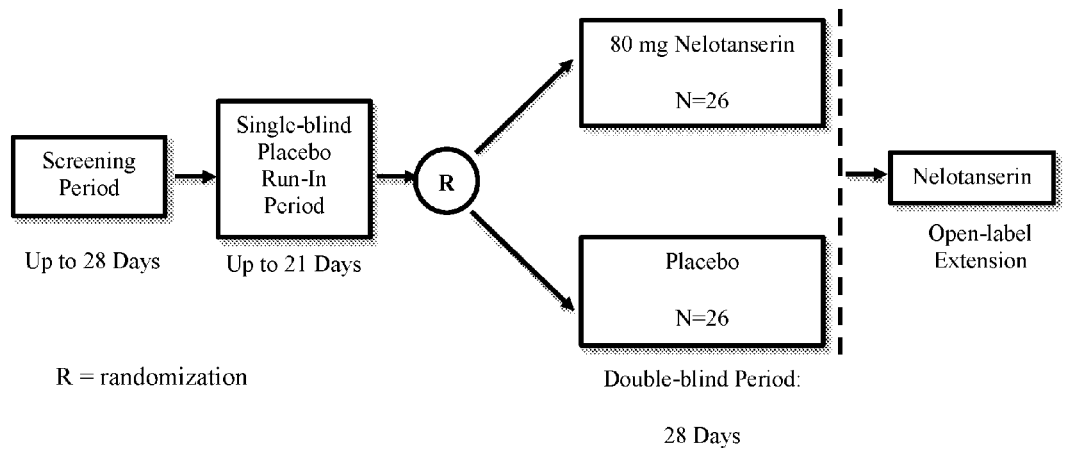
FIG. 1 shows the design of a multi-center, double-blind, randomized, placebo-controlled, cross-over study in DLB subjects with REM sleep behavior disorder.

Although any methods and materials similar or equivalent to those described herein can be used in the practice or testing of embodiments of the present invention, the exemplary methods, devices, and materials are now described.

In each of the embodiments described herein, the method may comprise administering a therapeutically effective amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof. In some embodiments, 1-[3-(4-bromo-2-methyl-2H-pyrazol-3-yl)-4-methoxy-phenyl]-3-(2,4-difluoro-phenyl)-urea may also be known as nelotanserin or RVT-102 and these terms may be used interchangeably. In each of the embodiments described herein, the method may consist essentially of administering a therapeutically effective amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof. In each of the embodiments described herein, the method may consist of administering a therapeutically effective amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof. The term "comprising" means "including, but not limited to." The term "consisting essentially of" means the method or composition includes the steps or components specifically recited, and may also include those that do not materially affect the basic and novel characteristics of the present invention. The term "consisting of" means the method or composition includes only the steps or components specifically recited. It must be noted that, as used herein, and in the appended claims, the singular forms "a", "an" and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the described includes instances where the event occurs and instances where it does not.

"Administering" when used in conjunction with a therapeutic means to administer a therapeutic directly or indirectly into or onto a target tissue to administer a therapeutic to a patient whereby the therapeutic positively impacts the tissue to which it is targeted. "Administering" a composition may be accomplished by oral nasal, sublingual, buccal, transdermal, vaginal or rectal administration, injection, infusion, inhalation, absorption or by any method in combination with other known techniques. "Administering" may include the act of self-administration or administration by another person such as a health care provider.

The term "improves" is used to convey that the present invention changes the appearance, form, characteristics, structure, function and/or physical attributes of the tissue to which it is being provided, applied or administered. "Improves" may also refer to the overall physical state of an individual to whom an active agent has been administered. For example, the overall physical state of an individual may "improve" if one or more symptoms of the disease, condition or disorder are alleviated by administration of an active agent.

As used herein, the term "therapeutic" means an agent utilized to treat, combat, ameliorate or prevent an unwanted disease, condition or disorder of a patient.

In each of the embodiments disclosed herein, the compounds and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "patient" and "subject" or "individual" are interchangeable and may be taken to mean any living organism, which may be treated with compounds of the present invention. As such, the terms "patient" and "subject" may include, but are not limited to, any non-human mammal, primate or human. In some embodiments, the "patient" or "subject" is an adult, an elderly adult, child, infant, or fetus. In some embodiments, an elderly adult is an adult of about 50 years of age or older. In yet other embodiments, an elderly adult is an adult aged between about 50 and 85 years of age. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology). In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is from about 0.001 mg to about 1,000 mg, about 0.001 mg to about 160 mg or about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 20 mg, about 40 mg, or about 80 mg.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disease, disorder or condition.

"In Need Of Prophylaxis Or Treatment" as used herein refers to a judgment made by a caregiver (e.g. physician, nurse, nurse practitioner, etc. in the case of humans; veterinarian in the case of animals, including non-human mammals) that an individual or animal requires or will benefit from prophylaxis or treatment. This judgment is made based on a variety of factors that are in the realm of a caregiver's expertise, but that includes the knowledge that the individual or animal is ill, or will be ill, as the result of a disease, condition or disorder that is treatable by the compounds of the invention. In general, "in need of prophylaxis" refers to the judgment made by the caregiver that the individual will become ill. In this context, the compounds of the invention are used in a protective or preventive manner. However, "in need of treatment" refers to the judgment of the caregiver that the individual is already ill; therefore, the compounds of the present invention are used to alleviate, inhibit or ameliorate the disease, condition or disorder.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof as the active ingredient. Alternatively, a pharmaceutical composition may contain 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof as the active ingredient.

"Pharmaceutically acceptable salts, hydrates or solvates" is meant to indicate those salts, hydrates or solvates which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail. A pharmaceutical acceptable "salt" is any acid addition salt, preferably a pharmaceutically acceptable acid addition salt, including, but not limited to, halogenic acid salts such as hydrobromic, hydrochloric, hydrofloric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesufonic, acetic, malic, fumaric, succinic, citric, benzoic gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

As used herein, the term "daily dose" refers to the amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof, per day that is administered or prescribed to a patient. This amount can be administered in multiple unit doses or in a single unit dose, in a single time during the day or at multiple times during the day. Multiple doses may be administered during the day, for example 2, 3 or 4, doses. In some embodiments, the dose is administered once daily in the morning, afternoon, evening, or once daily about 1 hour prior to the subject's bedtime. In some embodiments, the dose is administered twice daily. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is from about 0.0001 to about 1,000 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is from about 10 to about 160 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is about 10 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is about 20 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is about 40 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is about 80 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate is about 160 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is from about 0.001 mg to about 1,000 mg, about 0.001 mg to about 160 mg or about 10 to about 160 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 20 mg, about 40 mg, or about 80 mg.

"Composition" shall mean a material comprising at least two compounds or two components; for example, and without limitation, a Pharmaceutical Composition is a Composition comprising a compound of the present invention and a pharmaceutically acceptable carrier.

"Compound Efficacy" shall mean a measurement of the ability of a compound to inhibit or stimulate receptor functionality, as opposed to receptor binding affinity.

"Constitutively Activated Receptor" shall mean a receptor subject to constitutive receptor activation.

"Constitutive Receptor Activation" shall mean stabilization of a receptor in the active state by means other than binding of the receptor with its endogenous ligand or a chemical equivalent thereof.

"Contact" or "Contacting" shall mean bringing the indicated moieties together, whether in an in vitro system or an in vivo system. Thus, "contacting" a 5-HT$_{2A}$ receptor with a compound of the invention includes the administration of a compound of the present invention to an individual, preferably a human, having a 5-HT$_{2A}$ receptor, as well as, for example, introducing a compound of the invention into a sample containing a cellular or more purified preparation containing a 5-HT$_{2A}$ receptor.

"Endogenous" shall mean a material that a mammal naturally produces. Endogenous in reference to, for example and without limitation, the term "receptor" shall mean that which is naturally produced by a mammal (for example, and without limitation, a human) or a virus.

In contrast, the term "Non-Endogenous" in this context shall mean that which is not naturally produced by a mammal (for example, and without limitation, a human) or a virus. For example, and without limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and without limitation, in a screening approach, the endogenous or non-endogenous receptor may be in reference to an in vitro screening system. As a further example and without limitation, where the genome of a mammal has been manipulated to include a non-endogenous constitutively activated receptor, screening of a candidate compound by means of an in vivo system is viable.

"Inhibit" or "Inhibiting", in relationship to the term "response" shall mean that a response is decreased or prevented in the presence of a compound as opposed to in the absence of the compound.

"Inverse Agonists" shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

"Ligand" shall mean an endogenous, naturally occurring molecule specific for an endogenous, naturally occurring receptor.

As used herein, the terms "Modulate" or "Modulating" shall mean to refer to an increase or decrease in the amount, quality, response or effect of a particular activity, function or molecule.

Before the present compositions and methods are described, it is to be understood that this invention is not limited to the particular processes, compositions, or methodologies described, as these may vary. Moreover, the processes, compositions, and methodologies described in particular embodiments are interchangeable. Therefore, for example, a composition, dosages regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

The scientific literature that has evolved around receptors has adopted a number of terms to refer to ligands having various effects on receptors. For clarity and consistency, the following definitions will be used throughout this patent document.

"Agonists" shall mean moieties that interact and activate the receptor, such as the $5\text{-}HT_{2A}$ receptor, and initiate a physiological or pharmacological response characteristic of that receptor. For example, when moieties activate the intracellular response upon binding to the receptor, or enhance GTP binding to membranes.

The term "Antagonists" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

The term "$C_{1-6}$ acyl" denotes a $C_{1-6}$ alkyl radical attached to a carbonyl wherein the definition of alkyl has the same definition as described herein; some examples include but are not limited to, acetyl, propionyl, n-butanoyl, iso-butanoyl, sec-butanoyl, t-butanoyl (i.e., pivaloyl), pentanoyl and the like.

The term "$C_{1-6}$ acyloxy" denotes an acyl radical attached to an oxygen atom wherein acyl has the same definition has described herein; some examples include but are not limited to acetyloxy, propionyloxy, butanoyloxy, iso-butanoyloxy, sec-butanoyloxy, t-butanoyloxy and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present, then the bonds may be all E or Z or a mixture of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2,4-hexadienyl and the like.

The term "$C_{1-6}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments are 1 to 6 carbons, some embodiments are 1 to 4 carbons, some embodiments are 1 to 3 carbons, and some embodiments are 1 or 2 carbons. Examples of an alkyl include, but are not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., $CH(CH_3)CH_2CH_2CH_3$], 2-methylbutyl [i.e., $-CH_2CH(CH_3)CH_2CH_3$], n-hexyl and the like.

The term "$C_{1-6}$ alkylcarboxamido" or "$C_{1-6}$ alkylcarboxamide" denotes a single $C_{1-6}$ alkyl group attached to the nitrogen of an amide group, wherein alkyl has the same definition as found herein. The $C_{1-6}$ alkylcarboxamido may be represented by Formula II:

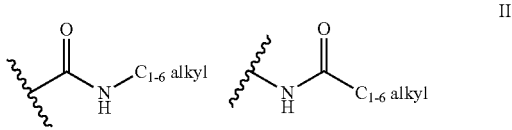

II

Examples include, but are not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —$CH_2$—, —$CH_2CH_2$—, —$CH_2CH_2CH_2$—, and the like. In some embodiments, $C_{1-3}$alkylene refers to —CH—, —$CHCH_2$—, —$CHCH_2CH_2$—, and the like wherein these examples relate generally to the variable or claim element "Q".

The term "$C_{1-6}$ alkylimino" denotes a $C_{1-6}$ alkyl radical attached directly to the carbon of the —C(=NH)— group wherein the definition of alkyl has the same definition as described herein; some examples include but are not limited to, 1-imino-ethyl [i.e., —C(=NH)$CH_3$], 1-imino-propyl [i.e., —C(=NH)$CH_2CH_3$], 1-imino-2-methyl-propyl [i.e., —C(=NH)CH($CH_3$)$_2$], and the like.

The term "$C_{1-6}$ alkylsulfinyl" denotes a $C_{1-6}$ alkyl radical attached to a sulfoxide radical of the formula: —S(O)— wherein the alkyl radical has the same definition as described herein. Examples include, but are not limited to, methylsulfinyl, ethylsulfinyl, n-propylsulfinyl, iso-propylsulfinyl, n-butylsulfinyl, sec-butylsulfinyl, iso-butylsulfinyl, t-butylsulfinyl, and the like.

The term "$C_{1-6}$ alkylsulfonamide" refers to the groups of Formula III:

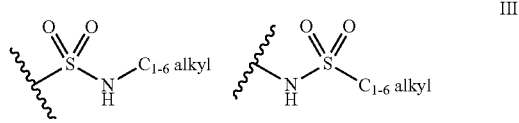

III wherein $C_{1-6}$ alkyl has the same definition as described herein.

The term "$C_{1-6}$ alkylsulfonyl" denotes a $C_{1-6}$ alkyl radical attached to a sulfone radical of the formula: —S(O)$_2$— wherein the alkyl radical has the same definition as described herein. Examples include, but are not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-6}$ alkylthio" denotes a $C_{1-6}$ alkyl radical attached to a sulfide of the formula: —S— wherein the alkyl radical has the same definition as described herein. Examples include, but are not limited to, methylsulfanyl (i.e., $CH_3$S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "$C_{1-6}$ alkylthiocarboxamide" denotes a thioamide of the following Formula IV:

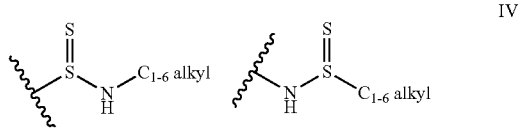

IV wherein $C_{1-4}$ alkyl has the same definition as described herein.

The term "$C_{1-6}$ alkylthioureyl" denotes the group of the formula: —NC(S)N— wherein one are both of the nitrogens are substituted with the same or different $C_{1-6}$ alkyl groups and alkyl has the same definition as described herein. Examples of an alkylthioureyl include, but are not limited to, $CH_3NHC(S)NH$—, $NH_2C(S)NCH_3$—, $(CH_3)_2N(S)NH$—, $(CH_3)_2N(S)NH$—, $(CH_3)_2N(S)NCH_3$—, $CH_3CH_2NHC(S)NH$—, $CH_3CH_2NHC(S)NCH_3$—, and the like.

The term "$C_{1-6}$ alkylureyl" denotes the group of the formula: —NC(O)N— wherein one are both of the nitrogens are substituted with the same or different $C_{1-6}$ alkyl group wherein alkyl has the same definition as described herein. Examples of an alkylureyl include, but are not limited to, $CH_3NHC(O)NH$—, $NH_2C(O)NCH_3$—, $(CH_3)_2NC(O)NH$—, $(CH_3)_2NC(O)NH$—, $(CH_3)_2NC(O)NCH_3$—, $CH_3CH_2NHC(O)NH$—, $CH_3CH_2NHC(O)NCH_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and triynes.

The term "amino" denotes the group —$NH_2$.

The term "$C_{1-6}$ alkylamino" denotes one alkyl radical attached to an amino radical wherein the alkyl radical has the same meaning as described herein. Some examples include, but are not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —$CH_2$—, —$CH_2CH_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. An example is N-phenylcarboxamide.

The term "arylureyl" denotes the group —NC(O)N— where one of the nitrogens are substituted with an aryl.

The term "benzyl" denotes the group —$CH_2C_6H_5$.

The term "carbo-$C_{1-6}$-alkoxy" refers to a $C_{1-6}$ alkyl ester of a carboxylic acid, wherein the alkyl group is as defined herein. Examples include, but are not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "$C_{4-7}$ cycloalkenyl" denotes a non-aromatic ring radical containing 4 to 7 ring carbons and at least one double bond; some embodiments contain 4 to 6 carbons; some embodiments contain 4 to 5 carbons; some embodiments contain 4 carbons. Examples include cyclobutenyl, cyclopentenyl, cyclopentenyl, cyclohexenyl, and the like.

The term "$C_{3-7}$ cycloalkyl" denotes a saturated ring radical containing 3 to 7 carbons; some embodiments contain 3 to 6 carbons; some embodiments contain 3 to 5 carbons; some embodiments contain 5 to 7 carbons; some embodiments contain 3 to 4 carbons. Examples include cyclopropyl, cyclobutyl, cyclopentyl, cyclohexyl, cycloheptyl and the like.

The term "$C_{2-8}$ dialkylamino" denotes an amino substituted with two of the same or different $C_{1-4}$ alkyl radicals wherein alkyl radical has the same definition as described herein. Some examples include, but are not limited to, dimethylamino, methylethylamino, diethylamino, methylpropylamino, methylisopropylamino, ethylpropyl amino, ethylisopropylamino, dipropylamino, propylisopropylamino and the like. Some embodiments are "$C_{2-4}$ dialkylamino."

The term "$C_{2-8}$ dialkylcarboxamido" or "$C_{2-8}$ dialkylcarboxamide" denotes two alkyl radicals, that are the same or different, attached to an amide group, wherein alkyl has the same definition as described herein. A $C_{2-8}$ dialkylcarboxamido may be represented by Formula V:

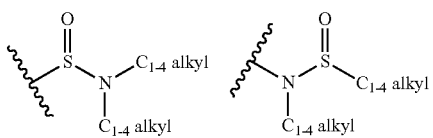

V wherein $C_{1-4}$ has the same definition as described herein. Examples of a dialkylcarboxamide include, but are not limited to, N,N-dimethylcarboxamide, N-methyl-N-ethylcarboxamide, N,N-diethylcarboxamide, N-methyl-N-isopropylcarboxamide, and the like.

The term "$C_{2-8}$ dialkylsulfonamide" refers to one of the following groups shown in Formula VI:

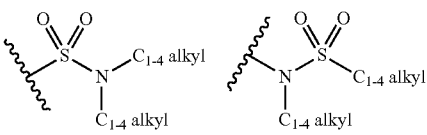

VI wherein $C_{1-4}$ has the same definition as described herein, for example but not limited to, methyl, ethyl, n-propyl, isopropyl, and the like.

The term "$C_{2-8}$ dialkylthiocarboxamido" or "$C_{2-8}$ dialkylthiocarbox-amide" denotes two alkyl radicals, that are the same or different, attached to a thioamide group, wherein alkyl has the same definition as described herein. A $C_{2-8}$ dialkylthiocarboxamido or $C_{2-8}$ dialkylthiocarboxamide may be represented by the Formula VII:

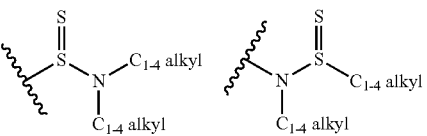

VII

Examples of a dialkylthiocarboxamide include, but are not limited to, N,N-dimethylthiocarboxamide, N-methyl-N-ethylthiocarboxamide and the like.

The term "ethynylene" refers to the carbon-carbon triple bond group as represented Formula VIII:

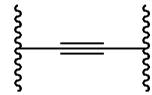

VIII

The term "formyl" refers to the group —CHO.

The term "$C_{1-6}$ haloalkoxy" denotes a haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_{1-6}$ haloalkyl" denotes an $C_{1-6}$ alkyl group, defined herein, wherein the alkyl is substituted with one halogen up to fully substituted and a fully substituted $C_{1-6}$ haloalkyl can be represented by the formula $C_nL_{2n+1}$ wherein L is a halogen and "n" is 1, 2, 3 or 4. When more than one halogen is present then they may be the same or different and selected from the group consisting of F, Cl, Br and I, preferably F. Examples of $C_{1-4}$ haloalkyl groups include, but are not limited to, fluoromethyl, difluoromethyl, trifluoromethyl, chlorodifluoromethyl, 2,2,2-trifluoroethyl, pentafluoroethyl and the like.

The term "$C_{1-6}$ haloalkylcarboxamide" denotes an alkylcarboxamide group, defined herein, wherein the alkyl is substituted with one halogen up to fully substituted represented by the formula $C_nL_{2n+1}$ wherein L is a halogen and "n" is 1, 2, 3 or 4. When more than one halogen is present they may be the same or different and selected from the group consisting of F, Cl, Br and I, preferably F.

The term "$C_{1-6}$ haloalkylsulfinyl" denotes a haloalkyl radical attached to a sulfoxide group of the formula: —S(O)— wherein the haloalkyl radical has the same definition as described herein. Examples include, but are not limited to, trifluoromethylsulfinyl, 2,2,2-trifluoroethylsulfinyl, 2,2-difluoroethylsulfinyl and the like.

The term "$C_{1-6}$ haloalkylsulfonyl" denotes a haloalkyl radical attached to a sulfone group of the formula: —S(O)$_2$— wherein haloalkyl has the same definition as described herein. Examples include, but are not limited to, trifluoromethylsulfonyl, 2,2,2-trifluoroethylsulfonyl, 2,2-difluoroethylsulfonyl and the like.

The term "$C_{1-6}$ haloalkylthio" denotes a haloalkyl radical directly attached to a sulfur wherein the haloalkyl has the same meaning as described herein. Examples include, but are not limited to, trifluoromethylthio (i.e., CF$_3$S—, also referred to as trifluoromethylsulfanyl), 1,1-difluoroethylthio, 2,2,2-trifluoroethylthio and the like.

The term "halogen" or "halo" denotes a fluoro, chloro, bromo or iodo group.

The term "heteroaryl" denotes an aromatic ring system that may be a single ring, two fused rings or three fused rings wherein at least one ring carbon is replaced with a heteroatom selected from, but are not limited to, the group consisting of O, S and N wherein the N can be optionally substituted with H, $C_{1-4}$ acyl or $C_{1-4}$ alkyl. Examples of heteroaryl groups include, but are not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH. Examples include, but are not limited to, pyrrole, indole, and the like. Other examples include, but are not limited to, those in Table 1, Table 2, and the like.

The term "heterocyclic" denotes a non-aromatic carbon ring (i.e., $C_{3-7}$ cycloalkyl or $C_{4-7}$ cycloalkenyl as defined herein) wherein one, two or three ring carbons are replaced by a heteroatom selected from, but are not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include, but are not limited to, aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term "heterocycliccarboxamido" denotes a heterocyclic group, as defined herein, with a ring nitrogen where the ring nitrogen is bonded directly to the carbonyl forming an amide. Examples include those in Formula IX, but are not limited to,

IX

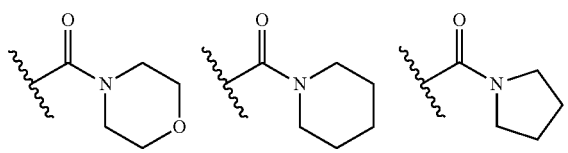

and the like.

The term "heterocyclicsulfonyl" denotes a heterocyclic group, as defined herein, with a ring nitrogen where the ring nitrogen is bonded directly to an —SO$_2$-group forming an sulfonamide. Examples include those in Formula X, but are not limited to,

X

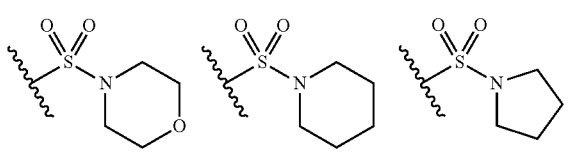

and the like.

The term "hydroxyl" refers to the group —OH.

The term "hydroxylamino" refers to the group —NHOH.

The term "nitro" refers to the group —NO$_2$.

The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the structures respectively in Formula XI:

XI

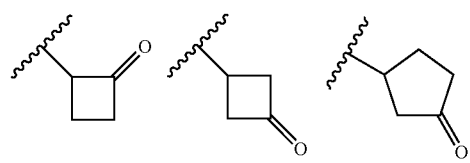

-continued

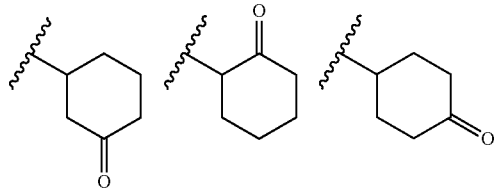

The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "phenoxy" refers to the group $C_6H_5O$—.

The term "phenyl" refers to the group $C_6H_5$—.

The term "sulfonic acid" refers to the group —$SO_3H$.

The term "thiol" denotes the group —SH.

"Codon" shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

Compounds of the Invention:

One aspect of the present invention encompasses certain diaryl and arylheteroaryl urea derivatives as shown in Formula I:

I

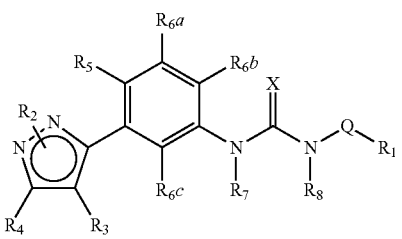

or a pharmaceutically acceptable salt, hydrate or solvate thereof, wherein $R_1$, $R_2$, $R_3$, $R_4$, $R_5$, $R_{6a}$, $R_{6b}$, $R_{6c}$, $R_7$, $R_8$, X, and Q have the same definitions as described herein, supra and infra.

Some embodiments of the present invention encompass certain diaryl and arylheteroaryl urea derivatives as shown in the following Formula II

II

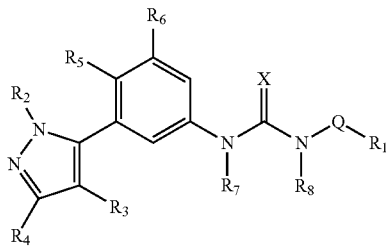

wherein:

i) $R_1$ is aryl or heteroaryl optionally substituted with $R_9$, $R_{10}$, $R_{11}$, $R_{12}$, $R_{13}$, $R_{14}$, and $R_{15}$ selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$haloalkylsulfinyl, $C_{1-6}$haloalkylsulfonyl, $C_{1-6}$ haloalkylthio, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein each of said $C_{2-6}$ alkenyl, $C_{1-6}$ alkyl, $C_{2-6}$ alkynyl and phenyl groups can be optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$haloalkylsulfinyl, $C_{1-6}$ haloalkylsulfonyl, $C_{1-6}$ haloalkylthio, hydroxyl, thiol and nitro;

ii) $R_2$ is selected from the group consisting of $C_{1-6}$ alkyl, $C_{2-6}$ alkenyl, $C_{2-6}$ alkynyl and $C_{3-7}$ cycloalkyl;

iii) $R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$dialkylcarboxamide, halogen, heteroaryl and phenyl; and wherein each of said $C_{2-6}$ alkenyl, $C_{1-6}$ alkyl, $C_{2-6}$alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

iv) $R_4$ is selected from the group consisting of H, $C_{1-6}$ acyl, $C_{1-6}$ acyloxy, $C_{2-6}$ alkenyl, $C_{1-6}$ alkoxy, $C_{1-6}$alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

v) $R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-4}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-5}$ alkyl, $C_{1-6}$alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$haloalkylsulfonyl, $C_{1-4}$ haloalkylthio, hydroxyl, nitro and phenyl, and wherein said phenyl is optionally substituted with 1 to 5 halogen atoms;

vi) $R_6$ is selected from the group consisting of H, $C_{1-6}$ acyl, $C_{1-6}$ acyloxy, $C_{2-6}$ alkenyl, $C_{1-6}$ alkoxy, $C_{1-6}$alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

vii) $R_7$ and $R_8$ are independently H or $C_{1-8}$ alkyl;

viii) X is O or S; and ix) Q is $C_{1-3}$ alkylene optionally substituted with 1 to 4 substituents selected from the group consisting of $C_{1-3}$alkyl, $C_{1-4}$ alkoxy, carboxy, cyano, $C_{1-3}$ haloalkyl, halogen and oxo; or Q is a bond; or a pharmaceutically acceptable salt, hydrate or solvate thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of the present invention may have one or more chiral centers, and therefore can exist as enantiomers and/or diastereomers. The invention is understood to extend to and embrace all such enantiomers, diastereomers and mixtures thereof, including but not limited to racemates. Accordingly, some embodiments of the present invention pertain to compounds of the present invention that are R enantiomers. Further, some embodiments of the present invention pertain to compounds of the present invention that are S enantiomers. In examples where more than one chiral center is present, some embodiments of the present invention include compounds that are RS or SR enantiomers. In further embodiments, compounds of the present invention are RR or SS enantiomers. It is understood that compounds of the present invention are intended to represent all individual enantiomers and mixtures thereof, unless stated or shown otherwise.

In some embodiments, $R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

Some embodiments of the present invention pertain to compounds wherein $R_1$ is phenyl or naphthyl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, carboxamide, cyano, $C_{3-7}$cycloalkyl, halogen, $C_{1-6}$ haloalkoxy, $C_{1-6}$ haloalkyl, and hydroxyl.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, $C_{1-6}$alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, and $R_{13}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, carboxamide, cyano, $C_{3-7}$ cycloalkyl, halogen, $C_{1-6}$haloalkoxy, $C_{1-6}$ haloalkyl, and hydroxyl.

Some embodiments of the present invention pertain to compounds wherein $R_1$ is phenyl or naphthyl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, amino, $C_{1-6}$ alkylamino, $C_{2-8}$ dialkylamino, $C_{1-6}$ alkylimino, cyano, halogen, $C_{1-6}$ haloalkoxy, $C_{1-6}$haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, amino, $C_{1-6}$alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, and $R_{13}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino [i.e., —N(CH$_3$)CH$_2$CH$_2$N(CH$_3$)$_2$], (3-dimethylamino-propyl)-methyl-amino [i.e., —N(CH$_3$)CH$_2$CH$_2$CH$_2$N(CH$_3$)$_2$], —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is phenyl optionally substituted with $R_9$, $R_{10}$, $R_{11}$, $R_{12}$, and $R_{13}$, $R_{14}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethyl-amino-ethyl)-methyl-amino [i.e., —N(CH$_3$)CH$_2$CH$_2$N(CH$_3$)$_2$], (3-dimethylamino-propyl)-methyl-amino [i.e., —N(CH$_3$)CH$_2$CH$_2$CH$_2$N(CH$_3$)$_2$], —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is phenyl and can be represented by the Formula XIII shown below:

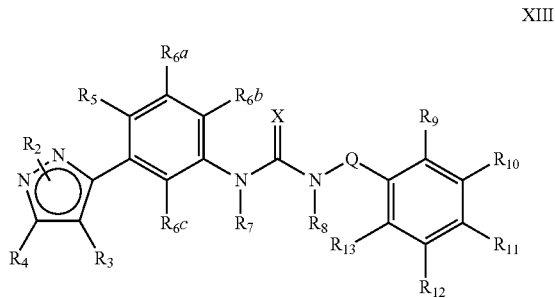

XIII wherein each variable in the above formula has the same meaning as described herein, supra and infra. In some embodiments, $R_7$ and $R_8$ are both —H, Q is a bond, and X is O.

Some embodiments of the present invention pertain to compounds wherein $R_1$ is phenyl and can be represented by Formula XIV as shown below:

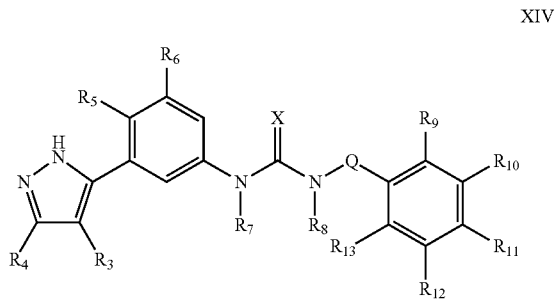

XIV wherein:
$R_9$ to $R_{13}$ substituents are each selected independently from the group consisting of H, $C_{1-6}$ acyl, $C_{1-6}$ acyloxy, $C_{1-6}$ alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$alkylamino, $C_{2-8}$ dialkylamino, carbo-$C_{1-6}$-alkoxy, carboxamide, carboxy, cyano, halogen, $C_{1-6}$ haloalkoxy, $C_{1-6}$ haloalkyl, hydroxyl, nitro and phenyl, or two adjacent substituents together with the phenyl form a $C_{5-7}$ cycloalkyl optionally comprising 1 to 2 oxygen atoms; and wherein each said $C_{1-6}$ alkyl and phenyl groups can be optionally substituted with 1 to 5 substituents selected independently from the group consisting of $C_{1-6}$ alkoxy, $C_{1-6}$ alkyl, amino, cyano, halogen, $C_{1-6}$haloalkoxy, $C_{1-6}$ haloalkyl, hydroxyl and nitro.

In some embodiments, $R_1$ is phenyl optionally substituted with $R_9$ to $R_{13}$ substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl; and wherein said phenyl can be optionally substituted with 1 to 5 substituents selected independently from the group consisting of $C_{1-6}$ alkoxy, $C_{1-6}$ alkyl, cyano, halogen, $C_{1-6}$ haloalkoxy, $C_{1-6}$ haloalkyl and nitro.

In some embodiments, $R_1$ is phenyl optionally substituted with $R_9$ to $R_{13}$ substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl.

In some embodiments, $R_1$ is phenyl optionally substituted with $R_9$ to $R_{13}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, F, Cl, Br, I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$, nitro and phenyl.

In some embodiments, $R_1$ is phenyl optionally substituted with $R_9$ to $R_{13}$ substituents are each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethyl amino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

In some embodiments, $R_1$ is phenyl optionally substituted with $R_9$, $R_{10}$, $R_{11}$, $R_{12}$ and $R_{13}$ substituents selected independently from the group consisting of —C(O)CH$_3$, —OCH$_3$, —CH$_3$, cyano, —F, —Cl, —Br, —OCF$_3$, —CF$_3$, nitro and phenyl.

Some embodiments of the present invention pertain to compounds wherein $R_1$ is naphthyl optionally substituted with $R_9R_{10}R_{11}R_{12}R_{13}R_{14}$ and $R_{15}$ substituents selected independently from the group consisting of $C_{1-6}$ acyl, $C_{1-6}$ acyloxy, $C_{1-6}$alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$ alkylamino, $C_{2-8}$ dialkylamino, carbo-$C_{1-6}$-alkoxy, carboxamide, carboxy, cyano, halogen, $C_{1-6}$ haloalkoxy, $C_{1-6}$haloalkyl, hydroxyl and nitro; and wherein said $C_{1-6}$ alkyl can be optionally substituted with 1 to 5 substituents selected independently from the group consisting of $C_{1-6}$ alkoxy, $C_{1-6}$ alkyl, amino, cyano, halogen, $C_{1-6}$ haloalkoxy, $C_{1-6}$ haloalkyl, hydroxyl and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$haloalkyl and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCHF$_2$CF$_3$, —CF$_3$, —CHF$_2$, —CFH$_2$, —CF$_2$CF$_3$, —CH$_2$CF$_3$ and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O) CH$_3$, —C(O)CH$_2$CH$_3$, —C(O)CH(CH$_3$)$_2$, —C(O) CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$ and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —OCH$_3$, —CH$_3$, cyano, —F, —Cl, —Br, —OCF$_3$, —CF$_3$ and nitro.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$alkyl, amino, $C_{1-6}$ alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethyl amino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of $C_{1-6}$ acyl, $C_{1-6}$ acyloxy, $C_{1-6}$ alkoxy, $C_{1-6}$alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$alkylamino, $C_{2-8}$ dialkylamino, carbo-$C_{1-6}$-alkoxy, carboxamide, carboxy, cyano, halogen, $C_{1-6}$ haloalkoxy, $C_{1-6}$ haloalkyl, hydroxyl, nitro and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group; and wherein each of said $C_{1-6}$ alkyl and phenyl groups can be optionally substituted with 1 to 5 substituents selected independently from the group consisting of $C_{1-6}$ alkoxy, $C_{1-6}$ alkyl, amino, cyano, halogen, $C_{1-6}$ haloalkoxy, $C_{1-6}$ haloalkyl, hydroxyl and nitro.

In some embodiments, $R_1$ is heteroaryl optionally substituted with $R_9$, $R_{10}$, $R_{11}$, $R_{12}$ and $R_{13}$ each selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl; and wherein said phenyl can be optionally substituted with 1 to 5 substituents selected independently from the group consisting of $C_{1-6}$ alkoxy, $C_{1-6}$ alkyl, cyano, halogen, $C_{1-6}$ haloalkoxy, $C_{1-6}$ haloalkyl and nitro.

In some embodiments, $R_1$ is heteroaryl optionally substituted with $R_9$, $R_{10}$, $R_{11}$, $R_{12}$ and $R_{13}$ each selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl.

In some embodiments, $R_1$ is heteroaryl optionally substituted with $R_9$, $R_{10}$, $R_{11}$, $R_{12}$, and $R_{13}$ each selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$, nitro and phenyl.

In some embodiments, $R_1$ is heteroaryl optionally substituted with $R_9$, $R_{10}$, $R_{11}$, $R_{12}$, and $R_{13}$ each selected independently from the group consisting of —C(O)CH$_3$, —OCH$_3$, —CH$_3$, cyano, —F, —Cl, —Br, —OCF$_3$, —CF$_3$, nitro and phenyl. In some embodiments, $R_1$ is heteroaryl optionally substituted with $R_9$, $R_{10}$, $R_{11}$, $R_{12}$, and $R_{13}$ selected independently from the group consisting of H, —C(O)CH$_3$, —OCH$_3$, —CH$_3$, cyano, —F, —Cl, —Br, —OCF$_3$, —CF$_3$, nitro and phenyl.

In some embodiments, $R_1$ is heteroaryl having 5-atoms in the aromatic ring, examples of which are represented by the following formulae in Table 1:

TABLE 1

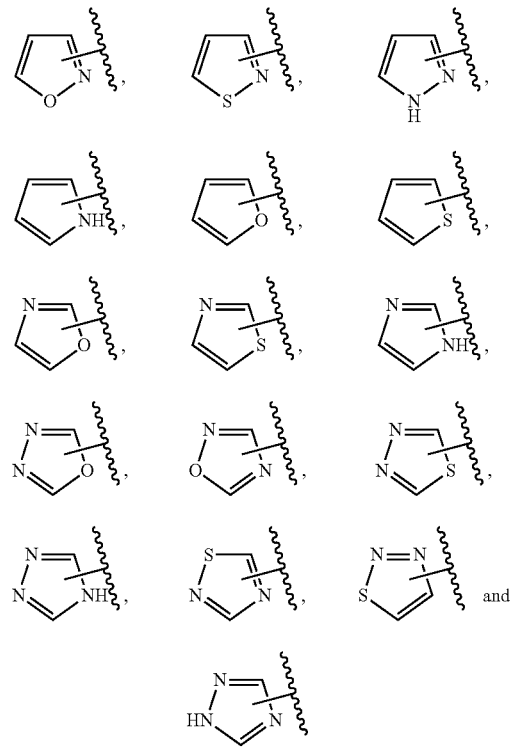

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imidazol-5-yl group).

In some embodiments, $R_1$ is a 6-membered heteroaryl, for example, a 6-membered heteroaryl as shown in Table 2:

TABLE 2

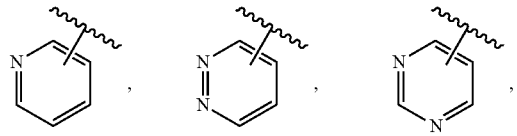

TABLE 2-continued

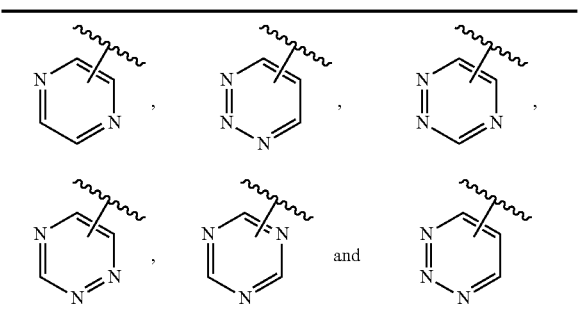

wherein the heteroaryl group is bonded at any ring carbon. In some embodiments, $R_1$ is selected from the group consisting of pyridinyl, pyridazinyl, pyrimidinyl and pyrazinyl. In some embodiments, $R_1$ is pyridinyl.

In some embodiments $R_1$ is a heteroaryl, for example but is not limited to those shown in Tables 1 and 2, optionally substituted with 1 to 3 substituents selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$haloalkylsulfonyl, $C_{1-6}$ haloalkylthio, hydroxyl, thiol, nitro, phenoxy and phenyl; and wherein each of said $C_{2-6}$ alkenyl, $C_{1-6}$alkyl, $C_{2-6}$ alkynyl and phenyl groups can be optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro.

Some embodiments of the present invention pertain to compounds wherein $R_2$ is H or $C_{1-6}$ alkyl.

Some embodiments of the present invention pertain to compounds wherein $R_2$ is $C_{1-6}$ alkyl. In some embodiments, $R_2$ is selected from the group consisting of —$CH_3$, —$CH_2CH_3$, —$CH(CH_3)_2$, —$CH_2CH_2CH_3$, —$CH_2CH(CH_3)_2$ and —$CH_2CH_2CH_2CH_3$. In some embodiments, $R_2$ is —$CH_3$ or —$CH(CH_3)_2$.

Some embodiments of the present invention can be represented by Formulae IIb and IIc respectively as shown below:

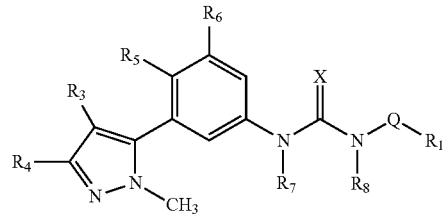

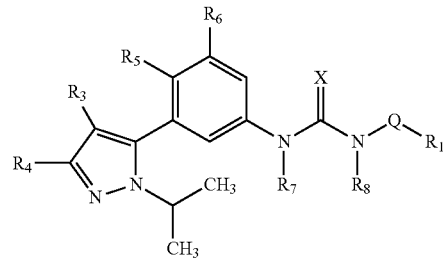

wherein each variable in Formulae IIb and IIc has the same meaning as described herein, supra and infra.

Some embodiments of the present invention pertain to compounds wherein $R_2$ is H.

It is understood that when $R_2$ is H, then tautomers are possible. It is well understood and appreciated in the art that pyrazoles can exist in various tautomeric forms. Two possible tautomeric forms are illustrated below as Formula IId and IId':

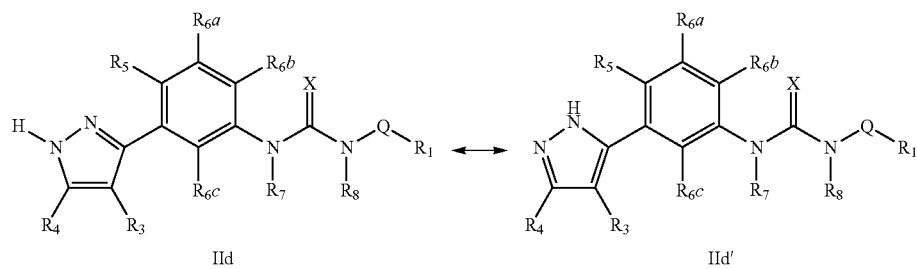

It is further understood that tautomeric forms can also have corresponding nomenclature for each represented tautomer, for example, Formula IId and Formula IId' can be represented by the general chemical names 1H-pyrazol-3-yl and 2H-pyrazole-3-yl respectively. Therefore, the present invention includes all tautomers and the various nomenclature designations.

Some embodiments of the present invention pertain to compounds wherein $R_2$ is $C_{2-6}$ alkenyl. In some embodiments, $R_2$ is —$CH_2CH$=$CH_2$.

Some embodiments of the present invention pertain to compounds wherein $R_2$ is $C_{2-6}$ alkynyl.

Some embodiments of the present invention pertain to compounds wherein $R_2$ is $C_{3-7}$ cycloalkyl. In some embodiments, $R_2$ is cyclopropyl.

Some embodiments of the present invention pertain to compounds wherein $R_3$ is selected from the group consisting of H, $C_{2-6}$ alkenyl, $C_{1-6}$ alkyl, $C_{1-6}$ alkylcarboxamide, $C_{2-6}$ alkynyl, carbo-$C_{1-6}$-alkoxy, carboxamide, carboxy, cyano, $C_{3-7}$cycloalkyl, halogen, heteroaryl or phenyl; and wherein each of said $C_{2-6}$ alkenyl, $C_{1-6}$ alkyl, $C_{2-6}$ alkynyl, heteroaryl and phenyl groups can be optionally substituted with 1 to 5 substituents selected independently from the group consisting of $C_{1-6}$ alkylamino, $C_{2-8}$ dialkylamino, $C_{2-6}$ alkenyl, $C_{1-4}$ alkoxy, $C_{1-8}$ alkyl, $C_{2-6}$ alkynyl, amino, halogen, $C_{1-4}$ haloalkoxy and hydroxyl.

In some embodiments, $R_3$ is selected from the group consisting of H, $C_{2-6}$ alkenyl, $C_{1-6}$ alkyl, $C_{2-6}$ alkynyl, carbo-$C_{1-6}$-alkoxy, carboxy, cyano, $C_{3-7}$ cycloalkyl, halogen, heteroaryl or phenyl; and wherein each of said $C_{2-6}$ alkenyl, $C_{1-6}$ alkyl, $C_{2-6}$ alkynyl and phenyl groups can be optionally substituted with 1 to 5 substituents selected independently from the group consisting of $C_{2-8}$ dialkylamino, $C_{2-6}$ alkenyl, $C_{1-4}$ alkoxy, $C_{2-6}$ alkynyl, halogen, $C_{1-4}$ haloalkoxy and hydroxyl.

In some embodiments, $R_3$ is selected from the group consisting of H, —CH=CH$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, —C≡CH, —C(O)OCH$_3$, —C(O)OCH$_2$CH$_3$, carboxy, cyano, cyclopropyl, F, Cl, Br, I, thiophen-2-yl, thiophen-3-yl, phenyl, —CH$_2$CH$_2$N(CH$_3$)$_2$, 2-methoxyphenyl, 3-methoxyphenyl, 4-methoxyphenyl, —CH=CH—C≡CH, 4-fluorophenyl, 4-trifluoromethoxyphenyl, —CH$_2$OH and —CH$_2$CH$_2$OH.

Some embodiments of the present invention pertain to compounds wherein $R_3$ is H or halogen.

In some embodiments, $R_3$ is H, F, Cl or Br.

Some embodiments of the present invention pertain to compounds of Formula IIe and Ie as shown below:

IIe

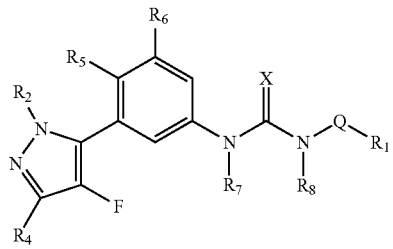

Ie

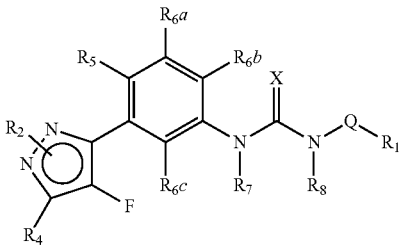

wherein each variable in Formula IIe and Ie has the same meaning as described herein, supra and infra.

Some embodiments of the present invention pertain to compounds of Formula IIf and If as shown below:

IIf

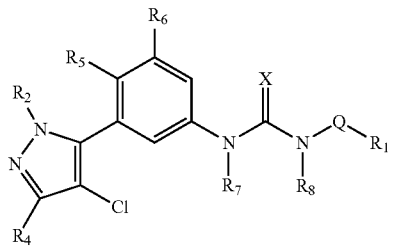

If

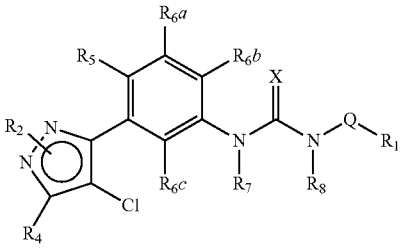

wherein each variable in Formula IIf and If has the same meaning as described herein, supra and infra.

Some embodiments of the present invention pertain to compounds of Formula IIg and Ig as shown below:

IIg

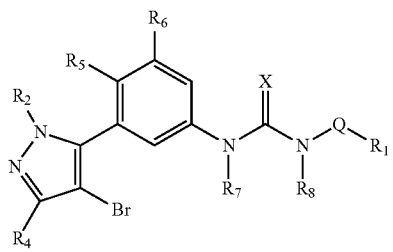

Ig wherein each variable in Formula IIg and Ig has the same meaning as described herein, supra and infra.

Some embodiments of the present invention pertain to compounds of Formula IIh or Ih as shown below:

IIh

-continued

Ih

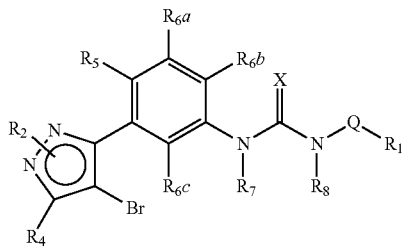

wherein each variable in Formula IIh and Ih has the same meaning as described herein, supra and infra.

Some embodiments of the present invention pertain to compounds wherein $R_4$ is selected from the group consisting of H, $C_{1-6}$ alkyl and $C_{1-6}$ haloalkyl.

In some embodiments, $R_4$ is selected from the group consisting of H, —$CH_3$, —$CH_2CH_3$, —$CH(CH_3)_2$, —$CH_2CH_2CH_3$, —$CH_2CH(CH_3)_2$, —$CH_2CH_2CH_2CH_3$, —$CF_3$, —$CHF_2$, —$CFH_2$, —$CF_2CF_3$ and —$CH_2CF_3$.

In some embodiments, $R_4$ is selected from the group consisting of H or —$CF_3$.

Some embodiments of the present invention can be represented by Formula IIi and IIj as shown below:

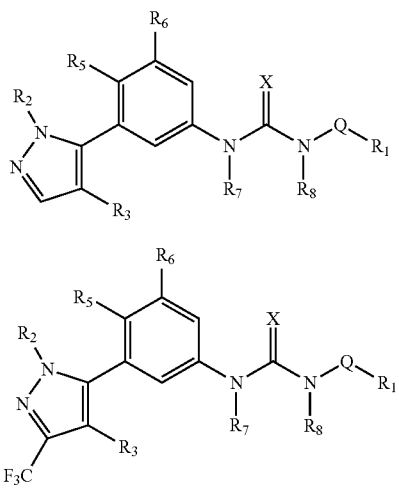

wherein each variable in Formula IIi and IIj has the same meaning as described herein, supra and infra.

Some embodiments of the present invention can be represented by Formula Ii and Ij as shown below:

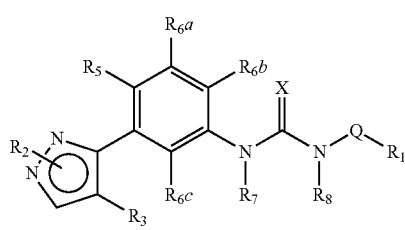

Ii

-continued

Ij

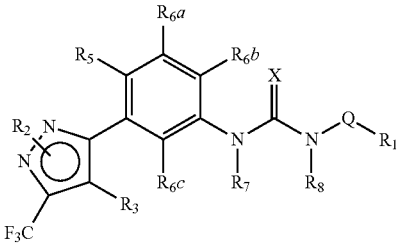

wherein each variable in Formula Ii and Ij has the same meaning as described herein, supra and infra.

Some embodiments of the present invention pertain to compounds wherein $R_5$ is selected from the group consisting of $C_{1-6}$ alkoxy, $C_{1-6}$ alkylthio, amino, $C_{1-6}$ alkylamino, $C_{2-8}$ dialkylamino, halogen, $C_{1-6}$ haloalkoxy, and hydroxyl, wherein said $C_{1-6}$ alkoxy group can be optionally substituted with 1 to 5 substituents selected independently from the group consisting of amino, $C_{1-6}$ alkylamino, $C_{2-8}$ dialkylamino, amino, carbo-$C_{1-6}$-alkoxy, carboxamide, carboxy, cyano, halogen, and phenyl, and wherein said amino and phenyl are each optionally substituted with 1 to 5 further substituents selected from the group consisting of halogen and carbo-$C_{1-6}$-alkoxy.

Some embodiments of the present invention pertain to compounds wherein $R_5$ is $C_{1-6}$ alkoxy, or hydroxyl, wherein said $C_{1-6}$ alkoxy group can be optionally substituted with 1 to 5 substituents selected independently from the group consisting of $C_{1-4}$ alkoxy, $C_{1-6}$ alkylamino, $C_{2-8}$ dialkylamino, alkylsulfinyl, $C_{1-4}$ alkylsulfonyl, $C_{1-4}$ alkylthio, amino, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and phenyl, and wherein said phenyl is optionally substituted with 1 to 5 halogen atoms.

Some embodiments of the present invention pertain to compounds wherein $R_5$ is selected from the group consisting of $C_{1-6}$ alkoxy, $C_{1-6}$ haloalkoxy, and hydroxyl, wherein said $C_{1-6}$ alkoxy group can be optionally substituted with 1 to 5 substituents selected independently from the group consisting of amino, $C_{2-8}$ dialkylamino, carboxy, and phenyl, and wherein said amino and phenyl are each optionally substituted with 1 to 5 further substituents selected from the group consisting of halogen and carbo-$C_{1-6}$-alkoxy.

In some embodiments, $R_5$ is $C_{1-6}$ alkoxy, or hydroxyl, and wherein said $C_{1-6}$ alkoxy group can be optionally substituted with 1 to 5 substituents selected independently from the group consisting of $C_{1-4}$ alkoxy, $C_{1-6}$ alkylamino, $C_{2-8}$ dialkylamino, amino, $C_{1-4}$ haloalkoxy, hydroxyl and phenyl, wherein said phenyl is optionally substituted with 1 to 5 halogen atoms.

Some embodiments of the present invention pertain to compounds wherein $R_5$ is selected from the group consisting of —$OCH_3$, —$OCH_2CH_3$, —$OCH(CH_3)_2$, —$OCF_3$, hydroxyl, benzyloxy, 4-chloro-benzyloxy, phenethyloxy, 2-dimethylamino-ethoxy [i.e., —$OCH_2CH_2N(CH_3)_2$], 3-dimethylamino-propoxy [i.e., —$OCH_2CH_2CH_2N(CH_3)_2$], carboxymethoxy [i.e., —$OCHC(O)OH$], and 2-tert-butoxycarbonylamino-ethoxy [i.e., —$OCH_2CH_2NHC(O)OC(CH_3)_3$].

In some embodiments, $R_5$ is selected from the group consisting of —$OCH_3$, —$OCH_2CH_3$, —$OCH(CH_3)_2$, —$OCH_2CH_2CH_3$, —$OCH_2CH(CH_3)_2$, hydroxyl, —$OCH_2CH_2OH$, —$OCH_2CH_2OCH_3$, —$OCH_2CH_2OCH_2CH_3$, —$OCH_2CH_2OCH(CH_3)_2$, —OCH$_2$CH$_2$OCH$_2$CH$_2$CH$_3$, —OCH$_2$CH$_2$OCH$_2$CH(CH$_3$)$_2$, —OCH$_2$CH$_2$NH$_2$, —OCH$_2$CH$_2$NHCH$_3$, —OCH$_2$CH$_2$N(CH$_3$)$_2$, —OCH$_2$CH$_2$OCF$_3$, —OCH$_2$CH$_2$OCHF$_2$, —OCH$_2$CH$_2$OCFH$_2$, —OCH$_2$C$_6$H$_5$, —OCH$_2$CH$_2$C$_6$H$_5$, —OCH$_2$C$_6$H$_5$-o-Cl, —OCH$_2$C$_6$H$_5$-m-Cl and —OCH$_2$C$_6$H$_5$-p-Cl.

In some embodiments, R$_5$ is selected from the group consisting of —OCH$_3$, —OCH$_2$CH$_3$, —OCH(CH$_3$)$_2$, hydroxyl, —OCH$_2$CH$_2$N(CH$_3$)$_2$, —OCH$_2$C$_6$H$_5$, —OCH$_2$CH$_2$C$_6$H$_5$ and —OCH$_2$C$_6$H$_5$-p-Cl.

In some embodiments, R$_5$ is —OCH$_3$.

Some embodiments of the present invention pertain to compounds wherein R$_6$ is selected from the group consisting of H, C$_{1-6}$ alkoxy, carbo-C$_{1-6}$-alkoxy, carboxamide, carboxy, cyano, halogen and hydroxyl.

In some embodiments, R$_6$ is H.

Some embodiments of the present invention pertain to compounds wherein R$_{6a}$, R$_{6b}$, and R$_{6c}$ are each independently selected from the group consisting of H, C$_{1-6}$ alkoxy, C$_{1-6}$ alkyl, amino, C$_{1-6}$ alkylamino, C$_{2-8}$ dialkylamino, cyano, halogen, C$_{1-6}$ haloalkoxy, C$_{1-6}$ haloalkyl, hydroxyl, and nitro.

Some embodiments of the present invention pertain to compounds wherein R$_{6a}$, R$_{6b}$, and R$_{6c}$ are each independently selected from the group consisting of H, —OCH$_3$, —CH$_3$, —N(CH$_3$)$_2$, cyano, —F, —Cl, —Br, —OCF$_3$, hydroxyl, and nitro.

Some embodiments of the present invention pertain to compounds wherein R$_{6a}$, R$_{6b}$, and R$_{6c}$ are each independently selected from the group consisting of H, C$_{1-6}$ alkoxy, carbo-C$_{1-6}$-alkoxy, carboxamide, carboxy, cyano, halogen and hydroxyl.

Some embodiments of the present invention pertain to compounds wherein R$_{6a}$, R$_{6b}$, and R$_{6c}$ are all H.

Some embodiments of the present invention pertain to compounds wherein R$_5$ is C$_{1-6}$ alkoxy and R$_{6a}$, R$_{6b}$, and R$_{6c}$ are all H.

In some embodiments, R$_5$ is —OCH$_3$.

Some embodiments of the present invention pertain to compounds represented by Formula IIk and Ik as shown below:

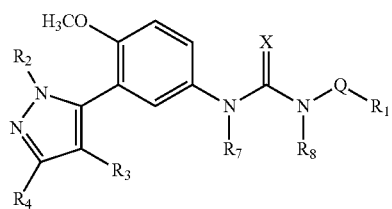

IIk

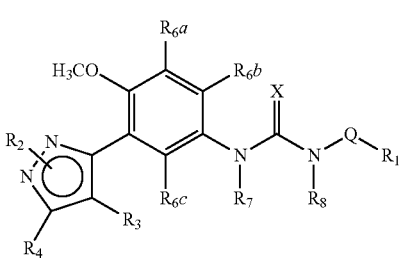

Ik wherein each variable in Formula IIK has the same meaning as described herein, supra and infra. In some embodiments, compounds of the present invention have Formula IIK and Q is a bond.

Some embodiments of the present invention pertain to compounds represented by Formula IK wherein each variable in Formula IK has the same meaning as described herein, supra and infra. In some embodiments, compounds of the present invention have Formula IK and Q is a bond.

Some embodiments of the present invention pertain to compounds wherein R$_7$ is H or C$_{1-8}$ alkyl.

In some embodiments, R is selected from the group consisting of H, —CH$_3$, —CH$_2$CH$_3$, —CH(CH$_3$)$_2$, —CH$_2$CH$_2$CH$_3$, —CH$_2$CH(CH$_3$)$_2$ and —CH$_2$CH$_2$CH$_2$CH$_3$.

In some embodiments, R$_7$ is H.

Some embodiments of the present invention pertain to compounds wherein R$_8$ is H or C$_{1-8}$ alkyl.

In some embodiments, R$_8$ is selected from the group consisting of H, —CH$_3$, —CH$_2$CH$_3$, —CH(CH$_3$)$_2$, —CH$_2$CH$_2$CH$_3$, —CH$_2$CH(CH$_3$)$_2$ and —CH$_2$CH$_2$CH$_2$CH$_3$.

In some embodiments, R$_8$ is H.

Some embodiments of the present invention pertain to compounds wherein both R$_7$ and R$_8$ are H.

Some embodiments of the present invention pertain to compounds represented by Formula IIm and Im as shown below:

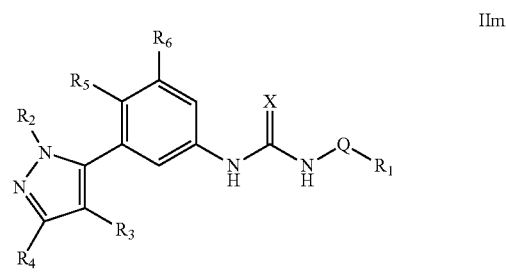

IIm

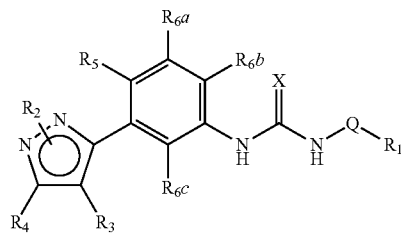

Im wherein each variable in Formula IIm and Im has the same meaning as described herein, supra and infra.

Some embodiments of the present invention pertain to compounds wherein X is O (i.e., oxygen).

Some embodiments of the present invention pertain to compounds wherein X is S (i.e., sulfur).

Some embodiments of the present invention pertain to compounds wherein Q is C$_{1-3}$ alkylene optionally substituted with C$_{1-3}$ alkyl, C$_{1-3}$ haloalkyl, halogen and oxo.

Some embodiments of the present invention pertain to compounds wherein Q is a C$_{1-3}$ alkylene optionally substituted with oxo. As used herein, oxo refers to a double bonded oxygen. In some embodiments, Q is —C(O)— (i.e., a carbonyl).

In some embodiments, Q is —CH$_2$—.

Some embodiments of the present invention pertain to compounds wherein Q is a bond.

Some embodiments of the present invention pertain to compounds represented by Formula IIn and In as shown below:

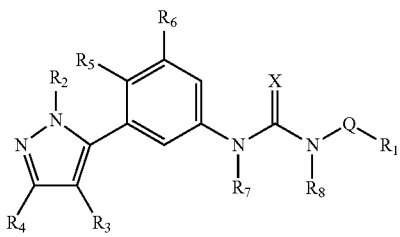

IIn

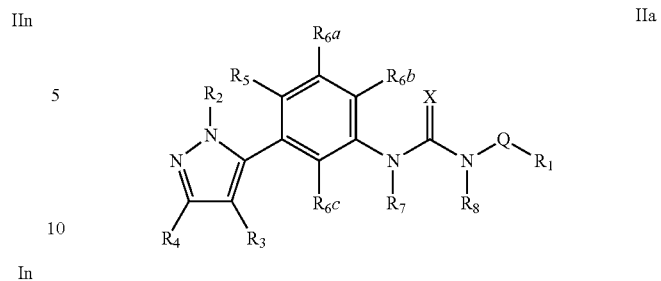

IIa

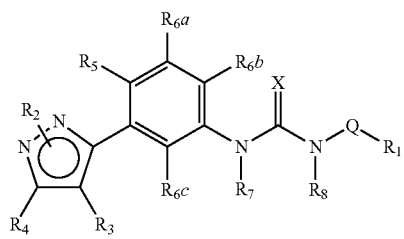

In wherein each variable in Formula IIn and In has the same meaning as described herein, supra and infra.

In some embodiments, R$_1$ is phenyl and can be represented by Formula XIIIa as shown below:

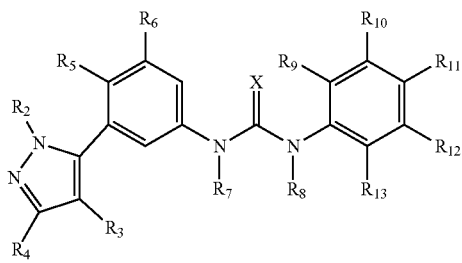

XIIIa wherein each variable in Formula XIIIa has the same meaning as described herein, supra and infra. In some embodiments, R$_7$ and R$_8$ are both H. In some embodiments, X is O (i.e., oxygen).

In some embodiments, R$_1$ is phenyl and can be represented by Formula XIVa as shown below:

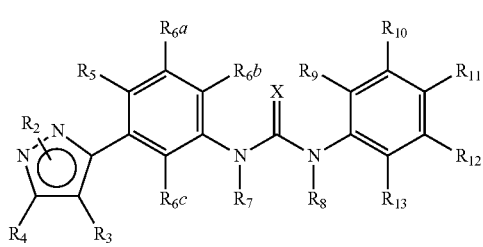

XIVa wherein each variable in Formula XIVa has the same meaning as described herein, supra and infra. In some embodiments, R$_7$ and R$_8$ are both H. In some embodiments, X is O (i.e., oxygen).

Some embodiments of the present invention pertain to compounds of Formula (IIa):

wherein:

R$_1$ is phenyl or naphthyl optionally substituted with R$_9$, R$_{10}$, R$_{11}$, R$_{12}$, R$_{13}$, R$_{14}$, and R$_{15}$ each selected independently from the group consisting of C$_{1-6}$ acyl, C$_{1-6}$ alkoxy, C$_{1-6}$ alkyl, amino, C$_{1-6}$ alkylamino, C$_{2-8}$ dialkylamino, C$_{1-6}$ alkylimino, cyano, halogen, C$_{1-6}$ haloalkoxy, C$_{1-6}$ haloalkyl, heterocyclic, hydroxyl, nitro, and phenyl, or two adjacent R$_9$, R$_{10}$, R$_{11}$, R$_{12}$, R$_{13}$, R$_{14}$, and R$_{15}$ together with the atoms to which they are attached form a C$_{5-7}$ cycloalkyl group or heterocyclic group each optionally substituted with F; and wherein said C$_{1-6}$ alkyl, C$_{1-6}$ alkylimino, and heterocyclic are each optionally substituted with 1 to 5 substituents selected independently from the group consisting of C$_{1-6}$ alkyl, amino, C$_{1-6}$ alkylamino, C$_{2-8}$ dialkylamino, and hydroxyl;

R$_2$ is C$_{1-6}$ alkyl;

R$_3$ is H or halogen;

R$_4$ is selected from the group consisting of H, C$_{1-6}$ alkyl and C$_{1-6}$ haloalkyl;

R$_5$ is selected from the group consisting of C$_{1-6}$ alkoxy, C$_{1-6}$ haloalkoxy, and hydroxyl, wherein said C$_{1-6}$ alkoxy group can be optionally substituted with 1 to 5 substituents selected independently from the group consisting of amino, C$_{2-8}$ dialkylamino, carboxy, and phenyl, and wherein said amino and phenyl are each optionally substituted with 1 to 5 further substituents selected from the group consisting of halogen and carbo-C$_{1-6}$-alkoxy;

R$_{6a}$, R$_{6b}$, and R$_{6c}$ are each independently selected from the group consisting of H, C$_{1-6}$ alkoxy, C$_{1-6}$ alkyl, amino, C$_{1-6}$ alkylamino, C$_{2-8}$ dialkylamino, cyano, halogen, C$_{1-6}$ haloalkoxy, C$_{1-6}$ haloalkyl, hydroxyl, and nitro R$_7$ and R$_8$ are both H;

X is O; and

Q is a bond.

Some embodiments of the present invention pertain to compounds of Formula (IIa):

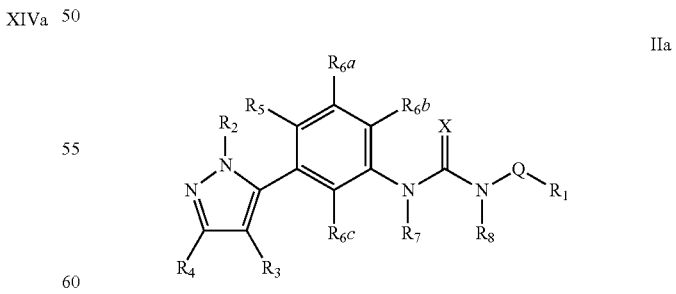

IIa wherein:

R$_1$ is phenyl or naphthyl optionally substituted with R$_9$, R$_{10}$, R$_{11}$, R$_{12}$, R$_{13}$, R$_{14}$, and R$_{15}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino, (3-dimethylamino-propyl)- methyl-amino, —C(=NOH)CH₃, cyano, —F, —Cl, —Br, —OCF₃, —CF₃, 4-methyl-piperazin-1-yl, morpholin-4-yl, 4-methyl-piperidin-1-yl, hydroxyl, nitro, and phenyl;
$R_2$ is —CH₃ or —CH(CH₃)₂;
$R_3$ is H, F, Cl, or Br;
$R_4$ is —H, or —CF₃;
$R_5$ is selected from the group consisting of —OCH₃, —OCH₂CH₃, —OCH(CH₃)₂, —OCF₃, hydroxyl, benzyloxy, 4-chloro-benzyloxy, phenethyloxy, 2-dimethylamino-ethoxy, 3-dimethylamino-propoxy, carboxymethoxy, and 2-tert-butoxycarbonylamino-ethoxy;
$R_{6a}$, $R_{6b}$, and $R_{6c}$ are each independently selected from the group consisting of H, —OCH₃, —CH₃, —N(CH₃)₂, cyano, —F, —Cl, —Br, —OCF₃, hydroxyl, and nitro;
$R_7$ and $R_8$ are both H;
X is O; and
Q is a bond.

Some embodiments of the present invention pertain to compounds of Formula (IIa):

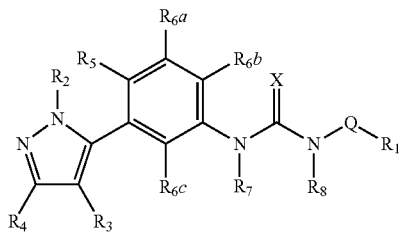

IIa wherein:
$R_1$ is phenyl optionally substituted with $R_9$, $R_{10}$, $R_{11}$, $R_{12}$, and $R_{13}$ each selected independently from the group consisting of —C(O)CH₃, —OCH₃, —CH₃, —CH(CH₃)₂, —CH(OH)CH₃, —N(CH₃)₂, (2-dimethylamino-ethyl)-methyl-amino, (3-dimethyl amino-propyl)-methyl-amino, —C(=NOH)CH₃, cyano, —F, —Cl, —Br, —OCF₃, —CF₃, 4-methyl-piperazin-1-yl, morpholin-4-yl, 4-methyl-piperidin-1-yl, hydroxyl, nitro, and phenyl;
$R_2$ is —CH₃ or —CH(CH₃)₂;
$R_3$ is —H, —F, —Cl, or —Br;
$R_4$ is —H, or —CF₃;

$R_5$ is selected from the group consisting of —OCH₃, —OCH₂CH₃, —OCH(CH₃)₂, —OCF₃, hydroxyl, benzyloxy, 4-chloro-benzyloxy, phenethyloxy, 2-dimethylamino-ethoxy, 3-dimethylamino-propoxy, carboxymethoxy, and 2-tert-butoxycarbonylamino-ethoxy;
$R_{6a}$, $R_{6b}$, and $R_{6c}$ are each independently selected from the group consisting of —H, —OCH₃, —CH₃, —N(CH₃)₂, cyano, F, Cl, Br, —OCF₃, hydroxyl, and nitro;
$R_7$ and $R_8$ are both H;
X is O; and
Q is a bond.

Some embodiments of the present invention pertain to compounds of Formula (IIa):

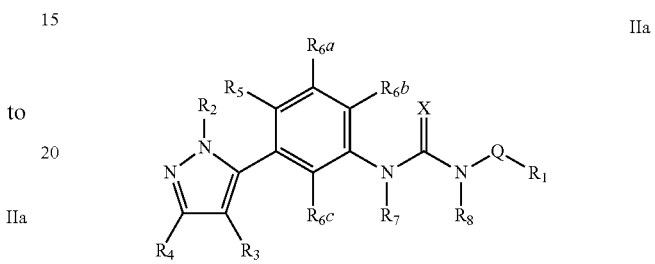

IIa wherein:
$R_1$ is phenyl optionally substituted with $R_9$, $R_{10}$, $R_{11}$, $R_{12}$, and $R_{13}$ each selected independently from the group consisting of —C(O)CH₃, —OCH₃, —CH₃, —CH(CH₃)₂, —N(CH₃)₂, cyano, —F, —Cl, —Br, —OCF₃, —CF₃, hydroxyl, and nitro;
$R_2$ is —CH₃;
$R_3$ is —H, —F, —Cl, or —Br;
$R_4$ is —H;
$R_5$ is selected from the group consisting of —OCH₃, —OCH₂CH₃, —OCH(CH₃)₂, —OCF₃, hydroxyl, benzyloxy, 4-chloro-benzyloxy, phenethyloxy, 2-dimethylamino-ethoxy, 3-dimethylamino-propoxy, carboxymethoxy, and 2-tert-butoxycarbonylamino-ethoxy;
$R_{6a}$, $R_{6b}$, and $R_{6c}$ are each —H;
$R_7$ and $R_8$ are both —H;
X is O; and
Q is a bond.

Some embodiments of the present invention include compounds illustrated in Table 3 as shown below:

TABLE 3

| Cmpd # | Structure | Chemical Name |
|---|---|---|
| 1 | 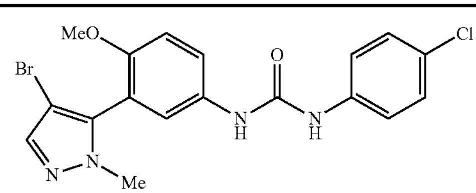 | 1-[3-(4-Bromo-2-methyl-2H-pyrazol-3-yl)-4-methoxy-phenyl]-3-(4-chloro-phenyl)-urea |
| 2 | 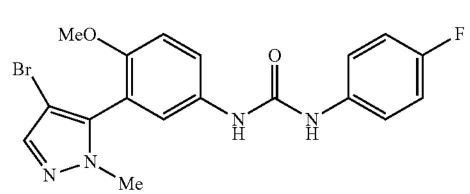 [SMILES: COc1ccc(NC(=O)Nc2ccc(F)cc2)cc1-c1c(Br)cnn1C] | 1-[3-(4-Bromo-2-methyl-2H-pyrazol-3-yl)-4-methoxy-phenyl]-3-(4-fluoro-phenyl)-urea |

TABLE 3-continued

| Cmpd # | Structure | Chemical Name |
|---|---|---|
| 3 | 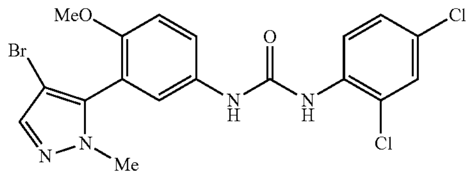 | 1-[3-(4-Bromo-2-methyl-2H-pyrazol-3-yl)-4-methoxy-phenyl]-3-(2,4-dichloro-phenyl)-urea |
| 4 | 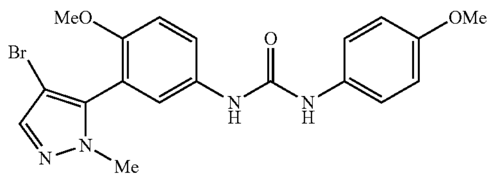 [SMILES: COc1ccc(NC(=O)Nc2ccc(OC)c(-c3c(Br)cnn3C)c2)cc1] | 1-[3-(4-Bromo-2-methyl-2H-pyrazol-3-yl)-4-methoxy-phenyl]-3-(4-methoxy-phenyl)-urea |
| 5 | 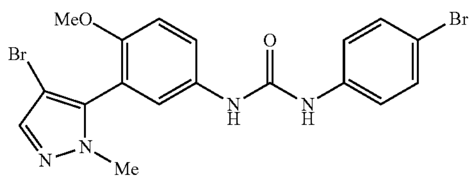 | 1-[3-(4-Bromo-2-methyl-2H-pyrazol-3-yl)-4-methoxy-phenyl]-3-(4-bromo-phenyl)-urea |
| 6 | 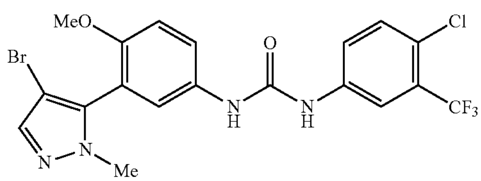 [SMILES: COc1ccc(NC(=O)Nc2ccc(Cl)c(C(F)(F)F)c2)cc1-c1c(Br)cnn1C] | 1-[3-(4-Bromo-2-methyl-2H-pyrazol-3-yl)-4-methoxy-phenyl]-3-(4-chloro-3-trifluoromethyl-phenyl)-urea |
| 7 | 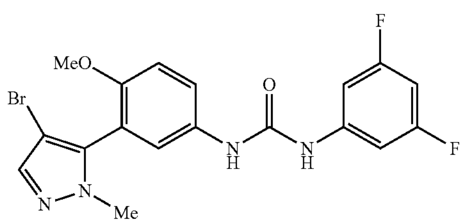 [SMILES: COc1ccc(NC(=O)Nc2cc(F)cc(F)c2)cc1-c1c(Br)cnn1C] | 1-[3-(4-Bromo-2-methyl-2H-pyrazol-3-yl)-4-methoxy-phenyl]-3-(3,5-difluoro-phenyl)-urea |
| 8 | 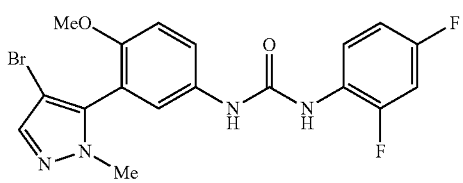 | 1-[3-(4-Bromo-2-methyl-2H-pyrazol-3-yl)-4-methoxy-phenyl]-3-(2,4-difluoro-phenyl)-urea |
| 9 | 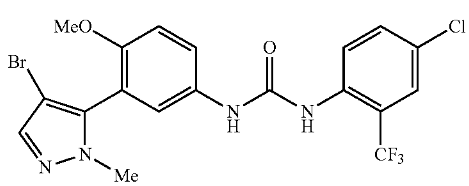 | 1-[3-(4-Bromo-2-methyl-2H-pyrazol-3-yl)-4-methoxy-phenyl]-3-4-chloro-2-trifluoromethyl-phenyl)-urea |
| 10 | 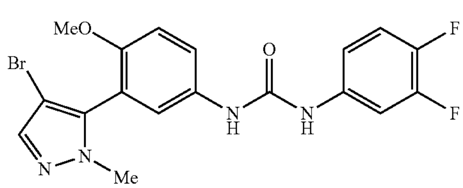 [SMILES: COc1ccc(NC(=O)Nc2ccc(F)c(F)c2)cc1-c1c(Br)cnn1C] | 1-[3-(4-Bromo-2-methyl-2H-pyrazol-3-yl)-4-methoxy-phenyl]-3-(3,4-difluoro-phenyl)-urea |

TABLE 3-continued

| Cmpd # | Structure | Chemical Name |
|---|---|---|
| 11 | 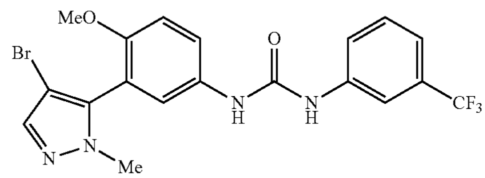 [SMILES: COc1ccc(NC(=O)Nc2cccc(C(F)(F)F)c2)cc1-c1c(Br)cnn1C] | 1-[3-(4-Bromo-2-methyl-2H-pyrazol-3-yl)-4-methoxy-phenyl]-3-(3-trifluoromethyl-phenyl)-urea |
| 12 | 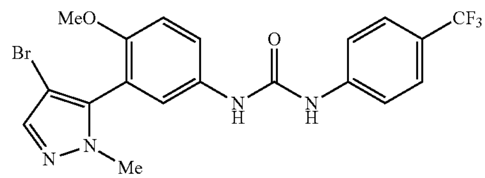 [SMILES: COc1ccc(NC(=O)Nc2ccc(C(F)(F)F)cc2)cc1-c1c(Br)cnn1C] | 1-[3-(4-Bromo-2-methyl-2H-pyrazol-3-yl)-4-methoxy-phenyl]-3-(4-trifluoromethyl-phenyl)-urea |
| 13 | 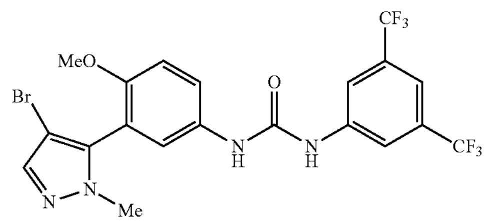 [SMILES: COc1ccc(NC(=O)Nc2cc(C(F)(F)F)cc(C(F)(F)F)c2)cc1-c1c(Br)cnn1C] | 1-(3,5-Bis-trifluoromethyl-phenyl)-3-[3-(4-bromo-2-methyl-2H-pyrazol-3-yl)-4-methoxy-phenyl]-urea |
| 14 | 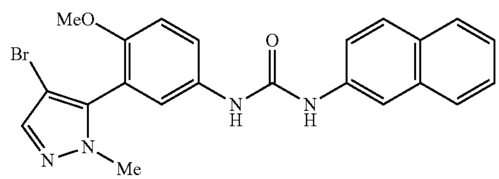 [SMILES: COc1ccc(NC(=O)Nc2ccc3ccccc3c2)cc1-c1c(Br)cnn1C] | 1-[3-(4-Bromo-2-methyl-2H-pyrazol-3-yl)-4-methoxy-phenyl]-3-naphthalen-2-yl-urea |
| 15 | 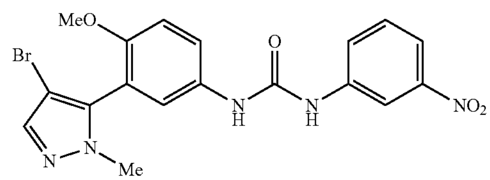 [SMILES: COc1ccc(NC(=O)Nc2cccc([N+](=O)[O-])c2)cc1-c1c(Br)cnn1C] | 1-[3-(4-Bromo-2-methyl-2H-pyrazol-3-yl)-4-methoxy-phenyl]-3-(3-nitro-phenyl)-urea |
| 16 | 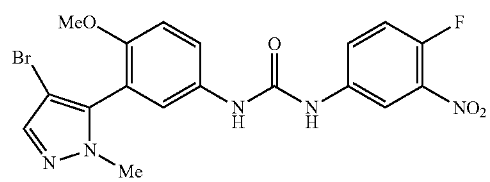 [SMILES: COc1ccc(NC(=O)Nc2ccc(F)c([N+](=O)[O-])c2)cc1-c1c(Br)cnn1C] | 1-[3-(4-Bromo-2-methyl-2H-pyrazol-3-yl)-4-methoxy-phenyl]-3-(4-fluoro-3-nitro-phenyl)-urea |
| 17 | 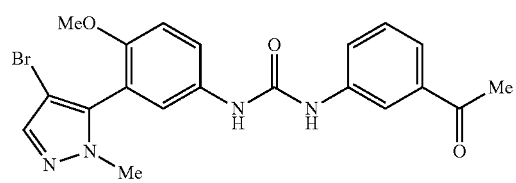 | 1-(3-Acetyl-phenyl)-3-[3-(4-bromo-2-methyl-2H-pyrazol-3-yl)-4-methoxy-phenyl]-urea |
| 18 | 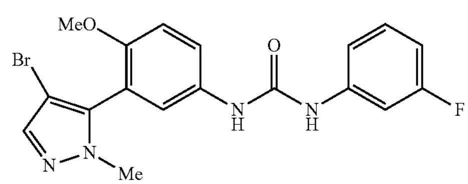 | 1-[3-(4-Bromo-2-methyl-2H-pyrazol-3-yl)-4-methoxy-phenyl]-3-(3-fluoro-phenyl)-urea |

TABLE 3-continued

| Cmpd # | Structure | Chemical Name |
|---|---|---|
| 19 | 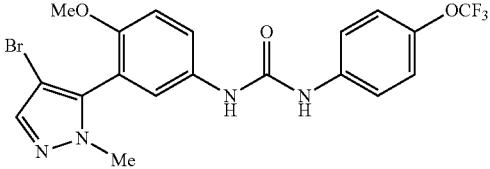 [SMILES: COc1ccc(NC(=O)Nc2ccc(OC(F)(F)F)cc2)cc1-c1c(Br)cnn1C] | 1-[3-(4-Bromo-2-methyl-2H-pyrazol-3-yl)-4-methoxy-phenyl]-3-(4-trifluoromethoxy-phenyl)-urea |
| 20 | 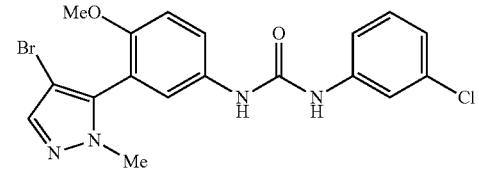 [SMILES: COc1ccc(NC(=O)Nc2cccc(Cl)c2)cc1-c1c(Br)cnn1C] | 1-[3-(4-Bromo-2-methyl-2H-pyrazol-3-yl)-4-methoxy-phenyl]-3-(3-chloro-phenyl)-urea |
| 21 | 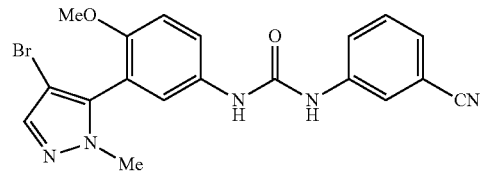 | 1-[3-(4-Bromo-2-methyl-2H-pyrazol-3-yl)-4-methoxy-phenyl]-3-(3-cyano-phenyl)-urea |
| 22 | 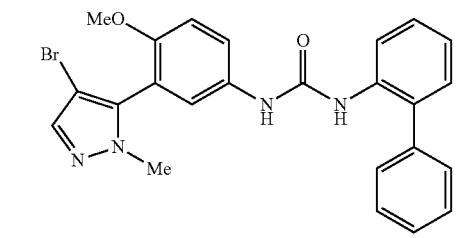 [SMILES: COc1ccc(NC(=O)Nc2ccccc2-c2ccccc2)cc1-c1c(Br)cnn1C] | 1-Biphenyl-2-yl-3-[3-(4-bromo-2-methyl-2H-pyrazol-3-yl)-4-methoxy-phenyl]-urea |
| 23 | 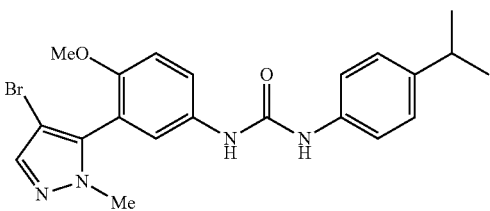 [SMILES: COc1ccc(NC(=O)Nc2ccc(C(C)C)cc2)cc1-c1c(Br)cnn1C] | 1-[3-(4-Bromo-2-methyl-2H-pyrazol-3-yl)-4-methoxy-phenyl]-3-(4-isopropyl-phenyl)-urea |
| 24 | 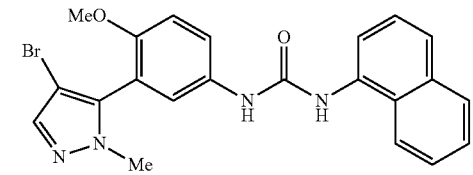 [SMILES: COc1ccc(NC(=O)Nc2cccc3ccccc23)cc1-c1c(Br)cnn1C] | 1-[3-(4-Bromo-2-methyl-2H-pyrazol-3-yl)-4-methoxy-phenyl]-3-naphthalen-1-yl-urea |
| 25 | 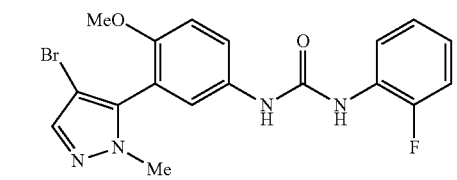 | 1-[3-(4-Bromo-2-methyl-2H-pyrazol-3-yl)-4-methoxy-phenyl]-3-(2-fluoro-phenyl)-urea |
| 26 | 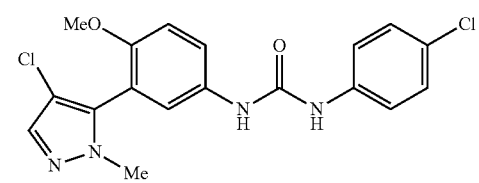 [SMILES: COc1ccc(NC(=O)Nc2ccc(Cl)cc2)cc1-c1c(Cl)cnn1C] | 1-[3-(4-Chloro-2-methyl-2H-pyrazol-3-yl)-4-methoxy-phenyl]-3-(4-chloro-phenyl)-urea |

TABLE 3-continued

| Cmpd # | Structure | Chemical Name |
|---|---|---|
| 27 | 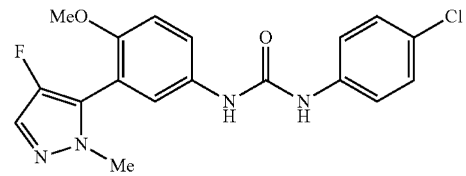 [SMILES: COc1ccc(NC(=O)Nc2ccc(Cl)cc2)cc1-c1c(F)cnn1C] | 1-(4-Chloro-phenyl)-3-[3-(4-fluoro-2-methyl-2H-pyrazol-3-yl)-4-methoxy-phenyl]-urea |
| 28 | 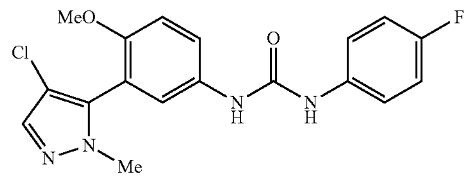 [SMILES: COc1ccc(NC(=O)Nc2ccc(F)cc2)cc1-c1c(Cl)cnn1C] | 1-[3-(4-Chloro-2-methyl-2H-pyrazol-3-yl)-4-methoxy-phenyl]-3-(4-fluoro-phenyl)-urea |
| 29 | 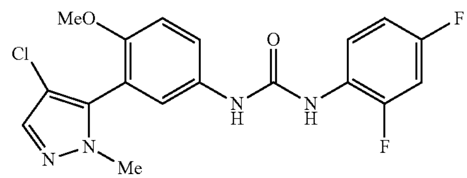 [SMILES: COc1ccc(NC(=O)Nc2ccc(F)cc2F)cc1-c1c(Cl)cnn1C] | 1-[3-(4-Chloro-2-methyl-2H-pyrazol-3-yl)-4-methoxy-phenyl]-3-(2,4-difluoro-phenyl)-urea |
| 30 | 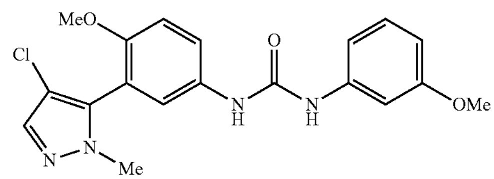 [SMILES: COc1cccc(NC(=O)Nc2ccc(OC)c(-c3c(Cl)cnn3C)c2)c1] | 1-[3-(4-Chloro-2-methyl-2H-pyrazol-3-yl)-4-methoxy-phenyl]-3-(3-methoxy-phenyl)-urea |
| 31 | 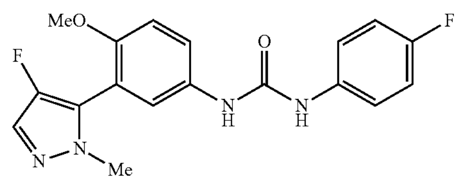 [SMILES: COc1ccc(NC(=O)Nc2ccc(F)cc2)cc1-c1c(F)cnn1C] | 1-[3-(4-Fluoro-2-methyl-2H-pyrazol-3-yl)-4-methoxy-phenyl]-3-(4-fluoro-phenyl)-urea |
| 32 | 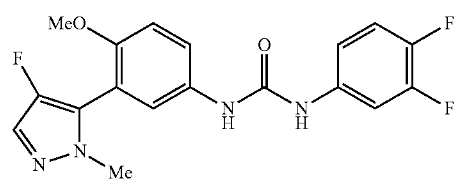 [SMILES: COc1ccc(NC(=O)Nc2ccc(F)c(F)c2)cc1-c1c(F)cnn1C] | 1-(3,4-Difluoro-phenyl)-3-[3-(4-fluoro-2-methyl-2H-pyrazol-3-yl)-4-methoxy-phenyl]-urea |
| 33 | 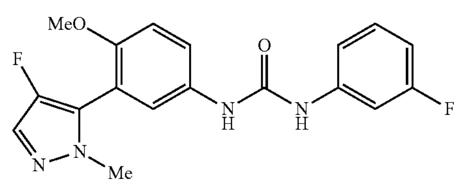 [SMILES: COc1ccc(NC(=O)Nc2cccc(F)c2)cc1-c1c(F)cnn1C] | 1-[3-(4-Fluoro-2-methyl-2H-pyrazol-3-yl)-4-methoxy-phenyl]-3-(3-fluoro-phenyl)-urea |
| 34 | 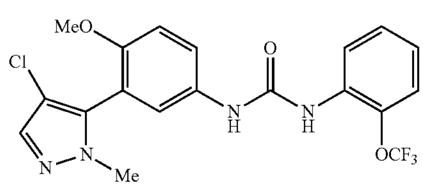 [SMILES: COc1ccc(NC(=O)Nc2ccccc2OC(F)(F)F)cc1-c1c(Cl)cnn1C] | 1-[3-(4-Chloro-2-methyl-2H-pyrazol-3-yl)-4-methoxy-phenyl]-3-(2-trifluoromethoxy-phenyl)-urea |

TABLE 3-continued

| Cmpd # | Structure | Chemical Name |
|---|---|---|
| 35 | 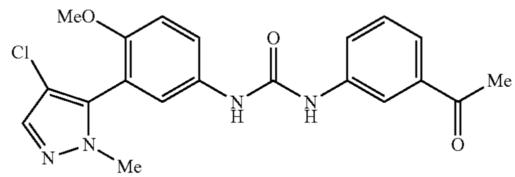 [SMILES: COc1ccc(NC(=O)Nc2cccc(C(C)=O)c2)cc1-c1c(Cl)cnn1C] | 1-(3-Acetyl-phenyl)-3-[3-(4-chloro-2-methyl-2H-pyrazol-3-yl)-4-methoxy-phenyl]-urea |
| 36 | 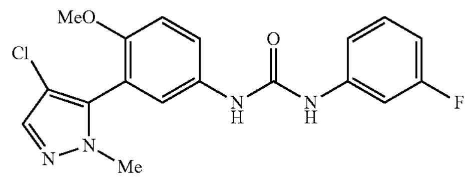 [SMILES: COc1ccc(NC(=O)Nc2cccc(F)c2)cc1-c1c(Cl)cnn1C] | 1-[3-(4-Chloro-2-methyl-2H-pyrazol-3-yl)-4-methoxy-phenyl]-3-(3-fluoro-phenyl)-urea |
| 37 | 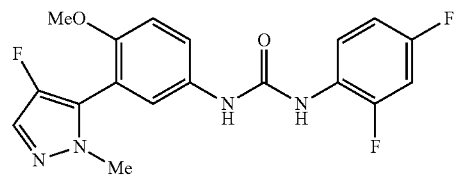 [SMILES: COc1ccc(NC(=O)Nc2ccc(F)cc2F)cc1-c1c(F)cnn1C] | 1-(2,4-Difluoro-phenyl)-3-[3-(4-fluoro-2-methyl-2H-pyrazol-3-yl)-4-methoxy-phenyl]-urea |
| 38 | 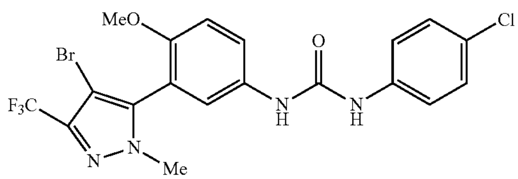 [SMILES: COc1ccc(NC(=O)Nc2ccc(Cl)cc2)cc1-c1c(Br)c(C(F)(F)F)nn1C] | 1-[3-(4-Bromo-2-methyl-5-trifluoromethyl-2H-pyrazol-3-yl)-4-methoxy-phenyl]-3-(4-chloro-phenyl)-urea |
| 39 | 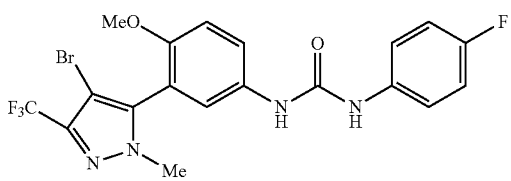 [SMILES: COc1ccc(NC(=O)Nc2ccc(F)cc2)cc1-c1c(Br)c(C(F)(F)F)nn1C] | 1-[3-(4-Bromo-2-methyl-5-trifluoromethyl-2H-pyrazol-3-yl)-4-methoxy-phenyl]-3-(4-fluoro-phenyl)-urea |
| 40 | 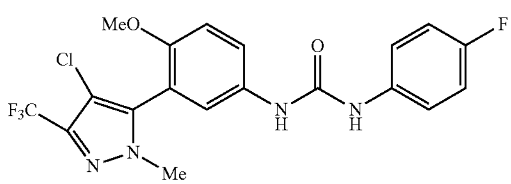 [SMILES: COc1ccc(NC(=O)Nc2ccc(F)cc2)cc1-c1c(Cl)c(C(F)(F)F)nn1C] | 1-[3-(4-Chloro-2-methyl-5-trifluoromethyl-2H-pyrazol-3-yl)-4-methoxy-phenyl]-3-(4-fluoro-phenyl)-urea |
| 41 | 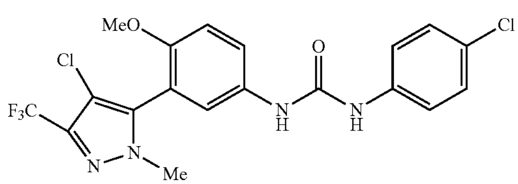 [SMILES: COc1ccc(NC(=O)Nc2ccc(Cl)cc2)cc1-c1c(Cl)c(C(F)(F)F)nn1C] | 1-[3-(4-Chloro-2-methyl-5-trifluoromethyl-2H-pyrazol-3-yl)-4-methoxy-phenyl]-3-(4-chloro-phenyl)-urea |
| 42 | 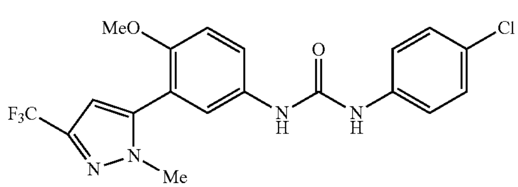 [SMILES: COc1ccc(NC(=O)Nc2ccc(Cl)cc2)cc1-c1cc(C(F)(F)F)nn1C] | 1-(4-Chloro-phenyl)-3-[4-methoxy-3-(2-methyl-5-trifluoromethyl-2H-pyrazol-3-yl)-phenyl]-urea |

TABLE 3-continued

| Cmpd # | Structure | Chemical Name |
| --- | --- | --- |
| 43 | 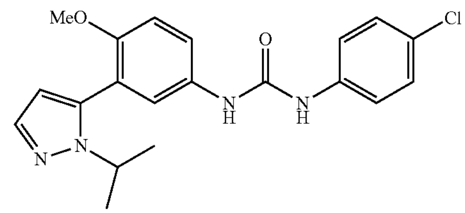 [SMILES: COc1ccc(NC(=O)Nc2ccc(Cl)cc2)cc1-c1ccnn1C(C)C] | 1-(4-Chloro-phenyl)-3-[3-(2-isopropyl-2H-pyrazol-3-yl)-4-methoxy-phenyl]-urea |
| 44 | 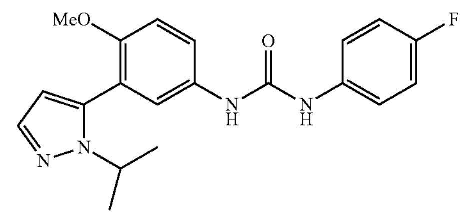 [SMILES: COc1ccc(NC(=O)Nc2ccc(F)cc2)cc1-c1ccnn1C(C)C] | 1-(4-Fluoro-phenyl)-3-[3-(2-isopropyl-2H-pyrazol-3-yl)-4-methoxy-phenyl]-urea |
| 45 | 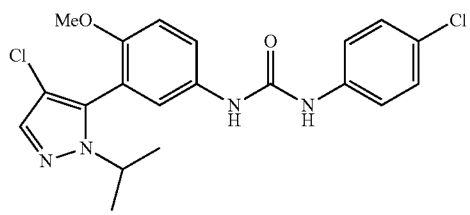 [SMILES: COc1ccc(NC(=O)Nc2ccc(Cl)cc2)cc1-c1c(Cl)cnn1C(C)C] | 1-[3-(4-Chloro-2-isopropyl-2H-pyrazol-3-yl)-4-methoxy-phenyl]-3-(4-chloro-phenyl)-urea |
| 46 | 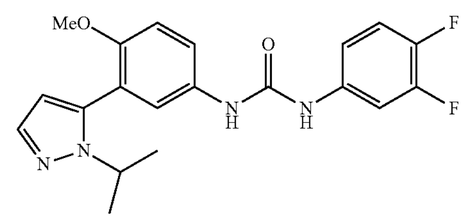 [SMILES: COc1ccc(NC(=O)Nc2ccc(F)c(F)c2)cc1-c1ccnn1C(C)C] | 1-(3,4-Difluoro-phenyl)-3-[3-(2-isopropyl-2H-pyrazol-3-yl)-4-methoxy-phenyl]-urea |
| 47 | 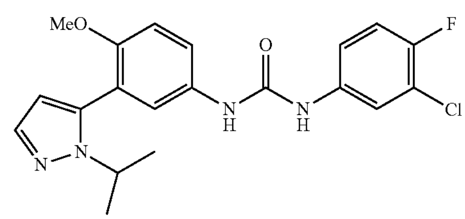 [SMILES: COc1ccc(NC(=O)Nc2ccc(F)c(Cl)c2)cc1-c1ccnn1C(C)C] | 1-(3-Chloro-4-fluoro-phenyl)-3-[3-(2-isopropyl-2H-pyrazol-3-yl)-4-methoxy-phenyl]-urea |
| 48 | 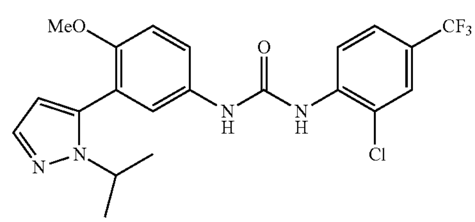 [SMILES: COc1ccc(NC(=O)Nc2ccc(C(F)(F)F)cc2Cl)cc1-c1ccnn1C(C)C] | 1-(2-Chloro-4-trifluoromethyl-phenyl)-3-[3-(2-isopropyl-2H-pyrazol-3-yl)-4-methoxy-phenyl]-urea |
| 49 | 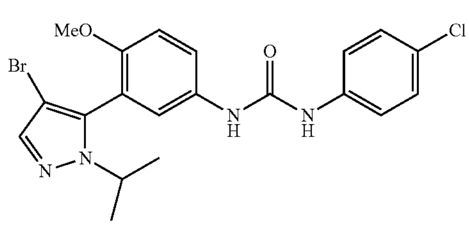 | 1-[3-(4-Bromo-2-isopropyl-2H-pyrazol-3-yl)-4-methoxy-phenyl]-3-(4-chloro-phenyl)-urea |

TABLE 3-continued

| Cmpd # | Structure | Chemical Name |
|---|---|---|
| 50 | 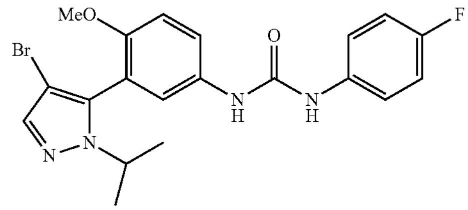 [SMILES: COc1ccc(NC(=O)Nc2ccc(F)cc2)cc1-c1c(Cl)cnn1C(C)C] | 1-[3-(4-Bromo-2-isopropyl-2H-pyrazol-3-yl)-4-methoxy-phenyl]-3-(4-fluoro-phenyl)-urea |
| 51 | 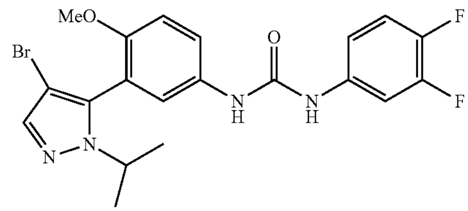 [SMILES: COc1ccc(NC(=O)Nc2ccc(F)c(F)c2)cc1-c1c(Cl)cnn1C(C)C] | 1-[3-(4-Bromo-2-isopropyl-2H-pyrazol-3-yl)-4-methoxy-phenyl]-3-(3,4-difluoro-phenyl)-urea |
| 52 | 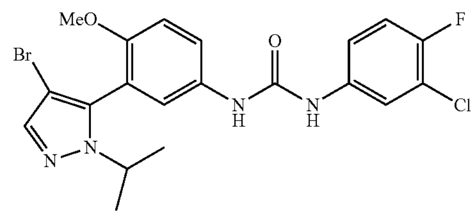 | 1-[3-(4-Bromo-2-isopropyl-2H-pyrazol-3-yl)-4-methoxy-phenyl]-3-(3-chloro-4-fluoro-phenyl)-urea |
| 53 | 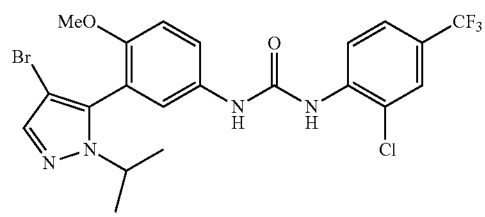 | 1-[3-(4-Bromo-2-isopropyl-2H-pyrazol-3-yl)-4-methoxy-phenyl]-3-(2-Chloro-4-trifluoromethyl-phenyl)-urea |
| 54 | 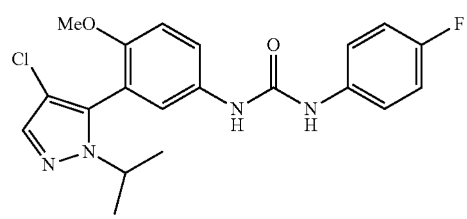 | 1-[3-(4-Chloro-2-isopropyl-2H-pyrazol-3-yl)-4-methoxy-phenyl]-3-(4-fluoro-phenyl)-urea |
| 55 | 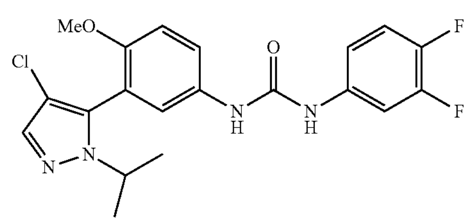 | 1-[3-(4-Chloro-2-isopropyl-2H-pyrazol-3-yl)-4-methoxy-phenyl]-3-(3,4-difluoro-phenyl)-urea |
| 56 | 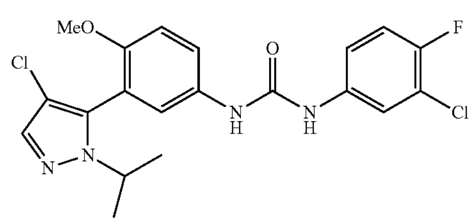 [SMILES: COc1ccc(NC(=O)Nc2ccc(F)c(Cl)c2)cc1-c1c(Cl)cnn1C(C)C] | 1-(3-Chloro-4-fluoro-phenyl)-3-[3-(4-Chloro-2-isopropyl-2H-pyrazol-3-yl)-4-methoxy-phenyl]-urea |

TABLE 3-continued

| Cmpd # | Structure | Chemical Name |
|---|---|---|
| 57 | 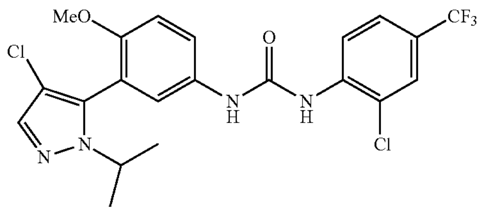 [SMILES: COc1ccc(NC(=O)Nc2ccc(C(F)(F)F)cc2Cl)cc1-c1c(Cl)cnn1C(C)C] | 1-[3-(4-Chloro-2-isopropyl-2H-pyrazol-3-yl)-4-methoxy-phenyl]-3-(2-Chloro-4-trifluoromethyl-phenyl)-urea |
| 58 | 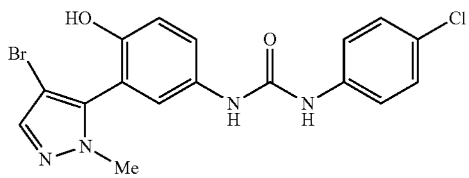 | 1-[3-(4-Bromo-2-methyl-2H-pyrazol-3-yl)-4-hydroxy-phenyl]-3-(4-chloro-phenyl)-urea |
| 59 | 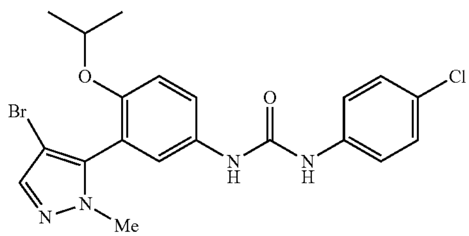 [SMILES: CC(C)Oc1ccc(NC(=O)Nc2ccc(Cl)cc2)cc1-c1c(Br)cnn1C] | 1-[3-(4-Bromo-2-methyl-2H-pyrazol-3-yl)-4-isopropoxy-phenyl]-3-(4-chloro-phenyl)-urea |
| 60 | 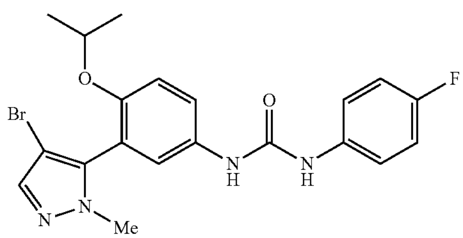 [SMILES: CC(C)Oc1ccc(NC(=O)Nc2ccc(F)cc2)cc1-c1c(Br)cnn1C] | 1-[3-(4-Bromo-2-methyl-2H-pyrazol-3-yl)-4-isopropoxy-phenyl]-3-(4-fluoro-phenyl)-urea |
| 61 | 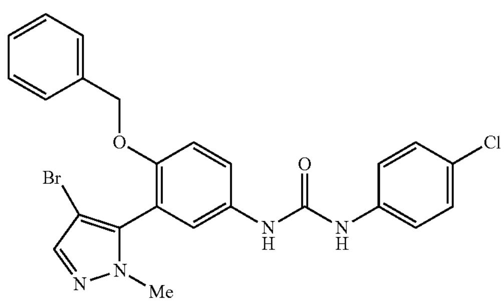 [SMILES: Cn1ncc(Br)c1-c1cc(NC(=O)Nc2ccc(Cl)cc2)ccc1OCc1ccccc1] | 1-[4-Benzyloxy-3-(4-bromo-2-methyl-2H-pyrazol-3-yl)-phenyl]-3-(4-chloro-phenyl)-urea |
| 62 | 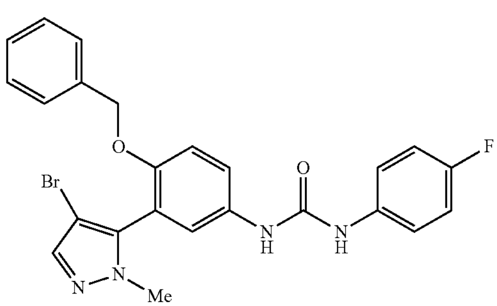 [SMILES: Cn1ncc(Br)c1-c1cc(NC(=O)Nc2ccc(F)cc2)ccc1OCc1ccccc1] | 1-[4-Benzyloxy-3-(4-bromo-2-methyl-2H-pyrazol-3-yl)-phenyl]-3-(4-fluoro-phenyl)-urea |

TABLE 3-continued

| Cmpd # | Structure | Chemical Name |
|---|---|---|
| 63 | 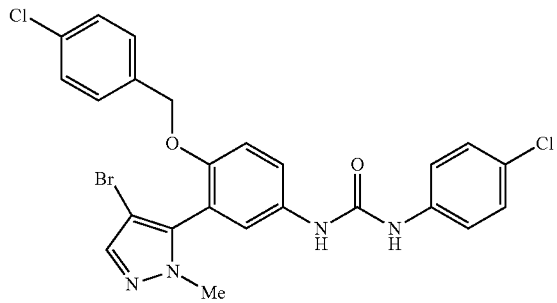 [SMILES: Cn1ncc(Br)c1-c1cc(NC(=O)Nc2ccc(Cl)cc2)ccc1OCc1ccc(Cl)cc1] | 1-[3-(4-Bromo-2-methyl-2H-pyrazol-3-yl)-4-(4-chloro-benzyloxy)-phenyl]-3-(4-chloro-phenyl)-urea |
| 64 | 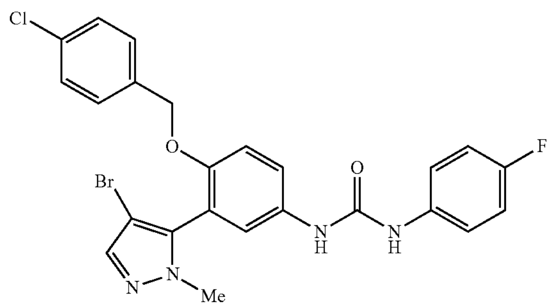 [SMILES: Cn1ncc(Br)c1-c1cc(NC(=O)Nc2ccc(F)cc2)ccc1OCc1ccc(Cl)cc1] | 1-[3-(4-Bromo-2-methyl-2H-pyrazol-3-yl)-4-(4-chloro-benzyloxy)-phenyl]-3-(4-fluoro-phenyl)-urea |
| 65 | 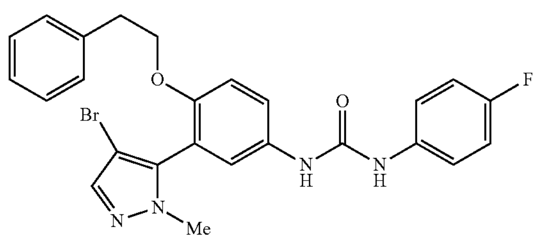 [SMILES: Cn1ncc(Br)c1-c1cc(NC(=O)Nc2ccc(F)cc2)ccc1OCCc1ccccc1] | 1-[3-(4-Bromo-2-methyl-2H-pyrazol-3-yl)-4-phenethyloxy-phenyl]-3-(4-fluoro-phenyl)-urea |
| 66 | 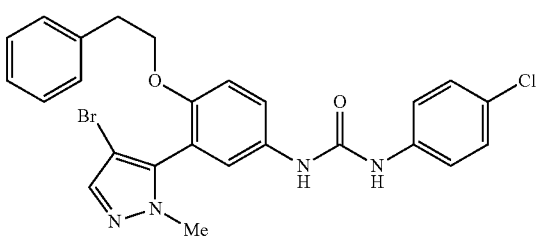 [SMILES: Cn1ncc(Br)c1-c1cc(NC(=O)Nc2ccc(Cl)cc2)ccc1OCCc1ccccc1] | 1-[3-(4-Bromo-2-methyl-2H-pyrazol-3-yl)-4-phenethyloxy-phenyl]-3-(4-chloro-phenyl)-urea |
| 67 | 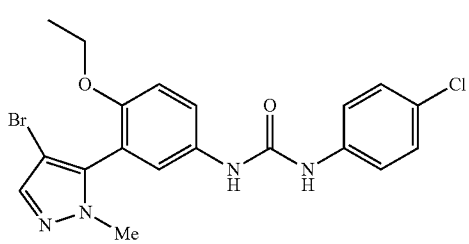 [SMILES: CCOc1ccc(NC(=O)Nc2ccc(Cl)cc2)cc1-c1c(Br)cnn1C] | 1-[3-(4-Bromo-2-methyl-2H-pyrazol-3-yl)-4-ethoxy-phenyl]-3-(4-chloro-phenyl)-urea |
| 68 | 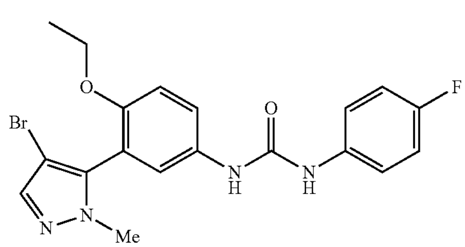 [SMILES: CCOc1ccc(NC(=O)Nc2ccc(F)cc2)cc1-c1c(Br)cnn1C] | 1-[3-(4-Bromo-2-methyl-2H-pyrazol-3-yl)-4-ethoxy-phenyl]-3-(4-fluoro-phenyl)-urea |

TABLE 3-continued

| Cmpd # | Structure | Chemical Name |
|---|---|---|
| 69 | 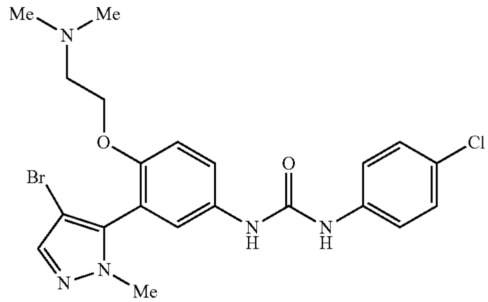 | 1-[3-(4-Bromo-2-methyl-2H-pyrazol-3-yl)-4-(2-dimethylamino-ethoxy)-phenyl]-3-(4-chloro-phenyl)-urea |
| 70 | 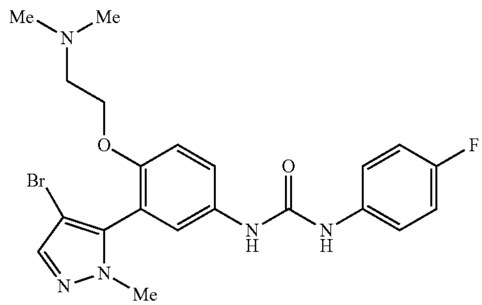 | 1-[3-(4-Bromo-2-methyl-2H-pyrazol-3-yl)-4-(2-dimethylamino-ethoxy)-phenyl]-3-(4-fluoro-phenyl)-urea |
| 71 | 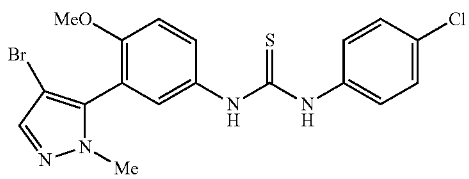 | 1-[3-(4-Bromo-2-methyl-2H-pyrazol-3-yl)-4-methoxy-phenyl]-3-(4-chloro-phenyl)-thiourea |
| 72 | 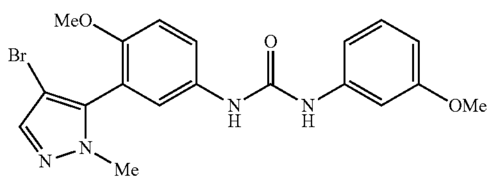 | 1-[3-(4-Bromo-2-methyl-2H-pyrazol-3-yl)-4-methoxy-phenyl]-3-(3-methoxy-phenyl)-urea |
| 73 | 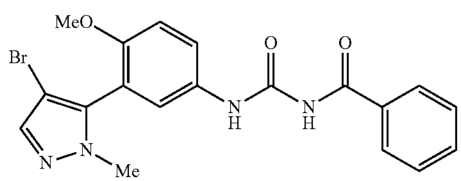 [SMILES: COc1ccc(NC(=O)NC(=O)c2ccccc2)cc1-c1c(Br)cnn1C] | 1-Benzoyl-3-[3-(4-bromo-2-methyl-2H-pyrazol-3-yl)-4-methoxy-phenyl]-urea |
| 74 | 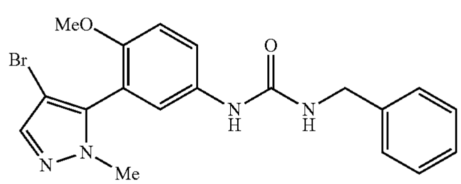 [SMILES: COc1ccc(NC(=O)NCc2ccccc2)cc1-c1c(Br)cnn1C] | 1-Benzyl-3-[3-(4-bromo-2-methyl-2H-pyrazol-3-yl)-4-methoxy-phenyl]-urea |
| 75 | 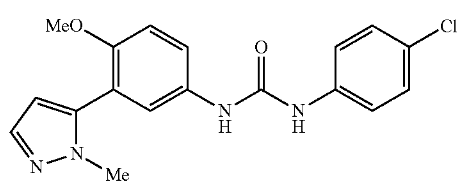 [SMILES: COc1ccc(NC(=O)Nc2ccc(Cl)cc2)cc1-c1ccnn1C] | 1-(4-Chloro-phenyl)-3-[4-methoxy-3-(2-methyl-2H-pyrazol-3-yl)-phenyl]-urea |

TABLE 3-continued

| Cmpd # | Structure | Chemical Name |
|---|---|---|
| 76 | 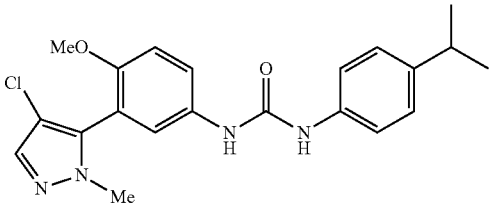 [SMILES: COc1ccc(NC(=O)Nc2ccc(C(C)C)cc2)cc1-c1c(Cl)cnn1C] | 1-[3-(4-Chloro-2-methyl-2H-pyrazol-3-yl)-4-methoxy-phenyl]-3-(4-isopropyl-phenyl)-urea |
| 77 | 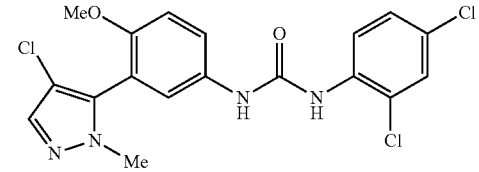 | 1-[3-(4-Chloro-2-methyl-2H-pyrazol-3-yl)-4-methoxy-phenyl]-3-(2,4-dichloro-phenyl)-urea |
| 78 | 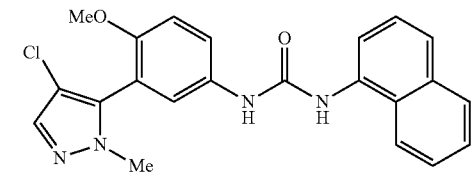 [SMILES: COc1ccc(NC(=O)Nc2cccc3ccccc23)cc1-c1c(Cl)cnn1C] | 1-[3-(4-Chloro-2-methyl-2H-pyrazol-3-yl)-4-methoxy-phenyl]-3-naphthalen-1-yl-urea |
| 79 | 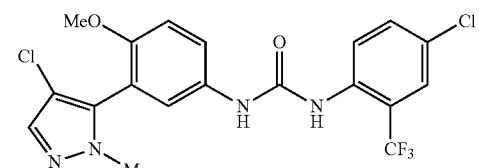 | 1-[3-(4-Chloro-2-methyl-2H-pyrazol-3-yl)-4-methoxy-phenyl]-3-(4-chloro-2-trifluoromethyl-phenyl)-urea |
| 80 | 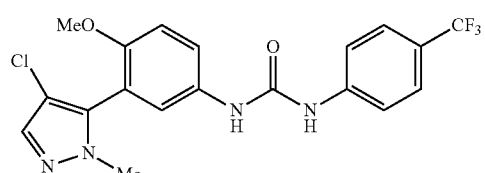 | 1-[3-(4-Chloro-2-methyl-2H-pyrazol-3-yl)-4-methoxy-phenyl]-3-(4-trifluoromethyl-phenyl)-urea |
| 81 | 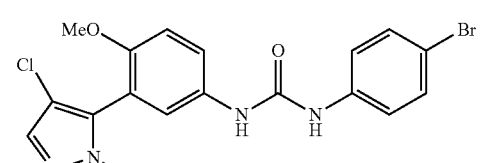 | 1-(4-Bromo-phenyl)-3-[3-(4-chloro-2-methyl-2H-pyrazol-3-yl)-4-methoxy-phenyl]-urea |
| 82 | 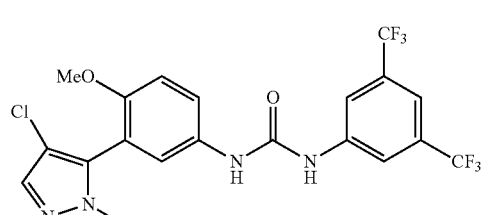 | 1-(3,5-Bis-trifluoromethyl-phenyl)-3-[3-(4-chloro-2-methyl-2H-pyrazol-3-yl)-4-methoxy-phenyl]-urea |
| 83 | 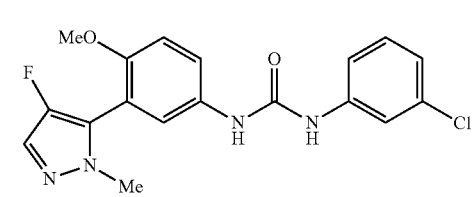 [SMILES: COc1ccc(NC(=O)Nc2cccc(Cl)c2)cc1-c1c(F)cnn1C] | 1-(3-Chloro-phenyl)-3-[3-(4-fluoro-2-methyl-2H-pyrazol-3-yl)-4-methoxy-phenyl]-urea |

TABLE 3-continued

| Cmpd # | Structure | Chemical Name |
|---|---|---|
| 84 | 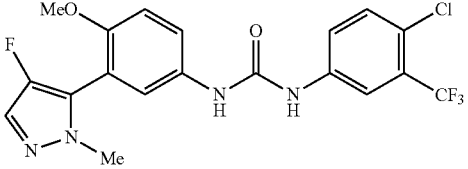 [SMILES: COc1ccc(NC(=O)Nc2ccc(Cl)c(C(F)(F)F)c2)cc1-c1c(F)cnn1C] | 1-(4-Chloro-3-trifluoromethyl-phenyl)-3-[3-(4-fluoro-2-methyl-2H-pyrazol-3-yl)-4-methoxy-phenyl]-urea |
| 85 | 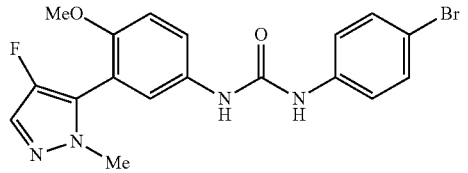 [SMILES: COc1ccc(NC(=O)Nc2ccc(Br)cc2)cc1-c1c(F)cnn1C] | 1-(4-Bromo-phenyl)-3-[3-(4-fluoro-2-methyl-2H-pyrazol-3-yl)-4-methoxy-phenyl]-urea |
| 86 | 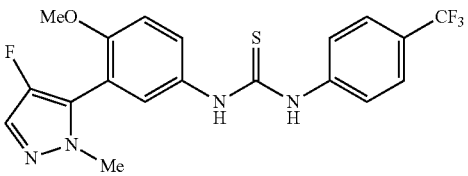 [SMILES: COc1ccc(NC(=O)Nc2ccc(C(F)(F)F)cc2)cc1-c1c(F)cnn1C] | 1-[3-(4-Fluoro-2-methyl-2H-pyrazol-3-yl)-4-methoxy-phenyl]-3-(4-trifluoromethyl-phenyl)-thiourea |
| 87 | 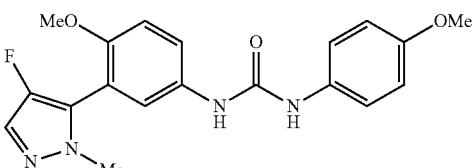 | 1-[3-(4-Fluoro-2-methyl-2H-pyrazol-3-yl)-4-methoxy-phenyl]-3-(4-methoxy-phenyl)-urea |
| 88 | 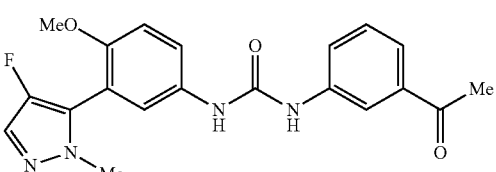 | 1-(3-Acetyl-phenyl)-3-[3-(4-fluoro-2-methyl-2H-pyrazol-3-yl)-4-methoxy-phenyl]-urea |
| 89 | 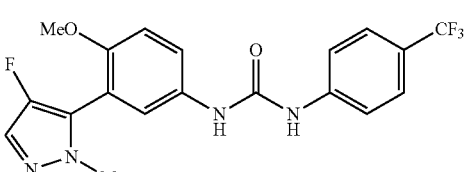 | 1-[3-(4-Fluoro-2-methyl-2H-pyrazol-3-yl)-4-methoxy-phenyl]-3-(4-trifluoromethyl-phenyl)-urea |
| 90 | 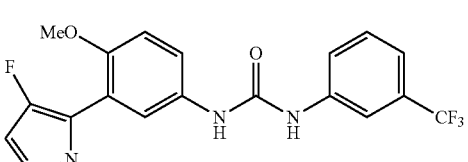 | 1-[3-(4-Fluoro-2-methyl-2H-pyrazol-3-yl)-4-methoxy-phenyl]-3-(3-trifluoromethyl-phenyl)-urea |
| 91 | 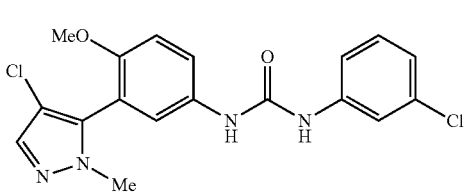 [SMILES: COc1ccc(NC(=O)Nc2cccc(Cl)c2)cc1-c1c(Cl)cnn1C] | 1-[3-(4-Chloro-2-methyl-2H-pyrazol-3-yl)-4-methoxy-phenyl]-3-(3-chloro-phenyl)-urea |

TABLE 3-continued

| Cmpd # | Structure | Chemical Name |
|---|---|---|
| 92 | 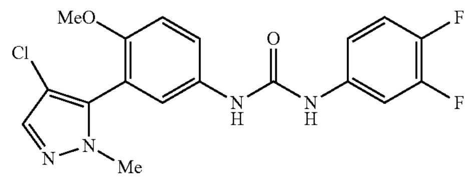 [SMILES: COc1ccc(NC(=O)Nc2ccc(F)c(F)c2)cc1-c1c(Cl)cnn1C] | 1-[3-(4-Chloro-2-methyl-2H-pyrazol-3-yl)-4-methoxy-phenyl]-3-(3,4-difluoro-phenyl)-urea |
| 93 | 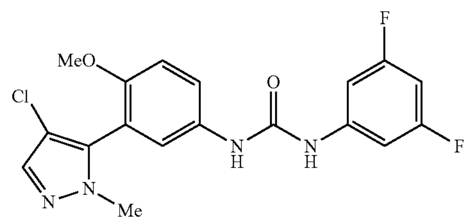 [SMILES: COc1ccc(NC(=O)Nc2cc(F)cc(F)c2)cc1-c1c(Cl)cnn1C] | 1-[3-(4-Chloro-2-methyl-2H-pyrazol-3-yl)-4-methoxy-phenyl]-3-(3,5-difluoro-phenyl)-urea |
| 94 | 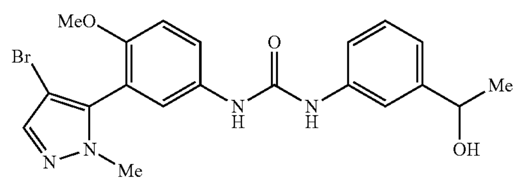 [SMILES: COc1ccc(NC(=O)Nc2cccc(C(C)O)c2)cc1-c1c(Br)cnn1C] | 1-[3-(4-Bromo-2-methyl-2H-pyrazol-3-yl)-4-methoxy-phenyl]-3-[3-(1-hydroxy-ethyl)-phenyl]-urea |
| 95 | 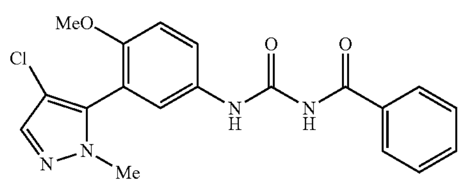 [SMILES: COc1ccc(NC(=O)NC(=O)c2ccccc2)cc1-c1c(Cl)cnn1C] | 1-Benzoyl-3-[3-(4-chloro-2-methyl-2H-pyrazol-3-yl)-4-methoxy-phenyl]-urea |
| 96 | 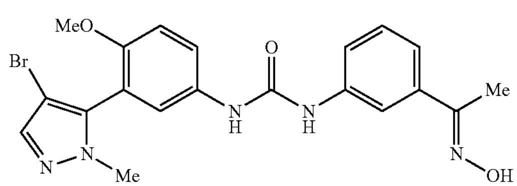 [SMILES: COc1ccc(NC(=O)Nc2cccc(/C(C)=N/O)c2)cc1-c1c(Br)cnn1C] | 1-[3-(4-Bromo-2-methyl]-2H-pyrazol-3-yl)-4-methoxy-phenyl]-3-[3-(1-hydroxyimino-ethyl)-phenyl]-urea |
| 97 | 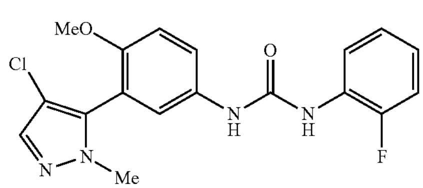 [SMILES: COc1ccc(NC(=O)Nc2ccccc2F)cc1-c1c(Cl)cnn1C] | 1-[3-(4-Chloro-2-methyl-2H-pyrazol-3-yl)-4-methoxy-phenyl]-3-(2-fluoro-phenyl)-urea |
| 98 | 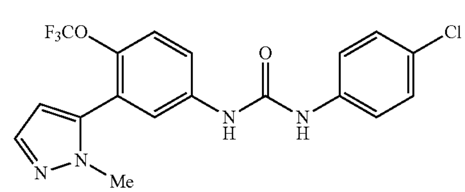 [SMILES: Cn1nccc1-c1cc(NC(=O)Nc2ccc(Cl)cc2)ccc1OC(F)(F)F] | 1-(4-Chloro-phenyl)-3-[3-(2-methyl-2H-pyrazol-3-yl)-4-trifluoromethoxy-phenyl]-urea |
| 99 | 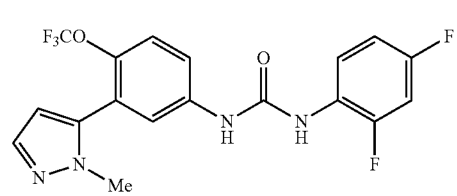 [SMILES: Cn1nccc1-c1cc(NC(=O)Nc2ccc(F)cc2F)ccc1OC(F)(F)F] | 1-(2,4-Difluoro-phenyl)-3-[3-(2-methyl-2H-pyrazol-3-yl)-4-trifluoromethoxy-phenyl]-urea |

TABLE 3-continued

| Cmpd # | Structure | Chemical Name |
|---|---|---|
| 100 | 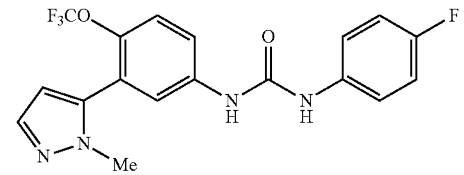 [SMILES: Cn1nccc1-c1cc(NC(=O)Nc2ccc(F)cc2)ccc1OC(F)(F)F] | 1-(4-Fluoro-phenyl)-3-[3-(2-methyl-2H-pyrazol-3-yl)-4-trifluoromethoxy-phenyl]-urea |
| 101 | 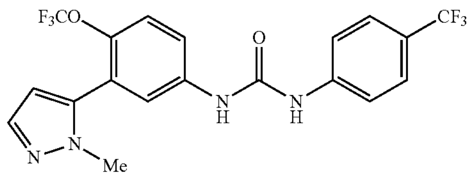 [SMILES: Cn1nccc1-c1cc(NC(=O)Nc2ccc(C(F)(F)F)cc2)ccc1OC(F)(F)F] | 1-[3-(2-Methyl-2H-pyrazol-3-yl)-4-trifluoromethoxy-phenyl]-3-(4-trifluoromethyl-phenyl)-urea |
| 102 | 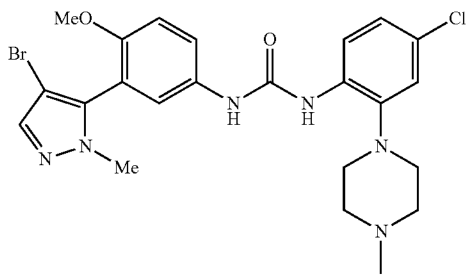 [SMILES: COc1ccc(NC(=O)Nc2ccc(Cl)cc2N2CCN(C)CC2)cc1-c1c(Br)cnn1C] | 1-[3-(4-Bromo-2-methyl-2H-pyrazol-3-yl)-4-methoxy-phenyl]-3-[4-chloro-2-(4-methyl-piperazin-1-yl)-phenyl]-urea |
| 103 | 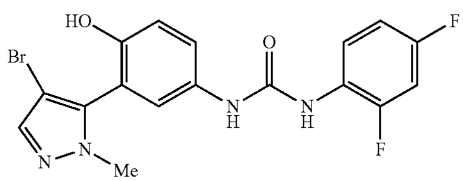 | 1-[3-(4-Bromo-2-methyl-2H-pyrazol-3-yl)-4-hydroxy-phenyl]-3-(2,4-difluoro-phenyl)-urea |
| 104 | 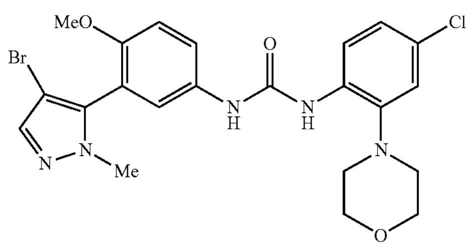 [SMILES: COc1ccc(NC(=O)Nc2ccc(Cl)cc2N2CCOCC2)cc1-c1c(Br)cnn1C] | 1-[3-(4-Bromo-2-methyl-2H-pyrazol-3-yl)-4-methoxy-phenyl]-3-(4-chloro-2-morpholin-4-yl-phenyl)-urea |
| 105 | 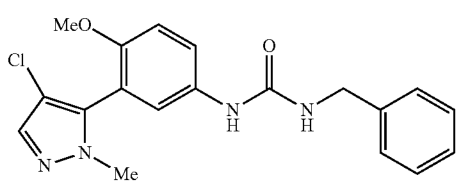 [SMILES: COc1ccc(NC(=O)NCc2ccccc2)cc1-c1c(Cl)cnn1C] | 1-Benzyl-3-[3-(4-chloro-2-methyl-2H-pyrazol-3-yl)-4-methoxy-phenyl]-urea |
| 106 | 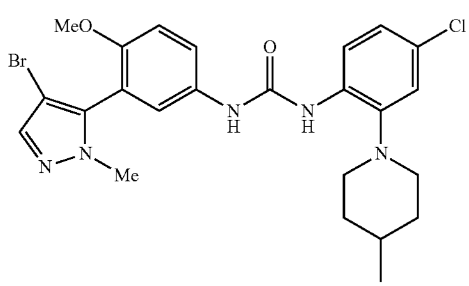 [SMILES: COc1ccc(NC(=O)Nc2ccc(Cl)cc2N2CCC(C)CC2)cc1-c1c(Br)cnn1C] | 1-[3-(4-Bromo-2-methyl-2H-pyrazol-3-yl)-4-methoxy-phenyl]-3-[4-chloro-2-(4-methyl-piperidin-1-yl)-phenyl]-urea |

TABLE 3-continued

| Cmpd # | Structure | Chemical Name |
|---|---|---|
| 107 | 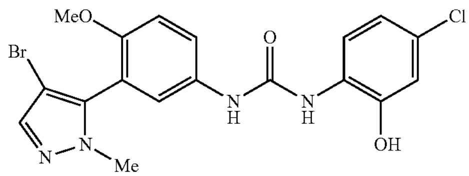 | 1-[3-(4-Bromo-2-methyl-2H-pyrazol-3-yl)-4-methoxy-phenyl]-3-(4-chloro-2-hydroxy-phenyl)-urea |
| 108 | 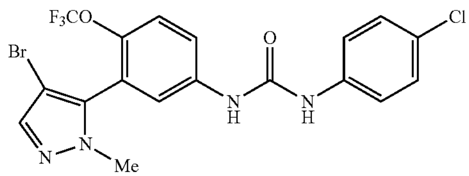 | 1-[3-(4-Bromo-2-methyl-2H-pyrazol-3-yl)-4-trifluoromethoxy-phenyl]-3-(4-chloro-phenyl)-urea |
| 109 | 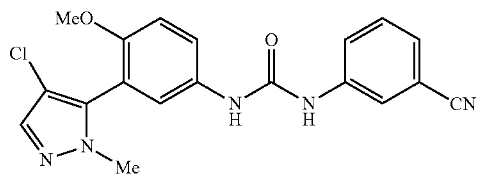 [SMILES: COc1ccc(NC(=O)Nc2cccc(C#N)c2)cc1-c1c(Cl)cnn1C] | 1-[3-(4-Chloro-2-methyl-2H-pyrazol-3-yl)-4-methoxy-phenyl]-3-(3-cyano-phenyl)-urea |
| 110 | 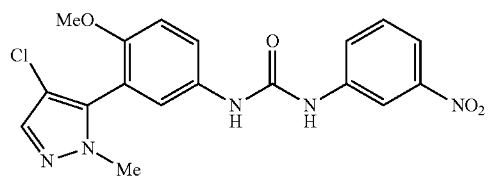 [SMILES: COc1ccc(NC(=O)Nc2cccc([N+](=O)[O-])c2)cc1-c1c(Cl)cnn1C] | 1-[3-(4-Chloro-2-methyl-2H-pyrazol-3-yl)-4-methoxy-phenyl]-3-(3-nitro-phenyl)-urea |
| 111 | 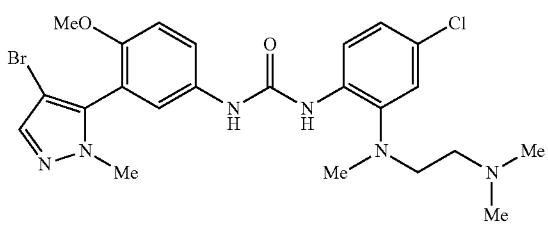 [SMILES: COc1ccc(NC(=O)Nc2ccc(Cl)cc2N(C)CCN(C)C)cc1-c1c(Br)cnn1C] | 1-[3-(4-Bromo-2-methyl-2H-pyrazol-3-yl)-4-methoxy-phenyl]-3-{4-chloro-2-[(2-dimethylamino-ethyl)-methyl-amino]-phenyl}-urea |
| 112 | 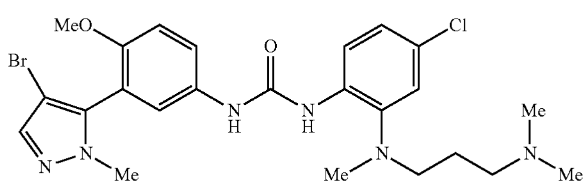 [SMILES: COc1ccc(NC(=O)Nc2ccc(Cl)cc2N(C)CCCN(C)C)cc1-c1c(Br)cnn1C] | 1-[3-(4-Bromo-2-methyl-2H-pyrazol-3-yl)-4-methoxy-phenyl]-3-{4-chloro-2-[(3-dimethylamino-propyl)-methyl-amino]-phenyl}-urea |
| 113 | 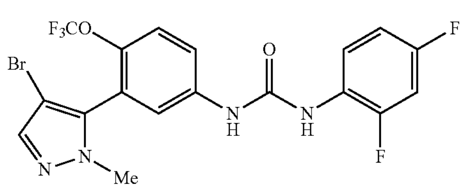 | 1-[3-(4-Bromo-2-methyl-2H-pyrazol-3-yl)-4-trifluoromethoxy-phenyl-3]-(2,4-difluoro-phenyl)-urea |
| 114 | 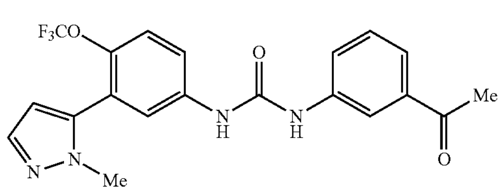 [SMILES: CC(=O)c1cccc(NC(=O)Nc2ccc(OC(F)(F)F)c(-c3ccnn3C)c2)c1] | 1-(3-Acetyl-phenyl)-3-[3-(2-methyl-2H-pyrazol-3-yl)-4-trifluoromethoxy-phenyl]-urea |

TABLE 3-continued

| Cmpd # | Structure | Chemical Name |
|---|---|---|
| 115 | 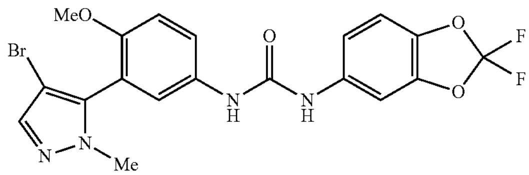 [SMILES: COc1ccc(NC(=O)Nc2ccc3c(c2)OC(F)(F)O3)cc1-c1c(Br)cnn1C] | 1-[3-(4-Bromo-2-methyl-2H-pyrazol-3-yl)-4-methoxy-phenyl]-3-(2,2-difluoro-benzo[1,3]dioxol-5-yl)-urea |
| 116 | 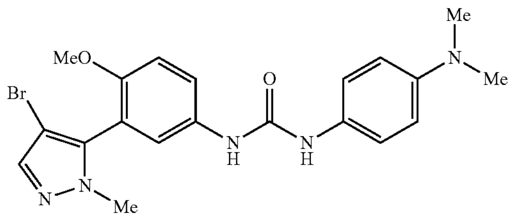 [SMILES: COc1ccc(NC(=O)Nc2ccc(N(C)C)cc2)cc1-c1c(Br)cnn1C] | 1-[3-(4-Bromo-2-methyl-2H-pyrazol-3-yl)-4-methoxy-phenyl]-3-(4-dimethylamino-phenyl)-urea |
| 117 | 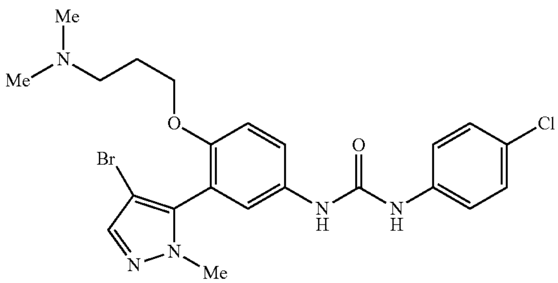 [SMILES: CN(C)CCCOc1ccc(NC(=O)Nc2ccc(Cl)cc2)cc1-c1c(Br)cnn1C] | 1-[3-(4-Bromo-2-methyl-2H-pyrazol-3-yl)-4-(3-dimethylamino-propoxy)-phenyl]-3-(4-chloro-phenyl)-urea |
| 118 | 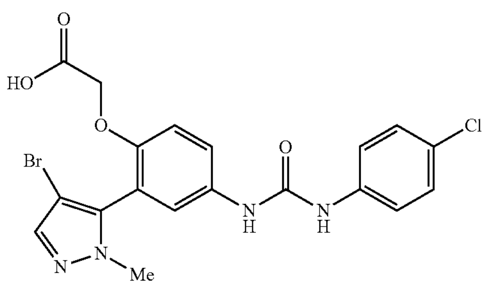 [SMILES: Cn1ncc(Br)c1-c1cc(NC(=O)Nc2ccc(Cl)cc2)ccc1OCC(=O)O] | {2-(4-Bromo-2-methyl-2H-pyrazol-3-yl)-4-[3-(4-chloro-phenyl)-ureido]-phenoxy}-acetic acid |
| 119 | 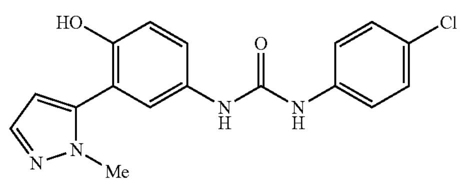 [SMILES: Cn1nccc1-c1cc(NC(=O)Nc2ccc(Cl)cc2)ccc1O] | 1-(4-Chloro-phenyl)-3-[4-hydroxy-3-(2-methyl-2H-pyrazol-3-yl)-phenyl]-urea |
| 120 | 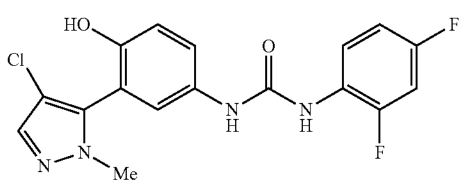 [SMILES: Cn1ncc(Cl)c1-c1cc(NC(=O)Nc2ccc(F)cc2F)ccc1O] | 1-[3-(4-Chloro-2-methyl-2H-pyrazol-3-yl)-4-hydroxy-phenyl]-3-(2,4-difluoro-phenyl)-urea |
| 121 | 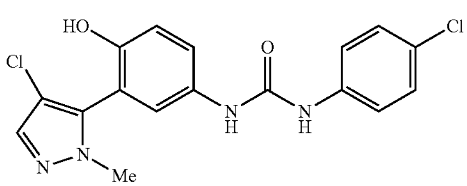 [SMILES: Cn1ncc(Cl)c1-c1cc(NC(=O)Nc2ccc(Cl)cc2)ccc1O] | 1-[3-(4-Chloro-2-methyl-2H-pyrazol-3-yl)-4-hydroxy-phenyl]-3-(4-chloro-phenyl)-urea |

TABLE 3-continued

| Cmpd # | Structure | Chemical Name |
| --- | --- | --- |
| 122 | 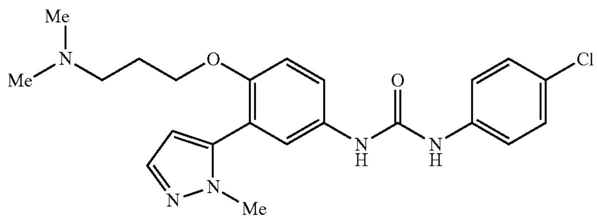 [SMILES: CN(C)CCCOc1ccc(NC(=O)Nc2ccc(Cl)cc2)cc1-c1ccnn1C] | 1-(4-Chloro-phenyl)-3-[4-(3-dimethylamino-propoxy)-3-(2-methyl-2H-pyrazol-3-yl)-phenyl]-urea |
| 123 | 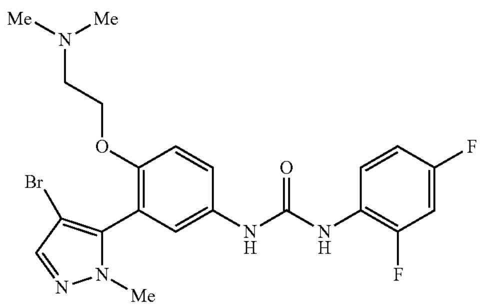 [SMILES: CN(C)CCOc1ccc(NC(=O)Nc2ccc(F)cc2F)cc1-c1c(Br)cnn1C] | 1-[3-(4-Bromo-2-methyl-2H-pyrazol-3-yl)-4-(2-dimethylamino-ethoxy)-phenyl]-3-(2,4-difluoro-pheny)-urea |
| 124 | 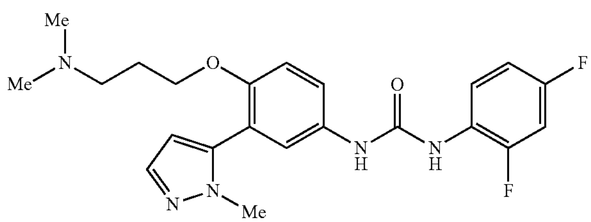 [SMILES: CN(C)CCCOc1ccc(NC(=O)Nc2ccc(F)cc2F)cc1-c1ccnn1C] | 1-(2,4-Difluoro-phenyl)-3-[4-(3-dimethylamino-propoxy)-3-(2-methyl-2H-pyrazol-3-yl)-phenyl]-urea |
| 125 | 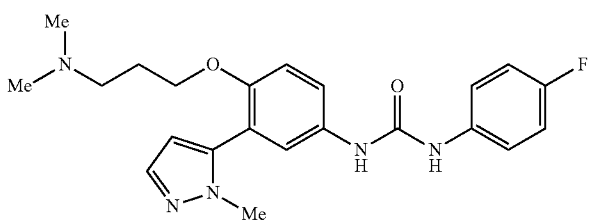 [SMILES: CN(C)CCCOc1ccc(NC(=O)Nc2ccc(F)cc2)cc1-c1ccnn1C] | 1-[4-(3-Dimethylamino-propoxy)-3-(2-methyl-2H-pyrazol-3-yl)-phenyl]-3-(4-fluoro-phenyl)-urea |
| 126 | 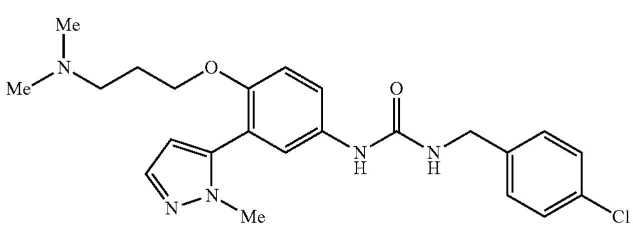 [SMILES: CN(C)CCCOc1ccc(NC(=O)NCc2ccc(Cl)cc2)cc1-c1ccnn1C] | 1-(4-Chloro-benzyl)-3-[4-(3-dimethylamino-propoxy)-3-(2-methyl-2H-pyrazol-3-yl)-phenyl]-urea |
| 127 | 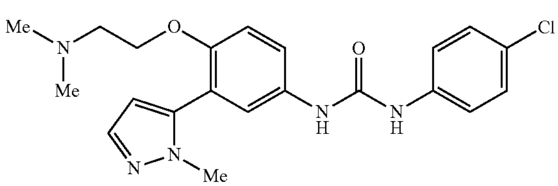 [SMILES: CN(C)CCOc1ccc(NC(=O)Nc2ccc(Cl)cc2)cc1-c1ccnn1C] | 1-(4-Chloro-phenyl)-3-[4-(2-dimethylamino-ethoxy)-3-(2-methyl-2H-pyrazol-3-yl)-phenyl]-urea |

TABLE 3-continued

| Cmpd # | Structure | Chemical Name |
|---|---|---|
| 128 | 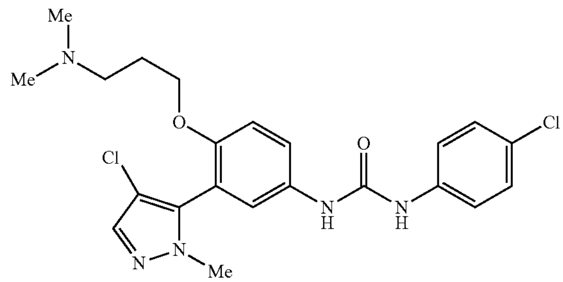 [SMILES: CN(C)CCCOc1ccc(NC(=O)Nc2ccc(Cl)cc2)cc1-c1c(Cl)cnn1C] | 1-[3-(4-Chloro-2-methyl-2H-pyrazol-3-yl)-4-(3-dimethylamino-(propoxy)-phenyl]-3-(4-chloro-phenyl)-urea |
| 129 | 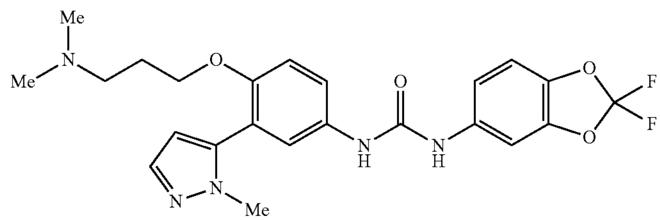 [SMILES: CN(C)CCCOc1ccc(NC(=O)Nc2ccc3c(c2)OC(F)(F)O3)cc1-c1ccnn1C] | 1-(2,2-Difluoro-benzo[1,3]dioxol-5-yl)-3-[4-(3-dimethylamino-propoxy)-3-(2-methyl-2H-pyrazol-3-yl)-phenyl]-urea |
| 130 | 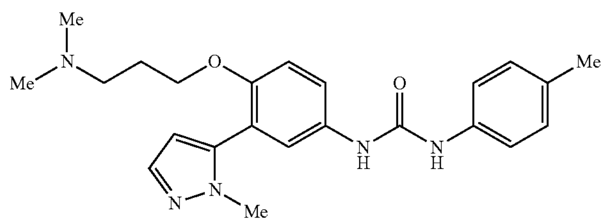 [SMILES: Cc1ccc(NC(=O)Nc2ccc(OCCCN(C)C)c(-c3ccnn3C)c2)cc1] | 1-[4-(3-Dimethylamino-propoxy)-3-(2-methyl-2H-pyrazol-3-yl)-phenyl]-3-p-tolyl-urea |
| 131 | 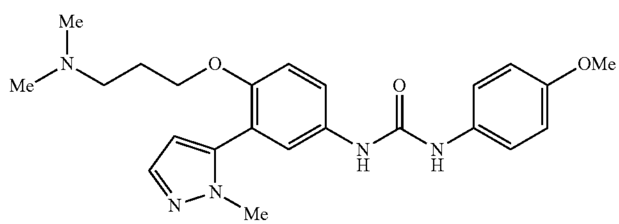 [SMILES: COc1ccc(NC(=O)Nc2ccc(OCCCN(C)C)c(-c3ccnn3C)c2)cc1] | 1-[4-(3-Dimethylamino-propoxy)-3-(2-methyl-2H-pyrazol-3-yl)-phenyl]-3-(4-methoxy-phenyl)-urea |
| 132 | 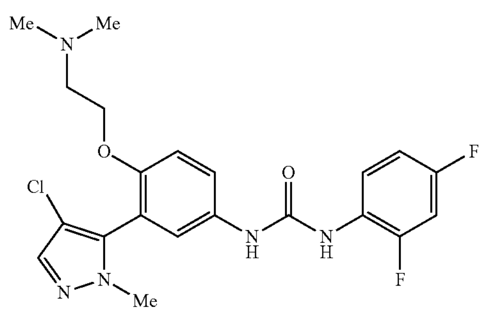 [SMILES: CN(C)CCOc1ccc(NC(=O)Nc2ccc(F)cc2F)cc1-c1c(Cl)cnn1C] | 1-[3-(4-Chloro-2-methyl-2H-pyrazol-3-yl)-4-(2-dimethylamino-ethoxy)-phenyl]-3-(2,4-difluoro-phenyl)-urea |
| 133 | 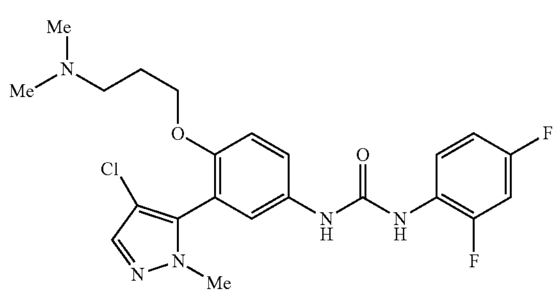 [SMILES: CN(C)CCCOc1ccc(NC(=O)Nc2ccc(F)cc2F)cc1-c1c(Cl)cnn1C] | 1-[3-(4-Chloro-2-methyl-2H-pyrazol-3-yl)-4-(3-dimethylamino-propoxy)-phenyl]-3-(2,4-difluoro-phenyl)-urea |

TABLE 3-continued

| Cmpd # | Structure | Chemical Name |
|---|---|---|
| 134 | 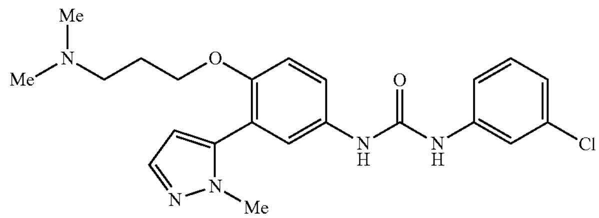 [SMILES: CN(C)CCCOc1ccc(NC(=O)Nc2cccc(Cl)c2)cc1-c1ccnn1C] | 1-(3-Chloro-phenyl)-3-[4-(3-dimethylamino-propoxy)-3-(2-methyl-2H-pyrazol-3-yl)-phenyl]-urea |
| 135 | 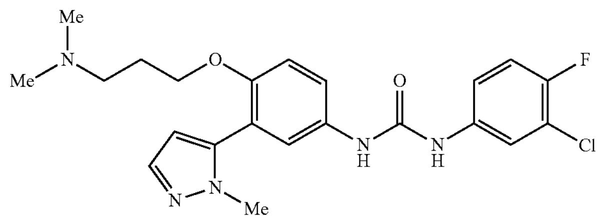 [SMILES: CN(C)CCCOc1ccc(NC(=O)Nc2ccc(F)c(Cl)c2)cc1-c1ccnn1C] | 1-(3-Chloro-4-fluoro-phenyl)-3-[4-(3-dimethylamino-propoxy)-3-(2-methyl-2H-pyrazol-3-yl)-phenyl]-urea |
| 136 | 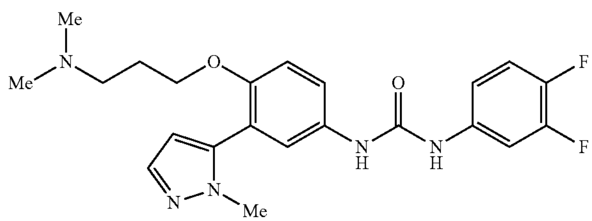 [SMILES: CN(C)CCCOc1ccc(NC(=O)Nc2ccc(F)c(F)c2)cc1-c1ccnn1C] | 1-(3,4-Difluoro-phenyl)-3-[4-(3-dimethylamino-propoxy)-3-(2-methyl-2H-pyrazol-3-yl)-phenyl]-urea |
| 137 | 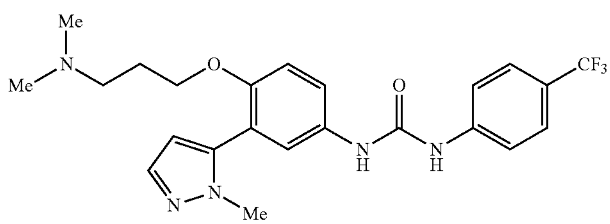 [SMILES: CN(C)CCCOc1ccc(NC(=O)Nc2ccc(C(F)(F)F)cc2)cc1-c1ccnn1C] | 1-[4-(3-Dimethylamino-propoxy)-3-(2-methyl-2H-pyrazol-3-yl)-phenyl]-3-(4-trifluoromethyl-phenyl)-urea |
| 138 | 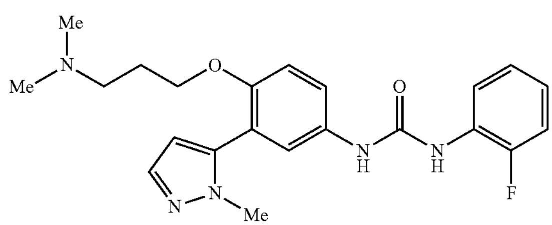 [SMILES: CN(C)CCCOc1ccc(NC(=O)Nc2ccccc2F)cc1-c1ccnn1C] | 1-[4-(3-Dimethylamino-propoxy)-3-(2-methyl-2H-pyrazol-3-yl)-phenyl]-3-(2-fluoro-phenyl)-urea |
| 139 | 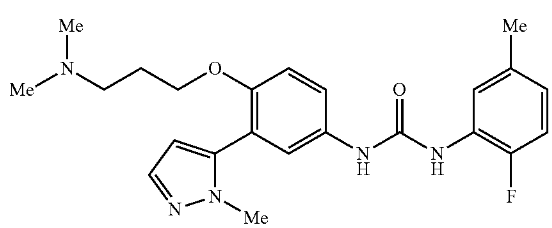 [SMILES: Cc1ccc(F)c(NC(=O)Nc2ccc(OCCCN(C)C)c(-c3ccnn3C)c2)c1] | 1-[4-(3-Dimethylamino-propoxy)-3-(2-methyl-2H-pyrazol-3-yl)-phenyl]-3-(2-fluoro-5-methyl-phenyl)-urea |
| 140 | 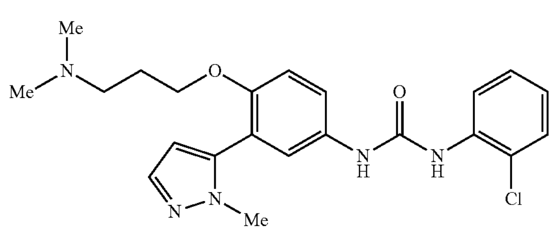 [SMILES: CN(C)CCCOc1ccc(NC(=O)Nc2ccccc2Cl)cc1-c1ccnn1C] | 1-(2-Chloro-phenyl)-3-[4-(3-dimethylamino-propoxy)-3-(2-methyl-2H-pyrazol-3-yl)-phenyl]-urea |

TABLE 3-continued

| Cmpd # | Structure | Chemical Name |
|---|---|---|
| 141 | 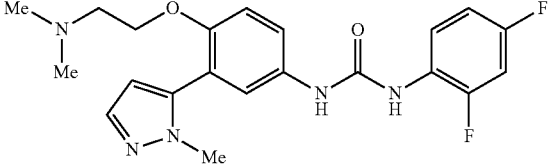 [SMILES: CN(C)CCOc1ccc(NC(=O)Nc2ccc(F)cc2F)cc1-c1ccnn1C] | 1-(2,4-Difluoro-phenyl)-3-[4-(2-dimethylamino-ethoxy)-3-(2-methyl-2H-pyrazol-3-yl)-phenyl]-urea |
| 142 | 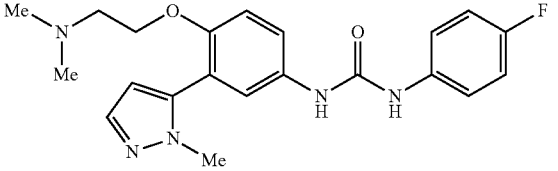 [SMILES: CN(C)CCOc1ccc(NC(=O)Nc2ccc(F)cc2)cc1-c1ccnn1C] | 1-[4-(2-Dimethylamino-ethoxy)-3-(2-methyl-2H-pyrazol-3-yl)-phenyl]-3-(4-fluoro-phenyl)-urea |
| 143 | 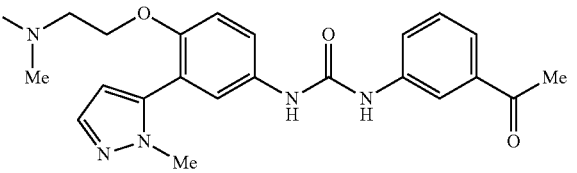 | 1-(3-Acetyl-phenyl)-3-[4-(2-dimethylamino-ethoxy)-3-(2-methyl-2H-pyrazol-3-yl)-pbenyl]-urea |
| 144 | 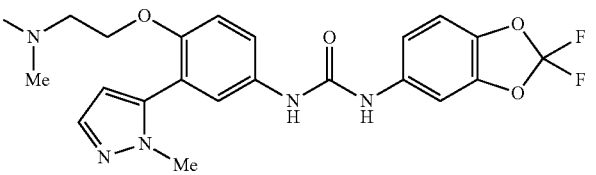 | 1-(2,2-Difluoro-benzo[1,3]dioxol-5-yl)-3-[4-(2-dimethylamino-ethoxy)-3-(2-methyl-2H-pyrazol-3-yl)-phenyl]-urea |
| 145 | 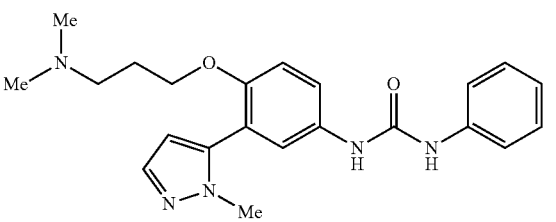 [SMILES: CN(C)CCCOc1ccc(NC(=O)Nc2ccccc2)cc1-c1ccnn1C] | 1-[4-(3-Dimethylamino-propoxy)-3-(2-methyl-2H-pyrazol-3-yl)-phenyl]-3-phenyl-urea |
| 146 | 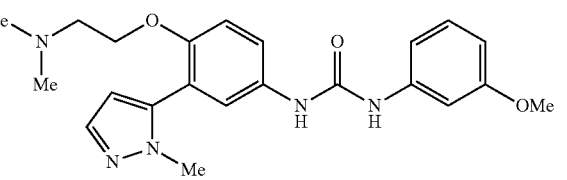 | 1-[4-(2-Dimethylamino-ethoxy)-3-(2-methyl-2H-pyrazol-3-yl)-phenyl]-3-(3-methoxy-phenyl)-urea |
| 147 | 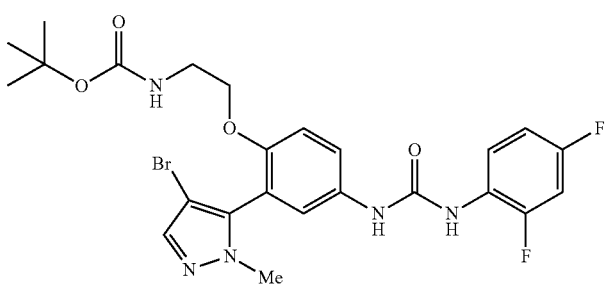 [SMILES: Cn1ncc(Br)c1-c1cc(NC(=O)Nc2ccc(F)cc2F)ccc1OCCNC(=O)OC(C)(C)C] | (2-{2-(4-Bromo-2-methyl-2H-pyrazol-3-yl)-4-[3-(2,4-difluoro-phenyl)-ureido]-phenoxy}-ethyl)-carbamic acid tert-butyl ester |

TABLE 3-continued

| Cmpd # | Structure | Chemical Name |
|---|---|---|
| 148 | 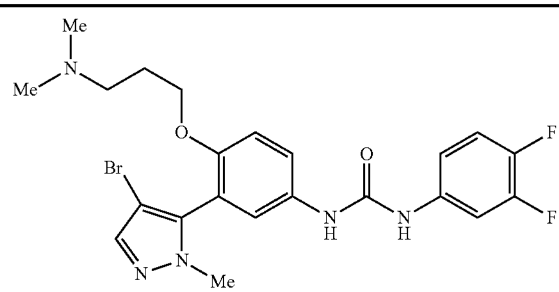 | 1-[3-(4-Bromo-2-methyl-2H-pyrazol-3-yl)-4-(3-dimethylamino-propoxy)-phenyl]-3-(3,4-difluoro-phenyl)-urea |
| 149 | 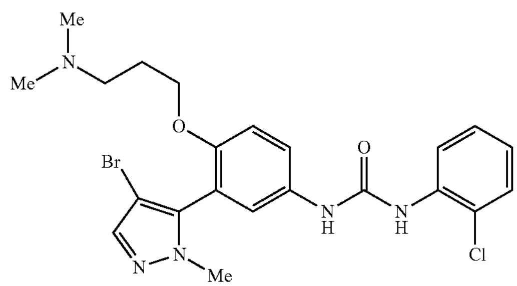 [SMILES: CN(C)CCCOc1ccc(NC(=O)Nc2ccccc2Cl)cc1-c1c(Br)cnn1C] | 1-[3-(4-Bromo-2-methyl-2H-pyrazol-3-yl)-4-(3-dimethylamino-propoxy)-phenyl]-3-(2-chloro-phenyl)-urea |
| 150 | 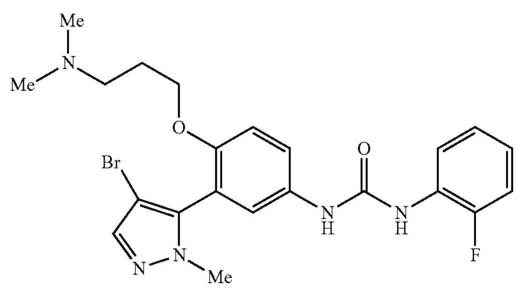 [SMILES: CN(C)CCCOc1ccc(NC(=O)Nc2ccccc2F)cc1-c1c(Br)cnn1C] | 1-[3-(4-Bromo-2-methyl-2H-pyrazol-3-yl)-4-(3-dimethylamino-propoxy)-phenyl]-3-(2-fluoro-phenyl)-urea |
| 151 | 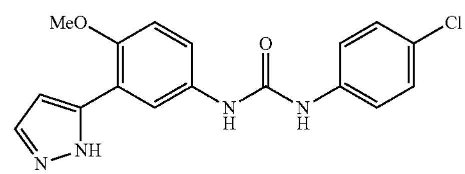 [SMILES: COc1ccc(NC(=O)Nc2ccc(Cl)cc2)cc1-c1ccn[nH]1] | 1-(4-Chloro-phenyl)-3-[4-methoxy-3-(2H-pyrazol-3-yl)-phenyl]-urea |
| 152 | 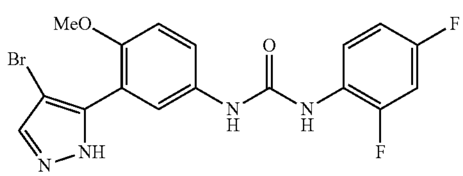 [SMILES: COc1ccc(NC(=O)Nc2ccc(F)cc2F)cc1-c1[nH]ncc1Br] | 1-[3-(4-Bromo-2H-pyrazol-3-yl)-4-methoxy-phenyl]-3-(2,4-difluoro-phenyl)-urea |
| 153 | 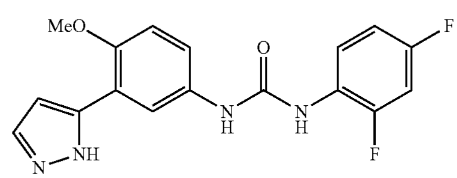 [SMILES: COc1ccc(NC(=O)Nc2ccc(F)cc2F)cc1-c1ccn[nH]1] | 1-(2,4-Difluoro-phenyl)-3-[4-methoxy-3-(2H-pyrazol-3-yl)-phenyl]-urea |
| 154 | 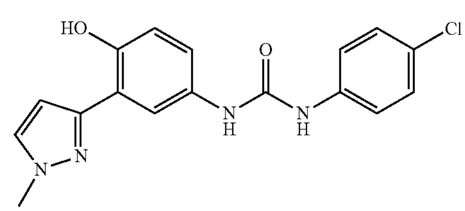 [SMILES: Cn1ccc(-c2cc(NC(=O)Nc3ccc(Cl)cc3)ccc2O)n1] | 1-(4-Chloro-phenyl)-3-[4-hydroxy-3-(1-methyl-1H-pyrazol-3-yl)-phenyl]-urea |

TABLE 3-continued

| Cmpd # | Structure | Chemical Name |
|---|---|---|
| 155 | 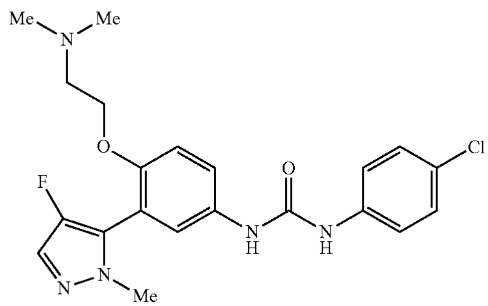 [SMILES: CN(C)CCOc1ccc(NC(=O)Nc2ccc(Cl)cc2)cc1-c1c(F)cnn1C] | 1-(4-Chloro-phenyl)-3-[4-(2-dimethylamino-ethoxy)-3-(4-fluoro-2-methyl-2H-pyrazol-3-yl)-phenyl]-urea |
| 156 | 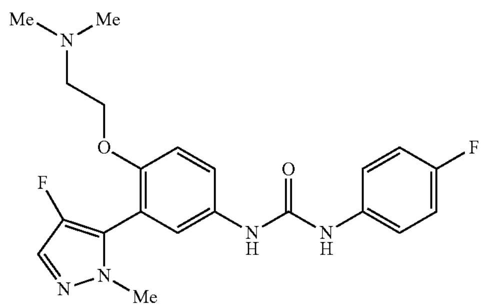 [SMILES: CN(C)CCOc1ccc(NC(=O)Nc2ccc(F)cc2)cc1-c1c(F)cnn1C] | 1-[4-(2-Dimethylamino-ethoxy)-3-(4-fluoro-2-methyl-2H-pyrazol-3-yl)-phenyl]-3-(4-fluoro-phenyl)-urea |
| 157 | 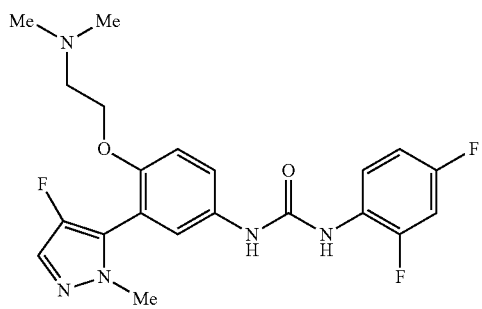 [SMILES: CN(C)CCOc1ccc(NC(=O)Nc2ccc(F)cc2F)cc1-c1c(F)cnn1C] | 1-(2,4-Difluoro-phenyl)-3-[4-(2-dimethylamino-ethoxy)-3-(4-fluoro-2-methyl-2H-pyrazol-3-yl)-phenyl]-urea |
| 158 | 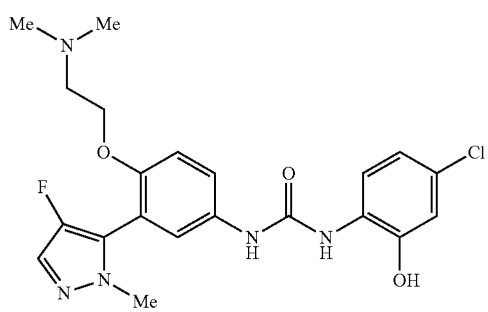 [SMILES: CN(C)CCOc1ccc(NC(=O)Nc2ccc(Cl)cc2O)cc1-c1c(F)cnn1C] | 1-(4-Chloro-2-hydroxy-pbenyl)-3-[4-(2-dimethylamino-ethoxy)-3-(4-fluoro-2-methyl-2H-pyrazol-3-yl)-phenyl]-urea |
| 159 | 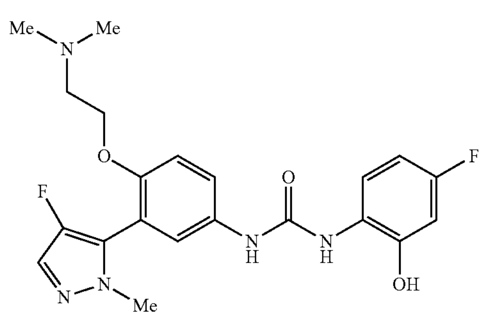 [SMILES: CN(C)CCOc1ccc(NC(=O)Nc2ccc(F)cc2O)cc1-c1c(F)cnn1C] | 1-[4-(2-Dimethylamino-ethoxy)-3-(4-fluoro-2-methyl-2H-pyrazol-3-yl)-phenyl]-3-(4-fluoro-2-hydroxy-phenyl)-urea |

TABLE 3-continued

| Cmpd # | Structure | Chemical Name |
|---|---|---|
| 160 | 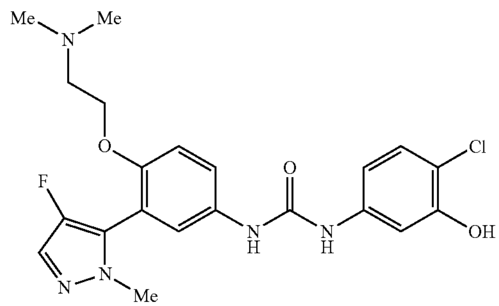 [SMILES: CN(C)CCOc1ccc(NC(=O)Nc2ccc(Cl)c(O)c2)cc1-c1c(F)cnn1C] | 1-(4-Chloro-3-hydroxy-phenyl)-3-[4-(2-dimethylamino-ethoxy)-3-(4-fluoro-2-methyl-2H-pyrazol-3-yl)-phenyl]-urea |
| 161 | 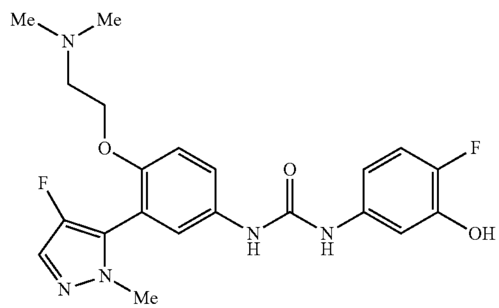 [SMILES: CN(C)CCOc1ccc(NC(=O)Nc2ccc(F)c(O)c2)cc1-c1c(F)cnn1C] | 1-[4-(2-Dimethylamino-ethoxy)-3-(4-fluoro-2-methyl-2H-pyrazol-3-yl)-phenyl]-3-(4-fluoro-3-hydroxy-phenyl)-urea |
| 162 | 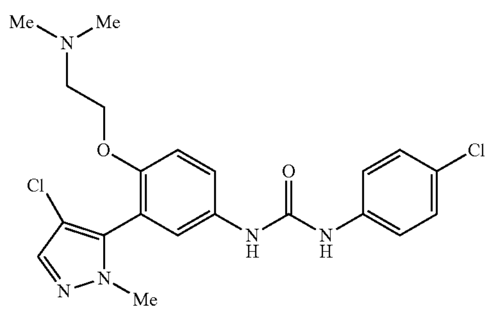 [SMILES: CN(C)CCOc1ccc(NC(=O)Nc2ccc(Cl)cc2)cc1-c1c(Cl)cnn1C] | 1-[3-(4-Chloro-2-methyl-2H-pyrazol-3-yl)-4-(2-dimethylamino-ethoxy)-phenyl]-3-(4-chloro-phenyl)-urea |
| 163 | 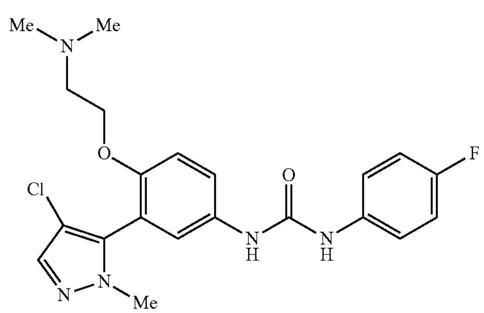 [SMILES: CN(C)CCOc1ccc(NC(=O)Nc2ccc(F)cc2)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-phenyl)-urea |
| 164 | 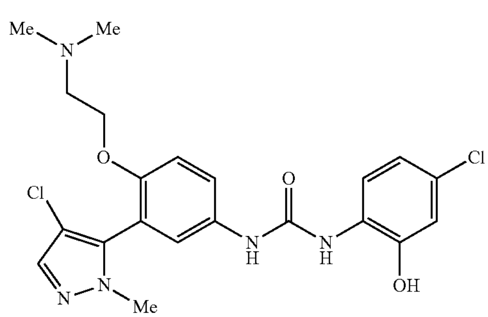 [SMILES: CN(C)CCOc1ccc(NC(=O)Nc2ccc(Cl)cc2O)cc1-c1c(Cl)cnn1C] | 1-(4-Chloro-2-hydroxy-phenyl)-3-[3-(4-chloro-2-methyl-2H-pyrazol-3-yl)-4-(2-dimethylamino-ethoxy)-phenyl]-urea |

TABLE 3-continued

| Cmpd # | Structure | Chemical Name |
|---|---|---|
| 165 | 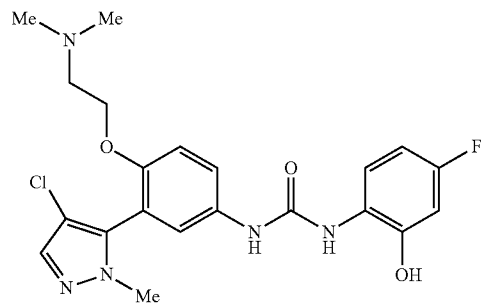 [SMILES: CN(C)CCOc1ccc(NC(=O)Nc2ccc(F)cc2O)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-2-hydroxy-phenyl)-urea |
| 166 | 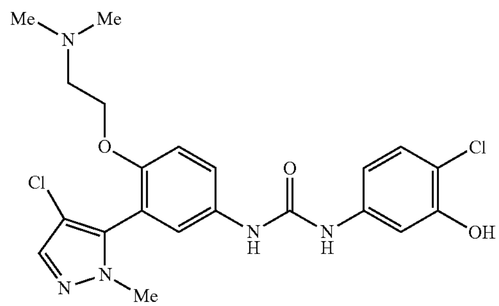 [SMILES: CN(C)CCOc1ccc(NC(=O)Nc2ccc(Cl)c(O)c2)cc1-c1c(Cl)cnn1C] | 1-(4-Chloro-3-hydroxy-phenyl)-3-[3-(4-chloro-2-methyl-2H-pyrazol-3-yl)-4-(2-dimethylamino-ethoxy)-phenyl]-urea |
| 167 | 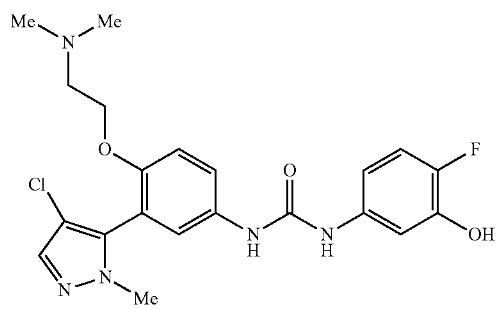 [SMILES: CN(C)CCOc1ccc(NC(=O)Nc2ccc(F)c(O)c2)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-3-hydroxy-phenyl)-urea |
| 168 | 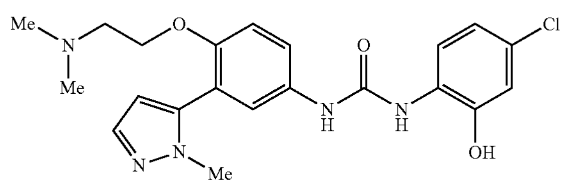 [SMILES: CN(C)CCOc1ccc(NC(=O)Nc2ccc(Cl)cc2O)cc1-c1ccnn1C] | 1-(4-Chloro-2-hydroxy-phenyl)-3-[4-(2-dimethylamino-ethoxy)-3-(2-methyl-2H-pyrazol-3-yl)-phenyl]-urea |
| 169 | 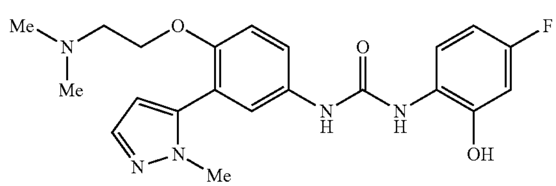 [SMILES: CN(C)CCOc1ccc(NC(=O)Nc2ccc(F)cc2O)cc1-c1ccnn1C] | 1-[4-(2-Dimethylamino-ethoxy)-3-(2-methyl-2H-pyrazol-3-yl)-phenyl]-3-(4-fluoro-2-hydroxy-phenyl)-urea |
| 170 | 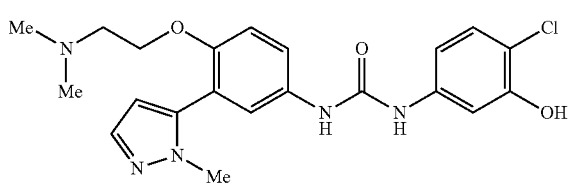 | 1-(4-Chloro-3-hydroxy-phenyl)-3-[4-(2-dimethylamino-ethoxy)-3-(2-methyl-2H-pyrazol-3-yl)-phenyl]-urea |

TABLE 3-continued

| Cmpd # | Structure | Chemical Name |
|---|---|---|
| 171 | 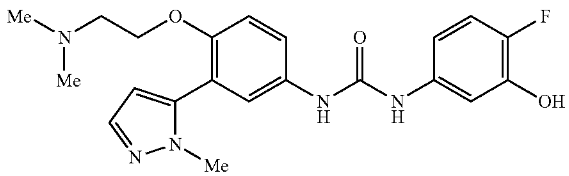 [SMILES: CN(C)CCOc1ccc(NC(=O)Nc2ccc(F)c(O)c2)cc1-c1ccnn1C] | 1-[4-(2-Dimethylamino-ethoxy)-3-(2-methyl-2H-pyrazol-3-yl)-phenyl]-3-(4-fluoro-3-hydroxy-phenyl)-urea |
| 172 | 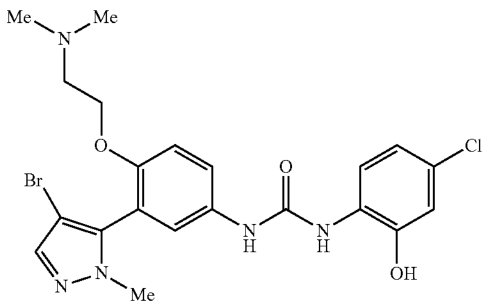 | 1-[3-(4-Bromo-2-methyl-2H-pyrazol-3-yl)-4-(2-dimethylamino-ethoxy)-phenyl]-3-(4-chloro-2-hydroxy-phenyl)-urea |
| 173 | 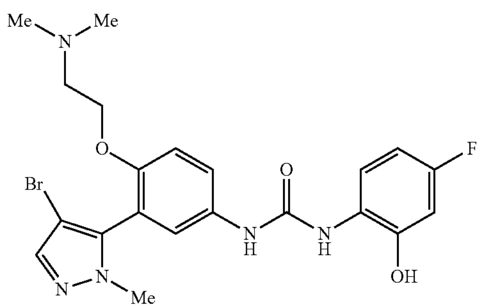 | 1-[3-(4-Bromo-2-methyl-2H-pyrazol-3-yl)-4-(2-dimethylamino-ethoxy)-phenyl]-3-(4-fluoro-2-hydroxy-phenyl)-urea |
| 174 | 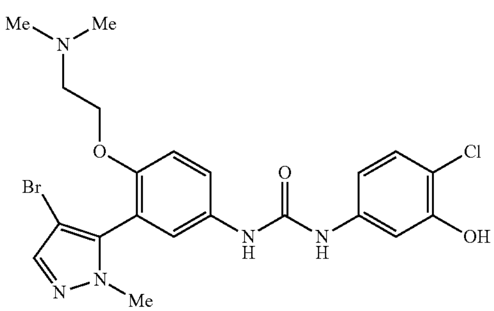 | 1-[3-(4-Bromo-2-methyl-2H-pyrazol-3-yl)-4-(2-dimethylamino-ethoxy)-phenyl]-3-(4-chloro-3-hydroxy-phenyl)-urea |
| 175 | 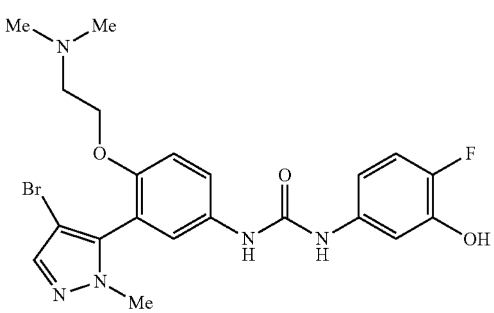 | 1-[3-(4-Bromo-2-methyl-2H-pyrazol-3-yl)-4-(2-dimethylamino-ethoxy)-phenyl]-3-(4-fluoro-3-hydroxy-phenyl)-urea |

TABLE 3-continued

| Cmpd # | Structure | Chemical Name |
|---|---|---|
| 176 | 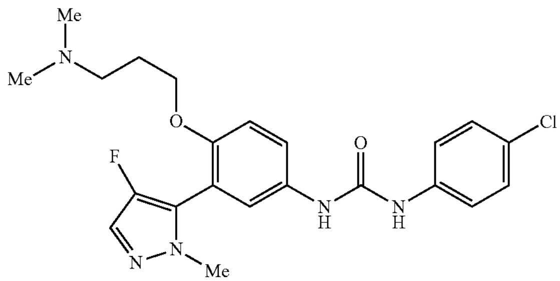 [SMILES: CN(C)CCCOc1ccc(NC(=O)Nc2ccc(Cl)cc2)cc1-c1c(F)cnn1C] | 1-(4-Chloro-phenyl)-3-[4-(3-dimethylamino-propoxy)-3-(4-fluoro-2-methyl-2H-pyrazol-3-yl)-phenyl]-urea |
| 177 | 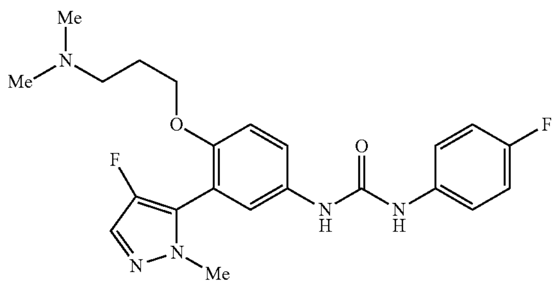 [SMILES: CN(C)CCCOc1ccc(NC(=O)Nc2ccc(F)cc2)cc1-c1c(F)cnn1C] | 1-[4-(3-Dimethylamino-propoxy)-3-(4-fluoro-2-methyl-2H-pyrazol-3-yl)-phenyl]-3-(4-fluoro-phenyl)-urea |
| 178 | 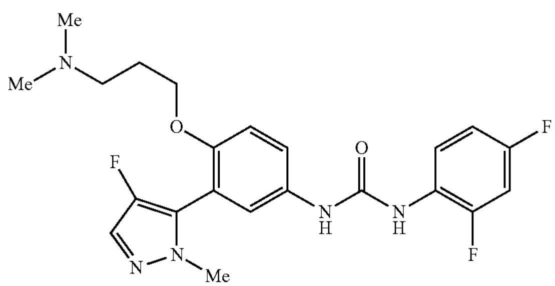 [SMILES: CN(C)CCCOc1ccc(NC(=O)Nc2ccc(F)cc2F)cc1-c1c(F)cnn1C] | 1-(2,4-Difluoro-phenyl)-3-[4-(3-dimethylamino-propoxy)-3-(4-fluoro-2-methyl-2H-pyrazol-3-yl)-phenyl]-urea |
| 179 | 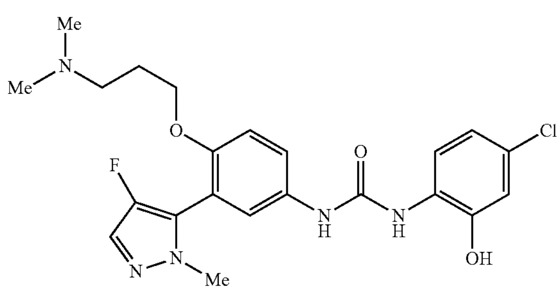 [SMILES: CN(C)CCCOc1ccc(NC(=O)Nc2ccc(Cl)cc2O)cc1-c1c(F)cnn1C] | 1-(4-Chloro-2-hydroxy-phenyl)-3-[4-(3-dimethylamino-propoxy)-3-(4-fluoro-2-methyl-2H-pyrazol-3-yl)-phenyl]-urea |
| 180 | 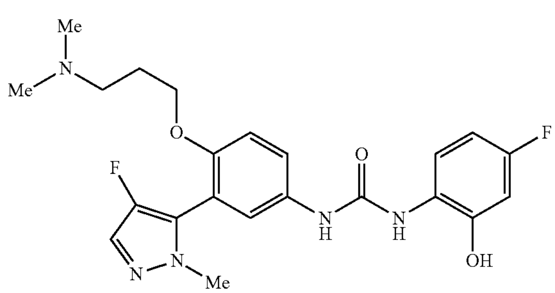 [SMILES: CN(C)CCCOc1ccc(NC(=O)Nc2ccc(F)cc2O)cc1-c1c(F)cnn1C] | 1-[4-(3-Dimethylamino-propoxy)-3-(4-fluoro-2-methyl-2H-pyrazol-3-yl)-phenyl]-3-(4-fluoro-2-hydroxy-phenyl)-urea |

TABLE 3-continued

| Cmpd # | Structure | Chemical Name |
|---|---|---|
| 181 | 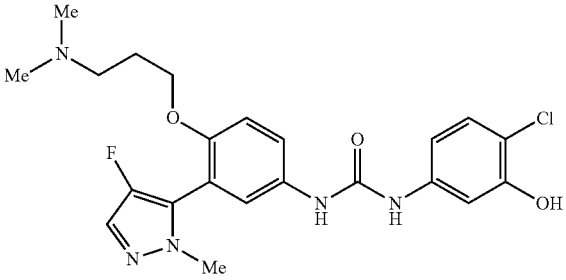 | 1-(4-Chloro-3-hydroxy-phenyl)-3-[4-(3-dimethylamino-propoxy)-3-(4-fluoro-2-methyl-2H-pyrazol-3-yl)-phenyl]-urea |
| 182 | 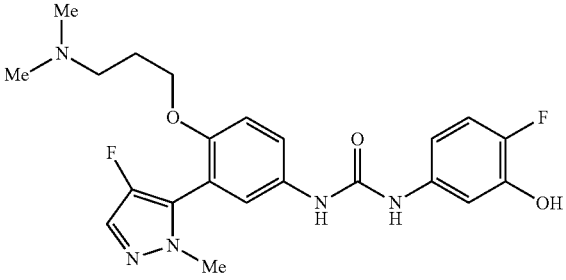 [SMILES: CN(C)CCCOc1ccc(NC(=O)Nc2ccc(F)c(O)c2)cc1-c1c(F)cnn1C] | 1-[4-(3-Dimethylamino-propoxy)-3-(4-fluoro-2-methyl-2H-pyrazol-3-yl)-phenyl]-3-(4-fluoro-3-hydroxy-phenyl)-urea |
| 183 | 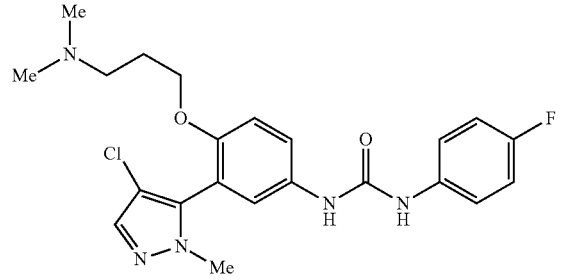 [SMILES: CN(C)CCCOc1ccc(NC(=O)Nc2ccc(F)cc2)cc1-c1c(Cl)cnn1C] | 1-[3-(4-Chloro-2-methyl-2H-pyrazol-3-yl)-4-(3-dimethylamino-propoxy)-phenyl]-3-(4-fluoro-phenyl)-urea |
| 184 | 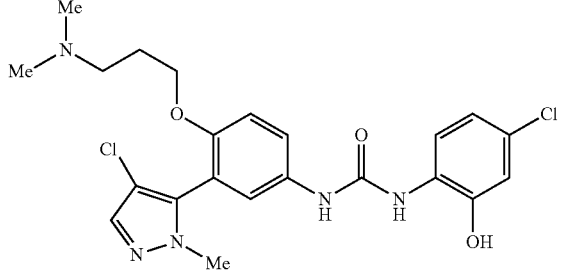 [SMILES: CN(C)CCCOc1ccc(NC(=O)Nc2ccc(Cl)cc2O)cc1-c1c(Cl)cnn1C] | 1-(4-Chloro-2-hydroxy-phenyl)-3-[3-(4-chloro-2-methyl-2H-pyrazol-3-yl)-4-(3-dimethylamino-propoxy)-phenyl]-urea |
| 185 | 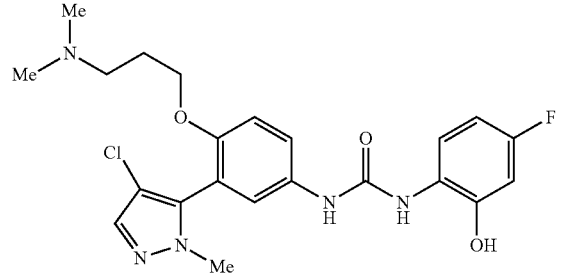 [SMILES: CN(C)CCCOc1ccc(NC(=O)Nc2ccc(F)cc2O)cc1-c1c(Cl)cnn1C] | 1-[3-(4-Chloro-2-methyl-2H-pyrazol-3-yl)-4-(3-dimethylamino-propoxy)-phenyl]-3-(4-fluoro-2-hydroxy-phenyl)-urea |

TABLE 3-continued

| Cmpd # | Structure | Chemical Name |
|---|---|---|
| 186 | 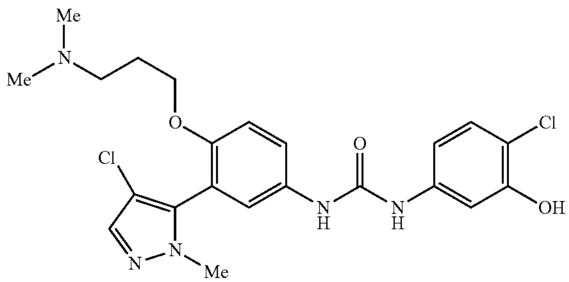 [SMILES: CN(C)CCCOc1ccc(NC(=O)Nc2ccc(Cl)c(O)c2)cc1-c1c(Cl)cnn1C] | 1-(4-Chloro-3-hydroxy-phenyl)-3-[3-(4-chloro-2-methyl-2H-pyrazol-3-yl)-4-(3-dimethylamino-propoxy)-phenyl]-urea |
| 187 | 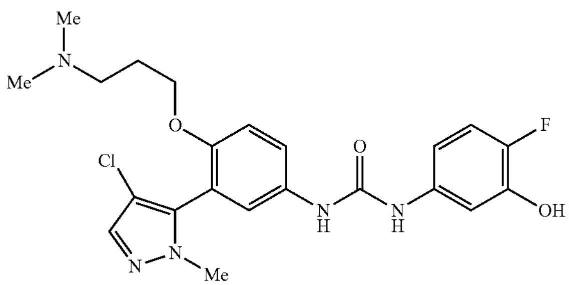 [SMILES: CN(C)CCCOc1ccc(NC(=O)Nc2ccc(F)c(O)c2)cc1-c1c(Cl)cnn1C] | 1-[3-(4-Chloro-2-methyl-2H-pyrazol-3-yl)-4-(3-dimethylamino-propoxy)-phenyl]-3-(4-fluoro-3-hydroxy-phenyl)-urea |
| 188 | 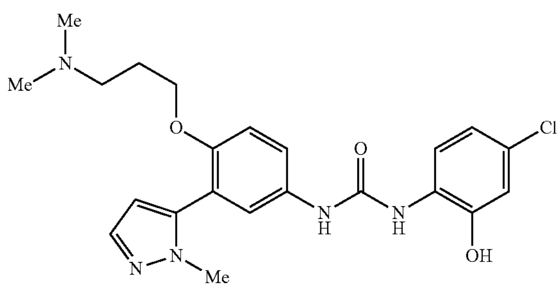 [SMILES: CN(C)CCCOc1ccc(NC(=O)Nc2ccc(Cl)cc2O)cc1-c1ccnn1C] | 1-(4-Chloro-2-hydroxy-phenyl)-3-[4-(3-dimethylamino-propoxy)-3-(2-methyl-2H-pyrazol-3-yl)-phenyl]-urea |
| 189 | 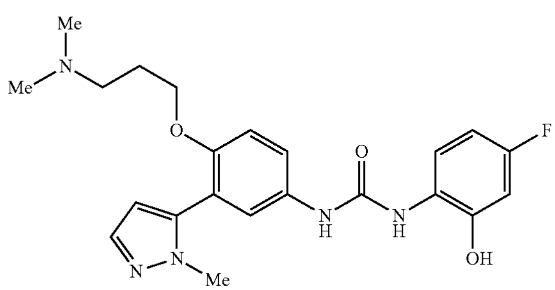 [SMILES: CN(C)CCCOc1ccc(NC(=O)Nc2ccc(F)cc2O)cc1-c1ccnn1C] | 1-[4-(3-Dimethylamino-propoxy)-3-(2-methyl-2H-pyrazol-3-yl)-phenyl]-3-(4-fluoro-2-hydroxy-phenyl)-urea |
| 190 | 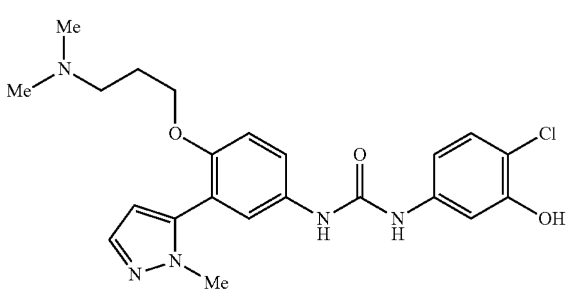 [SMILES: CN(C)CCCOc1ccc(NC(=O)Nc2ccc(Cl)c(O)c2)cc1-c1ccnn1C] | 1-(4-Chloro-3-hydroxy-phenyl)-3-[4-(3-dimethylamino-propoxy)-3-(2-methyl-2H-pyrazol-3-yl)-phenyl]-urea |

TABLE 3-continued

| Cmpd # | Structure | Chemical Name |
|---|---|---|
| 191 | 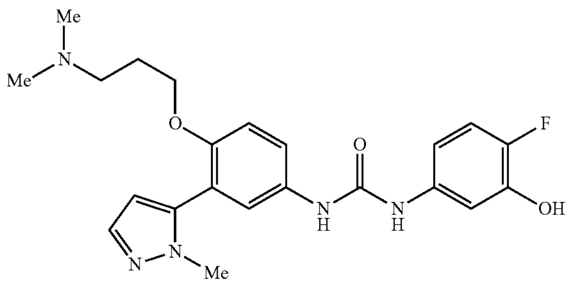 [SMILES: CN(C)CCCOc1ccc(NC(=O)Nc2ccc(F)c(O)c2)cc1-c1ccnn1C] | 1-[4-(3-Dimethylamino-propoxy)-3-(2-methyl-2H-pyrazol-3-yl)-phenyl]-3-(4-fluoro-3-hydroxy-phenyl)-urea |
| 192 | 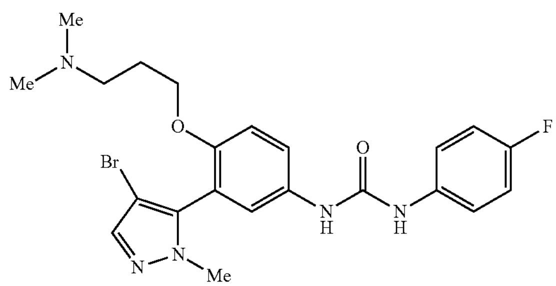 [SMILES: CN(C)CCCOc1ccc(NC(=O)Nc2ccc(F)cc2)cc1-c1c(Br)cnn1C] | 1-[3-(4-Bromo-2-methyl-2H-pyrazol-3-yl)-4-(3-dimethylamino-propoxy)-phenyl]-3-(4-fluoro-phenyl)-urea |
| 193 | 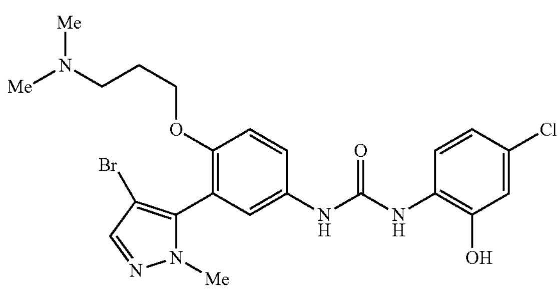 | 1-[3-(4-Bromo-2-methyl-2H-pyrazol-3-yl)-4-(3-dimethylamino-propoxy)-phenyl]-3-(4-chloro-2-hydroxy-phenyl)-urea |
| 194 | 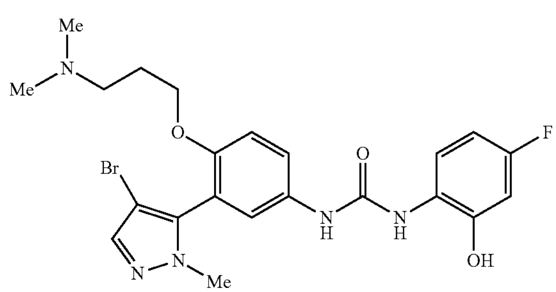 | 1-[3-(4-Bromo-2-methyl-2H-pyrazol-3-yl)-4-(3-dimethylamino-propoxy)-phenyl]-3-(4-fluoro-2-hydroxy-phenyl)-urea |
| 195 | 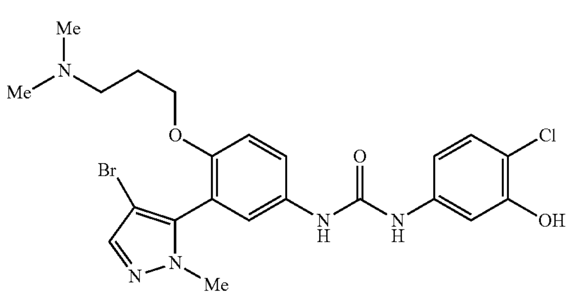 [SMILES: CN(C)CCCOc1ccc(NC(=O)Nc2ccc(Cl)c(O)c2)cc1-c1c(Br)cnn1C] | 1-[3-(4-Bromo-2-methyl-2H-pyrazol-3-yl)-4-(3-dimethylamino-propoxy)-phenyl]-3-(4-chloro-3-hydroxy-phenyl)-urea |

TABLE 3-continued

| Cmpd # | Structure | Chemical Name |
| --- | --- | --- |
| 196 | 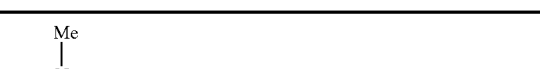 | 1-[3-(4-Bromo-2-methyl-2H-pyrazol-3-yl)-4-(3-dimethylamino-propoxy)-phenyl]-3-(4-fluoro-3-hydroxy-phenyl)-urea |

One aspect of the present invention pertains to certain compounds as shown in Formula 2a:

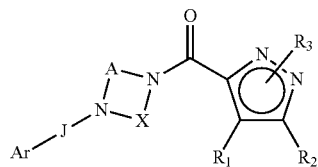

2a or a pharmaceutically acceptable salt, hydrate or solvate thereof; wherein $R_1$, $R_2$, $R_3$, Ar, A, X and J have the same definitions as described herein, supra and infra.

In some embodiments, the compounds of the present invention are other than 1-(4-(1H-pyrazole-3-carbonyl)piperazin-1-yl)-2-(4-fluoro-1H-indol-3-yl)ethane-1,2-dione, represented by the Formula 3 below:

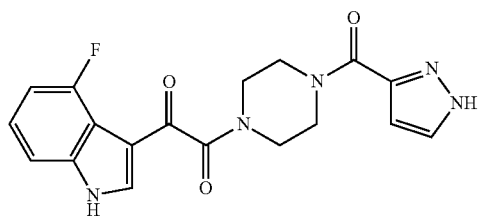

3

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R_1$, $R_2$, $R_3$, Ar, A, X and J) contained within the generic chemical formulae described herein, for example, (Ia, Ic and Ie) are specifically embraced by the present invention just as if they were explicitly disclosed, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each of such subcombination of chemical groups and subcombination of uses and medical indications were explicitly disclosed herein.

It is understood and appreciated that compounds of Formula 2a and formulae related therefrom may have one or more chiral centers, and therefore can exist as enantiomers and/or diastereomers. The invention is understood to extend to and embrace all such enantiomers, diastereomers and mixtures thereof, including but not limited to racemates. It is understood that compounds of Formula 2a and formulae used throughout this disclosure are intended to represent all individual enantiomers and mixtures thereof, unless stated or shown otherwise.

Some embodiments of the present invention pertain to compounds of Formula 2c:

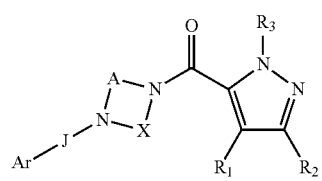

2c

Some embodiments of the present invention pertain to compounds of Formula 2e:

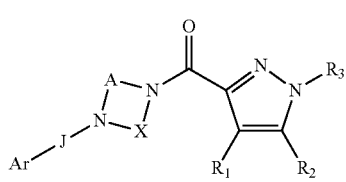

2e

In some embodiments, each $R_1$ and $R_2$ is selected independently from the group consisting of H, $C_1$-$C_6$ alkyl, $C_1$-$C_6$ alkylaryl, aryl, $C_3$-$C_7$ cycloalkyl, $C_1$-$C_6$ haloalkyl, halogen, heteroaryl, and nitro.

In some embodiments, $R_1$ and $R_2$ is selected independently from the group consisting of H, methyl, ethyl, isopropyl, t-butyl, 2-methylphenyl, phenyl, cyclopropyl, trifluoromethyl, fluoro, chloro, bromo, iodo, furan-2-yl and nitro.

In some embodiments, $R_1$ is H, halogen or $C_1$-$C_6$ alkylaryl; and $R_2$ is H, $C_1$-$C_6$ alkyl, aryl, $C_3$-$C_7$ cycloalkyl, $C_1$-$C_6$ haloalkyl, heteroaryl or nitro.

In some embodiments, $R_1$ is H, fluoro, chloro, bromo, iodo or 2-methylphenyl and $R_2$ is H, methyl, ethyl, isopropyl, t-butyl, phenyl, cyclopropyl, trifluoromethyl, furan-2-yl or nitro.

In some embodiments, $R_1$ and $R_2$ together with the carbon atoms to which they are bonded form a $C_3$-$C_7$ carbocyclyl.

In some embodiments, $R_1$ and $R_2$ together with the carbon atoms to which they are bonded form a $C_5$ carbocyclyl.

In some embodiments, $R_3$ is selected from the group consisting of H, $C_1$-$C_6$ alkyl and aryl; and wherein aryl is optionally substituted with $C_1$-$C_6$ alkoxy.

In some embodiments, $R_3$ is selected from the group consisting of H, $C_1$-$C_6$ alkyl and aryl; and wherein aryl is optionally substituted with methoxy.

In some embodiments, $R_3$ is selected from the group consisting of H, methyl, ethyl, t-butyl, phenyl and 4-methoxyphenyl.

In some embodiments, A and X are each —$CH_2CH_2$—, each optionally substituted with $C_1$-$C_3$ alkyl.

In some embodiments, A and X are each —$CH_2CH_2$—, each optionally substituted with methyl.

In some embodiments, A and X are each independently —$CH_2CH_2$— or —$CH(CH_3)CH_2$—.

In some embodiments, J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl.

In some embodiments, J is —$CH_2CH_2$— optionally substituted with 1, 2, 3 or 4 substituents selected independently from the group consisting of methyl, hydroxyl, oxo and =$NOCH_3$.

In some embodiments, J is —$CH_2CH_2$—, —C(=$NOCH_3$)$CH_2$—, —C=$OCH_2$—, —$CH(CH_3)CH_2$—, —$C(CH_3)_2CH_2$—, or —$CHOHCH_2$—.

In some embodiments, Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

In some embodiments, Ar is aryl or heteroaryl each optionally substituted with 1, 2, 3, 4 or 5 substituents selected independently from the group consisting of methoxy, methanesulfonyl, trifluoromethoxy, trifluoromethyl, fluoro, chloro and pyrrolidin-1-yl.

In some embodiments, Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

Some embodiments of the present invention pertain to compounds of Formula 2c:

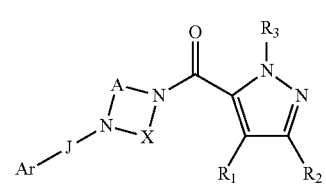

2c or a pharmaceutically acceptable salt, solvate or hydrate thereof;

wherein:
$R_1$ is H, halogen or $C_1$-$C_6$ alkylaryl;
$R_2$ is H, $C_1$-$C_6$ alkyl, aryl, $C_3$-$C_7$ cycloalkyl, $C_1$-$C_6$ haloalkyl, heteroaryl, or nitro; or
$R_1$ and $R_2$ together with the carbon atoms to which they are bonded form a $C_3$-$C_7$ carbocyclyl;
$R_3$ is H, $C_1$-$C_6$ alkyl, aryl, or aryl substituted with $C_1$-$C_6$ alkoxy;
A and X are each —$CH_2CH_2$—, each optionally substituted with $C_1$-$C_3$ alkyl;
J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl; and
Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

Some embodiments of the present invention pertain to compounds of Formula 2c:

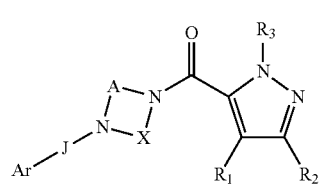

2c or a pharmaceutically acceptable salt, solvate or hydrate thereof;

wherein:
$R_1$ is H, fluoro, chloro, bromo, iodo or 2-methylphenyl;
$R_2$ is H, methyl, ethyl, isopropyl, t-butyl, phenyl, cyclopropyl, trifluoromethyl, furan-2-yl or nitro; or
$R_1$ and $R_2$ together with the carbon atoms to which they are bonded form a $C_5$ carbocyclyl;
$R_3$ is H, methyl, ethyl, t-butyl, phenyl or 4-methoxyphenyl;
A and X are each independently —$CH_2CH_2$— or —$CH(CH_3)CH_2$—;
J is —$CH_2CH_2$—, —C(=NOMe)$CH_2$—, —C=$OCH_2$—, —$CH(CH_3)CH_2$—, —$C(CH_3)_2CH_2$—, or —$CHOHCH_2$—; and
Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

Some embodiments of the present invention pertain to compounds of Formula 2e:

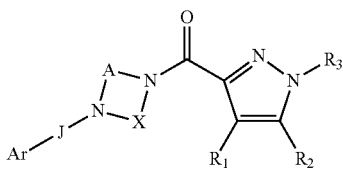

2e or a pharmaceutically acceptable salt, solvate or hydrate thereof;

wherein:

$R_1$ is H, halogen or $C_1$-$C_6$ alkylaryl;

$R_2$ is H, $C_1$-$C_6$ alkyl, aryl, $C_3$-$C_7$ cycloalkyl, $C_1$-$C_6$ haloalkyl, heteroaryl, or nitro; or $R_1$ and $R_2$ together with the carbon atoms to which they are bonded form a $C_3$-$C_7$ carbocyclyl;

$R_3$ is H, $C_1$-$C_6$ alkyl, aryl, or aryl substituted with $C_1$-$C_6$ alkoxy;

A and X are each —$CH_2CH_2$—, each optionally substituted with $C_1$-$C_3$ alkyl;

J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl; and Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

Some embodiments of the present invention pertain to compounds of Formula 2e:

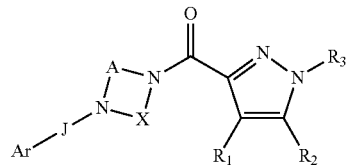

2e or a pharmaceutically acceptable salt, solvate or hydrate thereof;

wherein:

$R_1$ is H, fluoro, chloro, bromo, iodo or 2-methylphenyl;

$R_2$ is H, methyl, ethyl, isopropyl, t-butyl, phenyl, cyclopropyl, trifluoromethyl, furan-2-yl or nitro; or $R_1$ and $R_2$ together with the carbon atoms to which they are bonded form a $C_5$ carbocyclyl;

$R_3$ is H, methyl, ethyl, t-butyl, phenyl or 4-methoxyphenyl;

A and X are each independently —$CH_2CH_2$— or —CH($CH_3$)$CH_2$—;

J is —$CH_2CH_2$—, —C(=NOMe)$CH_2$—, —C=O$CH_2$—, —CH($CH_3$)$CH_2$—, —C($CH_3$)$_2$$CH_2$—, or —CHOH$CH_2$—; and Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

In some embodiments, where $R_1$, $R_2$ and $R_3$ are all H; and A and X are both —$CH_2CH_2$—; and J is (CO)$_2$; then Ar is a moiety other than heteroaryl substituted with halogen.

Some embodiments of the present invention include every combination of one or more compounds selected from the following group shown in TABLE 4.

TABLE 4

| Cmpd No. | Chemical Structure | Chemical Name |
| --- | --- | --- |
| 1 | 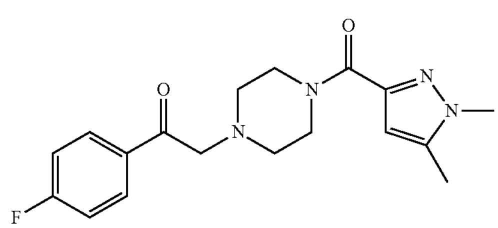 [SMILES: Cc1cc(C(=O)N2CCN(CC(=O)c3ccc(F)cc3)CC2)nn1C] | 2-[4-(1,5-Dimethyl-1H-pyrazole-3-carbonyl)-piperazin-1-yl]-1-(4-fluoro-phenyl)-ethanone |
| 2 | 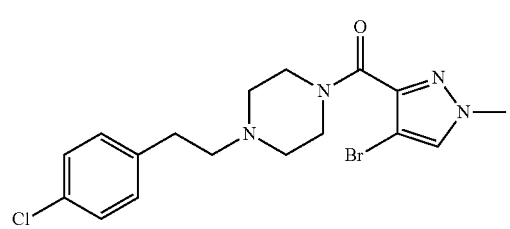 [SMILES: Cn1cc(Br)c(C(=O)N2CCN(CCc3ccc(Cl)cc3)CC2)n1] | (4-Bromo-1-methyl-1H-pyrazol-3-yl)-{4-[2-(4-chloro-phenyl)-ethyl]-piperazin-1-yl}-methanone |
| 3 | 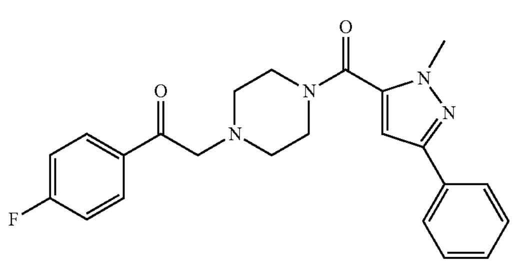 [SMILES: Cn1nc(-c2ccccc2)cc1C(=O)N1CCN(CC(=O)c2ccc(F)cc2)CC1] | 1-(4-Fluoro-phenyl)-2-[4-(2-methyl-5-phenyl-2H-pyrazole-3-carbonyl)-piperazin-1-yl]-ethanone |

TABLE 4-continued

| Cmpd No. | Chemical Structure | Chemical Name |
| --- | --- | --- |
| 4 | 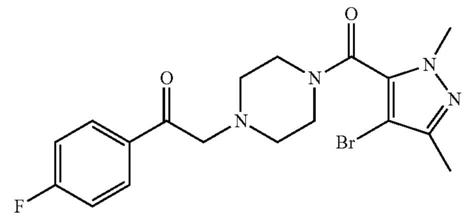 [SMILES: Cc1nn(C)c(C(=O)N2CCN(CC(=O)c3ccc(F)cc3)CC2)c1Br] | 2-[4-(4-Bromo-2,5-dimethyl-2H-pyrazole-3-carbonyl)-piperazin-1-yl]-1-(4-fluoro-phenyl)-ethanone |
| 5 | 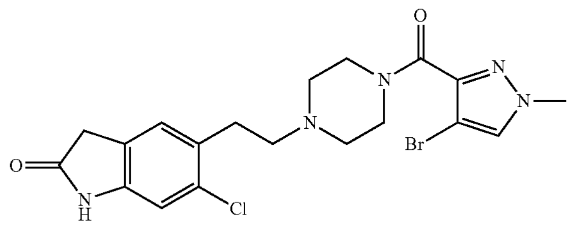 [SMILES: Cn1cc(Br)c(C(=O)N2CCN(CCc3cc4c(cc3Cl)NC(=O)C4)CC2)n1] | 5-{2-[4-(4-Bromo-1-methyl-1H-pyrazole-3-carbonyl)-piperazin-1-yl]-ethyl}-6-chloro-1,3-dihydro-indol-2-one |
| 6 | 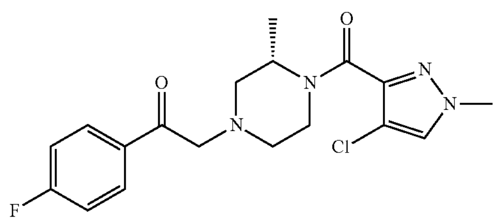 [SMILES: C[C@H]1CN(CC(=O)c2ccc(F)cc2)CCN1C(=O)c1nn(C)cc1Cl] | 2-[(S)-4-(4-Chloro-1-methyl-1H-pyrazole-3-carbonyl)-3-methyl-piperazin-1-yl]-1-(4-fluoro-phenyl)-ethanone |
| 7 | 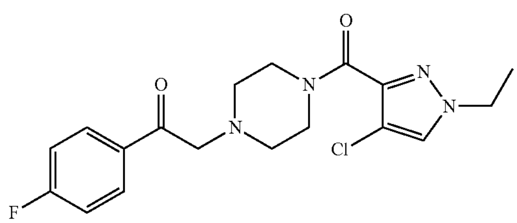 [SMILES: CCn1cc(Cl)c(C(=O)N2CCN(CC(=O)c3ccc(F)cc3)CC2)n1] | 2-[4-(4-Chloro-1-ethyl-1H-pyrazole-3-carbonyl)-piperazin-1-yl]-1-(4-fluoro-phenyl)-ethanone |
| 8 | 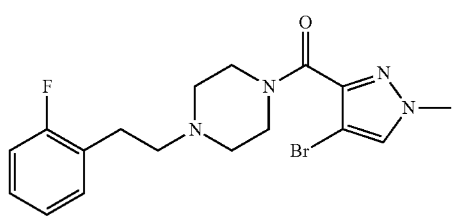 [SMILES: Cn1cc(Br)c(C(=O)N2CCN(CCc3ccccc3F)CC2)n1] | (4-Bromo-1-methyl-1H-pyrazol-3-yl)-{4-[2-(2-fluoro-phenyl)-ethyl]-piperazin-1-yl}-methanone |
| 9 | 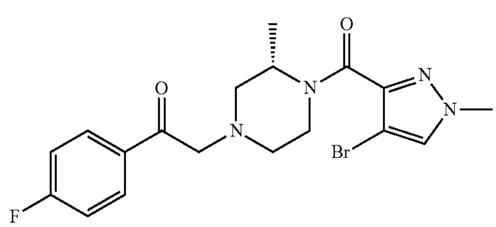 [SMILES: C[C@H]1CN(CC(=O)c2ccc(F)cc2)CCN1C(=O)c1nn(C)cc1Br] | 2-[(S)-4-(4-Bromo-1-methyl-1H-pyrazole-3-carbonyl)-3-methyl-piperazin-1-yl]-1-(4-fluoro-phenyl)-ethanone |
| 10 | 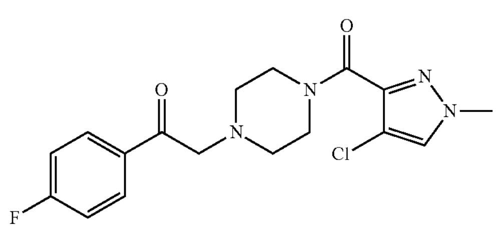 [SMILES: Cn1cc(Cl)c(C(=O)N2CCN(CC(=O)c3ccc(F)cc3)CC2)n1] | 2-[4-(4-Chloro-1-methyl-1H-pyrazole-3-carbonyl)-piperazin-1-yl]-1-(4-fluoro-phenyl)-ethanone |

TABLE 4-continued

| Cmpd No. | Chemical Structure | Chemical Name |
|---|---|---|
| 11 | 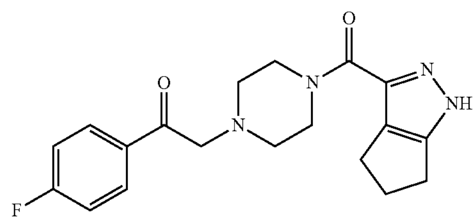 [SMILES: O=C(CN1CCN(C(=O)c2n[nH]c3c2CCC3)CC1)c1ccc(F)cc1] | 1-(4-Fluoro-phenyl)-2-[4-(1,4,5,6-tetrahydro-cyclopentapyrazole-3-carbonyl)-piperazin-1-yl]-ethanone |
| 12 | 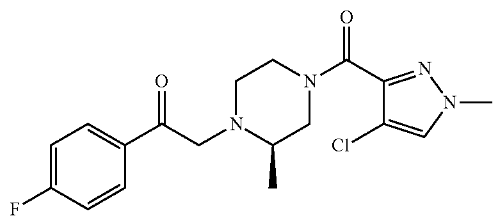 [SMILES: C[C@@H]1CN(C(=O)c2nn(C)cc2Cl)CCN1CC(=O)c1ccc(F)cc1] | 2-[(R)-4-(4-Chloro-1-methyl-1H-pyrazole-3-carbonyl)-2-methyl-piperazin-1-yl]-1-(4-fluoro-phenyl)-ethanone |
| 13 | 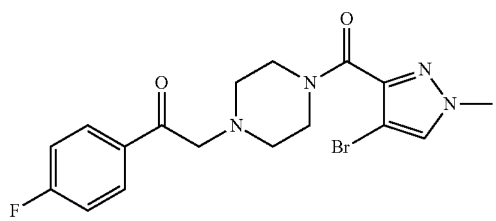 [SMILES: Cn1cc(Br)c(C(=O)N2CCN(CC(=O)c3ccc(F)cc3)CC2)n1] | 2-[4-(4-Bromo-1-methyl-1H-pyrazole-3-carbonyl)-piperazin-1-yl]-1-(4-fluoro-phenyl)-ethanone |
| 14 | 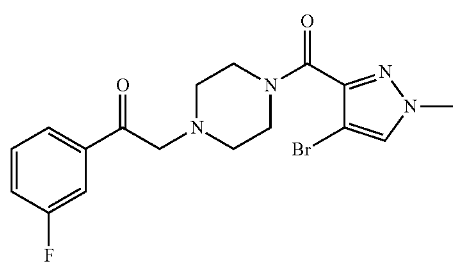 [SMILES: Cn1cc(Br)c(C(=O)N2CCN(CC(=O)c3cccc(F)c3)CC2)n1] | 2-[4-(4-Bromo-1-methyl-1H-pyrazole-3-carbonyl)-piperazin-1-yl]-1-(3-fluoro-phenyl)-ethanone |
| 15 | 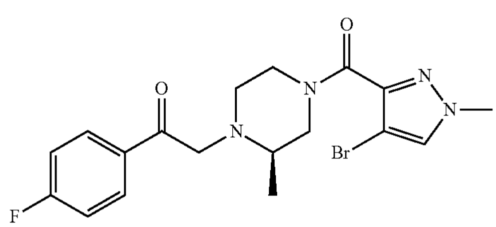 [SMILES: C[C@@H]1CN(C(=O)c2nn(C)cc2Br)CCN1CC(=O)c1ccc(F)cc1] | 2-[(R)-4-(4-Bromo-1-methyl-1H-pyrazole-3-carbonyl)-2-methyl-piperazin-1-yl]-1-(4-fluoro-phenyl)-ethanone |
| 16 | 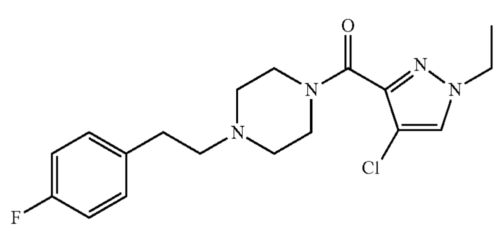 [SMILES: CCn1cc(Cl)c(C(=O)N2CCN(CCc3ccc(F)cc3)CC2)n1] | (4-Chloro-1-ethyl-1H-pyrazol-3-yl)-{4-[2-(4-fluoro-phenyl)-ethyl]-piperazin-1-yl}-methanone |
| 17 | 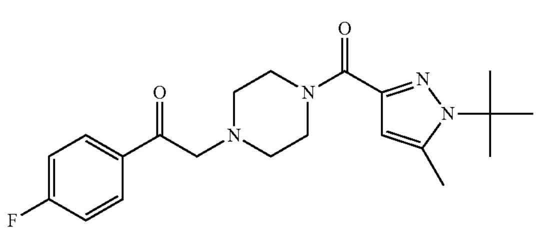 [SMILES: Cc1cc(C(=O)N2CCN(CC(=O)c3ccc(F)cc3)CC2)nn1C(C)(C)C] | 2-[4-(1-tert-Butyl-5-methyl-1H-pyrazole-3-carbonyl)-piperazin-1-yl]-1-(4-fluoro-phenyl)-ethanone |

TABLE 4-continued

| Cmpd No. | Chemical Structure | Chemical Name |
| --- | --- | --- |
| 18 | 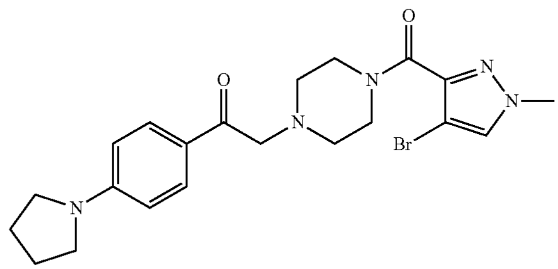 [SMILES: Cn1cc(Br)c(C(=O)N2CCN(CC(=O)c3ccc(N4CCCC4)cc3)CC2)n1] | 2-[4-(4-Bromo-1-methyl-1H-pyrazole-3-carbonyl)-piperazin-1-yl]-1-(4-pyrrolidin-1-yl-phenyl)-ethanone |
| 19 | 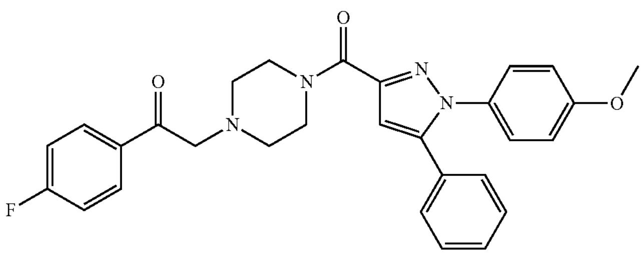 [SMILES: COc1ccc(-n2nc(C(=O)N3CCN(CC(=O)c4ccc(F)cc4)CC3)cc2-c2ccccc2)cc1] | 1-(4-Fluoro-phenyl)-2-{4-[1-(4-methoxy-phenyl)-5-phenyl-1H-pyrazole-3-carbonyl]-piperazin-1-yl}-ethanone |
| 20 | 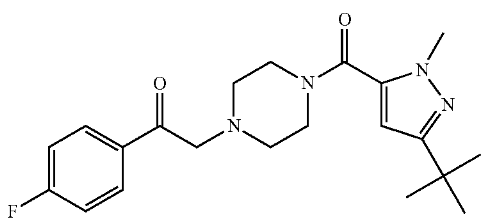 [SMILES: Cn1nc(C(C)(C)C)cc1C(=O)N1CCN(CC(=O)c2ccc(F)cc2)CC1] | 2-[4-(5-tert-Butyl-2-methyl-2H-pyrazole-3-carbonyl)-piperazin-1-yl]-1-(4-fluoro-phenyl)-ethanone |
| 21 | 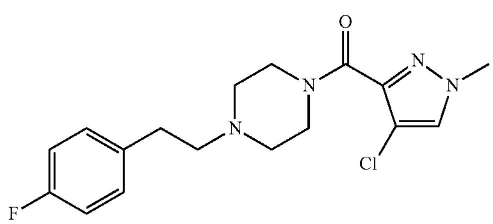 [SMILES: Cn1cc(Cl)c(C(=O)N2CCN(CCc3ccc(F)cc3)CC2)n1] | (4-Chloro-1-methyl-1H-pyrazol-3-yl)-{4-[2-(4-fluoro-phenyl)-ethyl]-piperazin-1-yl}-methanone |
| 22 | 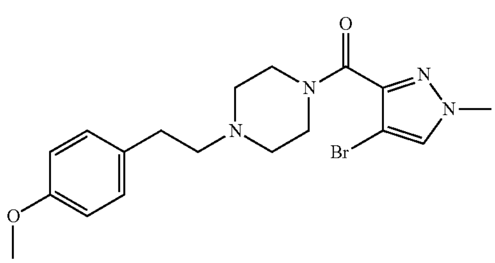 [SMILES: COc1ccc(CCN2CCN(C(=O)c3nn(C)cc3Br)CC2)cc1] | (4-Bromo-1-methyl-1H-pyrazol-3-yl)-{4-[2-(4-methoxy-phenyl)-ethyl]-piperazin-1-yl}-methanone |
| 23 | 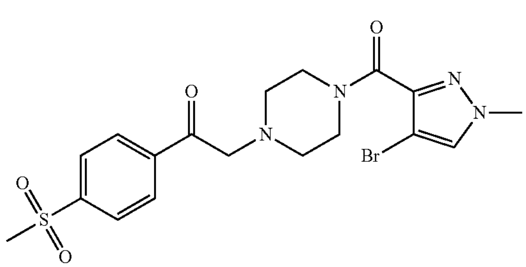 | 2-[4-(4-Bromo-1-methyl-1H-pyrazole-3-carbonyl)-piperazin-1-yl]-1-(4-methanesulfonyl-phenyl)-ethanone |

TABLE 4-continued

| Cmpd No. | Chemical Structure | Chemical Name |
|---|---|---|
| 24 | 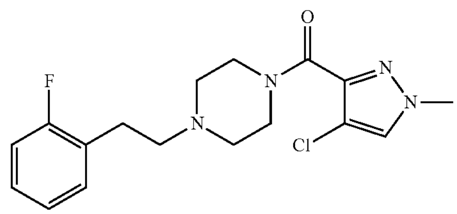 [SMILES: Cn1cc(Cl)c(C(=O)N2CCN(CCc3ccccc3F)CC2)n1] | (4-Chloro-1-methyl-1H-pyrazol-3-yl)-{4-[2-(2-fluoro-phenyl)-ethyl]-piperazin-1-yl}-methanone |
| 25 | 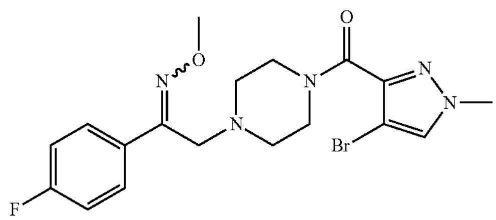 [SMILES: CON=C(CN1CCN(C(=O)c2nn(C)cc2Br)CC1)c1ccc(F)cc1] | 2-[4-(4-Bromo-1-methyl-1H-pyrazole-3-carbonyl)-piperazin-1-yl]-1-(4-fluoro-phenyl)-ethanone O-methyl-oxime |
| 26 | 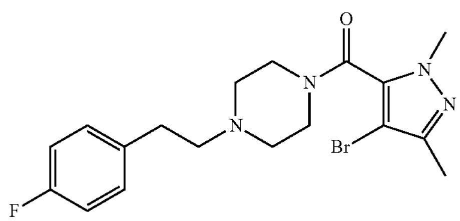 [SMILES: Cc1nn(C)c(C(=O)N2CCN(CCc3ccc(F)cc3)CC2)c1Br] | (4-Bromo-2,5-dimethyl-2H-pyrazol-3-yl)-{4-[2-(4-fluoro-phenyl)-ethyl]-piperazin-1-yl}-methanone |
| 27 | 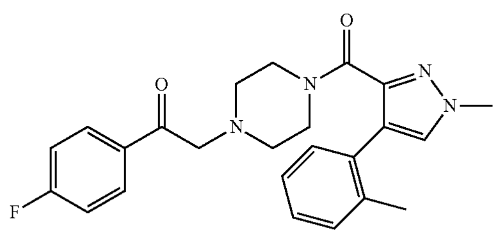 [SMILES: Cc1ccccc1-c1cn(C)nc1C(=O)N1CCN(CC(=O)c2ccc(F)cc2)CC1] | 1-(4-Fluoro-phenyl)-2-[4-(1-methyl-4-o-tolyl-1H-pyrazole-3-carbonyl)-piperazin-1-yl]-ethanone |
| 28 | 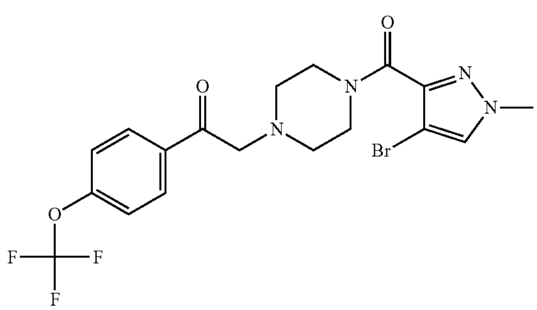 [SMILES: Cn1cc(Br)c(C(=O)N2CCN(CC(=O)c3ccc(OC(F)(F)F)cc3)CC2)n1] | 2-[4-(4-Bromo-1-methyl-1H-pyrazole-3-carbonyl)-piperazin-1-yl]-1-(4-trifluoromethoxy-phenyl)-ethanone |
| 29 | 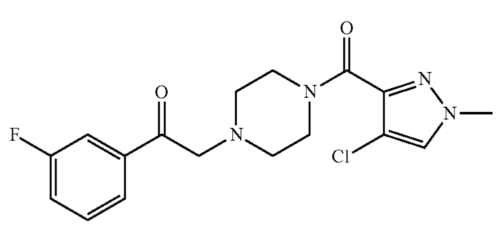 [SMILES: Cn1cc(Cl)c(C(=O)N2CCN(CC(=O)c3cccc(F)c3)CC2)n1] | 2-[4-(4-Chloro-1-methyl-1H-pyrazole-3-carbonyl)-piperazin-1-yl]-1-(3-fluoro-phenyl)-ethanone |

TABLE 4-continued

| Cmpd No. | Chemical Structure | Chemical Name |
| --- | --- | --- |
| 30 | 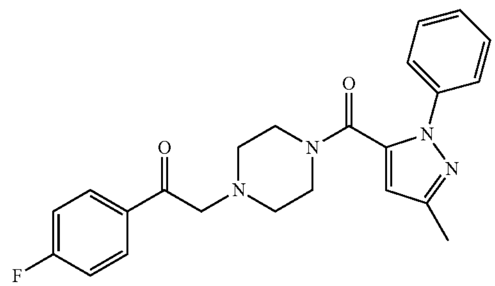 [SMILES: Cc1cc(C(=O)N2CCN(CC(=O)c3ccc(F)cc3)CC2)n(-c2ccccc2)n1] | 1-(4-Fluoro-phenyl)-2-[4-(5-methyl-2-phenyl-2H-pyrazole-3-carbonyl)-piperazin-1-yl]-ethanone |
| 31 | 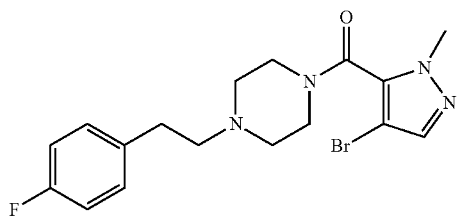 [SMILES: Cn1ncc(Br)c1C(=O)N1CCN(CCc2ccc(F)cc2)CC1] | (4-Bromo-2-methyl-2H-pyrazol-3-yl)-{4-[2-(4-fluoro-phenyl)-ethyl]-piperazin-1-yl}-methanone |
| 32 | 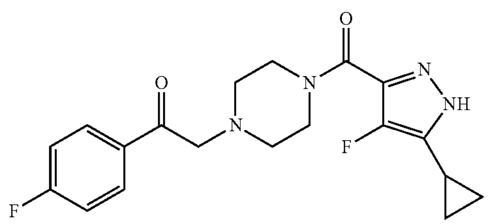 [SMILES: O=C(CN1CCN(C(=O)c2n[nH]c(C3CC3)c2F)CC1)c1ccc(F)cc1] | 2-[4-(5-Cyclopropyl-4-fluoro-1H-pyrazole-3-carbonyl)-piperazin-1-yl]-1-(4-fluorophenyl)-ethanone |
| 33 | 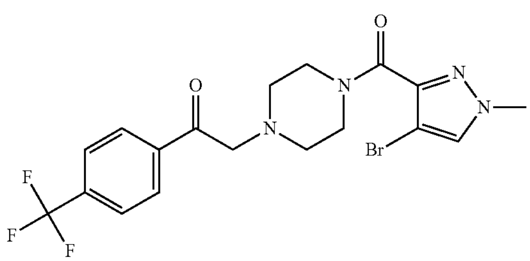 [SMILES: Cn1cc(Br)c(C(=O)N2CCN(CC(=O)c3ccc(C(F)(F)F)cc3)CC2)n1] | 2-[4-(4-Bromo-1-methyl-1H-pyrazole-3-carbonyl)-piperazin-1-yl]-1-(4-trifluoromethyl-phenyl)-ethanone |
| 34 | 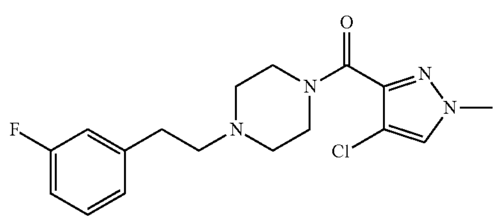 [SMILES: Cn1cc(Cl)c(C(=O)N2CCN(CCc3cccc(F)c3)CC2)n1] | (4-Chloro-1-methyl-1H-pyrazol-3-yl)-{4-[2-(3-fluoro-phenyl)-ethyl]-piperazin-1-yl}-methanone |
| 35 | 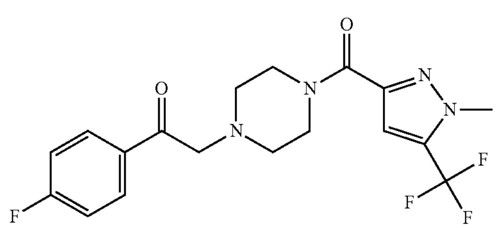 [SMILES: Cn1nc(C(=O)N2CCN(CC(=O)c3ccc(F)cc3)CC2)cc1C(F)(F)F] | 1-(4-Fluoro-phenyl)-2-[4-(1-methyl-5-trifluoromethyl-1H-pyrazole-3-carbonyl)-piperazin-1-yl]-ethanone |

TABLE 4-continued

| Cmpd No. | Chemical Structure | Chemical Name |
| --- | --- | --- |
| 36 | 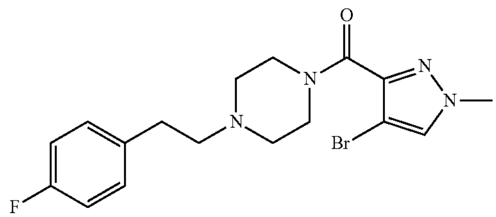 [SMILES: Cn1cc(Br)c(C(=O)N2CCN(CCc3ccc(F)cc3)CC2)n1] | (4-Bromo-1-methyl-1H-pyrazol-3-yl)-{4-[2-(4-fluoro-phenyl)-ethyl]-piperazin-1-yl}-methanone |
| 37 | 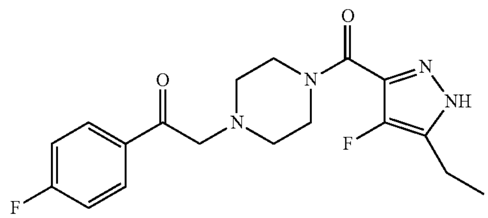 [SMILES: CCc1[nH]nc(C(=O)N2CCN(CC(=O)c3ccc(F)cc3)CC2)c1F] | 2-[4-(5-Ethyl-4-fluoro-1H-pyrazole-3-carbonyl)-piperazin-1-yl]-1-(4-fluoro-phenyl)-ethanone |
| 38 | 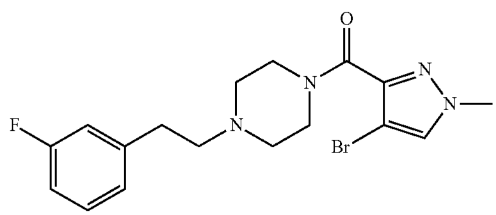 [SMILES: Cn1cc(Br)c(C(=O)N2CCN(CCc3cccc(F)c3)CC2)n1] | (4-Bromo-1-methyl-1H-pyrazol-3-yl)-{4-[2-(3-fluoro-phenyl)-ethyl]-piperazin-1-yl)-methanone |
| 39 | 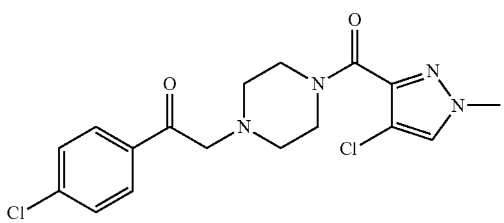 | 2-[4-(4-Chloro-1-methyl-1H-pyrazole-3-carbonyl)-piperazin-1-yl]-1-(4-chloro-phenyl)-ethanone |
| 40 | 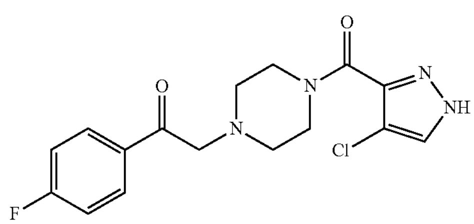 [SMILES: O=C(CN1CCN(C(=O)c2n[nH]cc2Cl)CC1)c1ccc(F)cc1] | 2-[4-(4-Chloro-1H-pyrazole-3-carbonyl)-piperazin-1-yl]-1-(4-fluoro-phenyl)-ethanone |
| 41 | 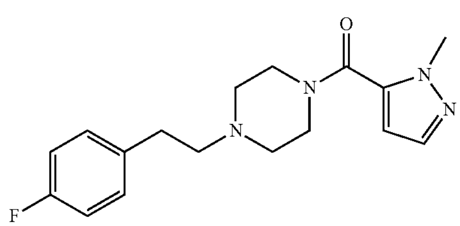 [SMILES: Cn1nccc1C(=O)N1CCN(CCc2ccc(F)cc2)CC1] | {4-[2-(4-Fluoro-phenyl)-ethyl]-piperazin-1-yl}-(2-methyl-2H-pyrazol-3-yl)-methanone |
| 42 | 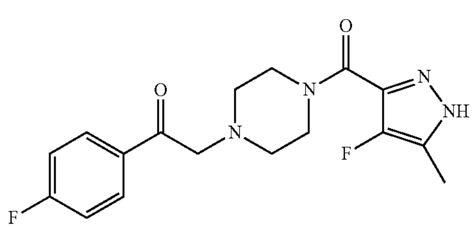 [SMILES: Cc1[nH]nc(C(=O)N2CCN(CC(=O)c3ccc(F)cc3)CC2)c1F] | 2-[4-(4-Fluoro-5-methyl-1H-pyrazole-3-carbonyl)-piperazin-1-yl]-1-(4-fluoro-phenyl)-ethanone |

TABLE 4-continued

| Cmpd No. | Chemical Structure | Chemical Name |
| --- | --- | --- |
| 43 | 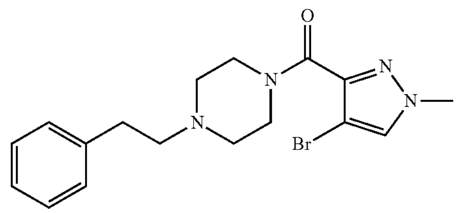 [SMILES: Cn1cc(Br)c(C(=O)N2CCN(CCc3ccccc3)CC2)n1] | (4-Bromo-1-methyl-1H-pyrazol-3-yl)-(4-phenethyl-piperazin-1-yl)-methanone |
| 44 | 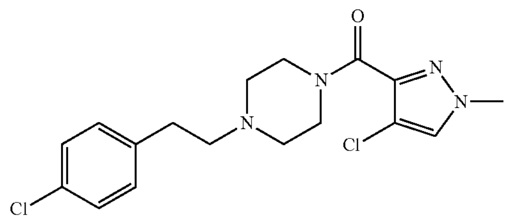 [SMILES: Cn1cc(Cl)c(C(=O)N2CCN(CCc3ccc(Cl)cc3)CC2)n1] | (4-Chloro-1-methyl-1H-pyrazol-3-yl)-{4-[2-(4-chloro-phenyl)-ethyl]-piperazin-1-yl}-methanone |
| 45 | 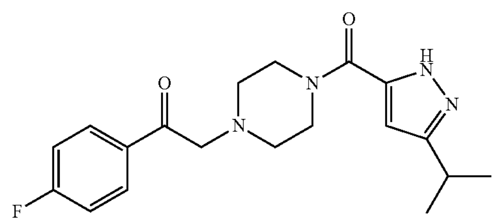 [SMILES: CC(C)c1cc(C(=O)N2CCN(CC(=O)c3ccc(F)cc3)CC2)[nH]n1] | 1-(4-Fluoro-phenyl)-2-[4-(5-isopropyl-2H-pyrazole-3-carbonyl)-piperazin-1-yl]-ethanone |
| 46 | 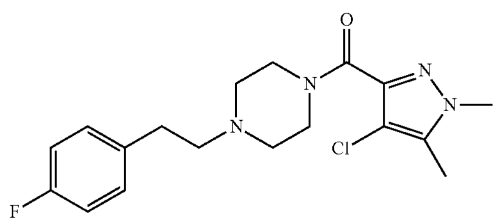 [SMILES: Cc1c(Cl)c(C(=O)N2CCN(CCc3ccc(F)cc3)CC2)nn1C] | (4-Chloro-1,5-dimethyl-1H-pyrazol-3-yl)-{4-[2-(4-fluoro-phenyl)-ethyl]-piperazin-1-yl}-methanone |
| 47 | 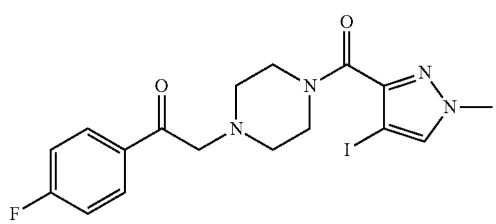 [SMILES: Cn1cc(I)c(C(=O)N2CCN(CC(=O)c3ccc(F)cc3)CC2)n1] | 1-(4-Fluoro-phenyl)-2-[4-(4-iodo-1-methyl-1H-pyrazole-3-carbonyl)-piperazin-1-yl]-ethanone |
| 48 | 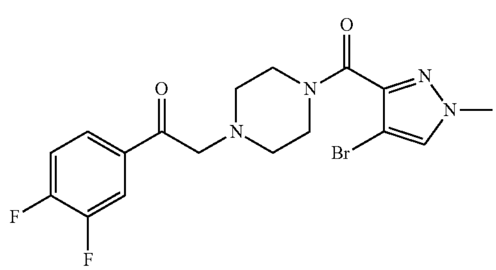 [SMILES: Cn1cc(Br)c(C(=O)N2CCN(CC(=O)c3ccc(F)c(F)c3)CC2)n1] | 2-[4-(4-Bromo-1-methyl-1H-pyrazole-3-carbonyl)-piperazin-1-yl]-1-(3,4-difluoro-phenyl)-ethanone |
| 49 | 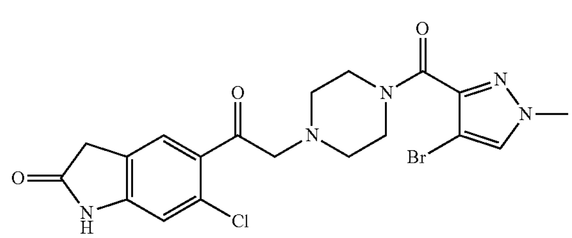 [SMILES: Cn1cc(Br)c(C(=O)N2CCN(CC(=O)c3cc4c(cc3Cl)NC(=O)C4)CC2)n1] | 5-{2-[4-(4-Bromo-1-methyl-1H-pyrazole-3-carbonyl)-piperazin-1-yl]-acetyl}-6-chloro-1,3-dihydro-indol-2-one |

TABLE 4-continued

| Cmpd No. | Chemical Structure | Chemical Name |
| --- | --- | --- |
| 50 | 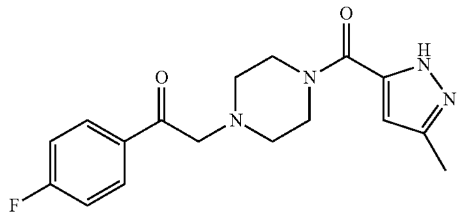 [SMILES: Cc1cc(C(=O)N2CCN(CC(=O)c3ccc(F)cc3)CC2)[nH]n1] | 1-(4-Fluoro-phenyl)-2-[4-(5-methyl-2H-pyrazole-3-carbonyl)-piperazin-1-yl]-ethanone |
| 51 | 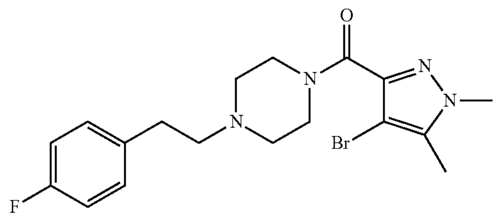 [SMILES: Cc1c(Br)c(C(=O)N2CCN(CCc3ccc(F)cc3)CC2)nn1C] | (4-Bromo-1,5-dimethyl-1H-pyrazol-3-yl)-{4-[2-(4-fluoro-phenyl)-ethyl]-piperazin-1-yl}-methanone |
| 52 | 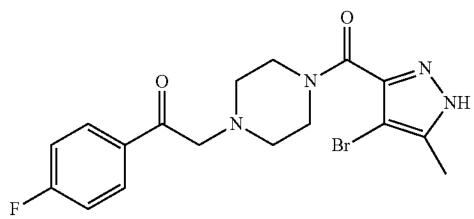 [SMILES: Cc1[nH]nc(C(=O)N2CCN(CC(=O)c3ccc(F)cc3)CC2)c1Br] | 2-[4-(4-Bromo-5-methyl-1H-pyrazole-3-carbonyl)-piperazin-1-yl]-1-(4-fluoro-phenyl)-ethanone |
| 53 | 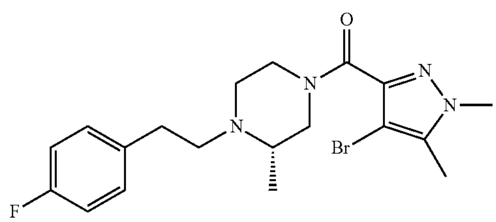 [SMILES: Cc1c(Br)c(C(=O)N2CCN(CCc3ccc(F)cc3)[C@@H](C)C2)nn1C] | (4-Bromo-1,5-dimethyl-1H-pyrazol-3-yl)-{(S)-4-[2-(4-fluoro-phenyl)-ethyl]-3-methyl-piperazin-1-yl}-methanone |
| 54 | 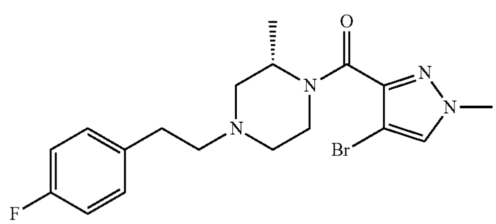 [SMILES: C[C@H]1CN(CCc2ccc(F)cc2)CCN1C(=O)c1nn(C)cc1Br] | (4-Bromo-1-methyl-1H-pyrazol-3-yl]-{(S)-4-[2-(4-fluoro-phenyl)-ethyl]-2-methyl-piperazin-1-yl}-methanone |
| 55 | 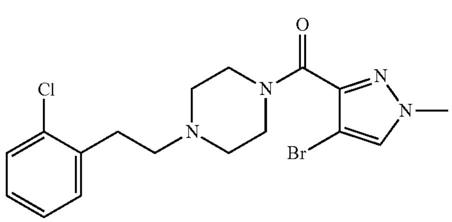 [SMILES: Cn1cc(Br)c(C(=O)N2CCN(CCc3ccccc3Cl)CC2)n1] | (4-Bromo-1-methyl-1H-pyrazol-3-yl)-{4-[2-(2-chloro-phenyl)-ethyl]-piperazin-1-yl}-methanone |
| 56 | 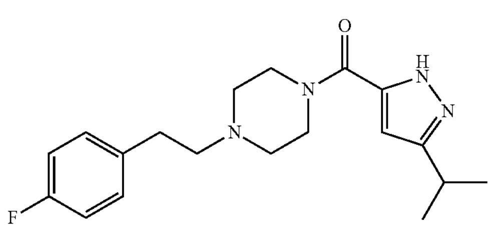 [SMILES: CC(C)c1cc(C(=O)N2CCN(CCc3ccc(F)cc3)CC2)[nH]n1] | {4-[2-(4-Fluoro-phenyl)-ethyl]-piperazin-1-yl}-(5-isopropyl-2H-pyrazol-3-yl)-methanone |

TABLE 4-continued

| Cmpd No. | Chemical Structure | Chemical Name |
|---|---|---|
| 57 | 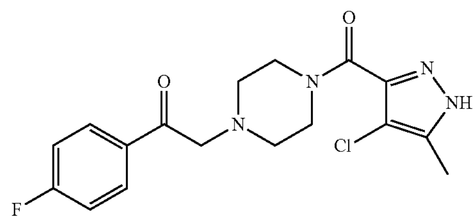 | 2-[4-(4-Chloro-5-methyl-1H-pyrazole-3-carbonyl)-piperazin-1-yl]-1-(4-fluoro-phenyl)-ethanone |
| 58 | 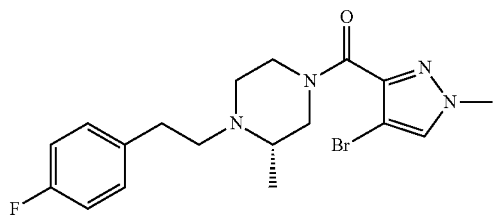 [SMILES: C[C@H]1CN(C(=O)c2nn(C)cc2Br)CCN1CCc1ccc(F)cc1] | (4-Bromo-1-methyl-1H-pyrazol-3-yl)-{(S)-4-[2-(4-fluoro-phenyl)-ethyl]-3-methyl-piperazin-1-yl}-methanone |
| 59 | 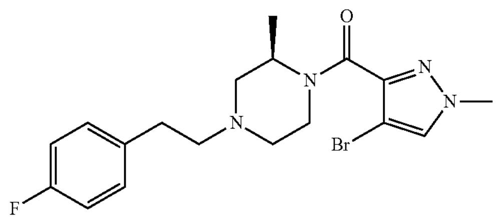 [SMILES: C[C@@H]1CN(CCc2ccc(F)cc2)CCN1C(=O)c1nn(C)cc1Br] | (4-Bromo-1-methyl-1H-pyrazol-3-yl)-{(R)-4-[2-(4-fluoro-phenyl)-ethyl]-2-methyl-piperazin-1-yl}-methanone |
| 60 | 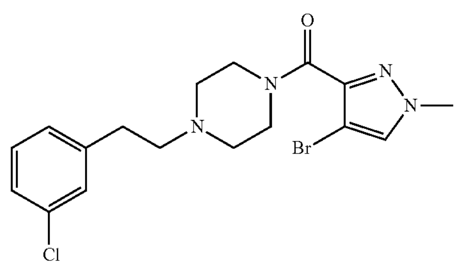 [SMILES: Cn1cc(Br)c(C(=O)N2CCN(CCc3cccc(Cl)c3)CC2)n1] | (4-Bromo-1-methyl-1H-pyrazol-3-yl)-{4-[2-(3-chloro-phenyl)-ethyl]-piperazin-1-yl}-methanone |
| 61 | 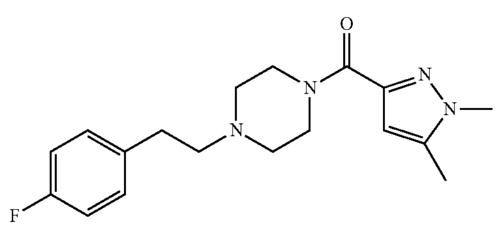 [SMILES: Cc1cc(C(=O)N2CCN(CCc3ccc(F)cc3)CC2)nn1C] | (1,5-Dimethyl-1H-pyrazol-3-yl)-{4-[2-(4-fluoro-phenyl)-ethyl]-piperazin-1-yl}-methanone |
| 62 | 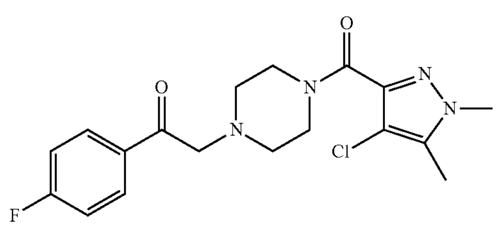 [SMILES: Cc1c(Cl)c(C(=O)N2CCN(CC(=O)c3ccc(F)cc3)CC2)nn1C] | 2-[4-(4-Chloro-1,5-dimethyl-1H-pyrazole-3-carbonyl)-piperazin-1-yl]-1-(4-fluoro-phenyl)-ethanone |
| 63 | 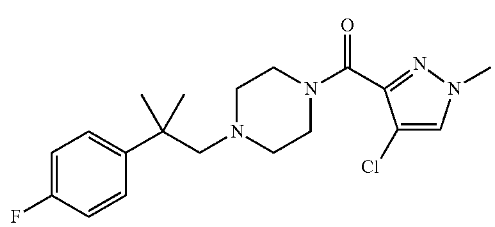 [SMILES: Cn1cc(Cl)c(C(=O)N2CCN(CC(C)(C)c3ccc(F)cc3)CC2)n1] | (4-Chloro-1-methyl-1H-pyrazol-3-yl)-{4-[2-(4-fluoro-phenyl)-2-methyl-propyl]-piperazin-1-yl}-methanone |

TABLE 4-continued

| Cmpd No. | Chemical Structure | Chemical Name |
| --- | --- | --- |
| 64 | 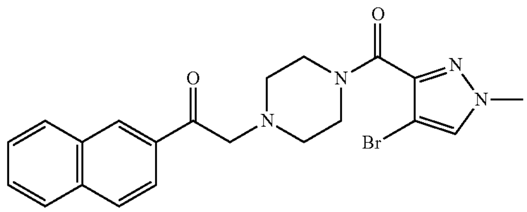 [SMILES: Cn1cc(Br)c(C(=O)N2CCN(CC(=O)c3ccc4ccccc4c3)CC2)n1] | 2-[4-(4-Bromo-1-methyl-1H-pyrazole-3-carbonyl)-piperazin-1-yl]-1-naphthalen-2-yl-ethanone |
| 65 | 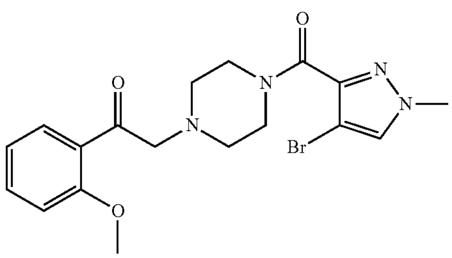 [SMILES: COc1ccccc1C(=O)CN1CCN(C(=O)c2nn(C)cc2Br)CC1] | 2-[4-(4-Bromo-1-methyl-1H-pyrazole-3-carbonyl)-piperazin-1-yl]-1-(2-methoxy-phenyl)-ethanone |
| 66 | 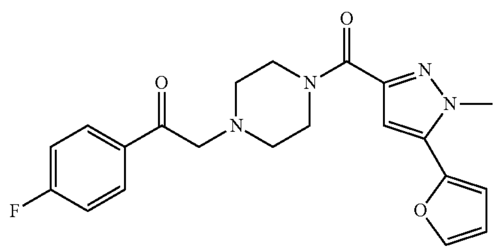 [SMILES: Cn1nc(C(=O)N2CCN(CC(=O)c3ccc(F)cc3)CC2)cc1-c1ccco1] | 1-(4-Fluoro-phenyl)-2-[4-(5-furan-2-yl-1-methyl-1H-pyrazole-3-carbonyl)-piperazin-1-yl]-ethanone |
| 67 | 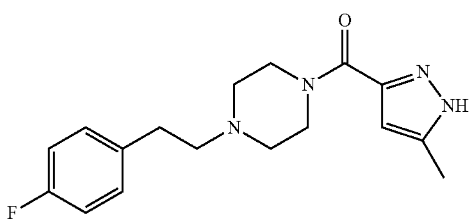 [SMILES: Cc1cc(C(=O)N2CCN(CCc3ccc(F)cc3)CC2)n[nH]1] | {4-[2-(4-Fluoro-phenyl)-ethyl]-piperazin-1-yl}-(5-methyl-1H-pyrazol-3-yl)-methanone |
| 68 | 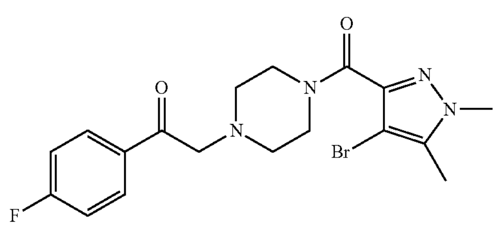 [SMILES: Cc1c(Br)c(C(=O)N2CCN(CC(=O)c3ccc(F)cc3)CC2)nn1C] | 2-[4-(4-Bromo-1,5-dimethyl-1H-pyrazole-3-carbonyl)-piperazin-1-yl]-1-(4-fluoro-phenyl)-ethanone |
| 69 | 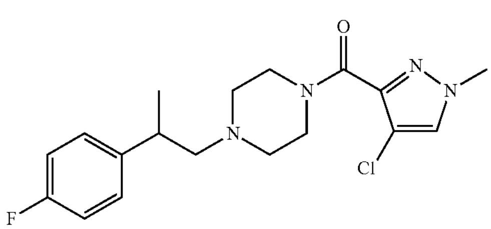 [SMILES: CC(CN1CCN(C(=O)c2nn(C)cc2Cl)CC1)c1ccc(F)cc1] | (4-Chloro-1-methyl-1H-pyrazol-3-yl)-{4-[2-(4-fluoro-phenyl)-propyl]-piperazin-1-yl}-methanone |

TABLE 4-continued

| Cmpd No. | Chemical Structure | Chemical Name |
| --- | --- | --- |
| 70 | 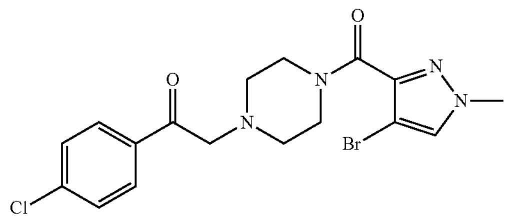 [SMILES: Cn1cc(Br)c(C(=O)N2CCN(CC(=O)c3ccc(Cl)cc3)CC2)n1] | 2-[4-(4-Bromo-1-methyl-1H-pyrazole-3-carbonyl)-piperazin-1-yl]-1-(4-chloro-phenyl)-ethanone |
| 71 | 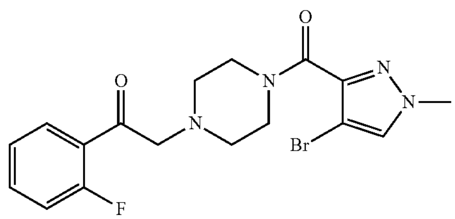 [SMILES: Cn1cc(Br)c(C(=O)N2CCN(CC(=O)c3ccccc3F)CC2)n1] | 2-[4-(4-Bromo-1-methyl-1H-pyrazole-3-carbonyl)-piperazin-1-yl]-1-(2-fluoro-phenyl)-ethanone |
| 72 | 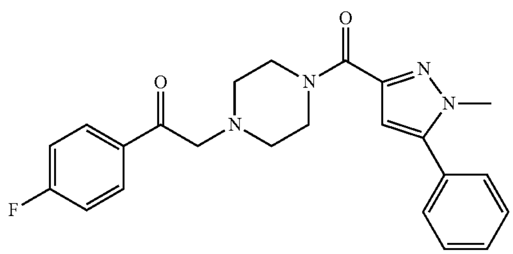 [SMILES: Cn1nc(C(=O)N2CCN(CC(=O)c3ccc(F)cc3)CC2)cc1-c1ccccc1] | 1-(4-Fluoro-phenyl)-2-[4-(1-methyl-5-phenyl-1H-pyrazole-3-carbonyl)-piperazin-1-yl]-ethanone |
| 73 | 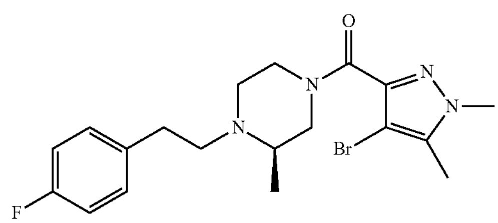 [SMILES: Cc1c(Br)c(C(=O)N2CCN(CCc3ccc(F)cc3)[C@H](C)C2)nn1C] | (4-Bromo-1,5-dimethyl-1H-pyrazol-3-yl)-{(R)-4-[2-(4-fluoro-phenyl)-ethyl]-3-methyl-piperazin-1-yl}-methanone |
| 74 | 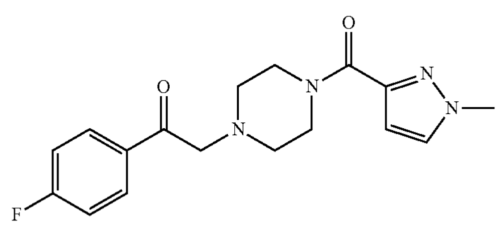 [SMILES: Cn1ccc(C(=O)N2CCN(CC(=O)c3ccc(F)cc3)CC2)n1] | 1-(4-Fluoro-phenyl)-2-[4-(1-methyl-1H-pyrazole-3-carbonyl)-piperazin-1-yl]-ethanone |
| 75 | 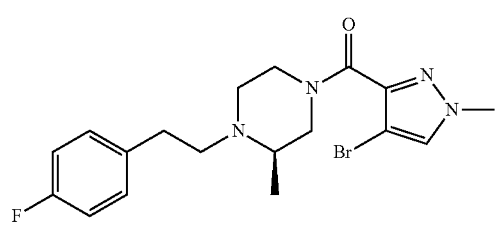 [SMILES: C[C@@H]1CN(C(=O)c2nn(C)cc2Br)CCN1CCc1ccc(F)cc1] | (4-Bromo-1-methyl-1H-pyrazol-3-yl)-{(R)-4-[2-(4-fluoro-phenyl)-ethyl]-3-methyl-piperazin-1-yl}-methanone |
| 76 | 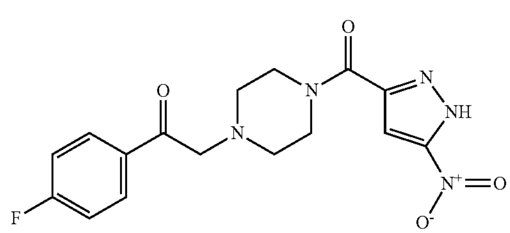 [SMILES: O=C(CN1CCN(C(=O)c2cc([N+](=O)[O-])[nH]n2)CC1)c1ccc(F)cc1] | 1-(4-Fluoro-phenyl)-2-[4-(5-nitro-1H-pyrazole-3-carbonyl)-piperazin-1-yl]-ethanone |

TABLE 4-continued

| Cmpd No. | Chemical Structure | Chemical Name |
|---|---|---|
| 77 | 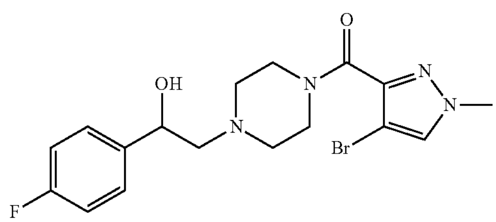 [SMILES: Cn1cc(Br)c(C(=O)N2CCN(CC(O)c3ccc(F)cc3)CC2)n1] | (4-Bromo-1-methyl-1H-pyrazol-3-yl)-{4-[2-(4-fluorophenyl)-2-hydroxy-ethyl]-piperazin-1-yl}-methanone |
| 78 | 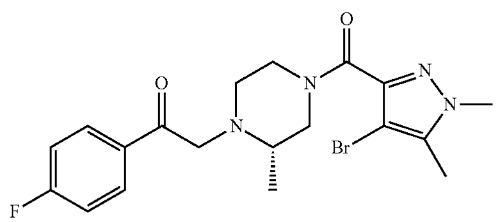 [SMILES: Cc1c(Br)c(C(=O)N2CCN(CC(=O)c3ccc(F)cc3)[C@@H](C)C2)nn1C] | 2-[(S)-4-(4-Bromo-1,5-dimethyl-1H-pyrazole-3-carbonyl)-2-methyl-piperazin-1-yl]-1-(4-fluoro-phenyl)-ethanone |
| 79 | 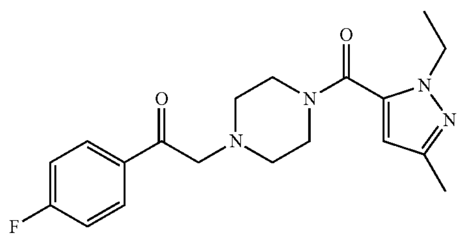 [SMILES: CCn1nc(C)cc1C(=O)N1CCN(CC(=O)c2ccc(F)cc2)CC1] | 2-[4-(2-Ethyl-5-methyl-2H-pyrazole-3-carbonyl)-piperazin-1-yl]-1-(4-fluoro-phenyl)-ethanone |
| 80 | 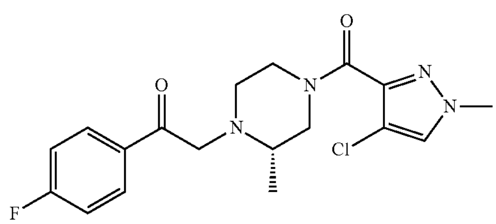 [SMILES: C[C@H]1CN(C(=O)c2nn(C)cc2Cl)CCN1CC(=O)c1ccc(F)cc1] | 2-[(S)-4-(4-Chloro-1-methyl-1H-pyrazole-3-carbonyl)-2-methyl-piperazin-1-yl]-1-(4-fluorophenyl)-ethanone |
| 81 | 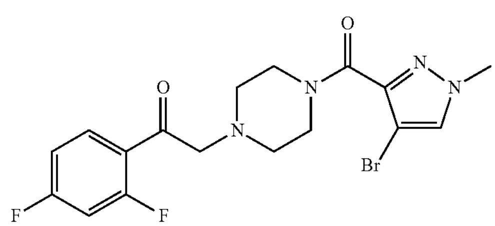 [SMILES: Cn1cc(Br)c(C(=O)N2CCN(CC(=O)c3ccc(F)cc3F)CC2)n1] | 2-[4-(4-Bromo-1-methyl-1H-pyrazole-3-carbonyl)-piperazin-1-yl]-1-(2,4-difluoro-phenyl)-ethanone |
| 82 | 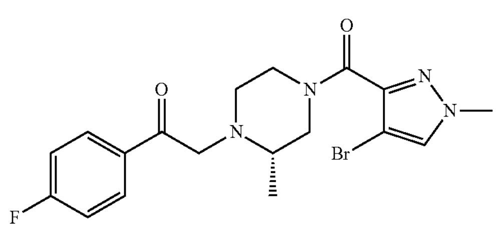 | 2-[(S)-4-(4-Bromo-1-methyl-1H-pyrazole-3-carbonyl)-2-methyl-piperazin-1-yl]-1-(4-fluoro-phenyl)-ethanone |
| 83 | 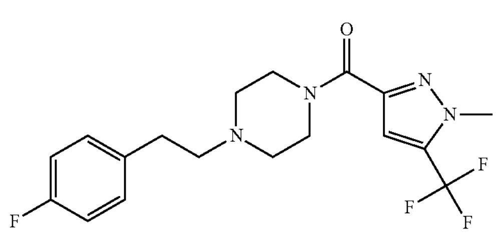 [SMILES: Cn1nc(C(=O)N2CCN(CCc3ccc(F)cc3)CC2)cc1C(F)(F)F] | {4-[2-(4-Fluoro-phenyl)-ethyl]-piperazin-1-yl}-(1-methyl-5-trifluoromethyl-1H-pyrazol-3-yl)-methanone |

TABLE 4-continued

| Cmpd No. | Chemical Structure | Chemical Name |
|---|---|---|
| 84 | 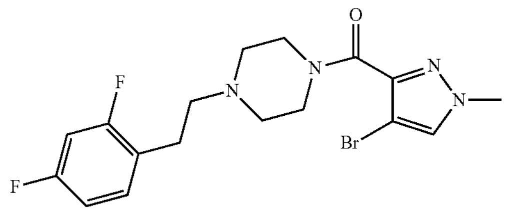 [SMILES: Cn1cc(Br)c(C(=O)N2CCN(CCc3ccc(F)cc3F)CC2)n1] | (4-Bromo-1-methyl-1H-pyrazol-3-yl)-{4-[2-(2,4-difluoro-phenyl)-ethyl]-piperazin-1-yl}-methanone |
| 85 | 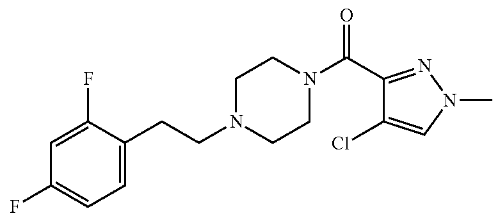 [SMILES: Cn1cc(Cl)c(C(=O)N2CCN(CCc3ccc(F)cc3F)CC2)n1] | (4-Chloro-1-methyl-1H-pyrazol-3-yl)-{4-[2-(2,4-difluoro-phenyl)-ethyl]-piperazin-1-yl}-methanone |

Additionally, individual compounds and chemical genera of the present invention, for example those compounds found in Table 4 including diastereomers and enantiomers thereof, encompass all pharmaceutically acceptable salts, solvates, and particularly hydrates, thereof.

Some embodiments of the present invention pertain to 1-[3-(4-Bromo-2-methyl-2H-pyrazol-3-yl)-4-methoxy-phenyl]-3-(2,4-difluoro-phenyl)-urea.

One aspect of the present invention relates to novel, solid-dosage formulations of 1-[3-(4-Bromo-2-methyl-2H-pyrazol-3-yl)-4-methoxy-phenyl]-3-(2,4-difluoro-phenyl)-urea which provide one or more of the following: (a) high oral-bioavailability, comparable to that of liquid formulations; (b) physical stability with respect to crystalline form; and (c) chemical stability better than that of liquid formulations. Consequently, the solid-dosage formulations disclosed herein are useful for treating certain 5-HT$_{2A}$ serotonin receptor-related disorders, such as REM sleep behavior disorder.

Some embodiments of the present invention pertain to N-(4-fluorophenylmethyl)-N-(1-methylpiperidin-4-yl)-N'-(4-(2-methylpropyloxy)phenylmethyl)carbamide or a pharmaceutically acceptable salt, hydrate, polymorph, or solvate thereof, which is also known as pimavanserin. Some embodiments of the present invention pertain to pruvanserin, eplivanserin, volinanserin, glemanserin, ketanserin, ritanserin, clozapine, or a pharmaceutically acceptable salt, hydrate, polymorph, or solvate thereof.

Additionally, compounds of the present invention, such as Formula (I) and related formulae, encompass all pharmaceutically acceptable salts, solvates, polymorphs, and particularly hydrates, thereof.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Prophylaxis and/or Treatment of REM Sleep Behavior Disorder

The normal sleep cycle is divided into 5 stages: Non-REM Stage 1, Non-REM Stage 2, Non-REM Stage 3, Non-REM Stage 4, and REM. Table 5 summarizes the characteristics of each stage.

TABLE 5

Sleep Stages

| Stage | Characteristics | Time spent | Sleep Disorder Associated with Stage |
|---|---|---|---|
| Awake (stage 0) | Eyes open, responsive to external stimuli, can hold intelligible conversation | 16-18 hours per day | Narcolepsy Hallucinations |
| Non-REM | | 4-7 hours per night | Insomnia NREM-related parasomnias: confusional arousals, sleep terror, somnambulism (sleepwalking) |
| *Stage 1- light sleep | Transition between waking and sleep, if awakened person will claim not asleep | | |

TABLE 5-continued

Sleep Stages

| Stage | Characteristics | Time spent | Sleep Disorder Associated with Stage |
|---|---|---|---|
| *Stage 2-light sleep | Main body of light sleep | | |
| *Stage 3 & 4-deep sleep | Slow (delta) waves on EEG readings, deepest and most restorative sleep | | |
| REM* (Rapid Eye Movement) | Brain waves similar to waking, most vivid dreams happen in this stage, body paralyzed | 90-120 minutes per night | REM Sleep Behavior Disorder |

*Cycle through 5 stages each night

Distinct Sleep Disorders are associated with Non-REM and REM, each with distinct pathophysiology. For example, somnambulism (sleepwalking) and related disorders are not related to dream enactment but occur following incomplete arousals from slow-wave sleep. All Non-REM parasomnias share a common pathophysiology that relies on the breakdown of the boundaries between the wakefulness and sleep regulatory systems during slow-wave sleep. Compared with Rapid Eye Movement (REM) Sleep Behavior Disorder (RBD) which occurs during REM sleep and can be related to dream enactment.

Dementia with Lewy bodies (DLB) is a progressive neurocognitive illness characterized pathologically by the presence of diffuse clusters comprised of alpha synuclein and other proteins that aggregate in the brain and disrupt cognitive function. DLB is considered to be the second most prevalent cause of degenerative dementia in the elderly population, accounting for up to 15%-25% of dementia presentations and 15%-20% of all autopsy confirmed dementias in old age. Between 50% and 80% of subjects with Parkinson's disease may experience dementia over the course of their illness. While few studies of the exact prevalence of DLB have been published, the Lewy Body Dementia Association estimates that 1.1 million individuals are affected by DLB in the U.S. alone. While cognitive dysfunction manifested as deficits and fluctuation in attention is a core component of DLB, subjects also exhibit prominent behavioral disturbances early in the disease, including RBD behaviors. RBD affects between 50% and 80% of patients with DLB and is characterized by the presence of abnormal behaviors and vocalizations during the phase of sleep associated with REM and during sleep phase transitions. While individuals are normally paralyzed during REM sleep, individuals with RBD lack muscle atonia during otherwise intact REM sleep. Hence, patients exhibit violent behaviors that mirror their dream content, including screaming and running during sleep, and kicking, punching, or strangling their bed partners. Patients have limited recall of these behaviors, which are often observed only by their bed partners. While the pathophysiology of RBD is poorly understood, the condition has been linked with visual hallucinations in Lewy body diseases. The presence of RBD has been associated with an increased risk of hallucinations and delusions in Parkinson's disease. Moreover, dream content during sleep-onset REM periods can resemble the content of daytime hallucinations, with patients reacting to the content of dreams that often involve themes of being chased or attacked. In addition, it has been shown that visual hallucinations can coincide with periods of REM. Thus, a drug that reduces visual hallucinations may also have the potential to reduce REM sleep behaviors. Despite the high prevalence of RBD and its dramatic impact on the quality of life of patients and their families, no medications are currently approved for its treatment. Indeed, there have been few randomized controlled trials to evaluate the efficacy and safety of drugs to treat RBD. Clonazepam, a long-acting benzodiazepine, is commonly used off-label to treat patients with RBD. The drug is associated with concerning side effects in elderly patients, including confusion, daytime sedation, and increased risk of falls. Moreover, the long-term use of benzodiazepines has been shown to be associated with cognitive impairment, a particularly concerning side effect in patients with dementia. There remains a significant unmet need for safe and effective new therapies for patients with RBD.

In addition to the foregoing beneficial uses for the modulators of $5-HT_{2A}$ receptor activity disclosed herein, the compounds disclosed herein are believed to be useful in the treatment of REM sleep behavior disorder, and in the amelioration of symptoms thereof.

Rapid eye movement (REM) sleep behavior disorder is a sleep disorder wherein subjects physically act out vivid, often unpleasant dreams with vocal sounds and sudden, often violent arm and leg movements during REM sleep, sometimes called dream-enacting behavior.

Subjects normally do not move during REM sleep, a normal stage of sleep that occurs many times during the night. About 20% of a subject's sleep is spent in REM sleep, the usual time for dreaming, which occurs primarily during the second half of the night. The onset of REM sleep behavior disorder is often sudden, and episodes may occur occasionally or several times a night. The disorder can get worse with time.

REM sleep behavior disorder often may be associated with other neurological conditions, such as Lewy body dementia (which includes dementia with Lewy bodies, Parkinson's disease dementia), Parkinson's disease or multiple system atrophy and Alzheimer's disease.

Representative Methods of the Invention

One aspect of the present invention encompasses methods for prophylaxis or treatment of REM sleep behavior disorder in an individual comprising administering to said individual in need thereof a therapeutically effective amount of a compound according to any of the embodiments described herein or a pharmaceutical composition. In some embodiments, the individual may also have another neurological condition, such as, but not limited to Lewy body dementia (which includes dementia with Lewy bodies), Parkinson's disease or multiple system atrophy.

One aspect of the present invention encompasses processes for preparing a composition comprising admixing a compound according to any embodiments described herein and a pharmaceutically acceptable carrier.

One aspect of the present invention is the use of a compound for the production of a medicament for use in the prophylaxis or treatment REM sleep behavior disorder.

One embodiment of the present invention is the use of a compound for the production of a medicament for use in the prophylaxis or treatment of REM sleep behavior disorder.

One aspect of the present invention are compounds according to any of the embodiments described herein for use in a method of treatment of the human or animal body by therapy.

One aspect of the present invention are compounds according to any of the embodiments described herein for use in a method for the prophylaxis or treatment of REM sleep behavior disorder, as described herein, in the human or animal body by therapy.

One aspect of the present invention pertains to pharmaceutical compositions comprising: (a) 1-[3-(4-bromo-2-methyl-2H-pyrazol-3-yl)-4-methoxy-phenyl]-3-(2,4-difluoro-phenyl)-urea; and (b) an excipient selected from: PVP and coPVP and their use in the treatment and prophylaxis of REM sleep behavior disorder.

One aspect of the present invention pertains to kits for the prophylaxis or treatment of REM sleep behavior disorder in an individual comprising a container and a pharmaceutical composition of the present invention.

One aspect of the present invention encompasses methods for the prophylaxis and/or treatment of REM sleep behavior disorder, idiopathic REM sleep behavior disorder, or a combination thereof, in an individual comprising administering to said individual in need thereof a therapeutically effective amount of a compound according to any of the embodiments described herein or a pharmaceutical composition.

Some embodiments are directed to methods for the prophylaxis and/or treatment of REM sleep behavior disorder, idiopathic REM sleep behavior disorder, or a combination thereof, in a subject in need thereof comprising administering to said subject a therapeutically effective amount of a 5-$HT_{2A}$ inverse agonist. In some embodiments, administration of a therapeutically effective amount of a 5-$HT_{2A}$ inverse agonist results in treatment, and/or prophylaxis of REM sleep behavior disorder, idiopathic REM sleep behavior disorder, or a combination thereof.

Some embodiments are directed to methods of decreasing the frequency, severity, or a combination thereof of REM sleep behavior disorder episodes in a subject in need thereof comprising administering to said subject a therapeutically effective amount of a 5-$HT_{2A}$ inverse agonist. Some embodiments are directed to methods of decreasing the frequency of abnormal vocalizations and motor behavior per sleep period in a subject in need thereof comprising administering to said subject a therapeutically effective amount of a 5-$HT_{2A}$ inverse agonist. Some embodiments are directed to methods of decreasing the amount of nightmare content per sleep period in a subject in need thereof comprising administering to said subject a therapeutically effective amount of a 5-$HT_{2A}$ inverse agonist. Some embodiments are directed to methods of decreasing the potential for injury or injury to said subject during a sleep period in a subject in need thereof comprising administering to said subject a therapeutically effective amount of a 5-$HT_{2A}$ inverse agonist. Some embodiments are directed to methods of increasing the quality of a subject's partner sleep comprising administering to said subject a therapeutically effective amount of a 5-$HT_{2A}$ inverse agonist. Some embodiments are directed to methods of improving subjective sleep quality, objective sleep quality measures, or a combination thereof, in a subject in need thereof, comprising administering to said subject a therapeutically effective amount of a 5-$HT_{2A}$ inverse agonist. Some embodiments are directed to methods of improving the clinician assessment of global change pertaining to REM sleep behavior disorder in a subject in need thereof, comprising administering to said subject a therapeutically effective amount of a 5-$HT_{2A}$ inverse agonist. Some embodiments are directed to methods of decreasing the frequency of REM sleep behavior disorder behaviors in a subject in need thereof, comprising administering to said subject a therapeutically effective amount of a 5-$HT_{2A}$ inverse agonist. Some embodiments are directed to methods of decreasing the severity of REM sleep behavior disorder behaviors in a subject in need thereof, comprising administering to said subject a therapeutically effective amount of a 5-$HT_{2A}$ inverse agonist. In some embodiments, REM sleep behavior disorder behaviors are selected from the group consisting of vocalizations, simple and complex motor behaviors, and any combination thereof. Some embodiments are directed to methods of decreasing the number of nights with injurious behaviors to subject or bed partner per week in a subject in need thereof, comprising administering to said subject a therapeutically effective amount of a 5-$HT_{2A}$ inverse agonist. In some embodiments, the injurious behaviors are selected from a group consisting of vocalizations, simple and complex motor behaviors, and any combination thereof. Some embodiments are directed to methods of decreasing the number of nightmares per week in a subject in need thereof, comprising administering to said subject a therapeutically effective amount of a 5-$HT_{2A}$ inverse agonist. Some embodiments are directed to methods of improving a subject's Mini-Mental State Examination score in a subject in need thereof, comprising administering to said subject a therapeutically effective amount of a 5-$HT_{2A}$ inverse agonist.

In some embodiments, the 5-$HT_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof. In some embodiments, the 5-$HT_{2A}$ inverse agonist is nelotanserin or a pharmaceutically acceptable salt, hydrate, polymorph, or solvate thereof. In some embodiments, the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof. In some embodiments, the therapeutically effective amount of nelotanserin or a pharmaceutically acceptable salt, hydrate, polymorph, or solvate thereof is from about 0.001 mg to about 1,000 mg, about 0.001 mg to about 160 mg or about 10 to about 160 mg. In some embodiments, the therapeutically effective amount of nelotanserin or a pharmaceutically acceptable salt, hydrate, polymorph, or solvate thereof is about 20 mg, about 40 mg, about 80 mg or about 160 mg. In some embodiments, the 5-$HT_{2A}$ inverse agonist is pimavanserin or a pharmaceutically acceptable salt, hydrate, polymorph, or solvate thereof. In some embodiments, the therapeutically effective amount of pimavanserin or a pharmaceutically acceptable salt, hydrate, polymorph, or solvate thereof is from about 0.001 mg to about 1,000 mg, about 17 mg to about 34 mg In some embodiments, the therapeutically effective amount of pimavanserin or a pharmaceutically acceptable salt, hydrate, polymorph, or solvate thereof is about 17 mg, or about 34 mg. In some embodiments, the therapeutically effective amount of the 5-HT$_{2A}$ inverse agonist is administered once a day, twice a day, or three times a day. In some embodiments, the 5-HT$_{2A}$ inverse agonist is configured for immediate release, for extended release, for delayed release, or any combination thereof. In some embodiments, the 5-HT2A inverse agonist is in a pharmaceutical composition, and wherein the pharmaceutical composition is formulated for oral administration. In some embodiments, the therapeutically effective amount of the 5-HT$_{2A}$ inverse agonist is administered once daily in the morning, twice daily, or once daily about 1 hour prior to the subject's bedtime.

In some embodiments, the subject is a human. In some embodiments, the subject is an elderly adult human. In some embodiments, the human is an adult diagnosed with a neurodegenerative disease. In some embodiments, the neurodegenerative disease is selected from the group consisting of probable dementia with Lewy Bodies, dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, and any combination thereof. In some embodiments, the human is an adult with a diagnosis of a condition selected from probable dementia with Lewy Bodies, dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof. In some embodiments, the human has a concurrent diagnosis of REM Sleep Behavior disorder, idiopathic REM Sleep Behavior disorder, or a combination thereof. In some embodiments, the human has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof. In some embodiments, the human has a Mini Mental State Examination score of greater than, or equal to about 18. In some embodiments, the human is an adult with a diagnosis of REM sleep behavior disorder, idiopathic REM sleep behavior disorder, or a combination thereof, associated with Dementia with Lewy Bodies. In some embodiments, the human is an adult aged 50-85 inclusive. In some embodiments, the human has experienced frequent episodes of REM sleep behavior disorder. In some embodiments, the human has experienced REM sleep behavior disorder on at least three to four days in a week.

Some embodiments are directed to methods for the prophylaxis and/or treatment of REM sleep behavior disorder, idiopathic REM sleep behavior disorder, or a combination thereof, in a subject in need thereof comprising administering to said subject a daily dose of about 40 mg of nelotanserin. In some embodiments, the daily dose of about 40 mg of nelotanserin is administered once a day, twice a day, three times a day or four times a day. In some embodiments, the subject has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, mild cognitive impairment, Parkinson's disease psychosis, Alzheimer's disease psychosis, a sleep disturbance, insomnia and a combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a daily oral dose of about 40 mg of nelotanserin. In some embodiments, the daily dose of about 40 mg of nelotanserin is administered once a day, twice a day, three times a day or four times a day. In some embodiments, the subject has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, mild cognitive impairment, Parkinson's disease psychosis, Alzheimer's disease psychosis, a sleep disturbance, insomnia and a combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a daily dose of about 80 mg of nelotanserin. In some embodiments, the daily dose of about 80 mg of nelotanserin is administered once a day, twice a day, three times a day or four times a day. In some embodiments, the subject has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, mild cognitive impairment, Parkinson's disease psychosis, Alzheimer's disease psychosis, a sleep disturbance, insomnia and a combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a daily oral dose of about 80 mg of nelotanserin. In some embodiments, the daily dose of about 80 mg of nelotanserin is administered once a day, twice a day, three times a day or four times a day. In some embodiments, the subject is a human adult with a diagnosis of a condition selected from probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

Some embodiments are directed to methods for the prophylaxis and/or treatment of REM sleep behavior disorder, idiopathic REM sleep behavior disorder, or a combination thereof, in a subject in need thereof comprising administering to said subject a dose of about 40 mg of nelotanserin for a first time period followed by administering to said subject a dose of about 80 mg of nelotanserin for a second time period. In some embodiments, the subject is a human adult with a diagnosis of a condition selected from probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

In some embodiments, the subject is concurrently receiving a therapeutically effective amount of at least one additional therapeutic agent selected from the group consisting of melatonin, quetiapine, clozapine, risperidone, clonazepam, levodopa, carbidopa, an antiparkinsonian drug, an acetylcholinesterase inhibitor, NMDA receptor antagonist, an atypical antipsychotic agent, a dopaminergic agent, a benzodiazepine, an antidepressant, and a combination thereof. In some embodiments, the therapeutically effective amount of melatonin is about 1 mg to about 5 mg. In some embodiments, the therapeutically effective amount of quetiapine is about 12.5 mg to about 100 mg. In some embodiments, the therapeutically effective amount of clonazepam is about 0.0625 mg to about 5 mg. In some embodiments, the antiparkinsonian drug is selected from an MAO-B inhibitor, a COMT inhibitor, a dopamine agonist or any combination thereof. In some embodiments, the therapeutically effective amount of levodopa or a pharmaceutically acceptable salt, hydrate, polymorph, or solvate thereof is from about 0.001 mg to about 10,000 mg, or about 0.001 mg to about 8,000 mg. In some embodiments, the therapeutically effective amount of levodopa or a pharmaceutically acceptable salt, hydrate, polymorph, or solvate thereof is about 285 mg, about 300 mg, about 400 mg, about 435 mg, 500 mg, about 585 mg, about 600 mg, about 700 mg, about 735 mg, about 750 mg, about 800 mg, about 980 mg, about 1,000 mg, about 1,225 mg, about 1,250 mg, about 1,470 mg, about 1,500 mg, about 1,715 mg, about 1,750 mg, about 1,960 mg, about 2,000 mg, about 2,205 mg, about 2,250 mg, about 2,450 mg, about 2,500 mg, about 2,750 mg, about 3,000 mg, about 3,250 mg, about 3,500 mg, about 3,750 mg, about 4,000 mg, about 4,250 mg, about 5,000 mg, about 5,250 mg, about 5,500 mg, about 5,750 mg, about 6,000 mg, about 6,250 mg, about 6,500 mg, about 6,750 mg, about 7,000 mg, about 7,250 mg, about 7,500 mg, about 7,750 mg, or about 8,000 mg. In some embodiments, the therapeutically effective amount of carbidopa or a pharmaceutically acceptable salt, hydrate, polymorph, or solvate thereof is configured for immediate release, extended release, for delayed release, or any combination thereof. In some embodiments, the therapeutically effective amount of carbidopa is from about 0.001 mg to about 1,000 mg, or from about 0.001 mg to about 700 mg. In some embodiments, the therapeutically effective amount of carbidopa is about 30 mg, about 40 mg, about 50 mg, about 60 mg, about 70 mg, about 71.25 mg, about 80 mg, about 108.75 mg, about 146.25 mg, 183.75 mg, about 245 mg, about 245 mg, about 306.25 mg, about 367.5 mg, about 428.75 mg, about 490 mg, about 551.25 mg, or about 612.5 mg. In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, the therapeutically effective amount of donepezil or a pharmaceutically acceptable salt, hydrate, polymorph, or solvate thereof is configured for immediate release, extended release, for delayed release, or any combination thereof. In some embodiments, the therapeutically effective amount of donepezil or a pharmaceutically acceptable salt, hydrate, polymorph, or solvate thereof is from about 0.001 mg to about 1,000 mg, or about 0.001 mg to about 30 mg. In some embodiments, the therapeutically effective amount of donepezil or a pharmaceutically acceptable salt, hydrate, polymorph, or solvate thereof is about 5 mg, 10 mg, or 23 mg. In some embodiments, the acetylcholinesterase inhibitor is rivastigmine or a pharmaceutically acceptable salt, hydrate, polymorph, or solvate thereof. In some embodiments, the therapeutically effective amount of rivastigmine or a pharmaceutically acceptable salt, hydrate, polymorph, or solvate thereof is from about 0.001 mg to about 1,000 mg, or about 0.001 mg to about 15 mg. In some embodiments, the therapeutically effective amount of rivastigmine or a pharmaceutically acceptable salt, hydrate, polymorph, or solvate thereof is about 1.5 mg, about 3 mg, about 4.5 mg, about 6 mg, about 9 mg, about 9.5 mg, about 12 mg, or about 13.3 mg. In some embodiments, the therapeutically effective amount of rivastigmine or a pharmaceutically acceptable salt, hydrate, polymorph, or solvate thereof is configured for immediate release, for extended release, for delayed release, or any combination thereof. In some embodiments, the acetylcholinesterase inhibitor is galantamine or a pharmaceutically acceptable salt, hydrate, polymorph, or solvate thereof. In some embodiments, the therapeutically effective amount of galantamine or a pharmaceutically acceptable salt, hydrate, polymorph, or solvate thereof is configured for immediate release, extended release, for delayed release, or any combination thereof. In some embodiments, the therapeutically effective amount of galantamine or a pharmaceutically acceptable salt, hydrate, polymorph, or solvate thereof is from about 0.001 mg to about 1,000 mg, or about 0.001 mg to about 30 mg. In some embodiments, the therapeutically effective amount of galantamine or a pharmaceutically acceptable salt, hydrate, polymorph, or solvate thereof is about 4 mg, about 8 mg, about 12 mg, about 16 mg, or about 24 mg. In some embodiments, NMDA receptor antagonist is selected from the group consisting of memantine, amantadine, ketamine, and pharmaceutically acceptable salts, hydrates, polymorphs, or solvates thereof. In some embodiments, the NMDA receptor antagonist is memantine or a pharmaceutically acceptable salt, hydrate, polymorph, or solvate thereof. In some embodiments, the therapeutically effective amount of memantine or a pharmaceutically acceptable salt, hydrate, polymorph, or solvate thereof is configured for immediate release, extended release, for delayed release, or any combination thereof. In some embodiments, the therapeutically effective amount of memantine or a pharmaceutically acceptable salt, hydrate, polymorph, or solvate thereof is from about 0.001 mg to about 1,000 mg, or about 0.001 mg to about 30 mg. In some embodiments, the therapeutically effective amount of memantine or a pharmaceutically acceptable salt, hydrate, polymorph, or solvate thereof is about 5 mg, about 7 mg, about 10 mg, about 14 mg, about 20 mg, about 21 mg, or about 28 mg. In some embodiments, the therapeutically effective amount of memantine or a pharmaceutically acceptable salt, hydrate, polymorph, or solvate thereof is configured for extended release, for delayed release or a combination thereof. In some embodiments, the NMDA receptor antagonist is amantadine or a pharmaceutically acceptable salt, hydrate, polymorph, or solvate thereof. In some embodiments, the therapeutically effective amount of amantadine or a pharmaceutically acceptable salt, hydrate, polymorph, or solvate thereof is configured for immediate release, extended release, for delayed release, or any combination thereof. In some embodiments, the therapeutically effective amount of amantadine or a pharmaceutically acceptable salt, hydrate, polymorph, or solvate thereof is from about 0.001 mg to about 1,000 mg, or about 0.001 mg to about 500 mg. In some embodiments, the therapeutically effective amount of amantadine or a pharmaceutically acceptable salt, hydrate, polymorph, or solvate thereof is from about 100 mg to about 400 mg. In some embodiments, the therapeutically effective amount of amantadine or a pharmaceutically acceptable salt, hydrate, polymorph, or solvate thereof is about 100 mg, 200 mg, 300 mg or about 400 mg.

In some embodiments, the at least one additional therapeutic agent is 3-phenylsulfonyl-8-piperazinyl-1yl-quinoline. In some embodiments, 3-phenylsulfonyl-8-piperazinyl-1yl-quinoline is administered in a therapeutically effective amount. In some embodiments, the therapeutically effective amount of 3-phenylsulfonyl-8-piperazinyl-1yl-quinoline or pharmaceutically acceptable salts, hydrates or solvates thereof is configured for extended release, and the additional therapeutic agent useful for treating a neurodegenerative disease is configured for immediate release, sustained release, extended release, or any combination thereof. In some embodiments, the therapeutically effective amount of 3-phenylsulfonyl-8-piperazinyl-1yl-quinoline or a pharmaceutically acceptable salt, hydrate, polymorph, or solvate thereof is from about 0.001 mg to about 1,000 mg, about 0.001 mg to about 200 mg, about 0.001 mg to about 175 mg, or 0.001 mg to about 70 mg. In some embodiments, the therapeutically effective amount of 3-phenylsulfonyl-8-piperazinyl-1yl-quinoline or a pharmaceutically acceptable salt, hydrate, polymorph, or solvate thereof is about 15 mg, about 35 mg, or about 70 mg.

In some embodiments, the at least one additional therapeutic agent is a monoclonal antibody. In some embodiments, the second therapeutic agent is a human monoclonal antibody. In some embodiments, the second therapeutic agent is a humanized monoclonal antibody. In some embodiments the monoclonal antibody targets beta amyloid. In some embodiments the beta amyloid may comprise aggregated beta amyloid such as but not limited to soluble oligomers, insoluble fibrils deposited into amyloid plaque, or a combination thereof. In some embodiments, the monoclonal antibody is Aducanumab (BIIB037), Gantenerumab, Bapineuzumab, Crenezumab, Ponezumab, Solanezumab, SAR228810, MEDI1814, BAN2401, or any combination thereof. In some embodiments, the monoclonal antibody targets alpha-synuclein. In some embodiments, the monoclonal antibody targeting alpha-synuclein is RG-7935, Posiphen, Affitope PD03A, Affitope PD01A, or any combination thereof.

In some embodiments, the at least one additional therapeutic agent is a BACE enzyme inhibitor. In some embodiments, the BACE enzyme inhibitor is CTS-21166, MK-8931, AZD3293, LY3314814, BI 1181181, LY2886721, E2609, RG7129, JNJ-5486911, TAK-070, or any combination thereof.

In some embodiments, the at least one additional therapeutic agent is a RAGE inhibitor. In some embodiments, the RAGE inhibitor is TTP488 (Azeliragon), TTP4000, FPS-ZM1, or any combination thereof.

In some embodiments, the at least one additional therapeutic agent is an antibody targeting Tau. In some embodiments, the antibody targeting Tau is AADVAC-1, AAD-VAC-2, ACI-35, BMS-986168, RG7345, TRx-237-015 (LMTX), AV-1451, AV-680, Posiphen, or any combination thereof.

In some embodiments, the at least one additional therapeutic agent is a α7 nicotinic acetylcholine receptor modulator. In some embodiments, the α7 nicotinic acetylcholine receptor modulator is Encenicline (EVP-6124), ABT-126, ABT 418, RG3487, Varenicline, A-867744, TC-5219, AVL3288, BMS933043, DSP-3748, or any combination thereof.

In some embodiments, the at least one additional therapeutic agent may include one or more treatments for Alzheimer's disease such as Namzaric™, Exelon®, Aricept® (donepezil hydrochloride), Namenda® (memantine hydrochloride), or galantamine hydrobromide. In some embodiments, described compositions and formulations may be administered in combination with one or more treatments for Parkinson's Disease such as ABT-126 (Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca pic), 11C-AZD-2995 (AstraZeneca pic), 18F-AZD-4694 (AstraZeneca pic), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-AD1 (Development Centre for Biotechnology), EGb-761 ((Dr Willmar Schwabe GmbH & Co), E-2012 (Eisai Co Ltd), ACC-001 (Elan Corp pic), bapineuzumab (Elan Corp pic), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FGLL (ENKAM Pharmaceuticals A/S), EHT-0202 (ExonHit Therapeutics SA), celecoxib (GD Searle & Co), GSK-933776A (GlaxoSmithKline pic), rosiglitazone XR (GlaxoSmithKline pic), SB-742457 (GlaxoSmithKline pic), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 123I-MNI-330 (Molecular Neuroimaging Lie), gantenerumab (MorphoSys AG), NIC5-15 (Mount Sinai School of Medicine), huperzine A (Neuro-Hitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm pic), Gero-46 (PN Gerolymatos SA), PBT-2 (Prana Biotechnology Ltd), PRX-03140 (Predix Pharmaceuticals Inc), Exebryl-l (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanofi-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 123I-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

In some embodiments, the at least one additional therapeutic agent may include one or more agents useful for the treatment of motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm pic), RPI-MN (ReceptoPharm Inc), SB-509 (Sangamo Biosciences Inc), olesoxime (Trophos SA), sodium phenylbutyrate (Ucyclyd Pharma Inc), and R-pramipexole (University of Virginia).

In some embodiments, the at least one additional therapeutic agent may be an agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT$_4$ receptor partial agonists or 5HT$_{1A}$ receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies, an antidepressants, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant). Examples of specific antidepressant compounds include amitriptyline, clomipramine, citalopram, dosulepin, doxepin, fluoxetine, imipramine, lofepramine, mirtazapine, moclobemide, nortriptyline, paroxetine, phenelzine, reboxetine, sertraline, tranylcypromine, trazodone, or venlafaxine. In some embodiments, additional therapeutic agents may include antipsychotic drugs, such as olanzapine, clozapine, risperidone, quetiapine, aripiprazole or paliperiden.

In some embodiments, treating or prophylaxis results in a decrease in the frequency, severity, or a combination thereof of REM sleep behavior disorder episodes. In some embodiments, treating or prophylaxis results in a decrease in the frequency of abnormal vocalizations and motor behavior per sleep period. In some embodiments, treatment results in a decrease in the amount of nightmare content per sleep period. In some embodiments, treating or prophylaxis results in a decrease in the potential for injury or injury to said subject during a sleep period. In some embodiments, treating or prophylaxis results in an increase in quality of partner sleep. In some embodiments, treating or prophylaxis results in an improvement in subjective sleep quality and objective sleep measures. In some embodiments, treating or prophylaxis results in an improvement in the clinician assessment of global change pertaining to REM sleep behavior disorder. In some embodiments, treating or prophylaxis results in a decrease in the frequency of REM sleep behavior disorder behaviors. In some embodiments, REM sleep behavior disorder behaviors are selected from the group consisting of vocalizations, complex motor behaviors, and any combination thereof. In some embodiments, treating or prophylaxis results in a decrease in the severity of REM sleep behavior disorder behaviors. In some embodiments, treating or prophylaxis results in a decrease in the number of nights with injurious behaviors to subject or bed partner per week. In some embodiments, injurious behaviors are selected from a group consisting of vocalizations, complex motor behaviors, and any combination thereof. In some embodiments, treating or prophylaxis results in a decrease in the number of nightmares per week. In some embodiments, treating or prophylaxis results in an improvement in subjective sleep quality and objective sleep measures. In some embodiments, treating or prophylaxis results in an improvement in Clinician's Global Impression of Change related to REM sleep behavior disorder behaviors. In some embodiments, treating or prophylaxis results in an improvement in the subject's Mini-Mental State Examination score.

One aspect of the present invention pertains to methods for the prophylaxis or treatment of REM sleep behavior disorder, idiopathic REM sleep behavior disorder, or a combination thereof, in an individual comprising administering to the individual in need thereof a therapeutically effective amount of a pharmaceutical composition of the present invention.

In some embodiments, the pharmaceutical composition is administered orally, nasally, sublingually, buccally, transdermally, vaginally or rectally.

In some embodiments, the pharmaceutical composition is administered orally.

One aspect of the present invention pertains to the use of a pharmaceutical composition of the present invention in the manufacture of a medicament for the treatment of a 5-HT$_{2A}$ serotonin receptor-related disorder.

One aspect of the present invention pertains to the use of a pharmaceutical composition of the present invention in the manufacture of a medicament for the treatment of REM sleep behavior disorder.

One aspect of the present invention is directed to methods for the prophylaxis or treatment of REM sleep behavior disorder, idiopathic REM sleep behavior disorder, or a combination thereof, in an individual comprising administering to the individual in need thereof a therapeutically effective amount of a composition of the present invention.

One aspect of the present invention pertains to the use of a composition of the present invention in the manufacture of a medicament for the prophylaxis or treatment of REM sleep behavior disorder.

One aspect of the present invention pertains to the use of a composition of the present invention in the manufacture of a medicament for the treatment of REM sleep behavior disorder.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

One aspect of the present invention pertains to pharmaceutical compositions comprising a therapeutically effective amount of 1-[3-(4-bromo-2-methyl-2H-pyrazol-3-yl)-4- methoxy-phenyl]-3-(2,4-difluoro-phenyl)-urea; and PVP, methyl cellulose, or a mixture thereof. One aspect of the present invention pertains to pharmaceutical compositions comprising a therapeutically effective amount of 1-[3-(4-bromo-2-methyl-2H-pyrazol-3-yl)-4-methoxy-phenyl]-3-(2,4-difluoro-phenyl)-urea. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

One aspect of the present invention pertains to methods for preparing a pharmaceutical composition of the present invention comprising: (a) 1-[3-(4-bromo-2-methyl-2H-pyrazol-3-yl)-4-methoxy-phenyl]-3-(2,4-difluoro-phenyl)-urea; and (b) an excipient selected from: PVP and coPVP; comprising blending the 1-[3-(4-bromo-2-methyl-2H-pyrazol-3-yl)-4-methoxy-phenyl]-3-(2,4-difluoro-phenyl)-urea and the excipient in a blender.

One aspect of the present invention pertains to dosage forms comprising a therapeutically effective amount of 1-[3-(4-bromo-2-methyl-2H-pyrazol-3-yl)-4-methoxy-phenyl]-3-(2,4-difluoro-phenyl)-urea; and PVP, methyl cellulose, or a mixture thereof. One aspect of the present invention pertains to dosage forms comprising a therapeutically effective amount of 1-[3-(4-bromo-2-methyl-2H-pyrazol-3-yl)-4-methoxy-phenyl]-3-(2,4-difluoro-phenyl)-urea. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg.

Conventional excipients, such as binding agents, fillers, acceptable wetting agents, tableting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the prophylaxis or treatment, a compound of the invention may, in an alternative use, be administered as a raw or pure chemical, it is preferable to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insulation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as 5-$HT_{2A}$ receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Representative doses of the present invention include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. In some embodiments, the dose is administered once daily in the morning, twice daily, or once daily about 1 hour prior to the subject's bedtime. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human; however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety of factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved, for example, by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well-known to a person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bio-availability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler:

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethanesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems," Vol. 14 of the A. C. S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the $5\text{-HT}_{2A}$ receptor modulators are utilized as active ingredients in a pharmaceutical composition, these are not intended for use only in humans, but in other non-human mammals as well. Indeed, recent advances in the area of animal healthcare mandate that consideration be given for the use of active agents, such as $5\text{-HT}_{2A}$ receptor modulators, for the treatment of a $5\text{-HT}_{2A}$ mediated disease or disorder in domestic animals (e.g., cats and dogs) and in other domestic animals (e.g., such as cows, chickens, fish, etc.). Those of ordinary skill in the art are readily credited with understanding the utility of such compounds in such settings.

One aspect of the present invention encompasses methods for the prophylaxis and/or treatment of REM sleep behavior disorder, idiopathic REM sleep behavior disorder, or a combination thereof, in an individual comprising administering to said individual in need thereof a therapeutically effective amount of a compound according to any of the embodiments described herein or a pharmaceutical composition. In some embodiments, the compound is 1-[3-(4-bromo-2-methyl-2H-pyrazol-3-yl)-4-methoxy-phenyl]-3-(2,4-difluoro-phenyl)-urea. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg.

In some embodiments, the individual is a mammal. In some embodiments, the subject is a human. In some embodiments, the subject is an elderly adult human. In some embodiments, the human is an adult diagnosed with a neurodegenerative disease. In some embodiments, the neurodegenerative disease is selected from the group consisting of probable dementia with Lewy Bodies, dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, and any combination thereof. In some embodiments, the human is an adult with a diagnosis of a condition selected from probable dementia with Lewy Bodies, dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof. In some embodiments, the human has a concurrent diagnosis of REM Sleep Behavior disorder, idiopathic REM Sleep Behavior disorder, or a combination thereof. In some embodiments, the human has a concurrent diagnosis of REM Sleep Behavior disorder, idiopathic REM Sleep Behavior disorder, or a combination thereof, and a condition selected from probable Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof. In some embodiments, the human has a Mini Mental State Examination score of greater than, or equal to, about 18. In some embodiments, the human is an adult with a diagnosis of REM sleep behavior disorder, idiopathic REM sleep behavior disorder, or a combination thereof, associated with Dementia with Lewy Bodies. In some embodiments, the human is an adult aged 50-85 inclusive. In some embodiments, the human has experienced frequent episodes of REM sleep behavior disorder. In some embodiments, the human has experienced REM sleep behavior disorder on at least three to four days in a week. In some embodiments, the human is an adult with a diagnosis of probable Dementia with Lewy Bodies based on DSM-5 criteria; Parkinson's disease, Parkinson's disease dementia, or any combination therof, and a diagnosis of REM Sleep Behavior Disorder based on DSM-5 criteria. In some embodiments, the human is an adult with a diagnosis of Dementia with Lewy Bodies. In some embodiments, the human is an adult with a diagnosis of REM sleep behavior disorder associated with Dementia with Lewy Bodies. In some embodiments, the human has a concurrent diagnosis of Dementia with Lewy Bodies and REM sleep behavior disorder based on DSM-5 criteria. In some embodiments, the human has a Mini Mental State Examination score of greater than, or equal to about 18. In some embodiments, the human has mild or optimally controlled obstructive sleep apnea (OSA) or any combination thereof.

In some embodiments, the human is an Adult aged 50-85 inclusive. In some embodiments, the human has experienced at least four episodes of RBD per week. In some embodiments, the individual is concurrently receiving stable melatonin treatment, clonazepam <5 mg per day, optimally controlled (obstructive sleep apnea) OSA; anti-parkinsonian drugs on stable dosage for at least 1 month, acetylcholinesterase inhibitors (AchEIs) on stable dosage for at least 1 month, memantine on stable dosage for at least 1 month.

In some embodiments, treatment results in a decrease in the frequency of abnormal vocalizations and motor behavior as monitored by diaries by the bed-partner after about 28 days of treatment. In some embodiments, treatment results in a decrease in the severity of abnormal vocalizations and motor behavior as recorded on a REM sleep behavior disorder visual analog scale by the caregiver/partner after about 28 days of treatment. In some embodiments, treatment results in a decrease in the amount of nightmare content per night as recorded by the patient after about 28 days of treatment. In some embodiments, treatment results in a decrease in the potential for injury and injury as measured by the caregiver/partner after about 28 days of treatment. In some embodiments, treatment results in an increase in quality of partner sleep as measured by a visual analog scale after about 28 days of treatment. In some embodiments, treatment results in a decrease in frequency and/or severity of visual hallucinations, as measured by a visual analog scale completed by the subject and his/her primary caregiver after about 28 days of treatment. In some embodiments, treatment results in a decrease in frequency and/or severity of visual hallucinations, as measured by the visual hallucinations component of the Scale for Assessment of Positive Symptoms after about 28 days of treatment. In some embodiments, treatment results in a decrease in hallucinations and delusions as measured by the Scale for Assessment of Positive Symptoms after about 28 days of treatment. In some embodiments, treatment results in an increase in cognition as measured by the Cognitive Drug Research Power of Attention computerized test after about 28 days of treatment.

In some embodiments, treatment results in a decrease in the nightly frequency of RBD behaviors. In some embodiments, RBD behaviors are selected from vocalizations, complex motor behaviors, and any combination thereof. In some embodiments, the nightly frequency of RBD behaviors are measured by video/audio assessment conducted at a sleep lab, video/audio assessment conducted in a controlled in-home environment, or any combination thereof. In some embodiments, treatment results in a decrease in the nightly severity of RBD behaviors. In some embodiments, RBD behaviors are selected from vocalizations, complex motor behaviors, and any combination thereof. In some embodiments, the nightly frequency of RBD behaviors are measured by video/audio assessment conducted at a sleep lab, video/audio assessment conducted in a controlled in-home environment, or any combination thereof. In some embodiments, treatment results in a decrease in the nightly frequency and severity of RBD behaviors. In some embodiments, RBD behaviors are selected from vocalizations, complex motor behaviors, and any combination thereof. In some embodiments, nightly frequency of RBD behaviors are measured by video/audio assessment conducted at a sleep lab, video/audio assessment conducted in a controlled in-home environment, or any combination thereof. In some embodiments, treatment results in a decrease in the number of nights with RBD behaviors per week. In some embodiments, RBD behaviors are selected from vocalizations, complex motor behaviors, and any combination thereof. In some embodiments, the nightly frequency of RBD behaviors are measured by video/audio assessment conducted at a sleep lab, video/audio assessment conducted in a controlled in-home environment, or any combination thereof. In some embodiments, treatment results in a decrease in the number of nights with injurious behaviors to subject or bed partner per week. In some embodiments, RBD behaviors are selected from vocalizations, complex motor behaviors, and any combination thereof. In some embodiments, the number of nights with injurious behaviors to subject or bed partner per week are measured by video/audio assessment conducted at a sleep lab, video/audio assessment conducted in a controlled in-home environment, study diary completed by subject and/or bed partner/caregiver, or any combination thereof. In some embodiments, treatment results in a decrease in the number of nights with nightmares per week. In some embodiments, the number of nights with nightmares are measured by video/audio assessment conducted at a sleep lab, video/audio assessment conducted in a controlled in-home environment, study diary completed by subject and/or bed partner/caregiver, or any combination thereof. In some embodiments, treatment results in an improvement in subjective sleep quality. In some embodiments, subjective sleep quality is measured by Scales for Outcomes in Parkinson's disease (SCOPA)—Sleep. In some embodiments, treatment results in an improvement in quality of bed partner sleep. In some embodiments, an improvement quality of bed partner sleep is measured by a VAS completed by the bed partner. In some embodiments, treatment results in an improvement in Clinician's Global Impression of Change related to RBD behaviors. In some embodiments, treatment results in an improvement in Clinician's Global Impression of Change related to RBD behaviors. In some embodiments, treatment results in a decrease in visual hallucinations. In some embodiments, a decrease in visual hallucinations is measured by study diary completed by subject and/or bed partner/caregiver. In some embodiments, treatment results in an improvement in the subject's Mini-Mental State Examination score.

Embodiments of the invention are not limited to any particular agent encompassed by the classes of agents described above, and any agent that falls within any of these categories may be utilized in embodiments of the invention. Non-limiting examples of such agents are provided for clarity. Any of the secondary agents described above may be useful in embodiments of the invention.

The embodiments for disease states, subject type, daily dose amounts, therapeutically effective amounts, no observable adverse effect level dose amounts, non-effective dose amounts, pharmaceutical compositions, and chiral purities for the methods of the invention, which are described herein separately for the sake of brevity, can be joined in any suitable combination.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

Example 1—A Phase 2, Double-Blind, Randomized Placebo-Controlled Cross-Over Study of Nelotanserin Versus Placebo in REM Behavior Disorder (RBD) in Patients with Lewy Body Dementia Primary Objective:
To assess the effects of nelotanserin versus placebo on the frequency of abnormal vocalizations and motor behavior as monitored by diaries by the bed-partner after 28 days of treatment.

Secondary Objectives:
To assess the effects of nelotanserin versus placebo on the severity of abnormal vocalizations and motor behavior as recorded on a RBD VAS by the caregiver/partner after 28 days of treatment;

To assess the effects of nelotanserin versus placebo on the amount of nightmare content per night as recorded by the patient after 28 days of treatment;

To assess the effects of nelotanserin versus placebo on the potential for injury and injury as measured by the caregiver/partner after 28 days of treatment;

To assess the effects of nelotanserin versus placebo on quality of partner sleep as measured by a VAS after 28 days of treatment;

To assess the effects of nelotanserin on subjective sleep quality as measured by change in the SCOPA-night and SCOPA day wake scores after 28 days of treatment; and To assess the safety and tolerability of nelotanserin as well as the effect of nelotanserin on motor symptoms as measured by UPDRS.

Target Population:
Adult subjects with a diagnosis of either probable Dementia with Lewy Bodies or Parkinson's disease and a diagnosis of REM Sleep Behavior Disorder as characterized by: Presence of REM sleep without atonia (RSWA) on polysomnography (PSG); The presence of at least one of the following conditions: (1) sleep-related behaviors, by history, that have been injurious, potentially injurious, or disruptive (e.g., dream enactment behavior); (2) abnormal REM sleep behavior documented during PSG monitoring; Absence of epileptiform activity on electroencephalogram (EEG) during REM sleep (unless RBD can be clearly distinguished from any concurrent REM sleep-related seizure disorder); Sleep disorder not better explained by another sleep disorder, a medical or neurologic disorder, a mental disorder, medication use, or a substance use disorder. In some instances, clonazepam rescue may be permitted and frequency of clonazepam measured as an endpoint.

Inclusion Criteria:

Diagnosis of RBD in patients with a concurrent diagnosis of DLB or PD; Diagnosis of PD-RBD; Diagnosis of PD-RBD which may be included where patients should be in the early stages of PD, defined as Hoehn & Yahr stages 1-3; stable melatonin treatment will be allowed, if at a stable dose for at least four weeks prior to screening; Consistently four or more RBD episodes per week for each of the past four weeks, as reported by bed partner; and Optimally controlled OSA;

Exclusion Criteria:

Known hypersensitivity to melatonin or clonazepam; therapy with clonazepam or any other benzodiazepine in the past four weeks; current use of sedative-hypnotic medication; current use of anti-epileptic medication of history of epilepsy; alcoholism; lack of bed partner/roommate/caretaker who sleeps in the same room; pregnancy; multiple system atrophy; narcolepsy; untreated or suboptimally treated OSA; bipolar disorder, psychosis, and major depression; patients taking β blockers and anti-depressants; or have been off anti-depressants for more than 3 months; patients with other parasomnias; patients with other sleep related movement disorders, i.e. rhythmic movement disorder; and patients with clinically relevant RLS.

Number of Subjects Planned:

Approximately 36 randomized subjects (Nelotanserin 80 mg: 18 subjects; Placebo: 18 subjects).

Number of Study Centers Planned:

Approximately 4.

Study Design:

This is a multi-center, double-blind, randomized, placebo-controlled, cross-over study in patients with RBD. The efficacy and safety of nelotanserin at doses of 80 mg daily will be evaluated over a 10-week period when given to patients who experience at least four episodes of RBD episodes per week for each of the past four weeks. The randomization ratio will be: 1:1; (80 mg nelotanserin: placebo). RBD subjects with a concurrent diagnosis of DLB or PD will be included in the study. All subjects will undergo a PSG to confirm presence of REM sleep without atonia. After screening, subjects will enter into a two-week placebo run-in period. At the end of this lead-in period, all subjects in the study will be randomized 1:1 to receive 80 mg of nelotanserin or placebo, once daily. Safety data will be collected throughout the study. Efficacy data on the primary and secondary endpoints will be collected at the pre-specified primary endpoints at 4 and 10 weeks of treatment, as well as at 6 week and baseline.

Duration of Treatment:

Study participation will last approximately 14 weeks: 0 to 14 days for Screening, a two-week placebo run-in period, a four-week randomized treatment period, a two-week wash-out phase, a four-week treatment period followed be a two week follow-up period. Following the second four-week treatment period, all subjects will be eligible to participate in a 40-week open-label extension study with nelotanserin.

Safety Evaluation:

Safety will be evaluated based on adverse events (AEs), physical examinations, vital signs, electrocardiograms (ECGs), and routine clinical laboratory assessments.

Example 2—A Phase 2, Double-Blind, Randomized, Placebo-Controlled Study of Nelotanserin Versus Placebo in Patients with Dementia with Lewy Bodies (DLB) Experiencing REM Sleep Behaviors (RBD)

Protocol Summary

| | |
|---|---|
| Study Title | A Phase 2, double-blind, randomized, placebo-controlled study of Nelotanserin versus placebo in patients with dementia with Lewy bodies (DLB) experiencing REM sleep behavior disorder (RBD) |
| Objectives | To determine if the efficacy of Nelotanserin is superior to placebo in the management of RBD in patients with DLB<br>To evaluate the safety and tolerability of Nelotanserin in patients with DLB |
| Study Phase | Phase 2 |
| Target Population | Inclusion Criteria:<br>1. Adult subjects aged 50-85, inclusive, with a diagnosis of probable major neurocognitive disorder (dementia) with Lewy bodies (DLB) based on DSM-5 criteria;<br>2. A concurrent diagnosis of REM sleep behavior disorder (RBD) based on DSM-5 criteria; subjects must<br>   a. experience frequent RBD episodes prior to Screening (Visit 1) and during the single-blind placebo run-in period; and<br>   b. have at least one qualifying night of REM sleep during the video-polysomnographic (video-PSG) study in the single-blind placebo run-in period. A qualifying night of REM sleep is defined as a night with REM sleep duration of ≥10 minutes;<br>   c. have 4 or more RBD episodes (one or more of which must include complex RBD events) per 10 minutes of REM sleep during 1 or more qualifying night(s) based on a central review of video-PSG data obtained from the sleep lab during the single-blind placebo run-in period;<br>3. Mini Mental state examination score ≥18;<br>4. Stable quetiapine treatment will be allowed, if at a stable dose of ≤25 mg/day for at least four weeks prior to screening and expect to continue the stable regimen throughout the study; |

-continued

|  |  |
|---|---|
|  | 5. Low dose clonazepam (≤1 mg/day) or melatonin treatment will be allowed, if at a stable dose for at least four weeks prior to screening and expect to continue the stable regimen throughout the study; Subjects taking antiparkinsonian drugs (e.g., levodopa) must be on stable dosage for at least 4 weeks prior to screening and expect to continue the stable regimen throughout the study;<br>6. Subjects taking acetylcholinesterase inhibitors (AchEIs) or memantine must be on stable dosage for at least 4 weeks prior to screening and expect to continue the stable regimen throughout the study;<br>7. Subjects must have a caregiver or family member who can serve as a collateral informant for study assessments and, if necessary, provide proxy consent to participate in the study;<br>8. Females who<br>    a. have undergone surgical removal of uterus or removal of both ovaries, or<br>    b. have been naturally postmenopausal for at least 24 consecutive months (i.e., no menses at any time during the preceding 24 consecutive months).<br>Exclusion Criteria:<br>1. Subjects' sleep behavioral symptoms are secondary to or better accounted for by another medical condition (eg, untreated or sub-optimally treated obstructive sleep apnea [OSA]), psychiatric disorder (eg, other non-REM parasomnias, multiple system atrophy), or substance abuse (eg, alcoholism);<br>2. Subjects have a current diagnosis of significant psychotic disorders including, but not limited to, schizophrenia or bipolar disorder;<br>3. Any significant change in the subject's environment within the past four weeks;<br>4. Subjects with a history of significant cerebrovascular events;<br>5. Subjects with a current serious and/or unstable cardiovascular, respiratory, thyroid, gastrointestinal, renal, hematologic or other medical disorder;<br>6. Use of any antipsychotic medication other than stable quetiapine at a dose of <25 mg/day;<br>7. Subjects with current use of sedative-hypnotic medication (other than stable low dose clonazepam and/or melatonin);<br>8. Subjects with medication-induced RBDs or receiving venlafaxine and mirtazapine that may induce RBD behaviors;<br>9. Subjects with current use of anti-epileptic medication or a history of epilepsy;<br>10. Subjects who are allergic or hypersensitive to nelotanserin;<br>11. Subjects with evidence of impaired liver function at screening (laboratory test values ≥3 times the upper limit of the laboratory reference (normal) range (ULN) for aspartate transaminase [AST/SGOT] or alanine transaminase [ALT/SGPT]);<br>12. Subjects who have used any investigational medication within 30 days prior to the first dose of study medication. |
| Number of Subjects Planned | A total of 52 randomized subjects:<br>1. Nelotanserin 80 mg: 26 subjects<br>2. Placebo: 26 subjects |
| Number of Study Centers Planned | Approximately 15-20 |
| Study Design | This is a multi-center, double-blind, randomized, placebo-controlled study in DLB subjects with RBD. Subjects will participate in a whole-night video-PSG study at a specified sleep lab during the single-blind placebo run-in period and at the end of the double-blind treatment. To allow subjects to acclimate to the sleep lab environment, subjects will spend a minimum of two (preferably consecutive) nights at the sleep lab. During this study, the subject must have at least one qualifying night of REM sleep (a qualifying night of REM sleep is defined as a night with REM sleep duration of ≥10 minutes). ActiGraph activity monitor will be used to assess physical activity during sleep during the study.<br>The primary objective of the study will be to evaluate the efficacy and safety of nelotanserin as compared to placebo in DLB subjects with a concurrent diagnosis of RBD who have frequent RBD behaviors.<br>Following an initial screening, eligible subjects will enter a single-blind placebo run-in period of up to 3 weeks in duration. At the end of this period, all subjects who continue to meet the eligibility criteria will enter a four-week double-blind treatment period. Each subject will be randomized 1:1 to either nelotanserin 80 mg or matching placebo. For subjects assigned to nelotanserin 80 mg, the dose will be titrated up to the 80 mg dose strength in a blinded fashion after initial 5 days of treatment with 40 mg nelotanserin. Following the final visit, all subjects who either have completed the study will be eligible to participate in an open-label extension period with nelotanserin. The study design is outlined in FIG. 1. |

-continued

| | |
|---|---|
| Duration of Treatment | Study participation will last approximately 7-11 weeks: 0-28 days for screening, an up to 3 week single-blind placebo run-in period to evaluate baseline status, and a four-week randomized double-blind treatment period. Following the final visit, eligible subjects will have the option to participate in an open-label extension period with nelotanserin. |
| Criteria for Evaluation | Primary Efficacy Measure:<br>To assess the effects of nelotanserin versus placebo on frequency per 10 minutes of REM sleep of characteristic RBD behaviors (both simple or major movements and vocalizations) based on video/audio assessment conducted at a sleep lab.<br>The primary endpoint is defined as the change in frequency per 10 minutes of REM sleep of RBD behaviors from baseline (the whole-night sleep study after 2 weeks of placebo run-in) to the end of treatment (the whole-night sleep study at the end of treatment).<br>Secondary Efficacy Measures:<br>To assess the effects of nelotanserin versus placebo on change in the proportion of severe RBD behaviors measured by video/audio assessment conducted at a sleep lab;<br>To assess the effects of nelotanserin versus placebo on change in a composite score based on both nightly severity and nightly frequency of RBD behaviors measured by video/audio assessment conducted at a sleep lab;<br>To assess the effects of nelotanserin versus placebo on change in the number of nights with injurious behaviors to subject or bed partner as recorded on study diary completed by subject and/or bed partner/caregiver;<br>To assess the effects of nelotanserin versus placebo on change in the number of nights with dramatic dreams per week as recorded on study diary completed by subject and/or bed partner/caregiver;<br>To assess the effects of nelotanserin versus placebo on change in subjective sleep quality as measured by Scales for Outcomes in Parkinson's disease (SCOPA) - Sleep;<br>To assess the effects of nelotanserin versus placebo on change in quality of bed partner sleep as measured by a visual analog scale (VAS) completed by the bed partner;<br>To assess the effects of nelotanserin versus placebo on Clinicians' Global Impression of Change (CGIC) related to RBD behaviors;<br>To assess the effects of nelotanserin versus placebo on change in objective sleep parameters obtained from PSG at a sleep lab;<br>To assess the effects of nelotanserin versus placebo on change in physical activity during sleep as measured by ActiGraph activity monitor;<br>To assess the effects of nelotanserin versus placebo on change in duration of VHs as recorded on study diary completed by subject and/or bed partner/caregiver;<br>To assess the effects of nelotanserin versus placebo on change in duration of auditory hallucinations as recorded on study diary completed by subject and/or bed partner/caregiver;<br>Safety Evaluation:<br>Safety will be evaluated based on adverse events (AEs), physical examinations, vital signs, electrocardiograms (ECGs), and routine clinical laboratory assessments. Extrapyramidal signs are assessed with the motor subsection of the Unified Parkinson's Disease Rating Scale (UPDRS, Parts II and III). Cognitive functioning is assessed with the Montreal Cognitive Assessment (MoCA) scale and the Mini-Mental State Examination (MMSE).<br>Pharmacokinetic Evaluation:<br>A blood sample for determination of plasma nelotanserin and M1 metabolite concentration will be collected after the last dose of study treatment. |
| Statistical Methods | Sample Size: A sample size of 52 subjects (26 subjects per treatment arm) would provide power of 0.80 to detect a 0.8 unit treatment group difference in the change from baseline to end of treatment in the nightly frequency of RBD behaviors (both simple and major movements and vocalizations) measured by video assessment conducted at a sleep lab, assuming SD of 1 unit using an analysis of covariance (ANCOVA) model with a single two-level between-groups fixed effect and two covariates and a significance level for Type-I error ($\alpha$) of 0.05.<br>Efficacy: For the change in frequency of RBD behaviors observed in the sleep lab during the single-blind placebo run-in period (visit 3 [V3]) and at the end of treatment, treatment arm comparisons between nelotanserin 80 mg and placebo in the change in frequency of RBD behaviors per 10 minutes of REM sleep from V3 to the end of treatment will be analysed using an ANCOVA model that includes treatment as a fixed effect and both the frequency of RBD behaviors at V3 and background treatment of melatonin/clonazepam as covariates.<br>For the change in severity of RBD behaviors observed in the sleep lab at V3 and at the end of treatment, treatment arm comparisons between nelotanserin 80 mg and placebo in the change in proportion of RBD behaviors classified as severe at V3 and at the end of treatment will be analysed using a generalized estimating equation (GEE) that includes treatment arm, visit, and the interaction of treatment arm and visit as fixed effects and background treatment of melatonin/clonazepam as a covariate. |

Treatment comparisons for end of treatment values of each continuous secondary efficacy endpoint that will be assessed at baseline and the final visit only will be analysed using an ANCOVA model that includes treatment as a fixed effect and both baseline value of the efficacy endpoint and background treatment of melatonin/clonazepam as covariates.
Treatment comparisons for end of treatment values of each continuous secondary efficacy endpoint that will be assessed at the final visit only (ie, CGIC) will be analysed using an ANCOVA model that includes treatment as a fixed effect and background treatment of melatonin/clonazepam as a covariate.
For continuous secondary efficacy endpoints that will be assessed daily over the course of the study, daily averages of the outcomes will be calculated for each week of the trial. Treatment comparisons in the change in average outcomes scores from the baseline week (over the last 7 days of placebo run-in) to the final week (over the last 7 days of treatment) will be analysed using an ANCOVA model that includes treatment as a fixed effect and background treatment of melatonin/clonazepam as a covariate.
Treatment comparisons for categorical secondary efficacy endpoints between groups will be analysed using Fisher's exact test.
Safety: Safety will be assessed by summarizing and analyzing AEs, laboratory analytes, vital signs, physical examination, and ECG parameters. For treatment comparisons of change in UPDRS II, UPDRS III, and UPDRS II and III composite scores, as well as change in MMSE and MoCA scores, statistical significance of treatment group differences in end of treatment values will be estimated using univariate ANCOVA models that include treatment arm as a fixed effect and both baseline value of the score and background treatment of melatonin/clonazepam as covariates.
Pharmacokinetics/pharmacodynamics (PK/PD): Plasma nelotanserin and M1 metabolite concentrations will be listed and summarized. Exploratory PK/PD analysis will include a plot of nelotanserin and M1 plasma concentrations versus the change in nightly frequency of RBD behaviors.

Rapid Eye Movement (REM) Sleep Behavior Disorder (RBD) in Dementia with Lewy Bodies (DLB): Dementia with Lewy bodies (DLB) is a progressive neurocognitive illness characterized pathologically by the presence of diffuse clusters comprised of alpha synuclein and other proteins that aggregate in the brain and disrupt cognitive function. DLB is considered to be the second most prevalent cause of degenerative dementia in the elderly population (McKeith 2004), accounting for up to 15%-25% of dementia presentations (McKeith 2000) and 15%-20% of all autopsy confirmed dementias in old age (Mosimann 2003). Between 50% and 80% of subjects with Parkinson's disease may experience dementia over the course of their illness (Alzheimer's Association 2015). While few studies of the exact prevalence of DLB have been published, the Lewy Body Dementia Association estimates that 1.1 million individuals are affected by DLB in the U.S. alone.

While cognitive dysfunction, manifested as deficits and fluctuation in attention is a core component of DLB, subjects also exhibit prominent behavioral disturbances early in the disease, including rapid eye movement (REM) sleep behavior disorder (RBD) behaviors. RBD affects between 50% and 80% of patients with DLB (Boeve 2007) and is characterized by the presence of abnormal behaviors and vocalizations during the phase of sleep associated with REM and during sleep phase transitions. While individuals are normally paralyzed during REM sleep, individuals with RBD lack muscle atonia during otherwise intact REM sleep. Hence, patients exhibit violent behaviors that mirror their dream content, including screaming and running during sleep, and kicking, punching, or strangling their bed partners. Patients have limited recall of these behaviors, which are often observed only by their bed partners.

While the pathophysiology of RBD is poorly understood, the condition has been linked with visual hallucinations (VHs) in Lewy body diseases. The presence of RBD has been associated with an increased risk of hallucinations and delusions in Parkinson's disease (Pacchetti 2005). Moreover, dream content during sleep-onset REM periods can resemble the content of daytime hallucinations (Pfeiffer 2013), with patients reacting to the content of dreams that often involve themes of being chased or attacked (Pfeiffer 2013). In addition, it has been shown that VHs can coincide with periods of REM (Pfeiffer 2013). Thus, a drug that reduces VHs may also have the potential to reduce REM sleep behaviors.

Despite the high prevalence of RBD and its dramatic impact on the quality of life of patients and their families, no medications are currently approved for its treatment. Indeed, there have been few randomized controlled trials to evaluate the efficacy and safety of drugs to treat RBD. Clonazepam, a long-acting benzodiazepine, is commonly used off-label to treat patients with RBD. The drug is associated with concerning side effects in elderly patients, including confusion, daytime sedation, and increased risk of falls (Anderson 2009). Moreover, the long-term use of benzodiazepines has been shown to be associated with cognitive impairment (Barker 2004), a particularly concerning side effect in patients with dementia. There remains a significant unmet need for safe and effective new therapies for patients with RBD.

Nelotanserin: Nelotanserin (RVT-102), previously known as APD-125, is a potent and selective 5HT2a receptor inverse agonist, and is currently being developed as an oral treatment for REM sleep behavior disorder in patients with DLB. Originally being developed for primary insomnia, seven clinical studies have been completed to date that included five Phase 1 and two Phase 2 studies, and 792 individuals have been exposed to nelotanserin over the dose range of 20 to 160 mg and up to 14 days. In the studies completed to date, nelotanserin has exhibited a favorable safety and tolerability profile.

Indication Rationale: Evaluation of nelotanserin for the treatment of RBD behaviors in patients with DLB is warranted by the following: (1) evidence in Phase 1 and Phase 2 studies that nelotanserin increases slow wave sleep and improves sleep maintenance and consolidation; (2) evidence that nelotanserin reduces the number of sleep phase transitions, which represent critical junctures at which RBD patients are particularly at risk of sleep behaviors; (3) overlap in the content of VHs and dreams experienced during RBD episodes, suggesting that a drug that reduces VHs may also impact dream content in a way that reduces the manifestation of violent behaviors; (4) evidence that other agents that block 5-HT2a neurotransmission, for example pimavanserin, may improve sleep quality in patients with Parkinson's disease (Cummings 2014; Friedman 2013), an illness that shares similar Lewy body pathology and clinical manifestations with DLB; and, (5) an acceptable safety and tolerability profile of nelotanserin based on previous clinical studies to date in the proposed dose range.

Dose Rationale: Based on the nonclinical studies conducted to date and the available clinical data, the 80 mg dose is considered a dose with sufficient safety margin to be evaluated in patients with DLB who experience RBD behaviors.

| Objectives | Endpoints |
|---|---|
| Primary | |
| To assess the effects of nelotanserin versus placebo on frequency of characteristic RBD behaviors (simple and major movements and vocalizations) based on video/audio assessment conducted at a sleep lab | The change in frequency of RBD behaviors per 10 minutes of REM sleep from baseline (the whole-night sleep study after 2 weeks of placebo run-in period) to the end of treatment (the whole-night sleep study on the end of treatment). |
| Secondary | |
| To assess the effects of nelotanserin versus placebo on severity of RBD behaviors measured by video/audio assessment conducted at a sleep lab | The change in the percentage of RBD behaviors rated as severe from baseline to the end of treatment. |
| To assess the effects of nelotanserin versus placebo on both severity and frequency of RBD behaviors measured by video/audio assessment conducted at a sleep lab | The change in the composite score based on both severity and frequency of RBD behaviors from baseline to the end of treatment. |
| To assess the effects of nelotanserin versus placebo on the number of injuries to subject or bed partner as recorded on study diary completed by subject and/or bed partner/caregiver | The change in the number of nights with injurious behaviors to subject or bed partner per week from baseline to the end of treatment. |
| To assess the effects of nelotanserin versus placebo on the number of nights with dramatic dreams per week as recorded on study diary completed by subject and/or bed partner/caregiver | The change in the number of nights with dramatic dreams per week from baseline to the end of treatment. |
| To assess the effects of nelotanserin versus placebo on subjective sleep quality | The change in sumscores of Scales for Outcomes in Parkinson's disease (SCOPA)-Night and SCOPA-Day subscales from baseline to the end of treatment. |
| To assess the effects of nelotanserin versus placebo on quality of bed partner sleep as measured by a visual analog scale (VAS) completed by the bed partner | The change in quality of bed partner sleep as measured by a VAS completed by the bed partner from baseline to the end of treatment. |
| To assess the effects of nelotanserin versus placebo on clinicians' rating of change in RBD behaviors | Comparison of Clinicians' Global Impression of Change in RBD Behaviors (CGIC-RBD) at the end of treatment. |
| To assess the effects of nelotanserin versus placebo on objective sleep parameters obtained at a sleep lab | The change in objective sleep parameters from baseline to the end of treatment. |
| To assess the effects of nelotanserin versus placebo on physical activity during sleep | The change in number of behaviors during sleep as measured by ActiGraph activity monitor from baseline to the end of treatment. |
| To assess the effects of nelotanserin versus placebo on visual hallucinations as recorded on study diary completed by subject and/or bed partner/caregiver | The change in total daily duration of VHs from baseline to the end of treatment. |
| To assess the effects of nelotanserin versus placebo on auditory hallucinations (AHs) as recorded on study diary completed by subject and/or bed partner/caregiver | The change in total daily duration of AHs from baseline to the end of treatment. |
| Safety | |
| To assess the safety of nelotanserin in DLB subjects with RBD behaviors | Safety will be assessed by analyzing adverse events (AEs), laboratory values, vital signs, and physical examinations. Extrapyramidal signs are assessed with the motor subsection of the Unified Parkinson's Disease Rating Scale (UPDRS, Parts II and III). Cognitive functioning is assessed with the Montreal Cognitive Assessment (MoCA) scale and the Mini-Mental State Examination (MMSE). |

| Objectives | Endpoints |
|---|---|
| Pharmacokinetic | |
| To assess the steady-state plasma exposure of nelotanserin and M1 metabolite, and relationship to primary endpoint | Plasma nelotanserin and M1 metabolite concentration on Day 29. Analysis of the relationship between plasma nelotanserin and M1 concentrations and the change in nightly frequency of RBD behaviors. |

Overall Design:

This is a multi-center, double-blind, randomized, placebo-controlled study in DLB subjects with RBD. Subjects will participate in a whole-night video-polysomnographic (video-PSG) study at a specified sleep lab during the single-blind placebo run-in period and at the end of the double-blind treatment. To allow subjects to acclimate to the sleep lab environment, subjects will spend a minimum of two (preferably consecutive) nights at the sleep lab. During this study, the subject must have at least one qualifying night of REM sleep (a qualifying night of REM sleep is defined as a night with REM sleep duration of ≥10 minutes). ActiGraph activity monitors worn on both wrists will be used to assess physical activity during sleep during the study.

The primary objective of the study will be to evaluate the efficacy and safety of nelotanserin as compared to placebo in DLB subjects with a concurrent diagnosis of RBD who have frequent RBD behaviors.

Following an initial screening, eligible subjects will enter a single-blind placebo run-in period of up to 3 weeks in duration. At the end of this period, all subjects who continue to meet the eligibility criteria will enter a four-week double-blind treatment period. Each subject will be randomized 1:1 to either nelotanserin 80 mg or matching placebo. For subjects assigned to nelotanserin 80 mg, the dose will be titrated up to the 80 mg dose strength in a blinded fashion after initial 5 days of treatment with 40 mg nelotanserin.

Following the final visit, all subjects who have completed the study will be eligible to participate in an open-label extension period with nelotanserin. The study design is outlined in FIG. 1.

Subject Population:

The study will randomize approximately 52 subjects with DLB who experience frequent RBD behaviors prior to screening and have 4 or more RBD episodes (one or more of which must include complex RBD events) per 10 minutes of REM sleep during 1 or more qualifying night(s) in the single-blind placebo run-in period (based on a central review of video-PSG data obtained from the sleep lab): Nelotanserin 80 mg-26 subjects, Placebo-26 subjects.

Inclusion Criteria: Adult subjects aged 50-85, inclusive, with a diagnosis of probable major neurocognitive disorder (dementia) with Lewy bodies (DLB) based on DSM-5 criteria; A concurrent diagnosis of REM sleep behavior disorder (RBD) based on DSM-5 criteria; subjects must: a) experience frequent RBD episodes prior to Screening (Visit 1) and during the single-blind placebo run-in period; and b) have at least 1 qualifying night of REM sleep during the video-PSG study in the single-blind placebo run-in period. A qualifying night of REM sleep is defined as a night with REM sleep duration of ≥10 minutes; have 4 or more RBD episodes (one or more of which must include complex RBD events) per 10 minutes of REM sleep during 1 or more qualifying night(s) based on a central review of video-PSG data obtained from the sleep lab during the single-blind placebo run-in period; Mini Mental State Examination score ≥18; Stable quetiapine treatment will be allowed, if at a stable dose of ≤25 mg/day for at least four weeks prior to screening and expect to continue the stable regimen throughout the study; Low dose clonazepam (≤1 mg/day) or melatonin treatment will be allowed, if at a stable dose for at least four weeks prior to screening and expect to continue the stable regimen throughout the study; Subjects taking anti-parkinsonian drugs (eg, levodopa) must be on stable dosage for at least 4 weeks prior to screening and expect to continue the stable regimen throughout the study; Subjects taking acetylcholinesterase inhibitors (AchEIs) or memantine must be on stable dosage for at least 4 weeks prior to screening and expect to continue the stable regimen throughout the study; Subjects must have a caregiver or family member who can serve as a collateral informant for study assessments and, if necessary, provide proxy consent to participate in the study; Females who have undergone surgical removal of uterus or removal of both ovaries, or have been naturally postmenopausal for at least 24 consecutive months (ie, no menses at any time during the preceding 24 consecutive months).

Exclusion Criteria: Subjects' sleep behavioral symptoms are secondary to or better accounted for by another medical condition (eg, untreated or sub-optimally treated obstructive sleep apnea [OSA]), psychiatric disorder (eg, other non-REM parasomnias, multiple system atrophy), or substance abuse (eg, alcoholism); Subjects have a current diagnosis of significant psychotic disorders including, but not limited to, schizophrenia or bipolar disorder; Any significant change in the subject's environment within the past 4 weeks; Subjects with a history of significant cerebrovascular events; Subjects with a current serious and/or unstable cardiovascular, respiratory, thyroid, gastrointestinal, renal, hematologic or other medical disorder; Use of any antipsychotic medication other than stable quetiapine at a dose of ≤25 mg/day; Subjects with current use of sedative-hypnotic medication (other than stable low dose clonazepam and/or melatonin); Subjects with medication-induced RBD or receiving venlafaxine and mirtazapine that may induce RBD behaviors; Subjects with current use of anti-epileptic medication or a history of epilepsy; Subjects who are allergic or hypersensitive to nelotanserin; Subjects with evidence of impaired liver function at screening (laboratory test values ≥3 times the upper limit of the laboratory reference (normal) range (ULN) for aspartate transaminase [AST/SGOT] or alanine transaminase [ALT/SGPT]); Subjects who have used any investigational medication within 30 days prior to the first dose of study medication.

Other Eligibility Criteria Considerations: To assess any potential impact on subject eligibility with regard to safety, the investigator must refer to the following document(s) for detailed information regarding warnings, precautions, contraindications, AEs, and other significant data pertaining to the investigational product(s) being used in this study: Nelotanserin Investigator's Brochure.

Screening Failures: Screen failures are defined as subjects who sign an informed consent form (ICF) for the study but are never subsequently randomized and who do not enter the single-blind placebo run-in period. A minimal set of screen failure information is required including demography, screen failure details, eligibility criteria, and any AEs. Subjects who are screen failures may be rescreened once only after approval by the study Medical Monitor.

Withdrawal Criteria: A withdrawal from the study is defined as withdrawing any time after entering the single-blind placebo run-in period and before completion of the end of study visit (Visit 5). Subjects who permanently discontinue use of investigational product will be considered to be withdrawn from the study. Subjects may withdraw from the study at any time and for any reason. The investigator (or designee) must document the reason for withdrawal in the Study Conclusion section of the case report form (CRF). Information related to AEs will continue to be collected as per usual procedures on subjects who have discontinued investigational product. Withdrawn subjects will not be replaced. The reasons for subject withdrawal will be recorded and may include, but are not limited to: Any clinical AE, laboratory abnormality, or other medical condition or situation occurs such that continued participation in the study would not be in the best interest of the subject in the opinion of the investigator; Significant protocol violation; Subject requests to discontinue for any reason; it is important to determine whether the withdrawal of consent is primarily due to an AE, lack of efficacy, or other reason; Subjects don't meet the eligibility criteria at baseline (Visit 4). The above reasons do not automatically lead to withdrawal from the study in all cases. The final decision will be based on consultation between the principal investigator and the study Medical Monitor, with the ultimate decision by the principal investigator or subject. If a subject meets discontinuation criteria during treatment, an Early Termination Visit will be required.

Subject Withdrawal Procedures: If a subject is prematurely discontinued from treatment with the investigational product(s), the investigator must make every effort to perform the evaluations scheduled for the Early Termination Visit (Table 8). In the case where the subject permanently discontinues study medication between scheduled clinic visits he/she should be recalled to the clinic as soon as possible and preferably within 7 days of stopping study medication for the Early Termination Visit; it is important to record the date of the last study dose.

Lost to follow-up: If a subject is lost to follow-up, every effort must be made by study center personnel to contact the subject, inquire about the reason for discontinuation/withdrawal, and follow up with any unresolved AEs/serious adverse events (SAEs). A minimum of 3 attempts at contact should be made with 1 contact being by certified letter. All measures taken to contact the subject and information received during those attempts must be documented.

Investigational Product and Other Study Treatment: Nelotanserin 20 mg tablets and matching placebo tablets are composed of an immediate-release, blue, oblong shaped tablet containing common pharmaceutical excipients in a compacted powder blend. The excipients used for the proposed clinical program are commonly available, generally regarded as safe, and tested against appropriate compendial acceptance criteria. The tablets are coated with a cosmetic colored film-coat. Lactose monohydrate is the only excipient used in the manufacture of RVT-102 tablets that is animal-sourced. The vendor source of this excipient has certified that ingredients used in the manufacture of lactose monohydrate are Bovine spongiform encephalopathy (BSE)/transmissible spongiform encephalopathy (TSE) free.

Randomization/Treatment Assignment: During the screening and the single-blind placebo run-in period, subjects will be identified by their initials, screening number and date of birth. Subjects who meet all screening eligibility criteria at Visit 2 will receive single-blind placebo (2× placebo tablets) for up to 3 weeks during the single-blind placebo run-in period. The tablet will be administered once-daily in the evening, at approximately 1 hour before bedtime. The subject will be instructed to take the study drug around the same time each day. If subjects continue to meet all eligibility criteria, they will be randomized and assigned a randomization identification number (three digits). Both screening and randomization numbers will be used to identify the subject on any related study documents. The Investigator will keep a record relating the names of the subjects to their identification numbers, to allow easy checking of data in subject files, when required. A central randomization process (IVRS) will be utilized. The investigative sites will be provided a 4 digit (e.g. 1001) randomization number (randnum) and a 3 digit (e.g. 123) kit ID (kitid). Both the randnum and kitid will be entered on the CRFs for each subject. Eligible subjects will be randomized (1:1) to either the nelotanserin 80 mg treatment group or the placebo group during the double-blind period. The randomization will be stratified by whether the subjects will continue to take clonazepam or melatonin concurrently with the study treatment. The study medications used in the trial are nelotanserin 20 mg and matching placebo tablets. Subjects randomized to nelotanserin 80 mg will receive two (2) 20 mg nelotanserin tablets (40 mg/day) for 5 days before the dose is titrated to four (4) 20 mg nelotanserin tablets (80 mg/day) for the remainder of the double-blind period. In order to mask the treatment assignment, subjects randomized to placebo will similarly receive two (2) placebo tablets for 5 days and then four (4) matching placebo tablets for the remainder of the double-blind period.

Blinding: The 20 mg Nelotanserin and matching placebo tablets will be identical in appearance.

Concomitant Medications and Non-Drug Therapies:

Permitted Medications and Non-Drug Therapies: Quetiapine <25 mg/day will be allowed if the dose is stabilized for at least 4 weeks prior to screening and the subject is expected to continue on this stable dose throughout the study; Low dose clonazepam (≤1 mg/day) or melatonin will be allowed if the dose is stabilized for at least four weeks prior to screening and the subject is expected to continue on this stable dose throughout the study; Subjects taking antiparkinsonian drugs (eg, levodopa) must be on stable dosage for at least 4 weeks prior to screening and expect to continue the stable regimen throughout the study; Subjects taking acetylcholinesterase inhibitors (AchEIs) or memantine must be on stable dosage for at least 4 weeks prior to screening and expect to continue the stable regimen throughout the study Prohibited Medications and Non-Drug Therapies: Prohibited medications include any medications that may interfere with study assessment during the single-blind placebo run-in and treatment periods as shown in Table 7.

TABLE 7

Medications That May Increase or Decrease Exposure to Nelotanserin

| CYP 3A4 inhibitors | CYP 3A4 Inducers |
| --- | --- |
| Boceprevir, clarithromycin, conivaptan, grapefruit juice, indinavir, itraconazole, ketoconazole, lopinavir/ritonavir, mibefradil, nefazodone, nelfinavir, posaconazole, ritonavir, saquinavir, telaprevir, telithromycin, voriconazole | Avasimibe, carbamazepine, phenytoin, rifampin, St. John's wort |

Any medications used to treat RBD behaviors other than those allowed in the study. Venlafaxine and mirtazapine which may induce RBD behaviors.

Meals and Dietary Restrictions: The study medication can be administered with or without food. Subjects should refrain from consumption of grapefruit or grapefruit juice due to potential to raise RVT102 concentrations.

Study Assessments and Procedures:

Time and Events: The Time and Events Schedule displays each study assessment and procedure along with the time of occurrence. All study assessments should be conducted by the investigator, and/or a suitably qualified designee approved and documented for this study. All raters will be trained and certified or otherwise deemed qualified by the Sponsor to perform the specific rating scales in this study. It is important that all efforts be made to ensure visits occur according to the protocol schedule. In the event there is a conflict with a required visit, a 10 day window can be exercised. This includes a −3 day and +7 day window. During the single blind placebo run-in period, the −3 day window is not allowed since critical data are required to be collected for a 2 week period in order to confirm eligibility into the double-blind randomized period. Visits should not be scheduled relative to the baseline visit. If the visit window is used, the subsequent visit or contact should be calculated from the date of the previous visit. Information will be recorded in the source documents and, where appropriate, the CRF. If medical assessments are scheduled for the same nominal time, then the assessments should be given after cognitive testing and occur in the following order whenever possible: 12-lead Electrocardiogram (ECG), Vital Signs, Blood draws.

Screening Period (up to 28 days before Visit 2): At Visit 1 and during the screening period, subjects will be screened for eligibility. An ICF will be signed by each subject, if they are able, or by the caregiver with subject assent. An ICF will also be signed by the caregiver before any study-specific procedures are performed. Subjects will be screened according to study inclusion/exclusion criteria. Subjects who do not qualify for the study during this period will be considered screen failures. Subjects who are screen failures during the Screening Period may be rescreened after discussion with the Medical Monitor. Note: subjects who are screen failures may be rescreened only once.

Single-Blind Run-In Period (Period A) (Period A, Up to 21 days): At Visit 2, subjects who meet all study screening criteria will enter a Single-Blind Placebo Run-In Period (Period A). Investigational product will be dispensed. Subjects will be instructed to take the investigational product (2 tablets) once daily in the evening, at approximately 1 hour before bedtime. Visit 2 assessments and procedures will be performed according to Table 8 below. Subjects will wear ActiGraph activity monitors on both of their wrists during sleep throughout the study.

Sleep Lab Visit (Visit 3): At Visit 3, after the subject completes 2 weeks of placebo run-in treatment, the subject will participate in a whole-night video-PSG study at a specified sleep lab, during which his/her RBD behaviors will be evaluated while continuing his/her placebo treatment. To allow subjects to acclimate to the sleep lab environment, subjects will spend a minimum of two (preferably consecutive) nights at the local sleep lab. During this study, the subject must have at least one qualifying night of REM sleep. A qualifying night of REM sleep is defined as a night with REM sleep duration of ≥10 minutes. If a subject cannot achieve one or more qualifying nights of REM sleep, the video-PSG study may be repeated for up to 2 nights as unscheduled visit(s). If a new diagnosis of sleep apnea is made during the sleep study, the sleep apnea may be treated, and up to 2 additional nights of sleep lab may be performed upon approval of the medical monitor. Should this occur, 2 qualifying nights of sleep study without apnea should be completed and sent to the central reviewer. The video-PSG data will be reviewed by a central reviewer to determine if the subject meets the randomization criteria. During this time, the subject will continue to receive placebo until being notified to return for the next visit. This period can be extended for 7 days to accommodate Visit 4 scheduling. Double-blind Treatment Period (Period B): Baseline/randomization (Visit 4-Day 0): At Visit 4 (Day 0), prior to ingestion of double-blind investigational product, baseline assessments will be performed to determine subject eligibility. To qualify for randomization at Visit 4, subjects must meet protocol-specified criteria for RBD behaviors at baseline, return unused study medication, be considered capable of completing study assessments, and continue to meet all other eligibility requirements. Eligible subjects will be randomized 1:1, stratified by use of clonazepam/melatonin, to either the nelotanserin 80 mg treatment group or the placebo group. During the four week double-blind treatment period (Period B), investigational product will be dispensed at Visit 4 (Day 0) and will be returned at Visit 5 (Day 28), the final study visit. Subjects randomized to nelotanserin 80 mg will receive two (2) 20 mg nelotanserin tablets (40 mg/day) for 5 days before the dose is titrated to four (4) 20 mg nelotanserin tablets (80 mg/day) for the remainder of the double-blind period. In order to mask the treatment assignment, subjects randomized to placebo will similarly receive two (2) placebo tablets for 5 days and then four (4) matching placebo tablets for the remainder of the double-blind period. Subjects will be reminded to take the blinded investigational product around the same time each evening, at approximately 1 hour before bedtime. During the double-blind period, study drug dose may be reduced only once at the decrement of one or more tablets at the discretion of the investigator for safety/tolerability reasons. The study drug dose may return to 80 mg after safety/tolerability events subside. All dose adjustments must take place after a safety evaluation at the study clinic.

Phone call (Day 14): There will be a phone contact approximately 14 days into the double-blind period during which safety/tolerability issues with study treatment, if any, will be addressed and AEs will be collected. The site personnel will also ensure that the subject is in compliance with study drug dosing and protocol procedures, including continuing to record sleep behaviors and to wear ActiGraph activity monitors nightly at home.

Final Study Visit (Visit 5 on Day 28): Subjects will return to the clinic for Visit 5 (Day 28) to complete final study assessments. The subject will participate in a whole-night video-PSG study at a specified sleep lab for least two (preferably consecutive) nights at the end of the double-blind period (Visit 5), during which his/her RBD behaviors will be evaluated. During this period, at least one qualifying night of REM sleep is required. A qualifying night of REM sleep is defined as REM sleep duration of 10 minutes or more. If a subject cannot achieve one or more qualifying nights of REM sleep, the video-PSG study may be repeated for up to two nights as unscheduled visit(s). Subjects who discontinue study drug treatment early must contact the study site personnel as soon as possible to schedule the whole-night video-PSG study. Study assessments and procedures will be performed according to Table 8 below. The order of assessments should remain consistent. If possible, other assessments, including ECG, vital signs, and blood draws, should be performed after cognition testing. Subjects will continue to wear ActiGraph activity monitors on both of their wrists during sleep during the double-blind period. Generally, a 10 day visit window (−3/+7 days) will be allowed to accommodate the scheduling. Subjects who prematurely discontinue double-blind investigational product should be encouraged to return to the clinic for an Early Termination Visit and the Visit 5 assessments and procedures will be completed.

Unscheduled Visit: The subject may be requested to return to the clinic for an unscheduled visit for the following reasons: Repeat the whole night sleep study; Reduce the dose due to tolerability or safety concerns (the dose decrement can be one or more tablets, and dose reduction can only occur once during the double-blind period); Titrate the dose back to 80 mg after dose reduction; Perform additional safety assessments as requested by the investigators. Follow-up Visit/Phone Call: For subjects who will not be participating in the open-label study, a follow-up visit or phone call (as deemed appropriate by the investigators) will occur approximately 14 days after the final study visit. During this visit/phone call, the investigator will review and record subjects' post-study medications and AEs. Additional safety assessments (eg, follow-up ECG and clinical lab assessments) as deemed necessary by the investigators may be performed at this visit.

TABLE 8

Time and Events Schedule

|  | Screening | Single-Blind Placebo Run-in (Period A) | | Baseline | Double-blind Treatment (Period B) | | Early Termination | Unscheduled Visit | Follow-up Visit/Phone Contact |
| --- | --- | --- | --- | --- | --- | --- | --- | --- | --- |
| Study Visit Number: | V1 | V2[1] | V3/Sleep lab | V4/Pre-dose[1,2] | Phone Contact[1] | V5[1] | | V99[3] | |
| Study Week: | W(−6) | W(−3) | W(−1) | W(0) | W(2) | W(4) | | | |
| Study Day: (relative to Baseline) | Up to −49 | −21 | −7 | 0 | 14 | 28 | | | |
| Informed consent | X | | | | | | | | |
| Inclusion and exclusion criteria | X | | | X | | | | | |
| Medical history/demographics | X | | | | | | | | |
| Concomitant medications review | X | X | | X | | X | X | X[3] | X |
| Blood alcohol and urine drug screen | X[4] | | | | | | | | |
| Dose up-titration instruction | | | | X | | | | | |
| Columbia Suicide Severity Rating Scale, physician administered | X[4] | | | | | X | X | | |
| Neurological examination | X[4] | | | X | | X | X | X[3] | X[3] |
| Physical exam | X[4] | X | | X | | X | X | X[3] | X[3] |
| 12-lead ECG | X[4] | | | X | | X | X | X[3] | X[3] |
| Vital signs[5] | X | X | | X | | X | X | X[3] | |
| Review adverse events | | X | | X | X | X | X | X[3] | X |
| Serum chemistry, hematology, urinalysis[6] | X[4] | | | X | | X | X | X[3] | X[3] |
| TSH and Vitamin B12[6] | X[4] | | | | | | | | |
| Syphilis Serology[6] | X[4] | | | | | | | | |
| HBsAg, hepatitis C antibody[6] | X[4] | | | | | | | | |

TABLE 8-continued

Time and Events Schedule

| | | | | | | | | |
|---|---|---|---|---|---|---|---|---|
| MMSE | X[4] | | | X | | X | X | | |
| MoCA | X[4] | | | X | | X | X | | |
| Video-polysomnography/sleep lab | | | X | | | X | X | X[3] | X[3] |
| ActiGraph activity monitor | | | ←———————————→ | | | | | | |
| Dispense/collect study diary | | X | | X | | X | X | | |
| Review study diary | | | | X | | X | X | | |
| SCOPA-Sleep | | | | X | | X | X | | |
| VAS bed partner sleep quality | | | | X | | X | X | | |
| Clinician Global Impression of Change-RBD | | | | | | X | X | | |
| Unified Parkinson's Disease Rating Scale, Part II and Part III | | | | X | | X | X | | |
| Dispense study drug | | X | | X | | | | | |
| Return study drug | | | | X | | X | X | | |

Abbreviations:
ALT = alanine aminotransferase;
AST = aspartate aminotransferase;
BUN = blood urea nitrogen;
CRF = case report form;
ECG = electrocardiogram;
GGT = gamma glutamyltransferase;
HBsAg = hepatisis B surface antigen;
MCH = mean corpuscular hemoglobin;
MCV = mean corpuscular volume;
MoCA = Montreal Cognitive Assessment;
TSH = thyroid stimulating hormone;
V = visit;
W = week.

[1] All efforts should be made to maintain the protocol schedule, however in cases where there are scheduling conflicts a 10 day window can be exercised as follows: −3 days or +7 days.
[2] Pre-dose assessments will be performed (to establish baseline for each treatment period).
[3] Assessments and procedures to be performed at unscheduled visits can be a subset of those in Table 2 at investigator's discretion.
[4] Assessments and procedures must be performed after the subject has been stabilized on the following medications for at least four weeks: quetiapine ≤25 mg/day, acetylcholinesterase inhibitors (AchEIs), memantine, antiparkinsonian drugs (eg, levodopa), clonazepam ≤1 mg/day, and/or melatonin
[5] Vital signs will be measured at every visit after the subject has been in the sitting position for 5 minutes and will include: temperature, pulse rate, respiratory rate, weight, height (only at baseline) and blood pressure will be measured in the supine and standing positions. Postural changes will be measured within 3 minutes of appropriate position change.
[6] A central lab will be utilized for this clinical study. Lab tests will include: hemotology (platelet count, red blood cell count, hemoglobin, hematocrit, MCV, MCH, neutrophils, lymphocytes, monocytes, eosinophils, basophils, Chemistry (BUN, creatinine, glucose, potassium, sodium, calcium, chloride, bicarbonate, AST, ALT, alkaline phosphatase, total and direct bilirubin, total protein, albumin, GGT), urinalysis (specific gravity, pH, glucose, protein, blood and ketones by dipstick—a microscopic examination will be needed if blood or protein is positive), drugs and alcohol screen, HBsAg, hepatitis C antibody, TSH, Vitamin B12, Syphilis serology. It is critical that all labs are completed as required by protocol for this patient population. Note that hepatitis screening performed within 3 months of Visit 2 is acceptable and will not require repeat testing for the purpose of this clinical study.
[7] A blood sample for pharmacokinetic analysis will be conducted at Visit 4 and Visit 5.

Critical Baseline Assessments: Subjects need to continue to meet the eligibility criteria for REM sleep behaviors: A subject must experience frequent RBD episodes prior to Screening (Visit 1). In addition, there are at least four (4) RBD episodes (one or more of which must include complex RBD events) per 10 minutes of REM sleep during 1 or more qualifying night(s) based on a central review of video-PSG data obtained from the sleep lab during the single-blind placebo run-in period.

Efficacy Assessments: All study assessments should be conducted by the investigator, and/or a suitably qualified designee, all of whom will be trained and certified to administer these measures for this study. Every effort should be made for the same person to conduct specific assessments on each individual subject at each study visit. Assessments will be monitored for quality. Screening and baseline assessments along with accompanying data will be reviewed to ensure that subjects meet the inclusion criteria. Other assessments will be monitored by using data collected.

Efficacy Assessments: All study assessments should be conducted by the investigator, and/or a suitably qualified designee, all of whom will be trained and certified to administer these measures for this study. Every effort should be made for the same person to conduct specific assessments on each individual subject at each study visit. Assessments will be monitored for quality. Screening and baseline assessments along with accompanying data will be reviewed to ensure that subjects meet the inclusion criteria. Other assessments will be monitored by using data collected.

REM Sleep Behaviors Observed with Video-Polysomnography in Sleep Lab: Whole-night video-PSG study will be performed according to the current standards. Video-PSG will provide the information on number of REMs, duration of REMs, and number and nature of RBD behaviors. The video data during REM will be reviewed centrally following a methodology included in the study manual. The procedures are briefly summarized below. The video recordings will be reviewed and analysed to determine behaviors characteristic of RBDs. A panel of 3 to 4 members will be assembled and will consist of board-certified neurologists with specialization in sleep medicine and video analysis experts. The video will be analyzed by one of the panel members with supervision by the panel. All ambiguous cases will be adjudicated by the panel. All visible movements regardless of type, amplitude, and duration will be analyzed. Every movement will be classified according to type of movement, topographical involvement (involvement of body parts), and presence of an associated arousal. All movements will be dichotomized into elementary/simple and complex/major. Elementary/simple movements are defined as small involuntary movements or stereotyped movements. Complex/major movements are defined as movements showing complexity of action and involving more muscle groups simultaneously or violent movements. Vocalizations (talking, crying, laughing, yelling, swearing) are also analyzed; the apparent emotional state (positive, e.g., when the subject is laughing; negative, e.g., when the subject is screaming or crying; neutral) will be assessed for complex/major behaviors and vocalizations. An RBD behavior is defined as a motor behavior and/or vocalization with a purposeful component, seemingly expressive of a subject's mentation. Comfort moves, neck myoclonus, respiratory noises, and events related to arousals will be excluded. The frequencies of RBD behaviors will be scaled to a function of time to compute the number of RBD behaviors per 10 minutes of REM sleep. The severity RBD behaviors will be based on viewer ratings. Specifically, each behavior will be rated separately into one of three severity categories: mild, moderate, or severe. A composite measure of both RBD behavior frequency and severity will be derived based on the weighting of each RBD behavior by its severity, with mild RBD behaviors receiving a weight of 1, moderate RBD behaviors receiving a weight of 2, and severe RBD behaviors receiving a weight of 3. The composite will then be calculated as the sum of products across all behaviors and scaled to a function of time to compute the severity-weighted RBD behaviors per 10 minutes of REM sleep. Clinician's Global Impression of Change-REM Sleep Behaviors: The Clinician's Global Impression of Change-RBD (CGIC-RBD) is an ordinal scale of global evaluation which assesses the change in overall status with RBD relative to the start of treatment. The scale has only 1 item that measures global change of overall status (improvement or worsening) with RBD by the investigator on a 7-point scale from 1 to 7, where 1=very much better and 7=very much worse. The CGIC-RBD will be assessed in accordance with the time and events schedule described in Table 8.

RBD-related Injuries: RBD-related injuries to the subject or the bed partner will be captured on a daily RBD diary to be completed by the bed partner or caregiver with information provided by the subject as needed. The number of injuries to either the subject or the bed partner will be recorded.

Dramatic Dreams: Dramatic dreams that are frightening, very unpleasant, and/or involve attacking or chasing scenes and their content will be captured on a daily RBD diary to be completed by the bed partner or caregiver with information provided by the subject as needed. The number of dramatic dreams will be recorded.

Scales for Outcomes of Parkinson's Disease—Sleep-Scales for Outcomes in Parkinson's disease (SCOPA)—Sleep is a validated short questionnaire that is used to assess nighttime sleep (NS) problems and daytime sleepiness (DS) in subjects with Parkinson's disease. It takes about 10 min to complete. The NS subscale addresses NS problems in the past month and includes 5 items with 4 response options. The maximum score of this subscale is 15, with higher scores reflecting more severe sleep problems. One additional question evaluates overall sleep quality on a 7-point scale (ranging from slept very well to slept very badly). The score on this item is not included in the score of the NS scale but is used separately as a global measure of sleep quality. The DS subscale evaluates DS in the past month and includes 6 items with 4 response options, ranging from 0 (never) to 3 (often). The maximum score is 18, with higher scores reflecting more severe sleepiness.

Visual Analog Scale for Bed Partner Sleep Quality: The bed partner's sleep quality will be assessed using a VAS, with one end of the VAS (marked with "0") representing "not able to sleep at all" and the other end of the VAS (marked with "10") representing "uninterrupted sleep". The bed partner will place an X on the scale indicating how well he/she has slept over the last 7 days. A bed partner is defined as the person who sleeps in the same bedroom as the subject.

Visual Hallucinations and Auditory Hallucinations: Subjects and caregivers will together complete a daily study diary, in which they will document the frequency and severity of visual and auditory hallucinations experienced by the subject. This diary will be completed each evening at a defined time (i.e. within one hour of the time at which the diary is first completed during the study). The subject and caregiver will note whether the subject experiences any hallucinations over the course of the day, and will describe the approximate number of hallucinations and their duration, the quality of the hallucinations, and the degree to which the hallucinations are disturbing to the subject and caregiver. This daily study diary will be reviewed by the investigator according to the time and events schedule described above.

Objective Sleep Parameters Measured by Polysomnography: Objective sleep parameters will be measured with PSG. These will include wake after sleep onset (WASO), number of arousals (AR), sleep efficiency (SE), % and duration of sleep stages (Stage 1 Non-REM [NREM] [N1], Stage 2 NREM [N2], Stage 3 NREM [N3], and REM), latency to Stage N1, Stage N2, Stage N3, and REM, latency to sleep, total sleep time (TST), REM start and end time(s), total recording time-"lights out" to "lights on" (TRT), duration of Stage W (wakefulness), periodic leg movements of sleep index (PLMSI), periodic leg movements of sleep arousal index (PLMSArI), total apnea hypopnea index (AHI), and REM AHI.

Physical Activity During Sleep Measured with ActiGraph: ActiGraph wGT3X-BT will be used to objectively measure physical activity during sleep. The subject will be instructed to wear the monitors on both wrists every night and record their sleep times. The "total count" captured during sleep time by the activity monitors will be used as the measure of physical activity during sleep.

Safety and Screening Assessments:

Adverse Events: The investigator or site staff is responsible for detecting, documenting, and reporting events that meet the definition of an AE or SAE.

Definition of Adverse Events:

An AE is any untoward medical occurrence associated with the use of a drug in humans, whether or not considered drug related. Therefore, an AE can be ANY unfavorable and unintended sign (including an abnormal laboratory finding or vital sign measurement), symptom, or disease temporally associated with the use of a medicinal product, without any judgment about causality.

Events meeting the definition of an AE include: Exacerbation of a chronic or intermittent pre-existing condition including either an increase in frequency and/or intensity of the condition; New conditions detected or diagnosed after investigational product administration even though it may have been present prior to the start of the study; Signs, symptoms, or the clinical sequelae of a suspected drug interaction; Signs, symptoms, or the clinical sequelae of a suspected overdose of either investigational product or a concomitant medication; Clinically significant abnormal findings (laboratory test results, vital signs, physical examination findings, ECGs, radiologic exams or other studies) should be recorded as AEs. A "clinically significant" finding is one that affects clinical management, including additional visits, monitoring or referrals, diagnostic tests or alteration of treatment, or that is considered clinically significant by the investigator. A clinically significant finding may be a change in a test that has previously been abnormal but now requires additional action; When a medical or surgical procedure is performed, the condition that leads to the procedure should be recorded as the AE.

Events that do not meet the definition of an AE include:

Anticipated day-to-day fluctuations or expected progression of pre-existing disease(s) or condition(s) present or detected at the start of the study unless judged by investigator to be more severe than expected for the subject's underlying condition; Abnormal laboratory, ECG, or vital sign measurements that are not labelled clinically significant (see definition above); Situations where an untoward medical occurrence did not occur (social and/or convenience admission to a hospital); Overdose in the absence of other AEs will not be reported as an AE in its own right; Changes in Columbia Suicide Severity Rating Scale (C-SSRS) during the course of the study indicating worsening should be evaluated by the investigator for clinical significance, and if clinically significant (e.g., alteration in medical care or intervention is required), an associated AE should be recorded, if present. The AE should be the primary underlying clinical manifestation assessed as clinically significant, and not the change in score itself; Adverse events are recorded from the time that informed consent is signed, including those that occur during the Single-Blind Placebo Run-in Period. Treatment emergent adverse events (TEAEs) are defined as those that occur on or after the date of the first dose of investigational product. Definition of Serious Adverse Event:

An AE is considered serious if, in the view of either investigator or sponsor, it results in any of the following outcomes: Death, A life-threatening AE, An AE is considered "life-threatening" if, in the view of either the investigator or sponsor, its occurrence places the patient or subject at immediate risk of death. It does not include an AE that, had it occurred in a more severe form, might have caused death. The determination of whether an AE is life threatening can be based on the opinion of either the investigator or sponsor. Thus, if either believes that it meets the definition of life-threatening, it must be considered life-threatening for reporting purposes. Inpatient hospitalization or prolongation of existing hospitalization, A persistent or significant incapacity or substantial disruption of the ability to conduct normal life functions, or A congenital anomaly/birth defect. Important medical events that may not result in death, be life threatening, or require hospitalization may be considered serious when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse. This definition of an SAE permits either the sponsor or the investigator to decide if an event is serious. Because SAEs are critically important for the identification of significant safety problems, the United States Food and Drug Administration (FDA) believes taking into account both the investigator's and the sponsor's assessment is important. For example, the investigator's perspective may be informed by having actually observed the event, and the sponsor is likely to have broader knowledge of the drug and its effects to inform its evaluation of the significance of the event. If either the sponsor or investigator believes that the event is serious, the event must be considered serious and evaluated by the sponsor for possible expedited reporting. Time Period and Frequency for Collecting Adverse Event and Serious Adverse Event Information: Collection of AEs and SAEs will begin at the time a subject signs informed consent and continues until the last study visit/follow-up phone contact, as shown in the Time and Events Schedule (Table 8). SAEs that are spontaneously reported by the subject or subject representative or discovered by the investigator or designee after the last study visit/follow-up phone contact and up to 30 days after the last dose of investigational product must be collected and reported. All SAEs will be recorded and reported to the Sponsor within 24 hours of the investigator becoming aware of the SAE. Investigators are not obligated to actively seek AEs or SAEs in former study subjects. However, if the investigator learns of any SAE, including a death, at any time after a subject has been discharged from the study, and he/she considers the event reasonably related to the investigational product or study participation, the investigator must promptly notify the sponsor or sponsor representative.

Assessment of Adverse Events: The severity of each AE will be assessed by the investigator, or designee approved and documented for this study, as mild, moderate, or severe based on the below definitions: Mild: Event that is usually transient and may require only minimal treatment or therapeutic intervention. The event does not generally interfere with usual activities of daily living. Moderate: Event that is usually alleviated with additional specific therapeutic intervention. The event interferes with usual activities of daily living, causing discomfort, but poses no significant or permanent risk of harm to the subject. Severe: Event that interrupts usual activities of daily living or significantly affects clinical status, or may require intensive therapeutic intervention. Outcome will be assessed using the following categories: recovered/resolved, not recovered/not resolved, recovered/resolved with sequelae, fatal, or unknown. In addition the investigator must determine the relationship between the administration of study medication and the occurrence of an AE/SAE as Not Suspected or Suspected as defined below: Not suspected: Means a causal relationship of the AE to study medication administration is unlikely or remote, or other medications, therapeutic interventions, or underlying conditions provide a sufficient explanation for the observed event. Suspected: Means there is a reasonable possibility that the administration of study medication caused the AE. "Reasonable possibility" means there is evidence to suggest a causal relationship between the study drug and the AE. Causality should be assessed and provided for every AE/SAE based on currently available information. Causality is to be reassessed and provided as additional information becomes available. Method of Detecting Adverse Events and Serious Adverse Events: Care will be taken not to introduce bias when detecting AEs and/or SAEs. Open-ended and non leading verbal questioning is the preferred method to inquire about AE occurrence. Appropriate questions include: "How are you feeling?", "Have you had any (other) medical problems since your last visit/ contact?", "Have you taken any new medicines, other than those provided in this study, since your last visit/contact?"

Follow-up of Adverse Events and Serious Adverse Events: After the initial AE/SAE report, the investigator is required to proactively follow each subject at subsequent visits/contacts. All AEs and SAEs will be followed until resolution, until the condition stabilizes, until the event is otherwise explained, or until the subject is lost to follow-up.

Physical Examinations: Physical examinations will be performed as indicated in Table 8. A complete physical examination will include, at a minimum, assessment of the cardiovascular, respiratory, gastrointestinal, and neurological systems. Neurological examinations will include assessment of gait, balance, coordination, cranial nerves and motor and sensory systems. A brief, symptoms-directed physical examination will include, at a minimum, assessments of the lungs, cardiovascular system, and abdomen (liver and spleen). Physical examinations at Screening and Visit 5/Early Termination will be full examinations; at all other study visits, an abbreviated physical examination is required. Any clinical significant findings at the screening visit will be considered medical history. The investigator will assess whether any changes from the screening visit in physical and neurological examinations reflect AEs.

Vital Signs: Vital signs will be measured after the subject has been in the seated position for 5 minutes and will include temperature, systolic and diastolic blood pressures, pulse rate, and respiratory rate. Body weight will also be recorded at each visit and height will be recorded at Screening. Blood pressure will also be measured in the supine and standing positions. Blood pressure in the supine position will be measured after the subject has been supine for a minimum of 3 minutes; blood pressure in the standing position will be measured after the subject has been standing for a minimum of 3 minutes. Both results will be reported on the appropriate CRF pages. The investigators will assess the clinical significance of any decline in blood pressure associated with the positional change. Any clinical significant findings at the screening visit will be considered medical history. The investigator will assess whether any changes from the screening visit in vital signs reflect AEs.

Electrocardiogram: Two tracings of 12-lead ECGs 15 min apart will be obtained at each time point during the study (Table 8) using an ECG machine that automatically calculates the heart rate and measures RR, PR, QRS, QT, QTcB (QT corrected for heart rate using Bazett's method), and QTcF (QT corrected for heart rate using Fridericia's method) intervals with the subject in the supine position. The investigator or designated qualified physician at the site will evaluate the Screening ECG for any abnormalities that should exclude the subject from the study or require acute additional evaluation or intervention. They should also evaluate the ECG printouts for all subsequent visits for any new abnormalities. Any abnormality should include a determination of clinical significance. A clinically significant ECG finding is one that requires additional medical evaluation or treatment. Abnormal ECG findings that are clinically significant should be recorded as AEs on the CRFs or Medical History if noted at the screening visit.

Clinical Safety Laboratory Assessments: All protocol-required laboratory assessments, as defined in Table 3, must be conducted in accordance with the Study Procedures Manual and Protocol Time and Events Schedule (Table 8). A central laboratory will be utilized for this clinical protocol. Abnormal laboratory tests that are clinically significant should also be recorded as AEs on the CRF or Medical History if noted during screening. Clinically significant means that the confirmed abnormal test result has an impact on patient management, including additional monitoring diagnostic tests, or changes in treatment. The same standard applies to additional non-protocol specified laboratory assessments that are performed at the institution's local laboratory and result in a change in subject management (i.e., monitoring, diagnostic tests, or any alteration in treatment). Hematology, clinical chemistry, urinalysis, and other screening laboratory parameters to be tested are listed in Table 9.

TABLE 9

Protocol-Required Screening and Safety Laboratory Assessments

| Laboratory Assessments | Parameters | | |
|---|---|---|---|
| Hematology | Platelet count | RBC Indices | WBC Count with |
| | RBC count | MCV | Differential |
| | Hemoglobin | MCH | Neutrophils |
| | Hematocrit | | Lymphocytes |
| | | | Monocytes |
| | | | Eosinophils |
| | | | Basophils |
| Clinical Chemistry | BUN | Potassium | AST |
| | Creatinine | Sodium | ALT |
| | Glucose | Calcium | Alkaline phosphatase |
| | | Chloride | Total and direct bilirubin |
| | | Bicarbonate | Total protein |
| | | | Albumin |
| | | | GGT |
| Routine Urinalysis | Specific gravity | | |
| | pH, glucose, protein, blood, and ketones by dipstick | | |
| | Microscopic examination (if blood or protein is abnormal) | | |
| Screening Tests only | Urine drug and serum alcohol screen | | |
| | HBsAg | | |
| | Hepatitis C antibody | | |
| | TSH | | |
| | Vitamin $B_{12}$ | | |
| | Syphilis serology | | |
| PK Sample Draws | A single steady state blood sample will be collected. Processing and shipping details are outlined in the lab manual | | |

Abbreviations: ALT = alanine aminotransferase; AST = aspartate aminotransferase; BUN = blood urea nitrogen; FSH = follicle stimulating hormone; GGT = gamma glutamyl-transferase; HBsAg = hepatitis B surface antigen; hCG = human chorionic gonadotropin; MCH = mean corpuscular hemoglobin; MCV = mean corpuscular volume; RBC = red blood cell; TSH = thyroid stimulating hormone; WBC = white blood cell.

All laboratory tests with values that are considered clinically significantly abnormal during participation in the study or within 7 days after the last dose of investigational product should be repeated until the values return to normal or baseline or until the value stabilizes. If such values do not return to normal within a period judged reasonable by the investigator, the etiology should be identified and the Medical Monitor notified.

Assessment of Suicidality: Subjects will be assessed for suicidality before and during the study using the Columbia Suicide Severity Rating Scale (C-SSRS). Subjects considered to be at significant risk will be excluded from the study. The C-SSRS is a brief measure which is designed to assess severity and change of suicidality by integrating both behavior and ideation. It assesses intensity of ideation (a potentially important marker of severity), specifically asking about frequency, duration, controllability, deterrents, and reasons for the ideation which was most severe during the respectively assessed timeframe. Suicidal behavior is also assessed by asking further questions to categorize the behaviors into actual, interrupted, or aborted attempts; as well as preparatory and non-suicidal self-injurious behavior. The C-SSRS will be completed by a rater trained and certified to administer this scale. Any change in C-SSRS score indicating the presence of suicidality should be evaluated by the investigator for clinical significance to determine continued study eligibility and appropriate clinical actions (including but not limited to a referral to a mental health professional). Clinically meaningful suicidal ideation, suicidal behavior and completed suicide should be recorded as AEs.

Assessment of Parkinsonism: Subjects will be assessed for signs of Parkinsonism before and during the study using the Unified Parkinson's Disease Rating Scale (UPDRS) Part II and Part III (Fahn 1987). The UPDRS Part II consists of 13 items for self-reported abilities on activities of daily life (ADLs), including speech, swallowing, handwriting, dressing, falling, salivating, walking, and tremor. The UPDRS Part III is a 14-item clinician-scored motor evaluation including rigidity, figure taps, tremor at rest, posture, leg agility, bradykinesia. UPDRS Part II yields a score range of 0 to 52 (inclusive), while UPDRS Part III scores range from 0 to 108 (inclusive), with higher scores indicating greater disability for both parts.

Mini-Mental State Examination: The MMSE (Folstein 1975) consists of 11 tests of orientation, memory (recent and immediate), concentration, language, and praxis. Scores range from 0 to 30, with lower scores indicating greater cognitive impairment. It is based on the performance of the subject and takes approximately 5 to 10 minutes to administer.

Montreal Cognitive Assessment Scale: The Montreal Cognitive Assessment (MoCA) scale (Nasreddine 2005) is designed to assess different cognitive domains: attention and concentration, executive functions, memory, language, visuo-constructional skills, conceptual thinking, calculations, and orientation. Ongoing work with Biundo et al and others suggests that in PD and DLB, MoCA is more sensitive to detect the earliest stage, whereas MMSE is more sensitive in the more advanced stage, leading to a recommendation by the EU Joint Programme-Neurodegenerative Disease Research (JPND) Working Group on Longitudinal Cohorts that both measures be included in studies of these patient populations. Time to administer the MoCA is approximately 10 minutes. The total possible score is 30 points; a score of 26 or above is considered normal.

Pregnancy: The study will allow female subjects who are postmenopausal for at least 24 consecutive months who have undergone surgical removal of uterus or removal of both ovaries.

Pharmacokinetic Assessments: Two blood samples for pharmacokinetic analysis of plasma nelotanserin and M1 metabolite concentration will be collected at the time points indicated in Table 8. The actual date and time of each blood sample collection, and the date and time of the dose of study treatment on the day of pharmacokinetic sampling will be recorded. For the pharmacokinetic sample at Visit 5, the date and time of the previous dose of study treatment also will be recorded.

Statistical Considerations and Data Analyses:

Hypotheses: For the primary efficacy endpoint analysis, the null hypothesis to be tested is that the magnitude of change in frequency per 10 minutes of REM sleep of RBD behaviors (simple and major movements and vocalizations), based on video assessment conducted at a sleep lab, from baseline (the whole-night sleep study on the last day of the single-blind placebo run-in period) to the end of treatment (the whole-night sleep study on the last day of treatment), will be statistically equivalent for nelotanserin and placebo treatment arms.

For the secondary efficacy endpoint analyses, the following null hypotheses will be tested: The proportion of RBD behaviors rated as severe, based on video assessment conducted at a sleep lab, from baseline to the end of treatment will be statistically equivalent for nelotanserin and placebo treatment arms. The magnitude of change on a composite of both severity and frequency of RBD behaviors, based on video assessment conducted at a sleep lab, from baseline to the end of treatment will be statistically equivalent for nelotanserin and placebo treatment arms. The magnitude of change in the number of nights with injurious behaviors to the subject or the bed partner per week, based on self or caregiver reports from the daily study diary, from baseline to the end of treatment will be statistically equivalent for nelotanserin and placebo treatment arms. The magnitude of change in the number of nights with dramatic dreams per week, based on self or caregiver reports from the daily study diary, from baseline to the end of treatment will be statistically equivalent for nelotanserin and placebo treatment arms. The magnitude of change in nighttime sleep quality, based on the SCOPA-Night subscale sumscore, from baseline to the end of treatment will be statistically equivalent for nelotanserin and placebo treatment arms. The magnitude of change in daytime sleepiness, based on the SCOPA-Day subscale sumscore, from baseline to the end of treatment will be statistically equivalent for nelotanserin and placebo treatment arms. The magnitude of change in quality of bed partner sleep, based on a VAS completed by the bed partner, from baseline to the end of treatment will be statistically equivalent for nelotanserin and placebo treatment arms. Clinicians' judgment of overall change in RBD behaviors, based on the CGIC-RBD administered at the end of treatment will be statistically equivalent for nelotanserin and placebo treatment arms. The magnitude of change in objective sleep parameters (including WASO; number of arousals; sleep efficiency; duration of total sleep time [TST]; duration and proportion of sleep time in Stage 1 NREM [N1], Stage 2 NREM [N2], Stage 3 NREM [N3], and REM; latency to sleep; latency to Stage N1, Stage N2, Stage N3, and REM; duration of wakefulness [Stage W]; periodic leg movements of sleep index [PLMSI]; periodic leg movements of sleep arousal index [PLMSArI]; total apnea hypopnea index [AHI]; and REM AHI.), based on assessments from PSG, from baseline to the end of treatment will be statistically equivalent for nelotanserin and placebo treatment arms. The magnitude of change in nightly physical activity during sleep time, based on total count assessment from the ActiGraph wGT3X-BT activity monitor worn during the study, from baseline to the end of treatment will be statistically equivalent for nelotanserin and placebo treatment arms. The magnitude of change in total daily duration of VHs, based on self and caregiver reports from the daily study diary, from baseline to the end of treatment will be statistically equivalent for nelotanserin and placebo treatment arms. The magnitude of change in total daily duration of AHs, based on self and caregiver reports from the daily study diary, from baseline to the end of treatment will be statistically equivalent for nelotanserin and placebo treatment arms.

For the safety endpoint analyses, the following null hypotheses will be tested: Changes in subject-reported ability to engage in ADLs, based on the UPDRS Part II, from baseline to the end of treatment will be statistically equivalent for nelotanserin and placebo treatment arms. Changes in clinician-reported extrapyramidal signs, based on the UPDRS Part III, from baseline to the end of treatment will be statistically equivalent for nelotanserin and placebo treatment arms. The magnitude of change in MMSE score from baseline to the end of treatment will be statistically equivalent for nelotanserin and placebo treatment arms. The magnitude of change in MoCA score from baseline to the end of treatment will be statistically equivalent for nelotanserin and placebo treatment arms.

Sample Size Considerations: The primary comparison of interest is to compare change in the nightly frequency of characteristic RBD behaviors in patients with LBD between nelotanserin and placebo arms after a four week treatment period. A sample size of 52 subjects (26 subjects per treatment arm) would provide power (1-β) of 0.80 to detect a 0.8 unit treatment group difference in the change from baseline to end of treatment in the nightly frequency of RBD behaviors measured by video assessment conducted at a sleep lab, assuming SD of 1 unit, using an analysis of covariance (ANCOVA) model with a single two-level between-groups fixed effect and two covariates and a significance level for Type-I error (α) of 0.05.

Analysis Populations: The efficacy analysis population will consist of all randomized subjects who have taken at least one dose of investigational product and who have at least one post-baseline efficacy assessment. This will be the primary population used for the efficacy analysis. The primary population for safety analyses will be the Safety Population, which will consist of all subjects who were randomized and took at least one dose of investigational product.

Key Elements of Analysis Plan: The primary objective of this study is to evaluate the efficacy and safety of nelotanserin in reducing the nightly frequency of characteristic RBD behaviors following four weeks of treatment. Descriptive statistics for all efficacy and safety measures over the course of the study will be presented. Continuous data will be summarized by means, SDs, standard errors (SEs), medians, interquartile ranges (IQRs), maximum observed value, minimum observed value, and number of subjects. Categorical data will be summarized by frequency counts and proportions. Listings will be sorted by sequence subject, period and time. Summaries will be presented by treatment and time. Version 9.2 or higher of the SAS system will be used to analyze the data as well as to generate tables, figures, and listings. Further details of analyses to be performed will be provided in the statistical analysis plan. Analysis datasets will be constructed using version SAS 9.2 or later following current CDISC guidelines. Missing data will be imputed using the last observation carried forward (LOCF) method. Details of imputation and any changes or refinements necessary will be documented in the statistical analysis plan (SAP). Depending on the extent of missing values, further investigation may be made into the sensitivity of the analysis results using different imputation methods.

Efficacy Analyses: Efficacy data will be summarized and listed by treatment and assessment time by period and overall. For treatment comparisons of change in efficacy endpoints of interest across two time points (ie, baseline and end of treatment), statistical significance of between-group differences in change in values from baseline to end of treatment visits will be estimated using univariate ANCOVA models that include treatment arm as a fixed effect and both baseline value of the efficacy endpoint and background treatment of melatonin/clonazepam as covariates. The least squares means and standard errors for change in values from baseline to end of treatment, the magnitude of least square mean differences and 95% CIs for differences in means between treatment arms, and p-values for the test of the fixed effect of treatment will be estimated from these models for the following efficacy endpoints: Change in frequency of RBD behaviors per 10 minutes of REM sleep, based on video assessment conducted at a sleep lab at baseline and at the end of treatment, Change in a composite of frequency and severity of RBD behaviors, based on video assessment conducted at a sleep lab at baseline and at the end of treatment, Change in the number of nights with one or more injurious behaviors, based on self or caregiver reports from the study daily diary, averaged over the last 7 days of the single-blind placebo run-in period and the last 7 days of the double-blind treatment period, Change in the number of nights with one or more dramatic dreams, based on self or caregiver reports from the study daily diary, averaged over the last 7 days of the single-blind placebo run-in period and the last 7 days of the double-blind treatment period, Change in nighttime sleep quality, based on SCOPA-Night subscale sumscore at baseline and at the end of treatment, Change in daytime sleepiness, based on SCOPA-Day subscale sumscore at baseline and at the end of treatment, Change in quality of bed partner sleep, based on a VAS completed by the bed partner at baseline and at the end of treatment, Change in clinicians' judgment of overall change in RBD behaviors, based on the CGIC-RBD administered at baseline and at the end of treatment, Change in duration (in minutes) of WASO, based on the PSG conducted at a sleep lab at baseline and at the end of treatment, Change in the number of arousals, based on the PSG conducted at a sleep lab at baseline and at the end of treatment, Change in sleep efficiency, based on the PSG conducted at a sleep lab at baseline and at the end of treatment, Change in duration (in minutes) of TST, based on the PSG conducted at a sleep lab at baseline and at the end of treatment, Change in duration (in minutes) of sleep time in sleep Stage 1, based on the PSG conducted at a sleep lab at baseline and at the end of treatment, Change in proportion of sleep time in sleep Stage N1, based on the PSG conducted at a sleep lab at baseline and at the end of treatment, Change in duration (in minutes) of sleep time in sleep Stage N2, based on the PSG conducted at a sleep lab at baseline and at the end of treatment, Change in proportion of sleep time in sleep Stage N2, based on the PSG conducted at a sleep lab at baseline and at the end of treatment, Change in duration (in minutes) of sleep time in sleep Stage N3, based on the PSG conducted at a sleep lab at baseline and at the end of treatment, Change in proportion of sleep time in sleep Stage 3, based on the PSG conducted at a sleep lab at baseline and at the end of treatment, Change in duration (in minutes) of sleep time in REM sleep, based on the PSG conducted at a sleep lab at baseline and at the end of treatment, Change in proportion of sleep time in REM sleep, based on the PSG conducted at a sleep lab at baseline and at the end of treatment, Change in latency (in minutes) to reach sleep Stage N1, based on the PSG conducted at a sleep lab at baseline and at the end of treatment, Change in latency (in minutes) to reach sleep Stage N2, based on the PSG conducted at a sleep lab at baseline and at the end of treatment, Change in latency (in minutes) to reach sleep Stage N3, based on the PSG conducted at a sleep lab at baseline and at the end of treatment, Change in latency (in minutes) to reach REM sleep, based on the PSG conducted at a sleep lab at baseline and at the end of treatment, Change in duration (in minutes) of wakefulness (Stage W), based on the PSG conducted at a sleep lab at baseline and at the end of treatment, Change in PLMSI, based on the PSG conducted at a sleep lab at baseline and at the end of treatment, Change in PLMSArI, based on the PSG conducted at a sleep lab at baseline and at the end of treatment, Change in total AHI, based on the PSG conducted at a sleep lab at baseline and at the end of treatment, Change in REM AHI, based on the PSG conducted at a sleep lab at baseline and at the end of treatment, Change in the total count of physical activity during sleep, based on assessment from the ActiGraph wGT3X-BT activity monitor at a sleep lab at baseline and at the end of treatment, Change in total count of physical activity, based on assessment from the ActiGraph wGT3X-BT activity monitor worn in a controlled sleep environment, averaged over the last 7 days of the single-blind placebo run-in period and the last 7 days of the double-blind treatment period, Change in the total daily duration (in minutes) of VHs, based on a study daily diary completed jointly by subject and caregiver, at baseline and at the end of treatment, Change in the total daily duration (in minutes) of AHs, based on a study daily diary completed jointly by subject and caregiver, at baseline and at the end of treatment. For treatment comparisons of change in severity of RBD behaviors, statistical significance of between-group differences in change in proportion of severe RBD behaviors from baseline to end of treatment visits will be estimated using a generalized estimating equation (GEE) that includes treatment arm, visit, and the interaction of treatment arm and visit as fixed effects and background treatment of melatonin/clonazepam as a covariate. The parameter coefficients and p-values for the tests of fixed effects on the proportion of severe RBD behaviors will be estimated. For treatment comparisons of change in efficacy endpoints of interest across more than two timepoints (ie, each week of the trial), statistical significance of between-group differences throughout the entire trial will be estimated using repeated-measures mixed-effects models that include treatment as a between-subjects fixed effect, week as a repeated-measures fixed effect, the interaction of treatment and week as a fixed-effect, subject as a random effect, and background treatment of melatonin/clonazepam as a covariate. Models that include treatment arm as a fixed effect and both baseline value of the efficacy endpoint and background treatment of melatonin/clonazepam as covariates. The least squares means and standard errors for values of each treatment arm at each week, p-values for omnibus tests of fixed effects, the magnitude of least square mean differences and 95% CIs for differences in means between treatment arms at each week, and p-values (adjusted for multiplicity) for post-hoc tests of pairwise comparisons across treatment arms and weeks will be estimated from these models for the following efficacy endpoints: The number of nights with one or more injury behaviors per week, based on self or caregiver reports from the RBD daily diary, The number of nights with one or more dramatic dreams per week, based on self or caregiver reports from the RBD daily diary, The total count of physical activity, based on assessment from the ActiGraph wGT3X-BT activity monitor worn in a controlled in-home environment.

Safety Analyses: The safety analyses will be based on the Safety Population. Safety will be assessed by summarizing and analyzing AEs, laboratory analytes, vital signs, ECG parameters, physical examination findings, and concomitant medications.

Adverse Events: AE verbatim text will be coded and classified by body system and preferred (coded) term using the Medical Dictionary for Regulatory Activities (Med-DRA). AEs will be assigned to the treatment based on the last dose received. All AEs will be listed. AEs, Drug related AEs, SAEs, AEs that lead to discontinuation of investigational product will be summarized by treatment group. AEs will be summarized separately for the Single-Blind Run-In Period and the Double-Blind Treatment Period. Clinical Laboratory Tests: Summaries of clinical laboratory data will be provided for subjects in the Safety Population. No inferential statistics will be provided. Quantitative values and change from baseline in quantitative values will be summarized by planned nominal time and treatment for each quantitative laboratory value. Listings of all laboratory results and reference ranges will be provided. For multiple lab assessments at the same time point, the worst value will be used for the data summaries. Laboratory values that fall outside of the reference range will be flagged as H=High or L=low. A lab shift table may be provided to show the baseline to the worst post value. Laboratory values that do not meet the laboratory abnormalities will be assigned N=normal in the shift table.

Vital Signs, Electrocardiograms, Physical Findings, and Other Safety Evaluations: Descriptive summaries of medical history, vital signs, weight, and ECG parameters will be presented separately for each study visit and treatment group. Clinically significant abnormal morphological ECG findings will be summarized by study visit. Abnormal physical examination findings will be summarized to include the number and percentage of subjects experiencing each treatment-emergent abnormal physical finding. These data will be summarized by treatment group.

Suicidal ideation and behavior (C-SSRS): Descriptive summaries of scores on the C-SSRS will be presented separately for each study visit and treatment group. Scores will consist of three composite values: suicidal ideations, suicidal behaviors, and suicidal ideations or behaviors. Each value will be binary: subjects answering 'yes' to one or more of the ideation items (items 1-5) will be classified as having suicidal ideations; subjects answering 'yes' to one or more of the behavior items (items 6-10) will be classified as having suicidal ideations; and subjects answering 'yes' to one or more of either set of items (items 1-10) will be classified as having suicidal ideations or behaviors.

Parkinsonism (UPDRS II and III): Descriptive summaries of scores on the UPDRS II, the UPDRS III, and a composite for the UPDRS II and III will be presented separately for each study visit and treatment group. For treatment comparisons of change in UPDRS II, UPDRS III, and UPDRS II and III composite scores, statistical significance of treatment group differences in change in values from baseline to end of treatment visits will be estimated using univariate ANCOVA models that include treatment arm as a fixed effect and both baseline value of UPDRS score and background treatment of melatonin/clonazepam as covariates. The least squares means and standard errors for change in values from baseline to end of treatment, the magnitude of least square mean differences and 95% CIs for differences in means between treatment arms, and p-values for the test of the fixed effect of treatment will be estimated from these models for each of these three measures. For each treatment group, mean change in UPDRS II and III composite scores from baseline to the end of treatment will be compared to the established threshold for minimal clinically important change of five points (Cummings 2014). Further, the proportion of subjects in each treatment arm with an increase in UPDRS II and III composite scores from baseline to end of treatment of at least 5 points will be calculated and compared using Fisher's exact test.

MMSE: Descriptive summaries of scores on the MMSE will be presented separately for each study visit and treatment group. For treatment comparisons of change in MMSE scores, statistical significance of treatment group differences in change in values from baseline to end of treatment visits will be estimated using a univariate ANCOVA model that includes treatment arm as a fixed effect and both baseline value of the MMSE score and background treatment of melatonin/clonazepam as covariates. The least squares means and standard errors for change in values from baseline to end of treatment, the magnitude of least square mean differences and 95% CIs for differences in means between treatment arms, and p-values for the test of the fixed effect of treatment will be estimated from this model.

MOCA: Descriptive summaries of scores on the MOCA will be presented separately for each study visit and treatment group. For treatment comparisons of change in MOCA scores, statistical significance of treatment group differences in change in values from baseline to end of treatment visits will be estimated using a univariate ANCOVA model that includes treatment arm as a fixed effect and both baseline value of the MOCA score and background treatment of melatonin/clonazepam as covariates. The least squares means and standard errors for change in values from baseline to end of treatment, the magnitude of least square mean differences and 95% CIs for differences in means between treatment arms, and p-values for the test of the fixed effect of treatment will be estimated from this model.

Pharmacokinetic/Pharmacodynamic (PK/PD) Analyses: Plasma nelotanserin and M1 metabolite concentrations will be listed and summarized by Visit. Exploratory PK/PD analysis will include a scatter plot of plasma nelotanserin and M1 concentrations collected at Visit 5 (Day 29) versus the change in nightly frequency of RBD behaviors from baseline to the end of treatment (primary efficacy endpoint). Additional analyses (if any) will be specified in the SAP.

Other Analyses: Additional analyses of the data may be conducted as deemed appropriate and will be detailed in the SAP. Further analyses of the data not specified in the SAP may be undertaken as post hoc analyses after completion of the study. Results of all study assessments will be included in an appendix to the study report.

Figure 2:
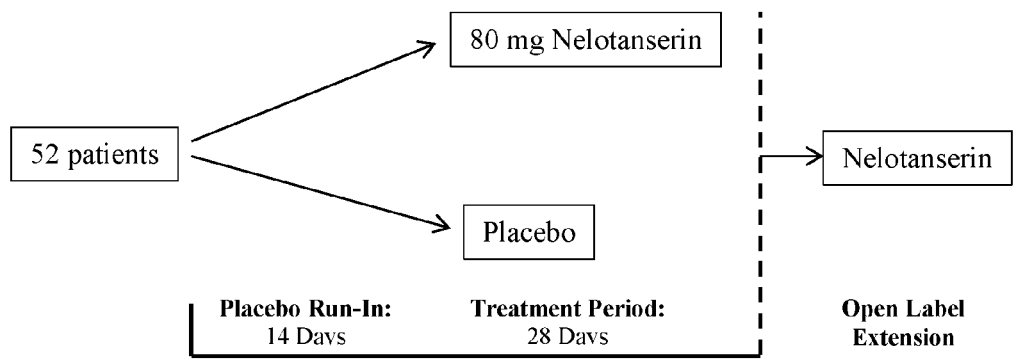
FIG. 2 shows the design for a video-PSG sleep lab study in DLB subjects with REM sleep behavior disorder.

Example 3—Double Blind Video-PSG in Sleep Lab and Home-Based Sleep Monitoring Study FIG. 2 displays the study design. The study will involve video-PSG in sleep lab at baseline (end of the placebo run-in period) and at the end of the double-blind treatment period. Home-based sleep monitoring (audio/video recording) nightly during the study; centrally read by an expert panel.

Endpoints include: Change in characteristic RBD behaviors observed on video recording in sleep lab; Change in characteristic RBD behaviors observed on home-based video recording.

Video Analysis Methodology

Primary outcome measure: change in nightly occurrence of complex scenic behaviours and vocalizations. These are defined as:

Complex scenic behaviours: These movements usually have a longer duration. When observing the videos, an apparent acting out of dreams or apparently intentional/finalistic behaviour can be seen.

Vocalizations: These will be subdivided based on type of vocalization

Other Data Captured:

Myoclonus-like movements: Very brief jerk-like movements without recognizable apparently intentional or finalistic movement Other simple motor events: Small excursion of head or limb without definitely jerk- or twitch-like appearance Inclusion criteria: Concurrent diagnosis of DLB and RBD based on DSM-5 criteria; Subjects must experience RBD behaviors >4 nights/week at screening and at the end of the placebo run-in period, and Subjects must have at least 6 RBD behaviors on video-PSG in the sleep lab, assessed by the methodology described previously, at the end of the placebo run-in period; Mini Mental State Examination score ≥18; Subjects with mild obstructive sleep apnea (OSA) or optimally controlled OSA allowed; Stable melatonin and low dose clonazepam (≤1 mg/day) allowed; Anti-parkinsonian drugs, acetylcholinesterase inhibitors, or memantine must be stable for at least 4 weeks prior to screening.

Exclusion Criteria: Subjects' RBD behaviours better accounted for by another medical condition (eg, untreated or sub-optimally treated obstructive sleep apnea [OSA]), psychiatric disorder (eg, other non-REM parasomnias, multiple system atrophy), or substance abuse (eg, alcoholism); Subjects with a history of significant cerebrovascular events; Subjects with current use of sedative-hypnotic medication (other than stable low dose clonazepam and/or melatonin); Subjects with medication-induced RBDs or receiving venlafaxine and/or amiodarone that may induce RBD behaviors; Subjects with current use of anti-epileptic medication or a history of epilepsy.

Although the present invention has been described in considerable detail with reference to certain preferred embodiments thereof, other versions are possible. Therefore, the sport and scope of the appended claims should not be limited to the description and the preferred versions contained within the specification.

What is claimed is:

1. A method for the prophylaxis and/or treatment of REM sleep behavior disorder, idiopathic REM sleep behavior disorder, or a combination thereof, in a subject in need thereof comprising administering to said subject a therapeutically effective amount of a 5-$HT_{2A}$ inverse agonist.

2. The method of claim 1, wherein the 5-$HT_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof.

3. The method of claim 2, wherein the 5-$HT_{2A}$ inverse agonist is nelotanserin or a pharmaceutically acceptable salt, hydrate, polymorph, or solvate thereof.

4. The method of claim 3, wherein the therapeutically effective amount of nelotanserin or a pharmaceutically acceptable salt, hydrate, polymorph, or solvate thereof is from 10 mg to about 160 mg.

5. The method of claim 3, wherein the therapeutically effective amount of nelotanserin or a pharmaceutically acceptable salt, hydrate, polymorph, or solvate thereof is about 10 mg, 20 mg, about 40 mg, 80 mg, or about 160 mg.

6. The method of claim 3, wherein the therapeutically effective amount of nelotanserin is about 10 mg, 20 mg, about 40 mg, 80 mg, or about 160 mg.

7. The method of claim 3, wherein the therapeutically effective amount of nelotanserin is about 10 mg.

8. The method of claim 3, wherein the therapeutically effective amount of nelotanserin is about 20 mg.

9. The method of claim 3, wherein the therapeutically effective amount of nelotanserin is about 40 mg.

10. The method of claim 3, wherein the therapeutically effective amount of nelotanserin is about 80 mg.

11. The method of claim 3, wherein the therapeutically effective amount of nelotanserin is about 160 mg.

12. The method of claim 1, wherein the therapeutically effective amount of the 5-$HT_{2A}$ inverse agonist is administered once a day, twice a day, three times a day, or four times a day.

13. The method of claim 1, wherein the 5-$HT_{2A}$ inverse agonist is configured for immediate release, for extended release, for delayed release, or any combination thereof.

14. The method of claim 1, wherein the 5-HT$_{2A}$ inverse agonist is in a pharmaceutical composition, and wherein the pharmaceutical composition is formulated for oral administration.

15. The method of claim 1, wherein the therapeutically effective amount of the 5-HT$_{2A}$ inverse agonist is administered about once daily in the morning, twice daily or once daily about 1 hour prior to the subject's bedtime.

16. The method of claim 1, wherein the subject is a human.

17. The method of claim 16, wherein the human is an adult with a diagnosis of a condition selected from Lewy Body dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

18. The method of claim 16, wherein the human has a concurrent diagnosis of REM Sleep Behavior disorder, idiopathic REM Sleep Behavior disorder, or a combination thereof, and a condition selected from Lewy Body dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and a combination thereof.

19. The method of claim 16, wherein the human has a Mini Mental State Examination score of greater than, or equal to, about 18.

20. The method of claim 16, wherein the human is an adult with a diagnosis of REM sleep behavior disorder associated with Dementia with Lewy Bodies.

21. The method of claim 16, wherein the human is an adult aged 50-85 inclusive.

22. The method of claim 16, wherein the human has experienced frequent episodes of REM sleep behavior disorder.

23. The method of claim 16, wherein the human has experienced episodes of REM sleep behavior disorder.

24. The method of claim 16, wherein the human has experienced episodes of REM sleep behavior disorder on at least three to four days in a week.

25. The method of claim 1, wherein the subject is concurrently receiving a therapeutically effective amount of at least one additional therapeutic agent selected from the group consisting of melatonin, quetiapine, clonazepam, levodopa, carbidopa, an antiparkinsonian drug, an acetylcholinesterase inhibitor, NMDA receptor antagonist, and a combination thereof.

26. The method of claim 25, wherein the antiparkinsonian drug is selected from an MAO-B inhibitor, a COMT inhibitor, a dopamine agonist or any combination thereof.

27. The method of claim 25, wherein the acetylcholinesterase inhibitor is selected from the group consisting of donepezil, rivastigmine, galantamine, and pharmaceutically acceptable salts, hydrates, polymorphs, or solvates thereof.

28. The method of claim 25, wherein the acetylcholinesterase inhibitor is donepezil or a pharmaceutically acceptable salt, hydrate, polymorph, or solvate thereof.

29. The method of claim 25, wherein the acetylcholinesterase inhibitor is rivastigmine or a pharmaceutically acceptable salt, hydrate, polymorph, or solvate thereof.

30. The method of claim 25, wherein the acetylcholinesterase inhibitor is galantamine or a pharmaceutically acceptable salt, hydrate, polymorph, or solvate thereof.

31. The method of claim 25, wherein NMDA receptor antagonist is selected from the group consisting of memantine, amantadine, ketamine, and pharmaceutically acceptable salts, hydrates, polymorphs, or solvates thereof.

32. The method of claim 31, wherein the NMDA receptor antagonist is memantine or a pharmaceutically acceptable salt, hydrate, polymorph, or solvate thereof.

33. The method of claim 25, wherein the NMDA receptor antagonist is amantadine or a pharmaceutically acceptable salt, hydrate, polymorph, or solvate thereof.

34. The method of claim 1, wherein administration of a therapeutically effective amount of a 5-HT$_{2A}$ inverse agonist results in treatment, and/or prophylaxis of REM sleep behavior disorder, idiopathic REM sleep behavior disorder, or a combination thereof.

35. The method of claim 1, wherein treating or prophylaxis results in a decrease in the frequency, severity, or a combination thereof of REM sleep behavior disorder episodes.

36. The method of claim 1, wherein treating or prophylaxis results in a decrease in the frequency of abnormal vocalizations and motor behavior per sleep period.

37. The method of claim 1, wherein treatment results in a decrease in the amount of nightmare content per sleep period.

38. The method of claim 1, wherein treating or prophylaxis results in a decrease in the potential for injury or injury to said subject during a sleep period.

39. The method of claim 1, wherein treating or prophylaxis results in an increase in quality of partner sleep.

40. The method of claim 1, wherein treating or prophylaxis results in an improvement in subjective sleep quality, objective sleep measures, or a combination thereof.

41. The method of claim 1, wherein treating or prophylaxis results in an improvement in the clinician assessment of global change pertaining to REM sleep behavior disorder.

42. The method of claim 1, wherein treating or prophylaxis results in a decrease in the frequency of REM sleep behavior disorder behaviors.

43. The method of claim 42, wherein REM sleep behavior disorder behaviors are selected from the group consisting of vocalizations, simple and complex motor behaviors, and any combination thereof.

44. The method of claim 1, wherein treating or prophylaxis results in a decrease in the severity of REM sleep behavior disorder behaviors.

45. The method of claim 1, wherein treating or prophylaxis results in a decrease in the number of nights with injurious behaviors to subject or bed partner per week.

46. The method of claim 45, wherein injurious behaviors are selected from a group consisting of vocalizations, simple and complex motor behaviors, and any combination thereof.

47. The method of claim 1, wherein treating or prophylaxis results in a decrease in the number of nightmares per week.

48. The method of claim 1, wherein treating or prophylaxis results in an improvement in the subject's Mini-Mental State Examination score.

49. A method for the prophylaxis and/or treatment of REM sleep behavior disorder, idiopathic REM sleep behavior disorder, or a combination thereof, in a subject in need thereof comprising administering to said subject a daily dose of about 40 mg of nelotanserin.

50. The method of claim 49, wherein the daily dose of about 40 mg of nelotanserin is administered once a day, twice a day, three times a day or four times a day.

51. The method of claim 49, wherein the subject has a concurrent diagnosis of REM Sleep Behavior disorder, idiopathic REM Sleep Behavior disorder, or a combination thereof, and a condition selected from Lewy Body dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and a combination thereof.

52. A method for the prophylaxis and/or treatment of REM sleep behavior disorder, idiopathic REM sleep behavior disorder, or a combination thereof, in a subject in need thereof comprising administering to said subject a daily oral dose of about 40 mg of nelotanserin.

53. The method of claim 52, wherein the daily dose of about 40 mg of nelotanserin is administered once a day, twice a day, three times a day or four times a day.

54. The method of claim 52, wherein the subject has a concurrent diagnosis of REM Sleep Behavior disorder, idiopathic REM Sleep Behavior disorder, or a combination thereof, and a condition selected from Lewy Body Dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and a combination thereof.

55. A method for the prophylaxis and/or treatment of REM sleep behavior disorder, idiopathic REM sleep behavior disorder, or a combination thereof, in a subject in need thereof comprising administering to said subject a daily dose of about 80 mg of nelotanserin.

56. The method of claim 55, wherein the daily dose of about 80 mg of nelotanserin is administered once a day, twice a day, three times a day or four times a day.

57. The method of claim 55, wherein the subject has a concurrent diagnosis of REM Sleep Behavior disorder, idiopathic REM Sleep Behavior disorder, or a combination thereof, and a condition selected from Lewy Body Dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and a combination thereof.

58. A method for the prophylaxis and/or treatment of REM sleep behavior disorder, idiopathic REM sleep behavior disorder, or a combination thereof, in a subject in need thereof comprising administering to said subject a daily oral dose of about 80 mg of nelotanserin.

59. The method of claim 58, wherein the daily dose of about 80 mg of nelotanserin is administered once a day, twice a day, three times a day or four times a day.

60. The method of claim 58, wherein the subject is a human adult with a diagnosis of a condition selected from Lewy Body Dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

61. A method for the prophylaxis and/or treatment of REM sleep behavior disorder, idiopathic REM sleep behavior disorder, or a combination thereof, in a subject in need thereof comprising administering to said subject a dose of about 40 mg of nelotanserin for a first time period followed by administering to said subject a dose of about 80 mg of nelotanserin for a second time period.

62. The method of claim 61, wherein the subject is a human adult with a diagnosis of a condition selected from Lewy Body Dementia, probable Dementia with Lewy Bodies, Dementia with Lewy Bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia and any combination thereof.

63. The method of claim 16, wherein the human is an adult with a diagnosis of REM sleep behavior disorder associated with Dementia with Lewy Bodies.

64. The method of claim 49, wherein the subject has a concurrent diagnosis of REM Sleep Behavior disorder, idiopathic REM Sleep Behavior disorder, or a combination thereof, and Lewy Body dementia.

65. The method of claim 52, wherein the subject has a concurrent diagnosis of REM Sleep Behavior disorder, idiopathic REM Sleep Behavior disorder, or a combination thereof, and Lewy Body Dementia.

66. The method of claim 55, wherein the subject has a concurrent diagnosis of REM Sleep Behavior disorder, idiopathic REM Sleep Behavior disorder, or a combination thereof, and Lewy Body Dementia.

67. The method of claim 58, wherein the subject is a human adult with a diagnosis of Lewy Body Dementia.

68. The method of claim 61, wherein the subject is a human adult with Lewy Body Dementia.

* * * * *